(12) United States Patent
Vu et al.

(10) Patent No.: US 10,683,369 B2
(45) Date of Patent: Jun. 16, 2020

(54) MONOCLONAL ANTIBODIES AGAINST BCMA

(71) Applicant: ENGMAB SARL, Boudry (CH)

(72) Inventors: Minh Diem Vu, Wollerau (CH); Klaus Strein, Weinheim (DE); Oliver Ast, Bassersdorf (CH); Marina Bacac, Zurich (CH); Camille Delon, Oberengstingen (CH); Lydia Jasmin Hanisch, Birmensdorf (CH); Anne Freimoser-Grundschober, Zurich (CH); Christian Klein, Bonstetten (CH); Ekkehard Moessner, Kreuzlingen (CH); Samuel Moser, Rotkreuz (CH); Pablo Umana, Wollerau (CH); Tina Weinzierl, Schlieren (CH)

(73) Assignee: EngMab Sàrl, Boudry (CH)

( * ) Notice: Subject to any disclaimer, the term of this patent is extended or adjusted under 35 U.S.C. 154(b) by 257 days.

(21) Appl. No.: 15/747,385

(22) PCT Filed: Aug. 3, 2016

(86) PCT No.: PCT/EP2016/068549
§ 371 (c)(1),
(2) Date: Jan. 24, 2018

(87) PCT Pub. No.: WO2017/021450
PCT Pub. Date: Feb. 9, 2017

(65) Prior Publication Data
US 2019/0352427 A1    Nov. 21, 2019

(30) Foreign Application Priority Data
Aug. 3, 2015 (EP) .................................. 15179549

(51) Int. Cl.
*A61K 39/395* (2006.01)
*C07K 16/46* (2006.01)
*A61P 35/02* (2006.01)
*C07K 16/28* (2006.01)

(52) U.S. Cl.
CPC ............ *C07K 16/468* (2013.01); *A61P 35/02* (2018.01); *C07K 16/2809* (2013.01); *C07K 16/2878* (2013.01); *C07K 2317/31* (2013.01); *C07K 2317/66* (2013.01); *C07K 2317/73* (2013.01); *C07K 2319/70* (2013.01)

(58) Field of Classification Search
None
See application file for complete search history.

(56) References Cited

U.S. PATENT DOCUMENTS

| | | |
|---|---|---|
| 5,273,743 A | 12/1993 | Ahlem et al. |
| 5,837,242 A | 11/1998 | Holliger et al. |
| 5,837,821 A | 11/1998 | Wu |
| 6,294,654 B1 | 9/2001 | Bogen et al. |
| 6,303,341 B1 | 10/2001 | Hiatt et al. |
| 6,551,592 B2 | 4/2003 | Lindhofer et al. |
| 6,602,684 B1 | 8/2003 | Umana et al. |
| 6,838,254 B1 | 1/2005 | Hamers et al. |
| 7,235,641 B2 | 6/2007 | Kufer et al. |
| 7,655,759 B2 | 2/2010 | Hamers et al. |
| 2009/0148438 A1 | 6/2009 | Nuttal et al. |

FOREIGN PATENT DOCUMENTS

| | | | |
|---|---|---|---|
| WO | 2014/122144 A1 | | 8/2014 |
| WO | WO2014122144 | * | 8/2014 |
| WO | 2014/140248 A1 | | 9/2014 |
| WO | 2016094304 A2 | | 6/2016 |

OTHER PUBLICATIONS

Klein, C., et al., Progress in overcoming the chain association issue in bispecific heterodimeric IgG antibodies, MAbs. Nov.-Dec. 2012;4(6):653-63.
Carpenter, R. O., et al., B-cell maturation antigen is a promising target for adoptive T-cell therapy of multiple myeloma, Clin Cancer Res. Apr. 15, 2013;19(8):2048-60.

* cited by examiner

*Primary Examiner* — Meera Natarajan
(74) *Attorney, Agent, or Firm* — Eckert Seamans Cherin & Mellott, LLC

(57) ABSTRACT

The invention relates to new antibodies against BCMA, their manufacture and use.

21 Claims, 32 Drawing Sheets
Specification includes a Sequence Listing.

Fig. 4 (Con't)
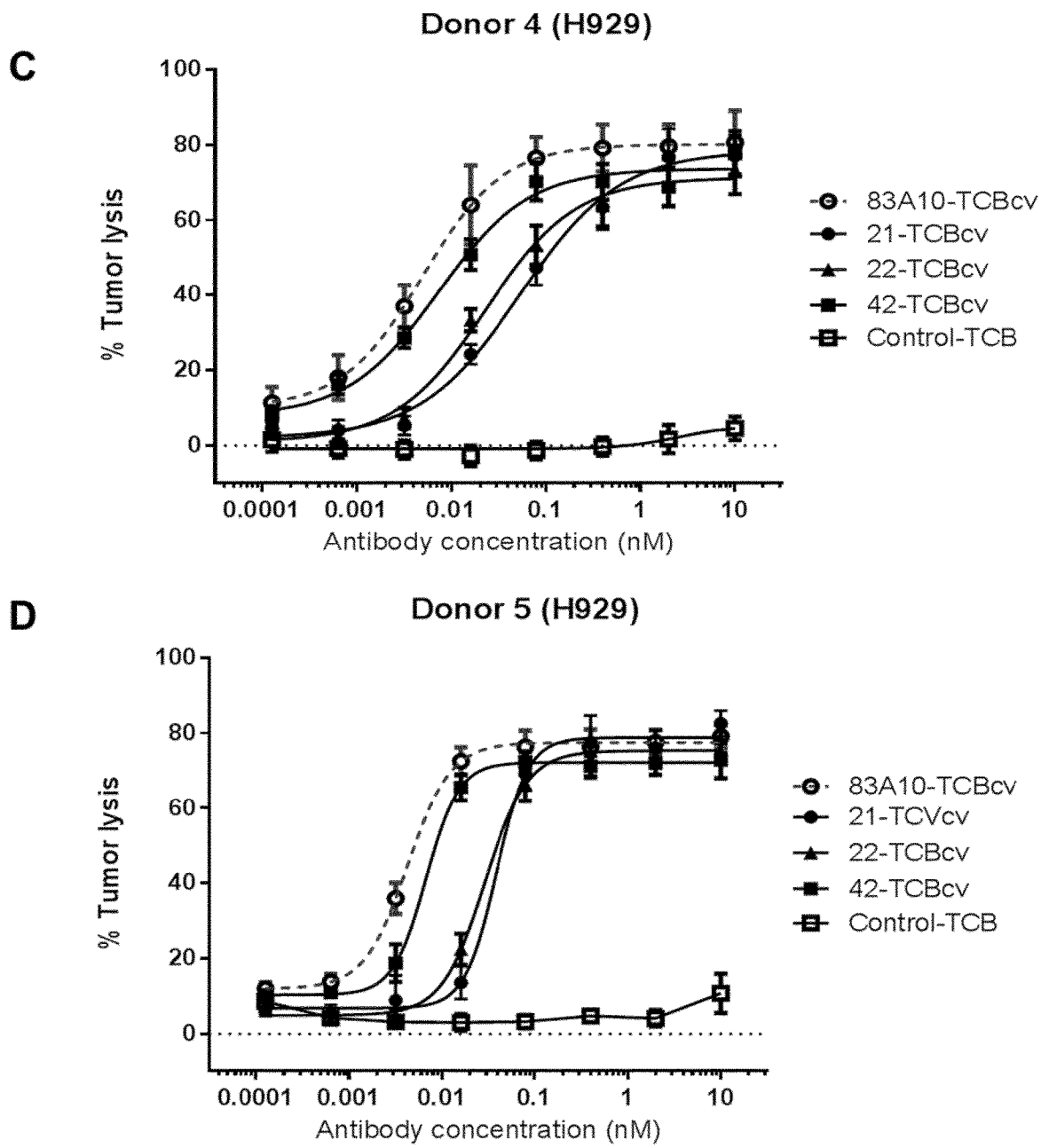

Fig. 5 (Con't)
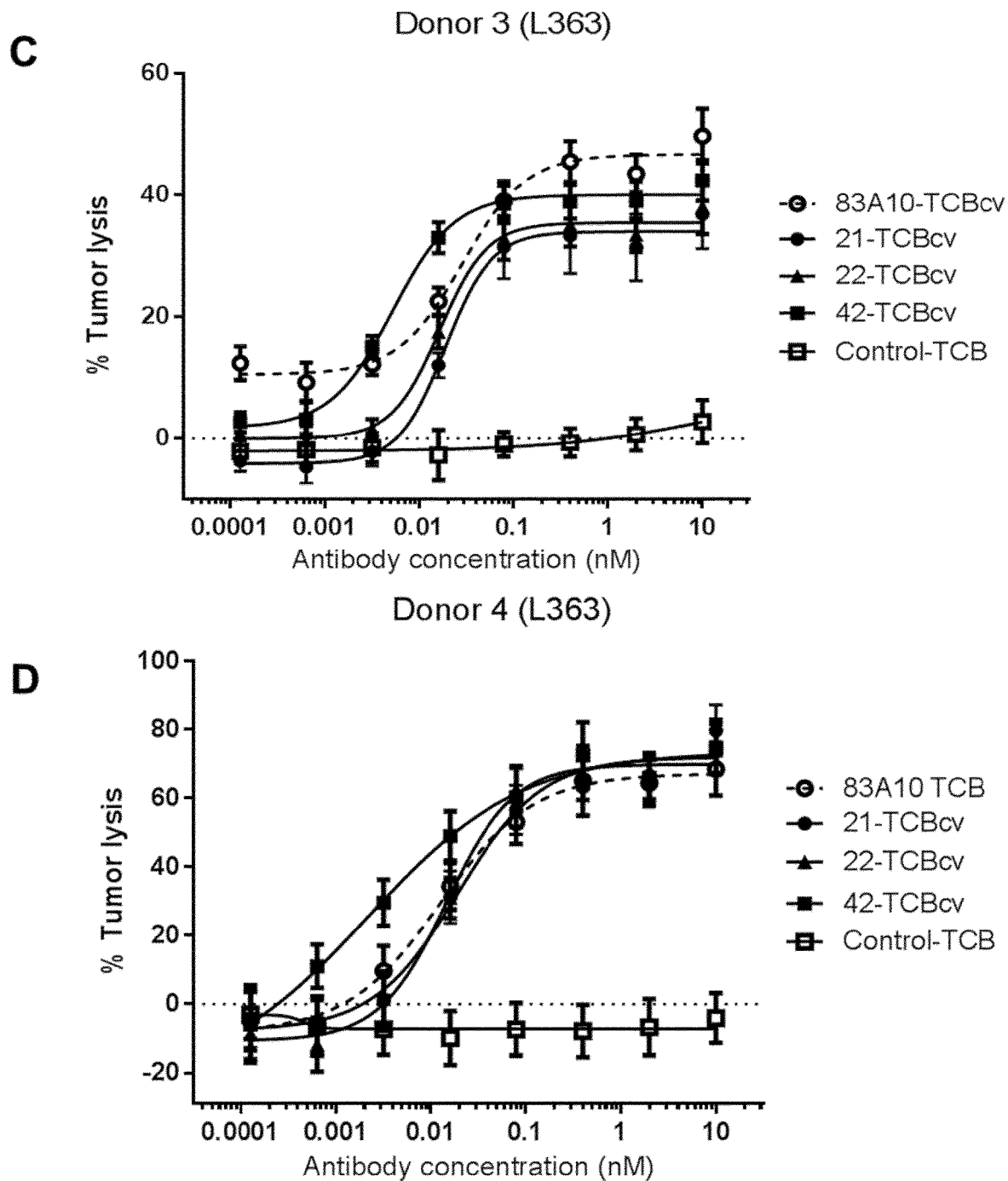

Fig. 5 (Con't)
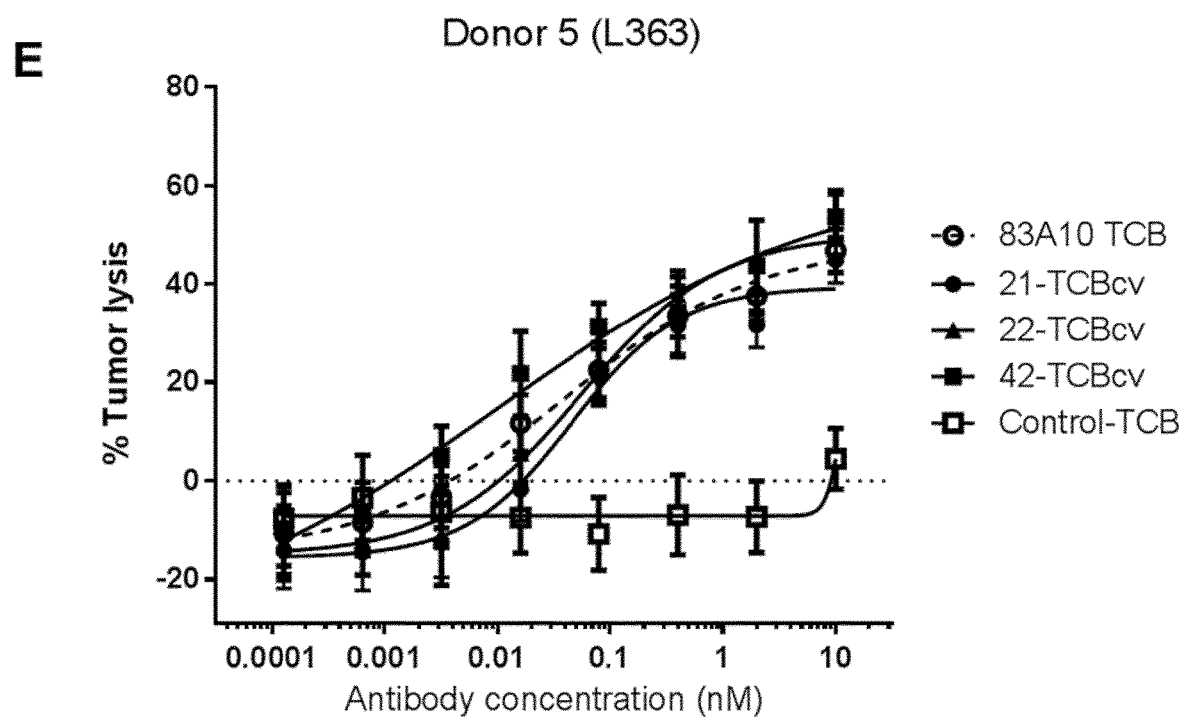

Fig. 6 (Con't)
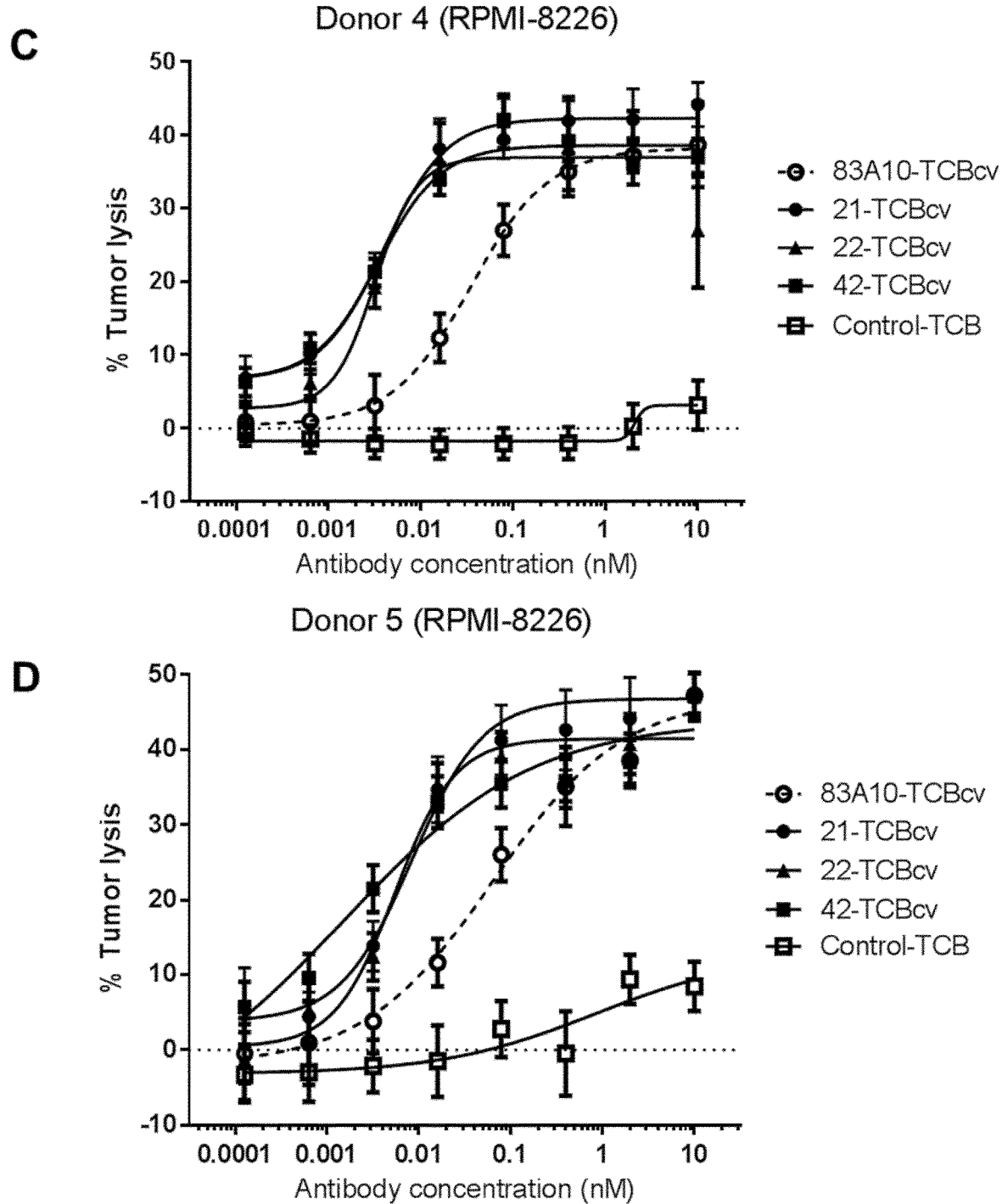

Fig. 7 (Con't)
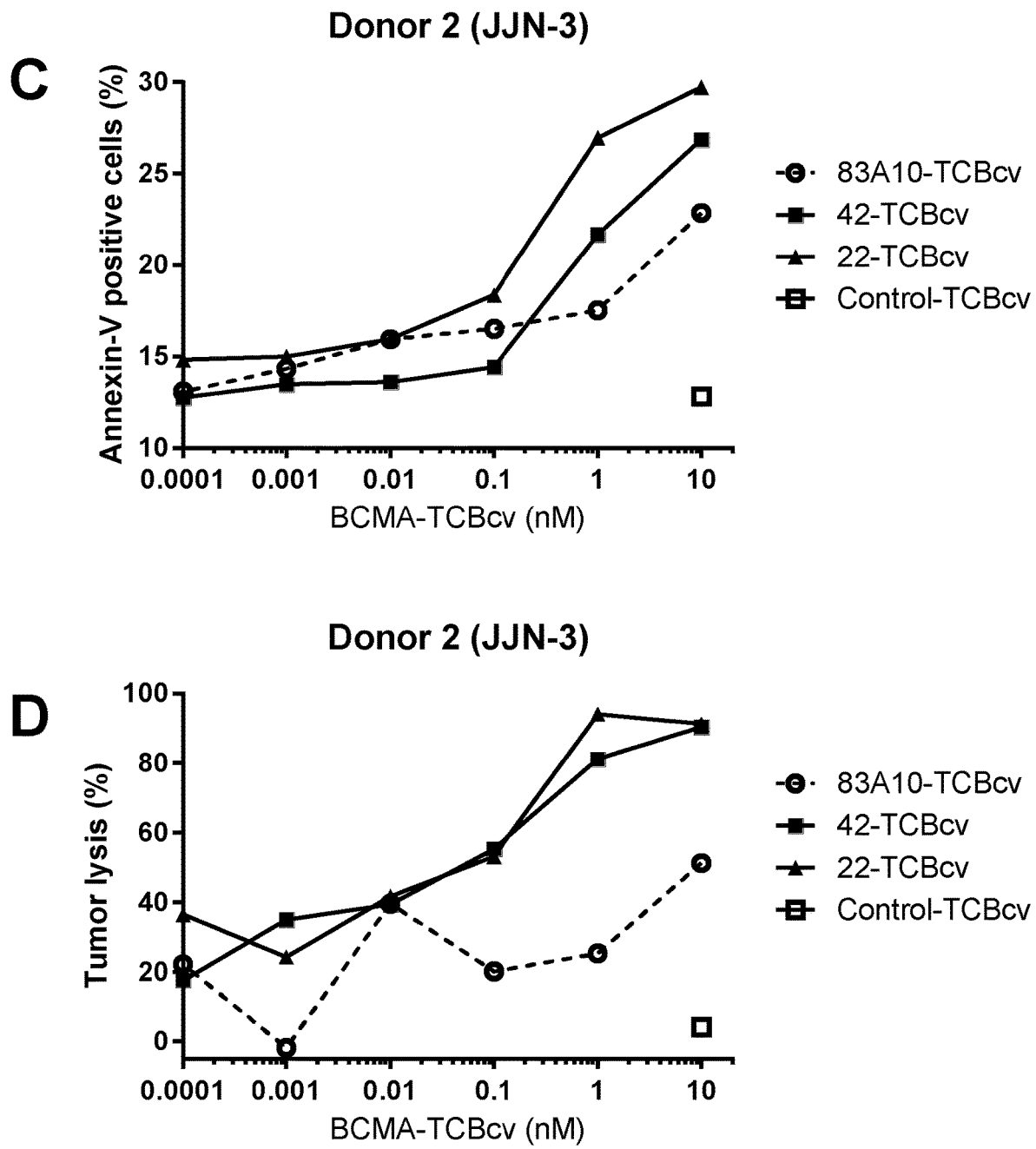

Fig. 10 (Con't)
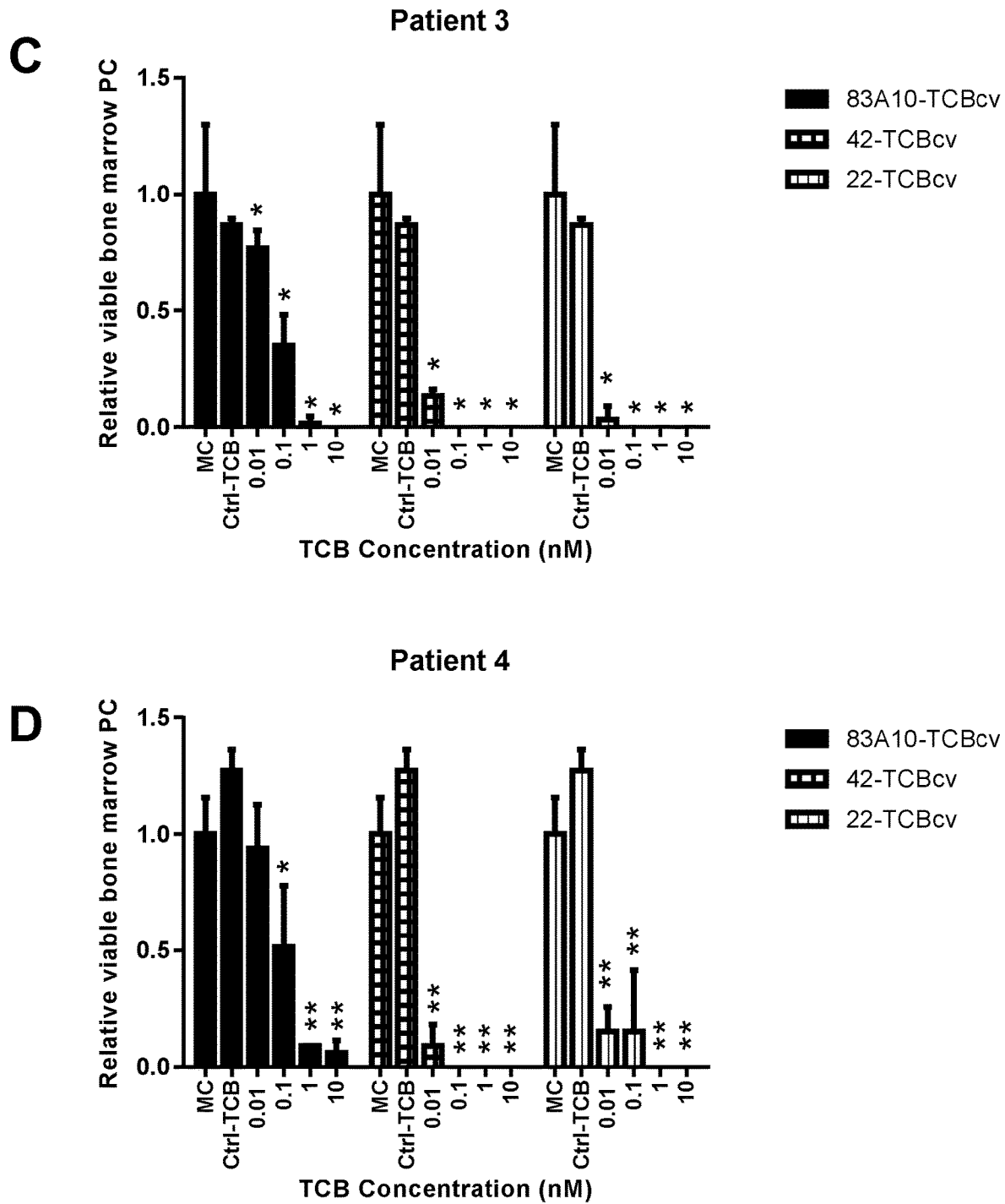

Fig. 10 (Con't)
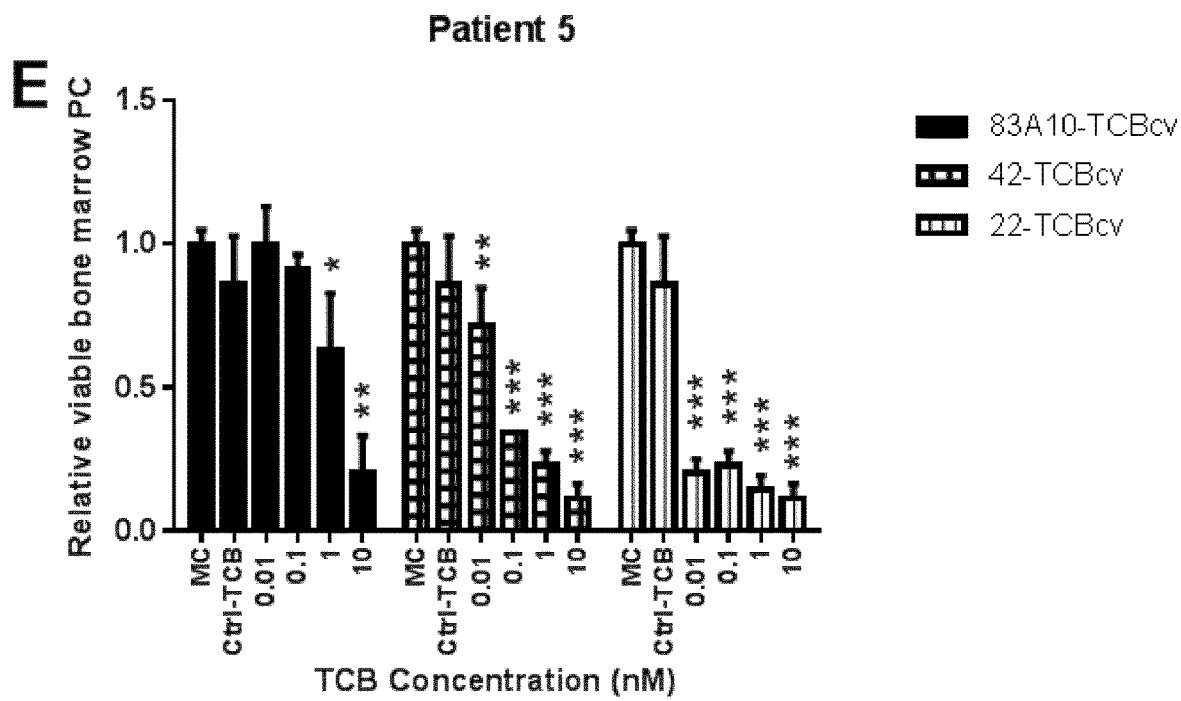
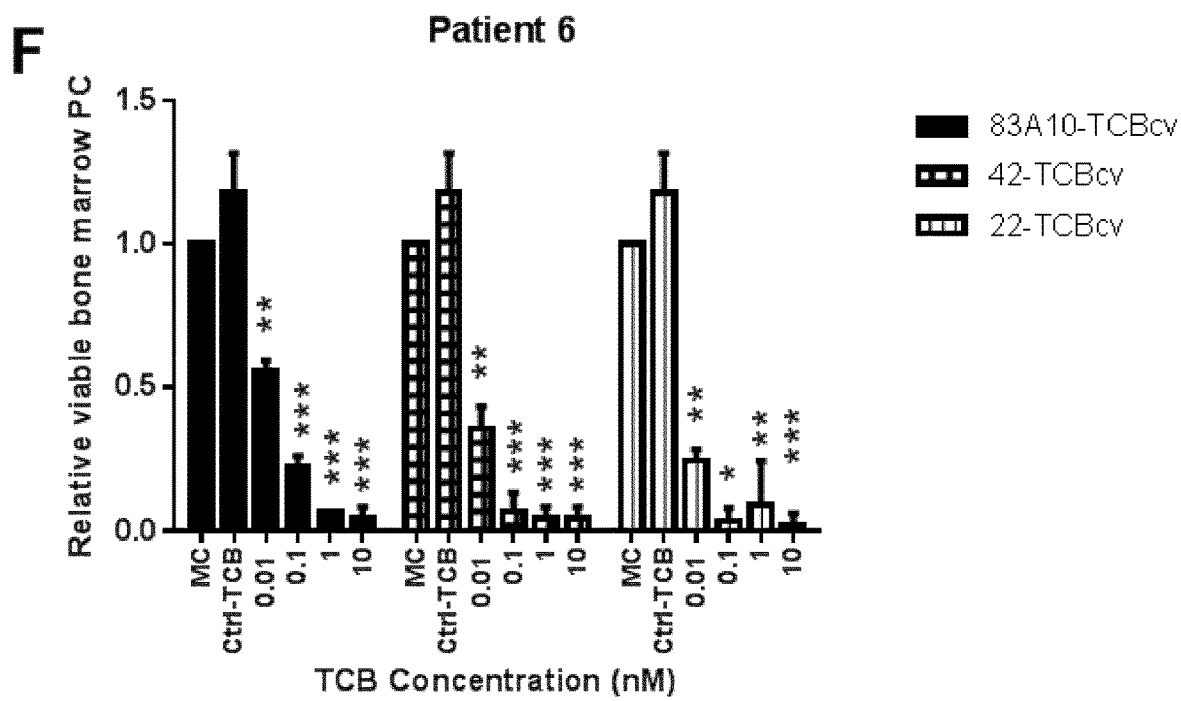

Fig. 10 (Con't)
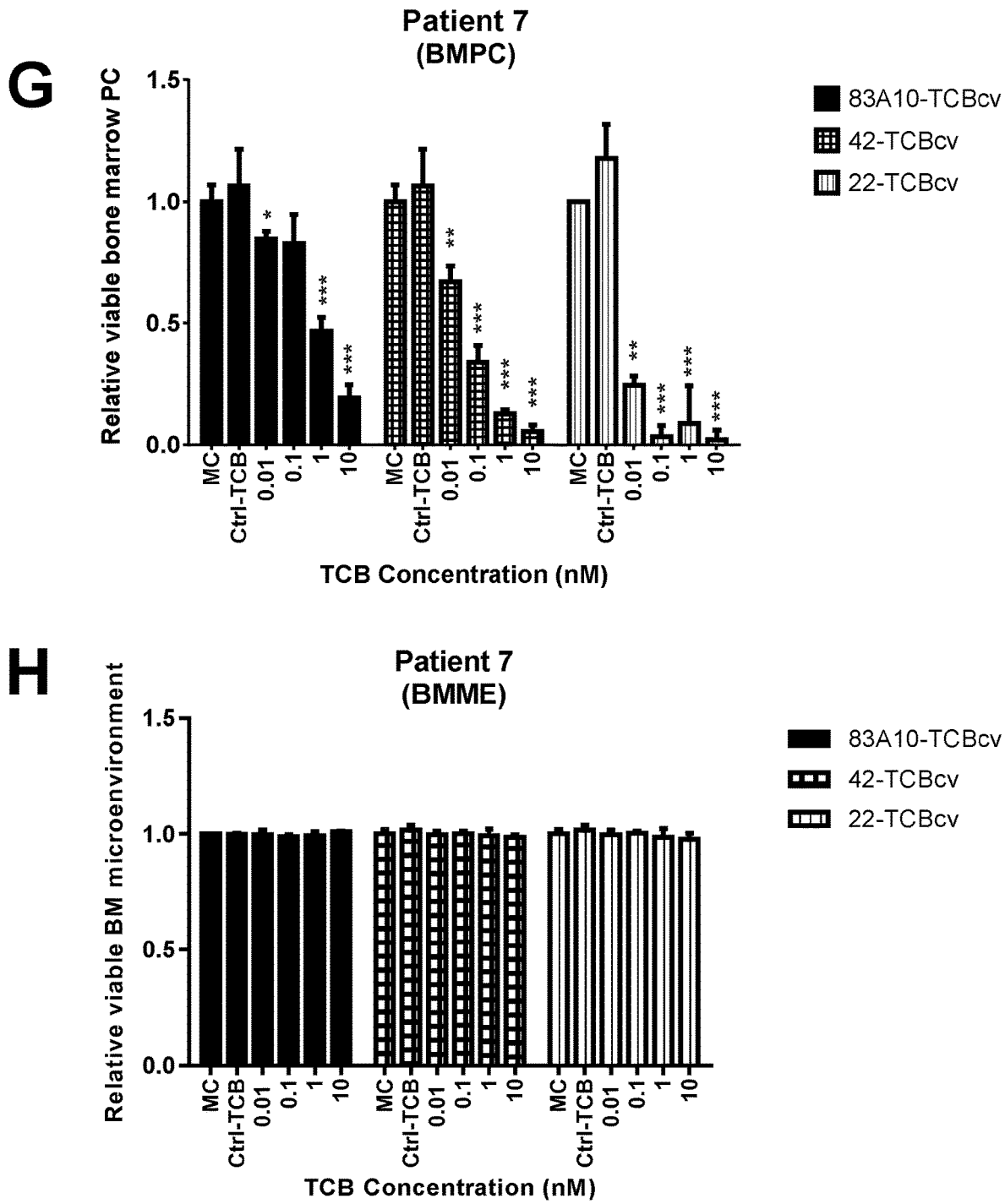

A

B

A

B

```
                       SEQUENCE LISTING

<160> NUMBER OF SEQ ID NOS: 57

<210> SEQ ID NO 1
<211> LENGTH: 5
<212> TYPE: PRT
<213> ORGANISM: Mus musculus

<400> SEQUENCE: 1

Thr Tyr Ala Met Asn
1               5

<210> SEQ ID NO 2
<211> LENGTH: 19
<212> TYPE: PRT
<213> ORGANISM: Mus musculus

<400> SEQUENCE: 2

Arg Ile Arg Ser Lys Tyr Asn Asn Tyr Ala Thr Tyr Tyr Ala Asp Ser
1               5                   10                  15

Val Lys Gly

<210> SEQ ID NO 3
<211> LENGTH: 14
<212> TYPE: PRT
<213> ORGANISM: Mus musculus

<400> SEQUENCE: 3

His Gly Asn Phe Gly Asn Ser Tyr Val Ser Trp Phe Ala Tyr
1               5                   10

<210> SEQ ID NO 4
<211> LENGTH: 14
<212> TYPE: PRT
<213> ORGANISM: Mus musculus

<400> SEQUENCE: 4

Gly Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Mus musculus

<400> SEQUENCE: 5
```

```
Gly Thr Asn Lys Arg Ala Pro
1               5
```

<210> SEQ ID NO 6
<211> LENGTH: 9
<212> TYPE: PRT
<213> ORGANISM: Mus musculus

<400> SEQUENCE: 6

```
Ala Leu Trp Tyr Ser Asn Leu Trp Val
1               5
```

<210> SEQ ID NO 7
<211> LENGTH: 125
<212> TYPE: PRT
<213> ORGANISM: Mus musculus

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 8
<211> LENGTH: 109
<212> TYPE: PRT
<213> ORGANISM: Mus musculus

<400> SEQUENCE: 8

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 9
<211> LENGTH: 116
<212> TYPE: PRT

-continued

<213> ORGANISM: Artificial Sequence
<220> FEATURE:
<223> OTHER INFORMATION: Variable region VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Variable region VH

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 11
<211> LENGTH: 109
<212> TYPE: PRT
<213> ORGANISM: Artificial Sequence
<220> FEATURE:
<223> OTHER INFORMATION: Variable region VL 83A10

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

```
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 12
<211> LENGTH: 109
<212> TYPE: PRT
<213> ORGANISM: Artificial Sequence
<220> FEATURE:
<223> OTHER INFORMATION: Variable region VL

<400> SEQUENCE: 12

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Glu Tyr
            20                  25                  30

Tyr Leu Ala Trp Tyr Gln Gln Lys Pro Gly Gln Ala Pro Arg Leu Leu
            35                  40                  45

Ile Glu His Ala Ser Thr Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 13
<211> LENGTH: 109
<212> TYPE: PRT
<213> ORGANISM: Artificial Sequence
<220> FEATURE:
<223> OTHER INFORMATION: Variable region VL Mab22

<400> SEQUENCE: 13

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Tyr Leu Ala Trp Tyr Gln Gln Lys Pro Gly Gln Ala Pro Arg Leu Leu
            35                  40                  45

Ile Ser Gly Ala Gly Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105
```

```
<210> SEQ ID NO 14
<211> LENGTH: 109
<212> TYPE: PRT
<213> ORGANISM: Artificial Sequence
<220> FEATURE:
<223> OTHER INFORMATION: Variable region VL Mab42

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Glu
            20                  25                  30

Tyr Leu Ser Trp Tyr Gln Gln Lys Pro Gly Gln Ala Pro Arg Leu Leu
        35                  40                  45

Ile His Ser Ala Ser Thr Arg Ala Thr Gly Ile Pro Asp Arg Phe Ser
    50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys
            100                 105

<210> SEQ ID NO 15
<211> LENGTH: 5
<212> TYPE: PRT
<213> ORGANISM: Homo sapiens
<220> FEATURE:
<223> OTHER INFORMATION: 83A10 CDR1H

<400> SEQUENCE: 15

Ser Tyr Ala Met Ser
1               5

<210> SEQ ID NO 16
<211> LENGTH: 17
<212> TYPE: PRT
<213> ORGANISM: Homo sapiens
<220> FEATURE:
<223> OTHER INFORMATION: 83A10 CDR2H

<400> SEQUENCE: 16

Ala Ile Ser Gly Ser Gly Gly Ser Thr Tyr Tyr Ala Asp Ser Val Lys
1               5                   10                  15

Gly

<210> SEQ ID NO 17
<211> LENGTH: 7
<212> TYPE: PRT
<213> ORGANISM: Homo sapiens
<220> FEATURE:
<223> OTHER INFORMATION: CDRH3

<400> SEQUENCE: 17

Val Leu Gly Trp Phe Asp Tyr
1               5

<210> SEQ ID NO 18
<211> LENGTH: 13
<212> TYPE: PRT
<213> ORGANISM: Homo sapiens
<220> FEATURE:
<223> OTHER INFORMATION: 83A10 CDR1L
```

-continued

<400> SEQUENCE: 18

Arg Ala Ser Gln Ser Val Ser Ser Ser Tyr Leu Ala Trp
1               5                   10

<210> SEQ ID NO 19
<211> LENGTH: 8
<212> TYPE: PRT
<213> ORGANISM: Homo sapiens
<220> FEATURE:
<223> OTHER INFORMATION: 83A10 CDR2L

<400> SEQUENCE: 19

Tyr Gly Ala Ser Ser Arg Ala Thr
1               5

<210> SEQ ID NO 20
<211> LENGTH: 10
<212> TYPE: PRT
<213> ORGANISM: Homo sapiens
<220> FEATURE:
<223> OTHER INFORMATION: CDRL3

<400> SEQUENCE: 20

Gln Gln Tyr Gly Tyr Pro Pro Asp Phe Thr
1               5                   10

<210> SEQ ID NO 21
<211> LENGTH: 5
<212> TYPE: PRT
<213> ORGANISM: Artificial Sequence
<220> FEATURE:
<223> OTHER INFORMATION: CDR1H

<400> SEQUENCE: 21

Asp Asn Ala Met Gly
1               5

<210> SEQ ID NO 22
<211> LENGTH: 17
<212> TYPE: PRT
<213> ORGANISM: Artificial Sequence
<220> FEATURE:
<223> OTHER INFORMATION: CDR2H

<400> SEQUENCE: 22

Ala Ile Ser Gly Pro Gly Ser Ser Thr Tyr Tyr Ala Asp Ser Val Lys
1               5                   10                  15

Gly

<210> SEQ ID NO 23
<211> LENGTH: 13
<212> TYPE: PRT
<213> ORGANISM: Artificial Sequence
<220> FEATURE:
<223> OTHER INFORMATION: Mab21 CDR1L

<400> SEQUENCE: 23

Arg Ala Ser Gln Ser Val Ser Glu Tyr Tyr Leu Ala Trp
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Mab21 CDR2L

```
<400> SEQUENCE: 24

Glu His Ala Ser Thr Arg Ala Thr
1               5

<210> SEQ ID NO 25
<211> LENGTH: 13
<212> TYPE: PRT
<213> ORGANISM: Artificial Sequence
<220> FEATURE:
<223> OTHER INFORMATION: Mab22 CDR1L

<400> SEQUENCE: 25

Arg Ala Ser Gln Ser Val Ser Ser Tyr Tyr Leu Ala Trp
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Mab22 CDR2L

<400> SEQUENCE: 26

Ser Gly Ala Gly Ser Arg Ala Thr
1               5

<210> SEQ ID NO 27
<211> LENGTH: 13
<212> TYPE: PRT
<213> ORGANISM: Artificial Sequence
<220> FEATURE:
<223> OTHER INFORMATION: Mab42 CDR1L

<400> SEQUENCE: 27

Arg Ala Ser Gln Ser Val Ser Asp Glu Tyr Leu Ser Trp
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Mab42 CDR2L

<400> SEQUENCE: 28

His Ser Ala Ser Thr Arg Ala Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Mab27 CDR1H

<400> SEQUENCE: 29

Ser Ala Pro Met Gly
1               5

<210> SEQ ID NO 30
<211> LENGTH: 16
<212> TYPE: PRT
<213> ORGANISM: Artificial Sequence
<220> FEATURE:
<223> OTHER INFORMATION: Mab27 CDR2H
```

```
<400> SEQUENCE: 30

Ala Ile Ser Tyr Ile Gly His Thr Tyr Tyr Ala Asp Ser Val Lys Gly
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: CDR1L

<400> SEQUENCE: 31

Arg Ala Ser Gln Ser Val Ser Glu Tyr Tyr Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: CDR2L

<400> SEQUENCE: 32

His Ala Ser Thr Arg Ala Thr
1               5

<210> SEQ ID NO 33
<211> LENGTH: 10
<212> TYPE: PRT
<213> ORGANISM: Artificial Sequence
<220> FEATURE:
<223> OTHER INFORMATION: CDR3L

<400> SEQUENCE: 33

Gln Gln Tyr Gly Tyr Pro Pro Asp Phe Thr
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Mab33 CDR1H

<400> SEQUENCE: 34

Thr Asn Ala Met Gly
1               5

<210> SEQ ID NO 35
<211> LENGTH: 17
<212> TYPE: PRT
<213> ORGANISM: Artificial Sequence
<220> FEATURE:
<223> OTHER INFORMATION: Mab33 CDR2H

<400> SEQUENCE: 35

Ala Ile Asn Arg Phe Gly Gly Ser Thr Tyr Tyr Ala Asp Ser Val Lys
1               5                   10                  15

Gly

<210> SEQ ID NO 36
<211> LENGTH: 5
<212> TYPE: PRT
<213> ORGANISM: Artificial Sequence
<220> FEATURE:
<223> OTHER INFORMATION: Mab39 CDR1H
```

```
<400> SEQUENCE: 36

Gln Asn Ala Met Gly
1               5

<210> SEQ ID NO 37
<211> LENGTH: 17
<212> TYPE: PRT
<213> ORGANISM: Artificial Sequence
<220> FEATURE:
<223> OTHER INFORMATION: Mab39 CDR2H

<400> SEQUENCE: 37

Ala Ile Ser Pro Thr Gly Phe Ser Thr Tyr Tyr Ala Asp Ser Val Lys
1               5                   10                  15

Gly

<210> SEQ ID NO 38
<211> LENGTH: 115
<212> TYPE: PRT
<213> ORGANISM: Artificial Sequence
<220> FEATURE:
<223> OTHER INFORMATION: Mab27 VH

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
                20                  25                  30

Pro Met Gly Trp Val Arg Gln Ala Pro Gly Lys Gly Leu Glu Trp Val
            35                  40                  45

Ser Ala Ile Ser Tyr Ile Gly His Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Val Leu Gly Trp Phe Asp Tyr Trp Gly Gln Gly Thr Leu Val Thr
            100                 105                 110

Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Mab33 VH

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Thr Asn
                20                  25                  30

Ala Met Gly Trp Val Arg Gln Ala Pro Gly Lys Gly Leu Glu Trp Val
            35                  40                  45

Ser Ala Ile Asn Arg Phe Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 40
<211> LENGTH: 116
<212> TYPE: PRT
<213> ORGANISM: Artificial Sequence
<220> FEATURE:
<223> OTHER INFORMATION: Mab39 VH

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Asn
            20                  25                  30

Ala Met Gly Trp Val Arg Gln Ala Pro Gly Lys Gly Leu Glu Trp Val
        35                  40                  45

Ser Ala Ile Ser Pro Thr Gly Phe Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 41
<211> LENGTH: 103
<212> TYPE: PRT
<213> ORGANISM: Artificial Sequence
<220> FEATURE:
<223> OTHER INFORMATION: CH1 domain

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys
            100

<210> SEQ ID NO 42
<211> LENGTH: 107
<212> TYPE: PRT

```
<213> ORGANISM: Artificial Sequence
<220> FEATURE:
<223> OTHER INFORMATION: CL domain

<400> SEQUENCE: 42

Arg Thr Val Ala Ala Pro Ser Val Phe Ile Phe Pro Pro Ser Asp Arg
1               5                   10                  15

Lys Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 43
<211> LENGTH: 103
<212> TYPE: PRT
<213> ORGANISM: Artificial Sequence
<220> FEATURE:
<223> OTHER INFORMATION: CD3 CH1

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 44
<211> LENGTH: 107
<212> TYPE: PRT
<213> ORGANISM: Artificial Sequence
<220> FEATURE:
<223> OTHER INFORMATION: CD3 CL

<400> SEQUENCE: 44

Ala Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 45
<211> LENGTH: 671
<212> TYPE: PRT
<213> ORGANISM: Artificial Sequence
<220> FEATURE:
<223> OTHER INFORMATION: 83A10 knob HC

<400> SEQUENCE: 45

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320
```

-continued

```
Ala Leu Trp Tyr Ser Asn Leu Trp Val Phe Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
            355                 360                 365

Leu Val Lys Asp Tyr Phe Pro Glu Pro Val Thr Val Ser Trp Asn Ser
            370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
            435                 440                 445

Thr Cys Pro Pro Cys Pro Ala Pro Glu Ala Ala Gly Gly Pro Ser Val
            450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
            515                 520                 525

Val Leu Thr Val Leu His Gln Asp Trp Leu Asn Gly Lys Glu Tyr Lys
            530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
            580                 585                 590

Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
            610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 46
<211> LENGTH: 446
<212> TYPE: PRT
<213> ORGANISM: Artificial Sequence
<220> FEATURE:
<223> OTHER INFORMATION: 83A10 hole HC

<400> SEQUENCE: 46

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly Lys
        435                 440                 445
```

<210> SEQ ID NO 47
<211> LENGTH: 216
<212> TYPE: PRT
<213> ORGANISM: Artificial Sequence
<220> FEATURE:
<223> OTHER INFORMATION: 83A10 LC

<400> SEQUENCE: 47

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 48
<211> LENGTH: 232
<212> TYPE: PRT
<213> ORGANISM: Artificial Sequence
<220> FEATURE:
<223> OTHER INFORMATION: CD3 LC

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80
```

-continued

```
Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 49
<211> LENGTH: 671
<212> TYPE: PRT
<213> ORGANISM: Artificial Sequence
<220> FEATURE:
<223> OTHER INFORMATION: Mab21 knob HC

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

-continued

Lys Val Asp Glu Lys Val Glu Pro Lys Ser Cys Asp Gly Gly Gly
    210             215             220

Ser Gly Gly Gly Ser Gln Ala Val Val Thr Gln Glu Pro Ser Leu
225             230             235             240

Thr Val Ser Pro Gly Gly Thr Val Thr Leu Thr Cys Gly Ser Ser Thr
                245             250             255

Gly Ala Val Thr Thr Ser Asn Tyr Ala Asn Trp Val Gln Glu Lys Pro
            260             265             270

Gly Gln Ala Phe Arg Gly Leu Ile Gly Gly Thr Asn Lys Arg Ala Pro
        275             280             285

Gly Thr Pro Ala Arg Phe Ser Gly Ser Leu Leu Gly Gly Lys Ala Ala
    290             295             300

Leu Thr Leu Ser Gly Ala Gln Pro Glu Asp Glu Ala Glu Tyr Tyr Cys
305             310             315             320

Ala Leu Trp Tyr Ser Asn Leu Trp Val Phe Gly Gly Gly Thr Lys Leu
                325             330             335

Thr Val Leu Ser Ser Ala Ser Thr Lys Gly Pro Ser Val Phe Pro Leu
            340             345             350

Ala Pro Ser Ser Lys Ser Thr Ser Gly Gly Thr Ala Ala Leu Gly Cys
        355             360             365

Leu Val Lys Asp Tyr Phe Pro Glu Pro Val Thr Val Ser Trp Asn Ser
    370             375             380

Gly Ala Leu Thr Ser Gly Val His Thr Phe Pro Ala Val Leu Gln Ser
385             390             395             400

Ser Gly Leu Tyr Ser Leu Ser Ser Val Val Thr Val Pro Ser Ser Ser
                405             410             415

Leu Gly Thr Gln Thr Tyr Ile Cys Asn Val Asn His Lys Pro Ser Asn
            420             425             430

Thr Lys Val Asp Lys Lys Val Glu Pro Lys Ser Cys Asp Lys Thr His
        435             440             445

Thr Cys Pro Pro Cys Pro Ala Pro Glu Ala Ala Gly Gly Pro Ser Val
    450             455             460

Phe Leu Phe Pro Pro Lys Pro Lys Asp Thr Leu Met Ile Ser Arg Thr
465             470             475             480

Pro Glu Val Thr Cys Val Val Val Asp Val Ser His Glu Asp Pro Glu
                485             490             495

Val Lys Phe Asn Trp Tyr Val Asp Gly Val Glu Val His Asn Ala Lys
            500             505             510

Thr Lys Pro Arg Glu Glu Gln Tyr Asn Ser Thr Tyr Arg Val Val Ser
        515             520             525

Val Leu Thr Val Leu His Gln Asp Trp Leu Asn Gly Lys Glu Tyr Lys
    530             535             540

Cys Lys Val Ser Asn Lys Ala Leu Gly Ala Pro Ile Glu Lys Thr Ile
545             550             555             560

Ser Lys Ala Lys Gly Gln Pro Arg Glu Pro Gln Val Tyr Thr Leu Pro
                565             570             575

Pro Cys Arg Asp Glu Leu Thr Lys Asn Gln Val Ser Leu Trp Cys Leu
            580             585             590

Val Lys Gly Phe Tyr Pro Ser Asp Ile Ala Val Glu Trp Glu Ser Asn
        595             600             605

Gly Gln Pro Glu Asn Asn Tyr Lys Thr Thr Pro Pro Val Leu Asp Ser
    610             615             620

```
Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
            645                 650                 655

His Asn His Tyr Thr Gln Lys Ser Leu Ser Leu Ser Pro Gly Lys
        660                 665                 670

<210> SEQ ID NO 50
<211> LENGTH: 446
<212> TYPE: PRT
<213> ORGANISM: Artificial Sequence
<220> FEATURE:
<223> OTHER INFORMATION: Mab21 hole HC

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Cys Thr Leu Pro Pro
        340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 51
<211> LENGTH: 216
<212> TYPE: PRT
<213> ORGANISM: Artificial Sequence
<220> FEATURE:
<223> OTHER INFORMATION: Mab21 LC

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Glu Tyr
            20                  25                  30

Tyr Leu Ala Trp Tyr Gln Gln Lys Pro Gly Gln Ala Pro Arg Leu Leu
        35                  40                  45

Ile Glu His Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 52
<211> LENGTH: 671
```

```
<212> TYPE: PRT
<213> ORGANISM: Artificial Sequence
<220> FEATURE:
<223> OTHER INFORMATION: Mab22 knob HC

<400> SEQUENCE: 52
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

```
Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
            405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
            435                 440                 445

Thr Cys Pro Pro Cys Pro Ala Pro Glu Ala Ala Gly Gly Pro Ser Val
450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
                500                 505                 510

Thr Lys Pro Arg Glu Glu Gln Tyr Asn Ser Thr Tyr Arg Val Val Ser
            515                 520                 525

Val Leu Thr Val Leu His Gln Asp Trp Leu Asn Gly Lys Glu Tyr Lys
530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
                580                 585                 590

Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
            610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 53
<211> LENGTH: 446
<212> TYPE: PRT
<213> ORGANISM: Artificial Sequence
<220> FEATURE:
<223> OTHER INFORMATION: Mab22 hole HC

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
            35                  40                  45

Ser Ala Ile Ser Gly Pro Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 54
<211> LENGTH: 216
<212> TYPE: PRT
<213> ORGANISM: Artificial Sequence
<220> FEATURE:
<223> OTHER INFORMATION: Mab22 LC

<400> SEQUENCE: 54
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Tyr Leu Ala Trp Tyr Gln Gln Lys Pro Gly Gln Ala Pro Arg Leu Leu
        35                  40                  45

Ile Ser Gly Ala Gly Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 55
<211> LENGTH: 671
<212> TYPE: PRT
<213> ORGANISM: Artificial Sequence
<220> FEATURE:
<223> OTHER INFORMATION: Mab42 knob HC

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140
```

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Glu Lys Val Glu Pro Lys Ser Cys Asp Gly Gly Gly
                210                 215                 220

Ser Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
                260                 265                 270

Gly Gln Ala Phe Arg Gly Leu Ile Gly Gly Thr Asn Lys Arg Ala Pro
                275                 280                 285

Gly Thr Pro Ala Arg Phe Ser Gly Ser Leu Leu Gly Gly Lys Ala Ala
                290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
                340                 345                 350

Ala Pro Ser Ser Lys Ser Thr Ser Gly Gly Thr Ala Ala Leu Gly Cys
                355                 360                 365

Leu Val Lys Asp Tyr Phe Pro Glu Pro Val Thr Val Ser Trp Asn Ser
370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
                420                 425                 430

Thr Lys Val Asp Lys Lys Val Glu Pro Lys Ser Cys Asp Lys Thr His
                435                 440                 445

Thr Cys Pro Pro Cys Pro Ala Pro Glu Ala Ala Gly Gly Pro Ser Val
450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
                500                 505                 510

Thr Lys Pro Arg Glu Glu Gln Tyr Asn Ser Thr Tyr Arg Val Val Ser
                515                 520                 525

Val Leu Thr Val Leu His Gln Asp Trp Leu Asn Gly Lys Glu Tyr Lys
                530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro

Pro Cys Arg Asp Glu Leu Thr Lys Asn Gln Val Ser Leu Trp Cys Leu
                580                 585                 590

Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
        610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 56
<211> LENGTH: 446
<212> TYPE: PRT
<213> ORGANISM: Artificial Sequence
<220> FEATURE:
<223> OTHER INFORMATION: Mab42 hole HC

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val

```
              260                 265                 270
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 57
<211> LENGTH: 216
<212> TYPE: PRT
<213> ORGANISM: Artificial Sequence
<220> FEATURE:
<223> OTHER INFORMATION: Mab42 LC

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Glu
            20                  25                  30

Tyr Leu Ser Trp Tyr Gln Gln Lys Pro Gly Gln Ala Pro Arg Leu Leu
        35                  40                  45

Ile His Ser Ala Ser Thr Arg Ala Thr Gly Ile Pro Asp Arg Phe Ser
    50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
```

-continued

```
            180             185             190
Val Tyr Ala Cys Glu Val Thr His Gln Gly Leu Ser Ser Pro Val Thr
        195                 200                 205

Lys Ser Phe Asn Arg Gly Glu Cys
    210                 215
```

MONOCLONAL ANTIBODIES AGAINST BCMA

The present invention relates to new antibodies against BCMA, their manufacture and use.

BACKGROUND OF THE INVENTION

Human B cell maturation antigen, also known as BCMA; TR17_HUMAN, TNFRSF17 (UniProt Q02223), is a member of the tumor necrosis receptor superfamily that is preferentially expressed in differentiated plasma cells (Laabi et al. 1992; Madry et al. 1998). BCMA is a non-glycosylated type III transmembrane protein, which is involved in B cell maturation, growth and survival. BCMA is a receptor for two ligands of the TNF superfamily: APRIL (a proliferation-inducing ligand), the high-affinity ligand to BCMA and the B cell activation factor BAFF, the low-affinity ligand to BCMA (THANK, BlyS, B lymphocyte stimulator, TALL-1 and zTNF4). APRIL and BAFF show structural similarity and overlapping yet distinct receptor binding specificity. The negative regulator TACI also binds to both BAFF and APRIL. The coordinate binding of APRIL and BAFF to BCMA and/or TACI activates transcription factor NF-κB and increases the expression of pro-survival Bcl-2 family members (e.g. Bch 2, Bcl-xL, Bcl-w, Mcl-1, A1) and the downregulation of pro-apoptotic factors (e.g. Bid, Bad, Bik, Bim, etc.), thus inhibiting apoptosis and promoting survival. This combined action promotes B cell differentiation, proliferation, survival and antibody production (as reviewed in Rickert R C et al, Immunol Rev (2011) 244 (1): 115-133).

Antibodies against BCMA are described e.g. in Gras M-P. et al. Int Immunol. 7 (1995) 1093-1106, WO200124811, WO200124812, WO2010104949 and WO2012163805. Antibodies against BCMA and their use for the treatment of lymphomas and multiple myeloma are mentioned e.g. in WO2002066516 and WO2010104949. WO2013154760 and WO2015052538 relate to chimeric antigen receptors (CAR) comprising a BCMA recognition moiety and a T-cell activation moiety. Ryan, M C et al., Mol. Cancer Ther. 6 (2007) 3009-3018 relate to anti BCMA antibodies with ligand blocking activity that could promote cytotoxicity of multiple myeloma (MM) cell lines as naked antibodies or as antibody-drug conjugates. Ryan showed that SG1, an inhibitory BCMA antibody, blocks APRIL-dependent activation of nuclear factor-KB in a dose-dependent manner in vitro. Ryan also mentioned antibody SG2 which inhibited APRIL binding to BCMA not significantly.

A wide variety of recombinant bispecific antibody formats have been developed in the recent past, e.g. by fusion of, e.g. an IgG antibody format and single chain domains (see e.g. Kontermann R E, mAbs 4:2, (2012) 1-16). Bispecific antibodies wherein the variable domains VL and VH or the constant domains CL and CH1 are replaced by each other are described in WO2009080251 and WO2009080252.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway J B, Presta L G, Carter P. Protein Eng. 9, 617-621 (1996); and WO1996027011). The percentage of heterodimer could be further increased by remodeling the interaction surfaces of the two CH3 domains using a phage display approach and the introduction of a disulfide bridge to stabilize the heterodimers (Merchant A. M, et al, Nature Biotech 16 (1998) 677-681; Atwell S, Ridgway J B, Wells J A, Carter P., J Mol. Biol 270 (1997) 26-35). New approaches for the knobs-into-holes technology are described in e.g. in EP 1870459A1. Although this format appears very attractive, no data describing progression towards the clinic are currently available. One important constraint of this strategy is that the light chains of the two parent antibodies have to be identical to prevent mispairing and formation of inactive molecules. Thus this technique is not appropriate for easily developing recombinant, bispecific antibodies against two targets starting from two antibodies against the first and the second target, as either the heavy chains of these antibodies and/or the identical light chains have to be optimized. Xie, Z., et al, J Immunol. Methods 286 (2005) 95-101 refers to a format of bispecific antibody using scFvs in combination with knobs-into-holes technology for the FC part.

The TCR/CD3 complex of T-lymphocytes consists of either a TCR alpha (α)/beta (β) or TCR gamma (γ)/delta (δ) heterodimer coexpressed at the cell surface with the invariant subunits of CD3 labeled gamma (γ), delta (δ), epsilon (E), zeta (0, and eta (q). Human CD3ε is described under UniProt P07766 (CD3E_HUMAN).

An anti CD3ε antibody described in the state of the art is SP34 (Yang S J, The Journal of Immunology (1986) 137; 1097-1100). SP34 reacts with both primate and human CD3. SP34 is available from Pharmingen. A further anti CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti et al., Transplantation 54: 844 (1992)). SP34 differs from UCHT-1 and BC-3 in that SP-34 recognizes an epitope present on solely the ε chain of CD3 (see Salmeron et al., (1991) J. Immunol. 147: 3047) whereas UCHT-1 and BC-3 recognize an epitope contributed by both the ε and γ chains. Further anti-CD3 antibodies are described in WO2008119565, WO2008119566, WO2008119567, WO2010037836, WO2010037837, WO2010037838, and U.S. Pat. No. 8,236,308 (WO2007042261). CDRs, VH and VL sequences of a further anti-CD3 antibody are shown in SEQ ID NO:7 and 8.

Bispecific antibodies against CD3 and BCMA are mentioned in WO2007117600, WO2009132058, WO2012066058, and WO2012143498. CAR compounds of antibodies against BCMA are mentioned in WO2013154760, WO2013154760, and WO2014140248.

Cell-mediated effector functions of monoclonal antibodies (like antibody dependent cellular cytotoxicity (ADCC)) can be enhanced by engineering their oligosaccharide composition at Asn297 as described in Umaña, P., et al., Nature Biotechnol. 17 (1999) 176-180; and U.S. Pat. No. 6,602,684. WO1999054342, WO2004065540, WO2007031875, and WO2007039818, Hristodorov D, Fischer R, Linden L., Mol Biotechnol. 2012 Oct. 25. (Epub) also relate to the glycosylation engineering of antibodies to enhance Fc-mediated cellular cytotoxicity.

Also several amino acid residues in the hinge region and the CH2 domain influence cell-mediated effector functions of monoclonal antibodies (Eur. J. Immunol., 23, 1098 (1993), Immunology, 86, 319 (1995), Chemical Immunology, 65, 88 (1997)] Chemical Immunology, 65, 88 (1997)]. Therefore modification of such amino acids can enhance cell-mediated effector functions. Such antibody modifications to increase cell-mediated effector functions are mentioned in EP1931709, WO200042072 and comprise in the Fc part substitutions at amino acid position(s) 234, 235, 236, 239, 267, 268, 293, 295, 324, 327, 328, 330, and 332. Further antibody modifications to increase cell-mediated effector functions are mentioned in EP1697415 and comprise amino acid replacement of EU amino acid positions 277, 289, 306, 344, or 378 with a charged amino acid, a polar amino acid, or a nonpolar amino acid.

Antibody formats and formats of bispecific and multispecific antibodies are also pepbodies (WO200244215), Novel Antigen Receptor ("NAR") (WO2003014161), diabody-diabody dimers "TandAbs" (WO2003048209), polyalkylene oxide-modified scFv (U.S. Pat. No. 7,150,872), humanized rabbit antibodies (WO2005016950), synthetic immunoglobulin domains (WO2006072620), covalent diabodies (WO2006113665), flexibodies (WO2003025018), domain antibodies, dAb (WO2004058822), vaccibody (WO2004076489), antibodies with new world primate framework (WO2007019620), antibody-drug conjugate with cleavable linkers (WO2009117531), IgG4 antibodies with hinge region removed (WO2010063785), bispecific antibodies with IgG4 like CH3 domains (WO2008119353), camelid Antibodies (U.S. Pat. No. 6,838,254), nanobodies (U.S. Pat. No. 7,655,759), CAT diabodies (U.S. Pat. No. 5,837,242), bispecific (scFv)$_2$ directed against target antigen and CD3 (U.S. Pat. No. 7,235,641), sIgA plAntibodies (U.S. Pat. No. 6,303,341), minibodies (U.S. Pat. No. 5,837,821), IgNAR (US2009148438), antibodies with modified hinge and Fc regions (US2008227958, US20080181890), trifunctional antibodies (U.S. Pat. No. 5,273,743), triomabs (U.S. Pat. No. 6,551,592), troybodies (U.S. Pat. No. 6,294,654).

WO2014122143 disclose anti-human BCMA antibodies characterized in that the binding of said antibody is not reduced by 100 ng/ml APRIL for more than 20% measured in an ELISA assay as OD at 405 nm compared to the binding of said antibody to human BCMA without APRIL, said antibody does not alter APRIL-dependent NF-κB activation for more than 20%, as compared to APRIL alone, and said antibody does not alter NF-κB activation without APRIL for more than 20%, as compared without said antibody. WO2014122144 discloses bispecific antibodies specifically binding to the two targets human CD3ε and human BCMA, comprising anti-human BCMA antibodies of WO2014122143. An anti-human BCMA antibody with unique properties, especially in regard to its therapeutic use as a bispecific T cell binder, is antibody 83A10, characterized by comprising as CDR regions CDR1H of SEQ ID NO:15, CDR2H of SEQ ID NO 16, CDR3H of SEQ ID NO:17, CDR1L of SEQ ID NO:18, CDR3L of SEQ ID NO:19, and CDR3L of SEQ ID NO:20, disclosed also in WO2014122143 and WO2014122144.

SUMMARY OF THE INVENTION

The invention comprises monoclonal antibodies specifically binding to human B cell maturation antigen (BCMA). The antibodies according to the invention comprise as CDR3H and CDR3L regions the same CDR regions as antibody 83A10.

The antibodies according to the invention comprise in an embodiment as CDR3H and CDR3L regions the same CDR regions as antibody 83A10, but show especially potent and efficient advantages in comparison to antibody 83A10 for killing of MM cells in patient bone marrow aspirates.

The invention comprises a monoclonal antibody specifically binding to BCMA, characterized in comprising a CDR3H region of SEQ ID NO:17 and a CDR3L region of SEQ ID NO:20 and a CDR1H, CDR2H, CDR1L, and CDR2L region combination selected from the group of a) CDR1H region of SEQ ID NO:21 and CDR2H region of SEQ ID NO:22, CDR1L region of SEQ ID NO:23, and CDR2L region of SEQ ID NO:24, b) CDR1H region of SEQ ID NO:21 and CDR2H region of SEQ ID NO:22, CDR1L region of SEQ ID NO:25, and CDR2L region of SEQ ID NO:26, c) CDR1H region of SEQ ID NO:21 and CDR2H region of SEQ ID NO:22, CDR1L region of SEQ ID NO:27, and CDR2L region of SEQ ID NO:28, d) CDR1H region of SEQ ID NO:29 and CDR2H region of SEQ ID NO:30, CDR1L region of SEQ ID NO:31, and CDR2L region of SEQ ID NO:32, e) CDR1H region of SEQ ID NO:34 and CDR2H region of SEQ ID NO:35, CDR1L region of SEQ ID NO:31, and CDR2L region of SEQ ID NO:32, and f) CDR1H region of SEQ ID NO:36 and CDR2H region of SEQ ID NO:37, CDR1L region of SEQ ID NO:31, and CDR2L region of SEQ ID NO:32, The invention comprises a monoclonal antibody specifically binding to BCMA, characterized in comprising a VH region comprising a CDR1H region of SEQ ID NO:21, a CDR2H region of SEQ ID NO:22 and a CDR3H region of SEQ ID NO:17 and a VL region comprising a CDR3L region of SEQ ID NO:20 and a CDR1L and CDR2L region combination selected from the group of a) CDR1L region of SEQ ID NO:23 and CDR2L region of SEQ ID NO:24, b) CDR1L region of SEQ ID NO:25 and CDR2L region of SEQ ID NO:26, or c) CDR1L region of SEQ ID NO:27 and CDR2L region of SEQ ID NO:28.

The invention provides an antibody according to the invention, characterized in comprising a VL region selected from the group consisting of VL regions of SEQ ID NO:12, 13, and 14 wherein amino acid 49 is selected from the group of amino acids tyrosine (Y), glutamic acid (E), serine (S), and histidine (H). In one embodiment amino acid 49 is E within SEQ ID NO:12, S within SEQ ID NO:13 or H within SEQ ID NO:14.

The invention provides an antibody according to the invention, characterized in comprising a VL region selected from the group consisting of VL regions of SEQ ID NO:12, 13, and 14 wherein amino acid 74 is threonine (T) or alanine (A). In one embodiment amino acid 74 is A within SEQ ID NO:14.

The antibodies according to the invention comprise in an embodiment as CDR3H, CDR1L, CDR2L, and CDR3L regions the same CDR regions as antibody 83A10. The invention comprises a monoclonal antibody specifically binding to BCMA, characterized in comprising a VH region comprising a CDR3H region of SEQ ID NO:17 and a VL region comprising a CDR1L region of SEQ ID NO:31, a CDR2L region of SEQ ID NO:32 and a CDR3L region of SEQ ID NO:20 and a CDR1L and CDR2L region combination selected from the group of a) CDR1H region of SEQ ID NO:29 and CDR2H region of SEQ ID NO:30, b) CDR1H region of SEQ ID NO:34 and CDR2H region of SEQ ID NO:35, or c) CDR1H region of SEQ ID NO:36 and CDR2H region of SEQ ID NO:37.

The invention provides in one embodiment an antibody according to the invention, characterized in comprising a VL region of SEQ ID NO:12 and a VH region selected from the group comprising the VH regions of SEQ ID NO:38, 39, and 40. The invention provides an antibody according to the invention, characterized in comprising a VL region SEQ ID NO:12, wherein amino acid 49 is selected from the group of amino acids tyrosine (Y), glutamic acid (E), serine (S), and histidine (H). In one embodiment amino acid 49 is E.

The invention provides in one embodiment an antibody according to the invention, characterized in comprising as VH region a VH region of SEQ ID NO:10. The invention provides in one embodiment an antibody according to the invention, characterized in comprising as VL region a VL region selected from the group consisting of VL regions of SEQ ID NO:12, 13, and 14. The invention provides in one embodiment an antibody according to the invention, characterized in that comprising as VH region a VH region of SEQ ID NO:10 and as VL region a VL region of SEQ ID NO:12. The invention provides in one embodiment an antibody according to the invention, characterized in that comprising as VH region a VH region of SEQ ID NO:10 and as VL region a VL region of SEQ ID NO:13. The invention provides in one embodiment an antibody according to the invention, characterized in that comprising as VH region a VH region of SEQ ID NO:10 and as VL region a VL region of SEQ ID NO:14.

The invention provides in one embodiment an antibody according to the invention, characterized in comprising as VH region a VH region selected from the group consisting of SEQ ID NO:38, 39, and 40. The invention provides in one embodiment an antibody according to the invention, characterized in that comprising as VH region a VH region of SEQ ID NO:38 and as VL region a VL region of SEQ ID NO:12. The invention provides in one embodiment an antibody according to the invention, characterized in that comprising as VH region a VH region of SEQ ID NO:39 and as VL region a VL region of SEQ ID NO:12. The invention provides in one embodiment an antibody according to the invention, characterized in that comprising as VH region a VH region of SEQ ID NO:40 and as VL region a VL region of SEQ ID NO:12.

In one embodiment the antibody according to the invention is further characterized in that it binds also specifically to cynomolgus BCMA. In one embodiment an antibody of the invention shows regarding binding to BCMA a cyno/human affinity gap between 1.5 and 5 or 1.5 and 10 or 1.5 and 16 (table 5).

The bispecific antibody according to the invention is therefore in one embodiment characterized in that it binds also specifically to cynomolgus CD3. In one embodiment the bispecific anti-BCMA/anti-CD3 antibody of the invention shows a cyno/human gap of Mab CD3 between 1.25 and 5 or between 0.8 and 1.0.

In a further embodiment of the invention the antibody according to the invention is an antibody with an Fc part or without an Fc part including a multispecific antibody, bispecific antibody, a single chain variable fragment (scFv) such as a bispecific T cells engager, diabody, or tandem scFv, an antibody mimetic such as DARPin, a naked monospecific antibody, or an antibody drug conjugate. In one embodiment a multispecific antibody, bispecific antibody, a bispecific T cells engager, diabody, or tandem scFv is specifically binding to BCMA and CD3.

Based on an antibody according to the invention it is possible to generate antibody-drug conjugates against BCMA and multispecific or bispecific antibodies against BCMA and one or more further targets in different formats with or without an Fc portion known in the state of the art (see e. g. above in "background of the invention"), single chain variable fragments (scFv) such as bispecific T cells engagers, diabodies, tandem scFvs, and antibody mimetics such as DARPins, all of them are also embodiments of the invention. Bispecific antibody formats are well known in the state of the art and e.g. also described in Kontermann R E, mAbs 4:2 1-16 (2012); Holliger P., Hudson P J, Nature Biotech. 23 (2005) 1126-1136 and Chan A C, Carter P J Nature Reviews Immunology 10, 301-316 (2010) and Cuesta A M et al., Trends Biotech 28 (2011) 355-362.

A further embodiment of the invention is a bispecific antibody against the two targets human CD3ε (further named also as "CD3") and the extracellular domain of human BCMA (further named also as "BCMA"), characterized in comprising as BCMA binding portion an anti-BCMA antibody according to the invention.

The invention relates in one embodiment to a bispecific antibody against BCMA and CD3, characterized in comprising within the BCMA binding portion a CDR3H region of SEQ ID NO:17 and a CDR3L region of SEQ ID NO:20 and a CDR1H, CDR2H, CDR1L, and CDR2L region combination selected from the group of
a) CDR1H region of SEQ ID NO:21 and CDR2H region of SEQ ID NO:22, CDR1L region of SEQ ID NO:23, and CDR2L region of SEQ ID NO:24,
b) CDR1H region of SEQ ID NO:21 and CDR2H region of SEQ ID NO:22, CDR1L region of SEQ ID NO:25, and CDR2L region of SEQ ID NO:26,
c) CDR1H region of SEQ ID NO:21 and CDR2H region of SEQ ID NO:22, CDR1L region of SEQ ID NO:27, and CDR2L region of SEQ ID NO:28,
d) CDR1H region of SEQ ID NO:29 and CDR2H region of SEQ ID NO:30, CDR1L region of SEQ ID NO:31, and CDR2L region of SEQ ID NO:32,
e) CDR1H region of SEQ ID NO:34 and CDR2H region of SEQ ID NO:35, CDR1L region of SEQ ID NO:31, and CDR2L region of SEQ ID NO:32, and
f) CDR1H region of SEQ ID NO:36 and CDR2H region of SEQ ID NO:37, CDR1L region of SEQ ID NO:31, and CDR2L region of SEQ ID NO:32, The invention relates in one embodiment to a bispecific antibody against BCMA and CD3, characterized in comprising a VH region of an antibody according to the invention (further named "BCMA VH") comprising a CDR1H region of SEQ ID NO:21, a CDR2H region of SEQ ID NO:22 and a CDR3H region of SEQ ID NO:17 and a VL region (further named "BCMA VL") comprising a CDR3L region of SEQ ID NO:20 and a CDR1L and CDR2L region combination selected from the group of
a) CDR1L region of SEQ ID NO:23 and CDR2L region of SEQ ID NO:24,
b) CDR1L region of SEQ ID NO:25 and CDR2L region of SEQ ID NO:26, or
c) CDR1L region of SEQ ID NO:27 and CDR2L region of SEQ ID NO:28.

The invention provides in one embodiment a bispecific antibody according to the invention, characterized in comprising as BCMA VH a VH region of SEQ ID NO:10.

The invention relates in one embodiment to a bispecific antibody against BCMA and CD3, characterized in that the BCMA VL is selected from the group consisting of VL regions of SEQ ID NO:12, 13, and 14. The invention provides in one embodiment an antibody according to the invention, characterized in comprising as BCMA VH region a VH region of SEQ ID NO:10 and as VL region a VL region of SEQ ID NO:12. The invention provides in one embodiment an antibody according to the invention, characterized in comprising as BCMA VH a VH region of SEQ ID NO:10 and as VL region a VL region of SEQ ID NO:13. The invention provides in one embodiment an antibody according to the invention, characterized in comprising as BCMA VH a VH region of SEQ ID NO:10 and as VL region a VL region of SEQ ID NO:14.

The invention provides a bispecific antibody according to the invention, characterized in comprising a VL region selected from the group consisting of VL regions of SEQ ID NO:12, 13, and 14 wherein amino acid 49 is selected from the group of amino acids tyrosine (Y), glutamic acid (E), serine (S), and histidine (H). In one embodiment amino acid 49 is E (SEQ ID NO:12), S (SEQ ID NO:13) or H (SEQ ID NO:14). The invention provides a bispecific antibody according to the invention, characterized in comprising a VL region selected from the group consisting of VL regions of SEQ ID NO:12, 13, and 14 wherein amino acid 74 is threonine (T) or alanine (A). In one embodiment amino acid 74 is A within SEQ ID NO:14.

The invention relates to a bispecific antibody against BCMA and CD3, characterized in comprising a BCMA VH comprising a CDR3H region of SEQ ID NO:17 and a BCMA VL comprising a CDR1L region of SEQ ID NO:31, a CDR2L region of SEQ ID NO:32 and a CDR3L region of SEQ ID NO:20 and a CDR1L and CDR2L region combination selected from the group of
a) CDR1H region of SEQ ID NO:29 and CDR2H region of SEQ ID NO:30,
b) CDR1H region of SEQ ID NO:34 and CDR2H region of SEQ ID NO:35, or
c) CDR1H region of SEQ ID NO:36 and CDR2H region of SEQ ID NO:37.

The bispecific antibody against BCMA and CD3 is characterized in one embodiment in comprising an anti BCMA antibody according to the invention and an anti CD3 antibody, wherein
a) the light chain and heavy chain of an antibody specifically binding to one of said targets CD3 and BCMA; and
b) the light chain and heavy chain of an antibody specifically binding to the other one of said targets, wherein the variable domains VL and VH or the constant domains CL and CH1 are replaced by each other.

In one embodiment a VH domain of said anti-CD3 antibody portion is linked to a CH1 or CL domain of said anti-BCMA antibody portion. In one embodiment a VL domain of said anti-CD3 antibody portion is linked to a CH1 or CL domain of said anti-BCMA antibody portion.

In one embodiment the bispecific antibody comprises not more than one Fab fragment of an anti-CD3 antibody portion, not more than two Fab fragments of an anti-BCMA antibody portion and not more than one Fc part, in one embodiment a human Fc part. In one embodiment not more than one Fab fragment of the anti-CD3 antibody portion and not more than one Fab fragment of the anti-BCMA antibody portion are linked to the Fc part and linking is performed via C-terminal binding of the Fab fragment(s) to the hinge region. In one embodiment the second Fab fragment of the anti-BCMA antibody portion is linked via its C-terminus either to the N-terminus of the Fab fragment of the anti-CD3 antibody portion or to the hinge region of the Fc part and therefore between the Fc part and the anti-CD3 antibody portion. The preferred bispecific antibodies are shown in FIGS. 1 to 3.

Especially preferred are the bispecific antibodies comprising only the Fab fragments and the Fc part as specified, with or without "aa substitution":
Fab BCMA-Fc-Fab CD3 (bispecific format FIG. 1A or 1B),
Fab BCMA-Fc-Fab CD3-Fab BCMA (bispecific format FIG. 2A or 2B),
Fab BCMA-Fc-Fab BCMA-Fab CD3 (bispecific format FIG. 2C or 2D),
Fc-Fab CD3-Fab BCMA (bispecific format FIG. 3A or 3B),
Fc-Fab BCMA-Fab CD3 (bispecific format FIG. 3C or 3D).

As shown in FIGS. 1 to 3 "Fab BCMA-Fc, "Fab BCMA-Fc-Fab CD3" and "Fab BCMA-Fc-Fab CD3" means that the Fab fragment(s) is (are) bound via its (their) C-terminus to the N-terminus of the Fc fragment. "Fab CD3-Fab BCMA" means that the Fab CD3 fragment is bound with its N-terminus to the C-terminus of the Fab BCMA fragment. "Fab BCMA-Fab CD3" means that the Fab BCMA fragment is bound with its N-terminus to the C-terminus of the Fab CD3 fragment.

In one embodiment the bispecific antibody comprises a second Fab fragment of said anti-BCMA antibody linked with its C-terminus to the N-terminus of the CD3 antibody portion of said bispecific antibody. In one embodiment a VL domain of said first anti-CD3 antibody portion is linked to a CH1 or CL domain of said second anti-BCMA antibody.

In one embodiment the bispecific antibody comprises a second Fab fragment of said anti-BCMA antibody linked with its C-terminus to the Fc part (like the first Fab fragment of said anti-BCMA antibody) and linked with its N-terminus to the C-terminus of the CD3 antibody portion. In one embodiment a CH1 domain of said anti-CD3 antibody portion is linked to the VH domain of said second anti-BCMA antibody portion.

In one embodiment the bispecific antibody comprises an Fc part linked with its N-terminus to the C-terminus of said CD3 antibody Fab fragment. In one embodiment the bispecific antibody comprises an Fc part linked with its first N-terminus to the C-terminus of said CD3 antibody Fab fragment and a second Fab fragment of said anti-BCMA antibody linked with its C-terminus to the second N-terminus of the Fc part. In one embodiment the CL domain of the CD3 antibody Fab fragment is linked to the hinge region of the Fc part. In one embodiment the CH1 domain of the BCMA antibody Fab fragment is linked to the hinge region of the Fc part.

The Fab fragments are chemically linked together by the use of an appropriate linker according to the state of the art. In one embodiment a (Gly4-Ser1)3 linker is used (Desplancq D K et al., Protein Eng. 1994 August; 7(8):1027-33 and Mack M. et al., PNAS Jul. 18, 1995 vol. 92 no. 15 7021-7025). "Chemically linked" (or "linked") means according to the invention that the fragments are linked by covalent binding. As the linker is a peptidic linker, such covalent binding is usually performed by biochemical recombinant means, using a nucleic acid encoding the VL and/or VH domains of the respective Fab fragments, the linker and if appropriate the Fc part chain.

The invention relates in one embodiment to a bispecific antibody against BCMA and CD3 according to the invention, characterized in that the variable domain VH of the anti-CD3 antibody portion (further named as "CD3 VH") comprises the heavy chain CDRs of SEQ ID NO: 1, 2 and 3 as respectively heavy chain CDR1H, CDR2H and CDR3H and the variable domain VL of the anti-CD3 antibody portion (further named as "CD3 VL") comprises the light chain CDRs of SEQ ID NO: 4, 5 and 6 as respectively light chain CDR1L, CDR2L and CDR3L.

In one embodiment such a bispecific antibody according to the invention is characterized in that the variable domains of the anti CD3ε antibody portion are of SEQ ID NO:7 and 8.

The invention relates to a bispecific antibody according to the invention, characterized in that the anti-CD3 antibody portion is linked at its N-terminus to the C-terminus of a of the anti-BCMA antibody portion and the variable domains VL and VH of the anti-CD3 antibody portion or the constant domains CL and CH1 are replaced by each other.

In one embodiment the VH domain of said anti-CD3 antibody portion is linked to a CH1 or CL domain of said anti-BCMA antibody portion. In one embodiment a VL domain of said anti-CD3 antibody portion is linked to a CH1 or CL domain of said anti-BCMA antibody portion.

An antibody portion according to the invention is in one embodiment a Fab fragment of the respective antibody.

In a further embodiment of the invention the bispecific antibody wherein the variable domains VL and VH in the light chain and the respective heavy chain of the anti-CD3 antibody portion or the anti-BCMA antibody portion are replaced by each other, is characterized in comprising a constant domain CL of the anti-CD3 antibody portion or the anti-BCMA antibody portion wherein the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D). In one embodiment the antibody is monovalent for CD3 binding. In one embodiment in addition to the amino acid replacement at position 124 in the constant domain CL the amino acid at position 123 is substituted independently by lysine (K), arginine (R) or histidine (H) (further called as "charge variant exchange"). In one embodiment the antibody is monovalent for CD3 binding and amino acid 124 is K, amino acid 147 is E, amino acid 213 is E, and amino acid 123 is R. In one embodiment the bispecific antibody comprises in addition the same anti-BCMA binding portion once more (in one embodiment a Fab fragment). That means also, that if the first anti-BCMA binding portion comprises the charge variant exchange, then the second anti-BCMA binding portion comprise the same charge variant exchange.

The invention relates to a bispecific antibody according to the invention, characterized in comprising
a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and
c) wherein in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 and the amino acid at position 213 is substituted independently by glutamic acid (E), or aspartic acid (D) (numbering according to EU index of Kabat) (see e.g. FIGS. 1A, 2A, 2C, 3A, 3C).

In one embodiment said bispecific antibody described in the last preceding paragraph is further characterized in that said bispecific antibody comprises in addition a Fab fragment of said first antibody (further named also as "BCMA-Fab") and in the constant domain CL said BCMA-Fab the amino acid at position 124 is substituted independently by lysine (K), arginine (R) or histidine (H) (numbering according to Kabat), and wherein in the constant domain CH1 of said BCMA-Fab the amino acid at positions 147 and the amino acid at position 213 is substituted independently by glutamic acid (E), or aspartic acid (D) (numbering according to EU index of Kabat) (see e.g. FIGS. 2A, 2C).

The invention further relates to a bispecific antibody according to the invention, characterized in comprising
a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and wherein
c) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at positions 147 and the amino acid at position 213 is substituted independently by glutamic acid (E), or aspartic acid (D) (numbering according to EU index of Kabat).

In one embodiment in addition to the amino acid replacement at position 124 in the constant domain CL of the first or second light chain the amino acid at position 123 is substituted independently by lysine (K), arginine (R) or histidine (H).

In one embodiment in the constant domain CL the amino acid at position 124 is substituted by lysine (K), in the constant domain CH1 the amino acid at position 147 and the amino acid at position 213 are substituted by glutamic acid (E). In one embodiment in addition in the constant domain CL in the amino acid at position 123 is substituted by arginine (R).

In a preferred embodiment of the invention the bispecific antibody according to the invention consists of one Fab fragment of an antibody specifically binding to CD3 (further named also as "CD3-Fab"), and one Fab fragment of an anti-BCMA antibody according to the invention (further named also as "BCMA-Fab(s)") and a Fc part, wherein the CD3-Fab and the BCMA-Fab are linked via their C-termini to the hinge region of said Fc part. Either the CD3-Fab or the BCMA-Fab comprises aa substitution and the CD3-Fab comprises crossover (FIGS. 1A and 1B).

In a preferred embodiment of the invention the bispecific antibody according to the invention consists of one CD3-Fab, and one BCMA-Fab and a Fc part, wherein the CD3-Fab and the BCMA-Fab are linked via their C-termini to the hinge region of said Fc part and a second BCMA-Fab, which is linked with its C-terminus to the N-terminus of the CD3-Fab. The CD3-Fab comprises crossover and either the CD3-Fab or both BCMA-Fabs comprise aa substitution (FIGS. 2A and 2B). Especially preferred is a bispecific antibody comprising BCMA-Fab-Fc-CD3-Fab-BCMA-Fab, wherein both BCMA-Fabs comprise aa substitution and the CD3-Fab comprises VL/VH crossover (FIG. 2A). Especially preferred is a bispecific antibody consisting of BCMA-Fab-Fc-CD3-Fab-BCMA-Fab, wherein both BCMA-Fabs comprise aa substitution Q124K, E123R, K147E and K213E and the CD3-Fab comprises VL/VH crossover. Especially preferred is that both BCMA-Fabs comprise as CDRs the CDRs of antibody 21, 22, or 42, or as VH/VL the VH/VL of antibody 21, 22, or 42.

In a preferred embodiment of the invention the bispecific antibody according to the invention consists of two BCMA-Fabs and an Fc part, wherein one BCMA-Fab and the CD3 Fab are linked via their C-termini to the hinge region of said Fc part and the second BCMA-Fab is linked with its C-terminus to the N-terminus of the CD3-Fab. The CD3-Fab comprises crossover and either the CD3-Fab or both BCMA-Fabs comprise aa substitution (FIGS. 2A and 2B).

In a preferred embodiment of the invention the bispecific antibody according to the invention consists of two BCMA-Fabs and an Fc part, wherein the BCMA-Fabs are linked via their C-termini to the hinge region of said Fc part and a CD3-Fab, which is linked with its C-terminus to the N-terminus of one BCMA-Fab. The CD3-Fab comprises crossover and either the CD3-Fab or both BCMA-Fabs comprise aa substitution (FIGS. 2C and 2D).

In a preferred embodiment of the invention the antibody according to the invention consists of one CD3-Fab, which is linked via its C-terminus to the hinge region of said Fc part and a BCMA-Fab, which is linked with its C-terminus to the N-terminus of the CD3-Fab. The CD3-Fab comprises crossover and either the CD3-Fab or the BCMA-Fab comprise aa substitution (FIGS. 1A and 1B).

In a preferred embodiment of the invention the antibody according to the invention consists of one CD3-Fab, which is linked via its C-terminus to the hinge region of said Fc part and a BCMA-Fab, which is linked with its C-terminus to the N-terminus of the CD3-Fab. The CD3-Fab comprises crossover and either the CD3-Fab or the BCMA-Fab comprise aa substitution (FIGS. 3A and 3B).

In a preferred embodiment of the invention the antibody according to the invention consists of one BCMA-Fab, which is linked via its C-terminus to the hinge region of said Fc part and a CD3-Fab, which is linked with its C-terminus to the N-terminus of the BCMA-Fab. The CD3-Fab comprises crossover and either the CD3-Fab or the BCMA-Fab comprise aa substitution (FIGS. 3C and 3D).

The Fab fragments are chemically linked together by the use of an appropriate linker according to the state of the art. In one embodiment a (Gly4-Ser1)3 linker is used (Desplancq D K et al., Protein Eng. 1994 August; 7(8):1027-33 and Mack M. et al., PNAS Jul. 18, 1995 vol. 92 no. 15 7021-7025). Linkage between two Fab fragments is performed between the heavy chains. Therefore the C-terminus of CH1 of a first Fab fragment is linked to the N-terminus of VH of the second Fab fragment (no crossover) or to VL (crossover). Linkage between a Fab fragment and the Fc part is performed according to the invention as linkage between CH1 and CH2.

The first and a second Fab fragment of an antibody specifically binding to BCMA are in one embodiment derived from the same antibody and in one embodiment identical in the CDR sequences, variable domain sequences VH and VL and/or the constant domain sequences CH1 and CL. In one embodiment the amino acid sequences of the first and a second Fab fragment of an antibody specifically binding to BCMA are identical. In one embodiment the BCMA antibody is an antibody comprising the CDR sequences of antibody 21, 22, or 42, an antibody comprising the VH and VL sequences of antibody 21, 22, or 42, or an antibody comprising the VH, VL, CH1, and CL sequences of antibody 21, 22, or 42.

In one embodiment the bispecific antibody comprises as Fab fragments and Fc part, not more than one Fab fragment of an anti-CD3 antibody, not more than two Fab fragments of an anti-BCMA antibody and not more than one Fc part, in one embodiment a human Fc part. In one embodiment the second Fab fragment of an anti-BCMA antibody is linked via its C-terminus either to the N-terminus of the Fab fragment of an anti-CD3 antibody or to the hinge region of the Fc part. In one embodiment linkage is performed between CH1 of BCMA-Fab and VL of CD3-Fab (VL/VH crossover).

In one embodiment the antibody portion specifically binding to human CD3, in one embodiment the Fab fragment, is characterized in comprising a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3 of the anti-CD3E antibody (CDR MAB CD3). In one embodiment the antibody portion specifically binding to human CD3 is characterized in that the variable domains are of SEQ ID NO:7 and 8 (VHVL MAB CD3).

The invention relates to a bispecific antibody specifically binding to the extracellular domain of human BCMA and to human CD3E, characterized in comprising a heavy and light chain set selected from the group consisting of polypeptides
i) SEQ ID NO:48, SEQ ID NO:49, SEQ ID NO:50, and SEQ ID NO:51 (2×); (set 1 TCB of antibody 21),
ii) SEQ ID NO:48, SEQ ID NO:52, SEQ ID NO:53, and SEQ ID NO:54 (2×) (set 2 TCB of antibody 22), and
iii) SEQ ID NO:48, SEQ ID NO:55, SEQ ID NO:56, and SEQ ID NO:57 (2×) (set 3 TCB of antibody 42).

In one embodiment the bispecific antibody according to the invention is characterized in that the CH3 domain of one heavy chain and the CH3 domain of the other heavy chain each meet at an interface which comprises an original interface between the antibody CH3 domains; wherein said interface is altered to promote the formation of the bispecific antibody, wherein the alteration is characterized in that:
  a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
  b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

In one embodiment such a bispecific antibody is characterized in that said amino acid residue having a larger side chain volume is selected from the group consisting of arginine (R), phenylalanine (F), tyrosine (Y), tryptophan (W).

In one embodiment such a bispecific antibody is characterized in that said amino acid residue having a smaller side chain volume is selected from the group consisting of alanine (A), serine (S), threonine (T), valine (V).

In one embodiment such a bispecific antibody is characterized in that both CH3 domains are further altered by the introduction of cysteine (C) as amino acid in the corresponding positions of each CH3 domain.

In one embodiment such a bispecific antibody is characterized in that one of the constant heavy chain domains CH3 of both heavy chains is replaced by a constant heavy chain domain CH1; and the other constant heavy chain domain CH3 is replaced by a constant light chain domain CL.

The invention relates further to an antibody according to the invention, comprising a modified Fc part inducing cell death of 20% or more cells of a preparation BCMA expressing cells after 24 hours at a concentration of said antibody of 100 nM by ADCC relative to a control under identical conditions using the same antibody with the parent Fc part as control. Such an antibody is in one embodiment a naked antibody.

In one embodiment the antibody according to the invention is an antibody with an amount of fucose of 60% or less of the total amount of oligosaccharides (sugars) at Asn297 (see e.g. US20120315268).

In one embodiment the Fc part comprises the amino acid substitutions which are introduced in a human Fc part and disclosed in SEQ ID NO:55 and 56.

A further embodiment of the invention is a chimeric antigen receptor (CAR) of an anti-BCMA antibody according to the invention. In such an embodiment the anti-BCMA antibody consists of a single chain VH and VL domain of an antibody according to the invention and a CD3-zeta transmembrane and endodomain. Preferably the CD3 zeta domain is linked via a spacer with the C-terminus of said VL domain and the N terminus of the VL domain is linked via a spacer to the C terminus of said VH domain Chimeric antigen receptors of BCMA antibodies, useful transmembrane domains and endodomains, and methods for the production are described e.g. in Ramadoss N S. et al., J. Am. Chem. Soc. J., DOI: 10.1021/jacs.5b01876 (2015), Carpenter R O et al., Clin. Cancer. Res. DOI: 10.1158/1078-0432.CCR-12-2422 (2013), WO2015052538 and WO2013154760.

Further embodiments of the invention are the antibodies Mab21, Mab22, Mab42, Mab27, Mab33, and Mab39 as described herein by their CDR sequences, and/or VH/VL sequences together with the described CL and CH1 sequences, as antigen binding fragments, especially Fab fragments, as bispecific antibodies binding to BCMA and CD3, with and without Fc part, as bispecific antibodies in the described formats, especially the 2+1 format, and the bispecific antibodies with the heavy and light chains as described herein, especially as described in table 1A.

A further embodiment of the invention is a method of generation an anti-BCMA antibody which depletes, in the bispecific format according to the invention, human malignant plasma cells in Multiple Myeloma MM bone marrow aspirates to at least 80% after a 48 hour treatment in a concentration of between 10 nM and 1 fM inclusively, characterized in panning a variable heavy chain (VH) and a variable light chain (VL) phage-display library of antibody 83A10 (VH library, VL library) with 1-50 nM cyno BCMA in 1-3 rounds and selecting a variable light chain and a variable heavy chain which have such properties as such bispecific T cell binder. Preferably panning is performed in 3 rounds, using 50 nM cynoBCMA for round 1, 25 nM cyBCMA for round 2 and 10 nM cyBCMA for round 3. Preferably the libraries are randomized in either the light chain CDR1 and CDR2 or the heavy chain CDR1 and CDR2. Preferably a light and heavy chain are identified which each bind as Fab fragment, comprising in addition the corresponding VH or VL of antibody 83A10, to huBCMA with a Kd of 50 pM to 5 nM and to cyno BCMA with a Kd of 0.1 nM to 20 nM. Preferably the bispecific format is the format of FIG. 2A, comprising the respective constant domains VL and VH of the CD3 Fab replacement by each other and within both BCMA Fabs amino acid exchanges K213E and K147E in the CH1 domain and amino acid exchanges E123R and Q124K in the CL domain.

A further embodiment of the invention is a method for the preparation of an antibody according to the invention comprising the steps of
   a) transforming a host cell with
   b) vectors comprising nucleic acid molecules encoding the light chain and heavy chain of an antibody according to the invention,
   c) culturing the host cell under conditions that allow synthesis of said antibody molecule; and
   d) recovering said antibody molecule from said culture.

A further embodiment of the invention is a method for the preparation of a bispecific antibody according to the invention comprising the steps of
   e) transforming a host cell with
   f) vectors comprising nucleic acid molecules encoding the light chain and heavy chain of an antibody specifically binding to the first target
   g) vectors comprising nucleic acid molecules encoding the light chain and heavy chain of an antibody specifically binding to the second target, wherein the variable domains VL and VH or the constant domains CL and CH1 are replaced by each other;
   h) culturing the host cell under conditions that allow synthesis of said antibody molecule; and
   i) recovering said antibody molecule from said culture.

A further embodiment of the invention is a host cell comprising vectors comprising nucleic acid molecules encoding an antibody according to the invention. A further embodiment of the invention is a host cell comprising vectors comprising nucleic acid molecules encoding the light chain and heavy chain of an antibody specifically binding to the first target and vectors comprising nucleic acid molecules encoding the light chain and heavy chain of an antibody specifically binding to the second target, wherein the variable domains VL and VH or the constant domains CL and CH1 are replaced by each other.

A further embodiment of the invention is a pharmaceutical composition comprising an antibody according to the invention and a pharmaceutically acceptable excipient.

A further embodiment of the invention is a pharmaceutical composition comprising an antibody according to the invention for use as a medicament.

A further embodiment of the invention is a pharmaceutical composition comprising an antibody according to the invention for use as a medicament in the treatment of plasma cell disorders.

A further embodiment of the invention is a pharmaceutical composition comprising an antibody according to the invention for use as a medicament in the treatment of Multiple Myeloma.

A further embodiment of the invention is pharmaceutical composition comprising an antibody according to the invention for use as a medicament in the treatment of systemic lupus erythematosus.

A further embodiment of the invention is pharmaceutical composition comprising an antibody according to the invention, including a monospecific antibody, an ADCC enhanced naked antibody, an antibody-drug conjugate, a multispecific antibody or a bispecific antibody for use as a medicament in the treatment of antibody-mediated rejection.

In one embodiment an antibody according to the invention can be used for the treatment of plasma cell disorders like Multiple Myeloma MM or other plasma cell disorders expressing BCMA as described below. MM is a plasma cell malignancy characterized by a monoclonal expansion and accumulation of abnormal plasma cells in the bone marrow compartment. MM also involves circulating clonal plasma cells cells with same IgG gene rearrangement and somatic hypermutation. MM arises from an asymptomatic, premalignant condition called monoclonal gammopathy of unknown significance (MGUS), characterized by low levels of bone marrow plasma cells and a monoclonal protein. MM cells proliferate at low rate. MM results from a progressive occurrence of multiple structural chromosomal changes (e.g. unbalanced translocations). MM involves the mutual interaction of malignant plasma cells and bone marrow microenvironment (e.g. normal bone marrow stromal cells). Clinical signs of active MM include monoclonal antibody spike, plasma cells overcrowding the bone marrow, lytic bone lesions and bone destruction resulting from overstimulation of osteoclasts (Dimopulos & Terpos, Ann Oncol 2010; 21 suppl 7: vii143-150). Another plasma cell disorder involving plasma cells i.e. expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol 2010; 6: 326-337). Further plasma cell disorders are plasma cell leukemia and AL-Amyloidosis (see also Examples 19 and 20). In all these plasma cell disorders depletion of plasma cells/malignant plasma cells by antibodies according to this invention is expected to be beneficial for the patients suffering from such a disease.

A further embodiment of this invention is an antibody according to the invention for the treatment of antibody-mediated allograft rejection involving plasma cells and alloantibodies including acute and chronic antibody-mediated rejection (AMR). Acute AMR is characterized by graft dysfunction that occurs over days and is the result of either pre-formed or de novo donor specific antibodies developed post-transplant. It occurs in about 5-7% of all kidney transplants and causes 20-48% of acute rejection episodes among pre-sensitized positive crossmatch patients (Colvin and Smith, Nature Rev Immunol 2005; 5 (10): 807-817). Histopathology in patients with acute AMR often reveals endothelial cell swelling, neutrophilic infiltration of glomeruli and peritubular capillaries, fibrin thrombi, interstitial edema, and hemorrhage (Trpkov et al. Transplantation 1996; 61 (11): 1586-1592). AMR can be identified with C4d-staining or other improved methods of antibody detection in allograft biopsies. Another form of AMR is also known as chronic allograft injury which also involves donor specific antibodies but manifests within months and even years after transplantation. It is seen as transplant glomerulopathy (also known as chronic allograft glomerulopathy) on kidney biopsies and is characterized by glomerular mesangial expansion and capillary basement membrane duplication (Regele et al. J Am Soc Nephrol 2002; 13 (9): 2371-2380). The clinical manifestations vary from patients being asymptomatic in the early stages to having nephrotic range proteinuria, hypertension, and allograft dysfunction in the advanced stages. Disease progression can be quite rapid, especially with ongoing acute AMR, resulting in graft failure within months (Fotheringham et al. Nephron—Clin Pract 2009; 113 (1): c1-c7). The prevalence of transplant glomerulopathy in patient biopsies varies between 5% at 1 yr to 20% at 5 years (Cosio et al. Am J Transplant 2008; 8: 292-296).

A further embodiment of the invention is an antibody according to the invention for use as a medicament.

A further embodiment of the invention is a pharmaceutical composition comprising an antibody according to the invention for use as a medicament.

A further embodiment of the invention is a pharmaceutical composition comprising a naked antibody or a bispecific antibody according to the invention for use as a medicament.

A further embodiment of the invention is a pharmaceutical composition comprising an antibody according to the invention with increased effector function for use as a medicament.

A further embodiment of the invention is a pharmaceutical composition comprising an antibody according to the invention with decreased effector function for use as a medicament.

A further embodiment of the invention is a pharmaceutical composition comprising an antibody according to the invention as bispecific antibody for use as a medicament.

A further embodiment of the invention is a pharmaceutical composition comprising an antibody according to the invention as multispecific antibody for use as a medicament.

A further embodiment of the invention is a pharmaceutical composition comprising an antibody according to the invention as conjugate with a therapeutic agent (drug conjugate) e.g. with a cytotoxic agent or radiolabel for use as a medicament.

A further embodiment of the invention is a pharmaceutical composition comprising an antibody according to the invention as a diabody for use as a medicament.

In one embodiment the antibody according to the invention, especially when being a bispecific antibody against CD3 and BCMA, is administered once or twice a week in one embodiment via subcutaneous administration (e.g. in one embodiment in the dose range of 0.1 to 2.5, preferably to 25 mg/m$^2$/week, preferably to 250 mg/m$^2$/week). Due to superior cytotoxicity activities of the antibody according to the invention it can be administered at least at the same magnitude of clinical dose range (or even lower) as compared to conventional monospecific antibodies or conventional bispecific antibodies that are not T cell bispecifics (i.e. do not bind to CD3 on one arm). It is envisaged that for an antibody according to the invention subcutaneous administration is preferred in the clinical settings (e.g. in the dose range of 0.1-250 mg/m$^2$/week). In addition, in patients with high levels of serum APRIL and BAFF (e.g. multiple myeloma patients) it may not be required to increase the dose for an antibody according to this invention as it may not be affected by ligand competition. In contrast, the doses for other ligand-blocking/competing anti-BCMA antibodies may need to be increased in those patients. Another advantage of the antibody according to the invention is an elimination half-life of about 4 to 12 days which allows at least once or twice/week administration.

In one embodiment the antibody according to the invention in the case of naked/unconjugated ADCC enhanced monospecific antibodies is an antibody with properties allowing for once/twice a week treatment by intravenous route but preferably via subcutaneous administration (e.g. a dosage in the range of 200-2000 mg/m/week for 4 weeks). It is envisaged that for an antibody according to the invention subcutaneous administration is possible and preferred in the clinical settings (e.g. in the dose range of 200-2000 mg/m$^2$/week, depending on the disease indications). In addition, in patients with high levels of serum APRIL and BAFF (e.g. multiple myeloma patients) it may not be required to increase the dose for an antibody according to this invention (e.g. non-ligand blocking/competing antibody) as it may not be affected by ligand competition. In contrast, the doses for other ligand-blocking/competing anti-BCMA antibodies may need to be increased in those patients, making subcutaneous administration technically more challenging (e.g. pharmaceutical). Another advantage of the antibody according to the invention is based on the inclusion of an Fc portion, which is associated with an elimination half-life of 4 to 12 days and allows at least once or twice/week administration.

A further preferred embodiment of the invention is a diagnostic composition comprising an antibody according to the invention.

DETAILED DESCRIPTION OF THE INVENTION

Figure 1:
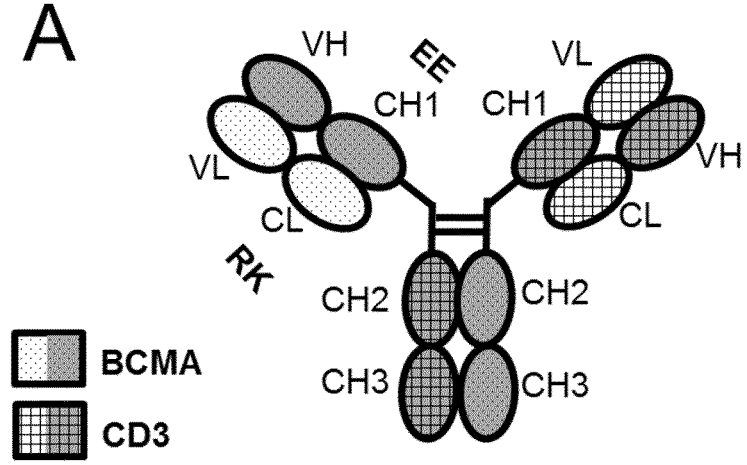
FIG. 1. Bispecific bivalent antibodies comprising only the Fab fragments (specific to CD3 and BCMA) and the Fc part as specified: (A) Fab BCMA(RK/EE)-Fc-Fab CD3; (B) Fab BCMA-Fc-Fab CD3(RK/EE). aa substitutions for RK/EE introduced in CL-CH1 to reduce LC mispairing/side products in production. The Fab CD3 includes a VL-VH crossover to reduce LC mispairing and side-products.
Figure 1:
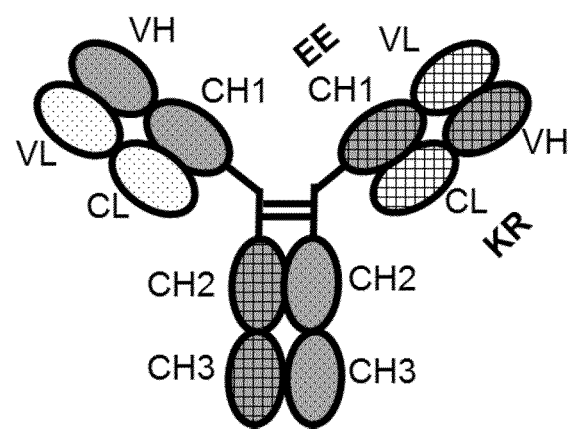

The term "BCMA, the target BCMA, human BCMA" as used herein relates to human B cell maturation antigen, also known as BCMA; TR17_HUMAN, TNFRSF17 (UniProt Q02223), which is a member of the tumor necrosis receptor superfamily that is preferentially expressed in differentiated plasma cells. The extracellular domain of BCMA consists according to UniProt of amino acids 1-54 (or 5-51). The term "antibody against BCMA, anti-BCMA antibody" as used herein relates to an antibody specifically binding to the extracellular domain of BCMA.

"Specifically binding to BCMA or binding to BCMA" refer to an antibody that is capable of binding to the target BCMA with sufficient affinity such that the antibody is useful as a therapeutic agent in targeting BCMA. In some embodiments, the extent of binding of an anti-BCMA antibody to an unrelated, non-BCMA protein is about 10-fold preferably >100-fold less than the binding of the antibody to BCMA as measured, e.g., by surface plasmon resonance (SPR) e.g. Biacore®, enzyme-linked immunosorbent (ELISA) or flow cytometry (FACS). In one embodiment the antibody that binds to BCMA has a dissociation constant (Kd) of 10 M or less, preferably from 10 M to $10^{-13}$ M, preferably from $10^{-9}$ M to $10^{-13}$ M. In one embodiment the anti-BCMA antibody binds to an epitope of BCMA that is conserved among BCMA from different species, preferably among human and cynomolgus, and in addition preferably also to mouse and rat BCMA. "Bispecific antibody specifically binding to CD3 and BCMA, bispecific antibody against CD3 and BCMA" refers to a respective definition for binding to both targets. An antibody specifically binding to BCMA (or BCMA and CD3) does not bind to other human antigens. Therefore in an ELISA, OD values for such unrelated targets will be equal or lower to that of the limit of detection of the specific assay, preferably >0.3 ng/mL, or equal or lower to OD values of control samples without plate-bound-BCMA or with untransfected HEK293 cells.

Preferably the anti-BCMA antibody is specifically binding to a group of BCMA, consisting of human BCMA and BCMA of non-human mammalian origin, preferably BCMA from cynomolgus, mouse and/or rat. "cyno/human gap" refer to the affinity ratio KD cynomolgus BCMA[M]/KD human BCMA[M] (details see example 3). "cyno/human gap of Mab CD3" as used herein refer to affinity ratio KD cynomolgus CD3[M]/KD human CD3[M]. In one embodiment the bispecific anti-BCMA/anti-CD3 antibody of the invention shows a cyno/human gap of Mab CD3 between 1.25 and 5 or between 0.8 and 1.0. The bispecific antibody according to the invention is in one embodiment characterized in that it binds also specifically to cynomolgus CD3. In one embodiment the bispecific anti-BCMA/anti-CD3 antibody of the invention shows a cyno/human gap of Mab CD3 between 1.25 and 5 or between 0.8 and 1.0. Preferably the cyno/human gap is in the same range for anti-BCMA- and the anti-CD3 antibody.

The term "APRIL" as used herein relates to recombinant, truncated murine APRIL (amino acids 106-241; NP_076006). APRIL can be produced as described in Ryan, 2007 (Mol Cancer Ther; 6 (11): 3009-18).

The term "BAFF" as used herein relates to recombinant, truncated human BAFF (UniProt Q9Y275

(TN13B_HUMAN) which can be produced as described in Gordon, 2003 (Biochemistry; 42 (20): 5977-5983). Preferably a His-tagged BAFF is used according to the invention. Preferably the His-tagged BAFF is produced by cloning a DNA fragment encoding BAFF residues 82-285 into an expression vector, creating a fusion with an N-terminal His-tag followed by a thrombin cleavage site, expressing said vector and cleaving the recovered protein with thrombin.

Anti-BCMA antibodies are analyzed by ELISA for binding to human BCMA using plate-bound BCMA. For this assay, an amount of plate-bound BCMA preferably 1.5 µg/mL and concentration(s) ranging from 0.1 pM to 200 nM of anti-BCMA antibody are used.

The term "NF-κB" as used herein relates to recombinant NF-κB p50 (accession number (P19838). NF-κB activity can be measured by a DNA-binding ELISA of an extract of NCI-H929 MM cells (CRL-9068™). NCI-H929 MM cells, untreated or treated with 0.1 µg/mL TNF-α, 1000 ng/mL heat-treated HT-truncated-BAFF, 1000 ng/mL truncated-BAFF, 0.1 pM to 200 nM isotype control, and with or without 0.1 pM to 200 nM anti-BCMA antibodies are incubated for 20 min. NF-κB activity can be assayed using a functional ELISA that detects chemiluminescent signal from p65 bound to the NF-κB consensus sequence (U.S. Pat. No. 6,150,090).

The term "further target" as used herein means preferably CD3ε. The term "first target and second target" means either CD3 as first target and BCMA as second target or means BCMA as first target and CD3 as second target.

The term "CD3E or CD3" as used herein relates to human CD3E described under UniProt P07766 (CD3E_HUMAN). The term "antibody against CD3E, anti CD3E antibody" relates to an antibody specifically binding to CD3E. In one embodiment the antibody comprises a variable domain VH comprising the heavy chain CDRs of SEQ ID NO: 1, 2 and 3 as respectively heavy chain CDR1H, CDR2H and CDR3H and a variable domain VL comprising the light chain CDRs of SEQ ID NO: 4, 5 and 6 as respectively light chain CDR1L, CDR2L and CDR3L. In one embodiment the antibody comprises the variable domains of SEQ ID NO:7 (VH) and SEQ ID NO:8 (VL).

The term "antibody" as used herein refers to a monoclonal antibody. An antibody consists of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. Each heavy chain comprises a heavy chain variable region (abbreviated herein as HCVR or VH) and a heavy chain constant region. The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The "constant domains" of the heavy chain and of the light chain are not involved directly in binding of an antibody to a target, but exhibit various effector functions. The term "antibody" as used herein refers comprises also the portion of an antibody which is needed at least for specific binding to the antigen CD3 resp. BCMA. Therefore such an antibody (or antibody portion) can be in one embodiment a Fab fragment, if said antibody portion is comprised in a bispecific antibody according to the invention. The antibody according to the invention can also be a Fab', F(ab')$_2$, a scFv, a di-scFv, or a bi-specific T-cell engager (BiTE).

The term "antibody" includes e.g. mouse antibodies, human antibodies, chimeric antibodies, humanized antibodies and genetically engineered antibodies (variant or mutant antibodies) as long as their characteristic properties are retained. Especially preferred are human or humanized antibodies, especially as recombinant human or humanized antibodies. Further embodiments are heterospecific antibodies (bispecific, trispecific etc.) and other conjugates, e.g. with cytotoxic small molecules.

The term "bispecific antibody" as used herein refers in one embodiment to an antibody in which one of the two pairs of heavy chain and light chain (HC/LC) is specifically binding to CD3 and the other one is specifically binding to BCMA. The term also refers to other formats of bispecific antibodies according to the state of the art, in one embodiment to bispecific single-chain antibodies.

Figure 2:
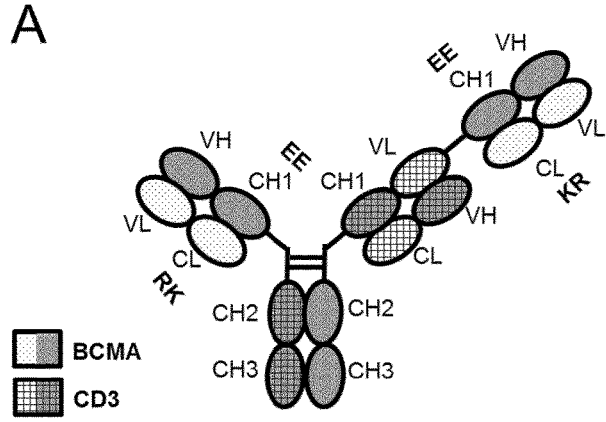
FIG. 2. Preferred bispecific trivalent antibodies comprising only the Fab fragments (specific to CD3 and BCMA) and the Fc part as specified: (A) Fab BCMA(RK/EE)-Fc-Fab CD3-Fab BCMA(RK/EE); (B) Fab BCMA-Fc-Fab CD3 (RK/EE)-Fab BCMA; (C) Fab BCMA(RK/EE)-Fc-Fab BCMA(RK/EE)-Fab CD3; (D) Fab BCMA-Fc-Fab BCMA-Fab CD3(RK/EE). aa substitutions for RK/EE introduced in CL-CH1 to reduce LC mispairing/side-products in production. Preferably, the Fab CD3 includes a VL-VH crossover to reduce LC mispairing and side-products. Preferably, Fab CD3 and Fab BCMA are linked to each other with flexible linkers.
Figure 2:
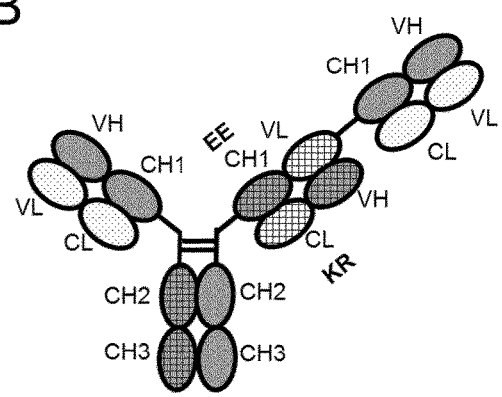
Figure 2:
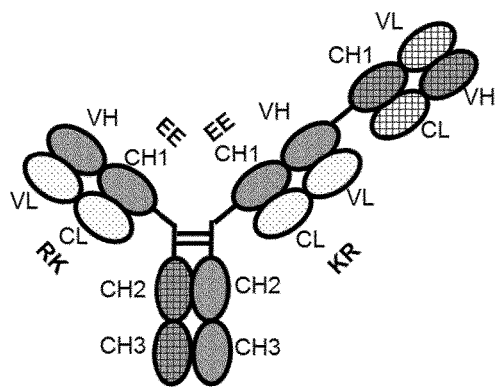
Figure 2:
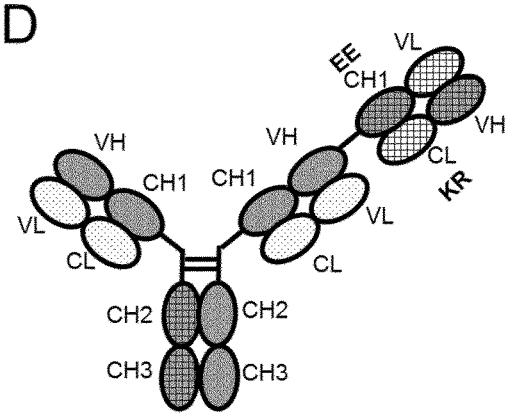
Figure 3:
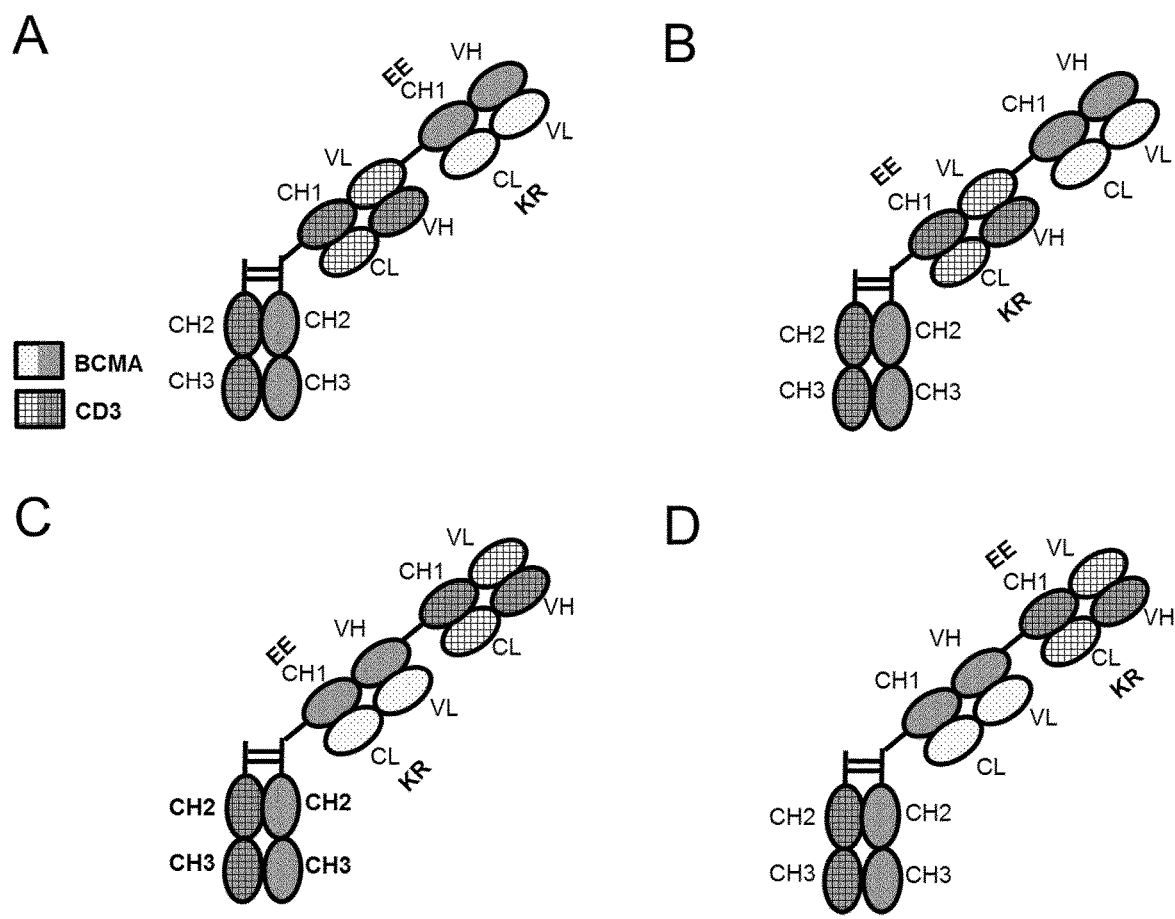
FIG. 3. Bispecific bivalent antibodies comprising only the Fab fragments (specific to CD3 and BCMA) and the Fc part as specified: (A) Fc-Fab CD3-Fab BCMA(RK/EE); (B) Fc-Fab CD3(RK/EE)-Fab BCMA; (C) Fc-Fab BCMA(RK/EE)-Fab CD3; (D) Fc-Fab BCMA-Fab CD3(RK/EE). Preferably, the Fabs CD3 include a VL-VH crossover to reduce LC mispairing and side-products. Fab CD3 and Fab BCMA are linked to each other with flexible linkers.

The term "TCB" as used herein refer to a bispecific antibody specifically binding to BCMA and CD3. The term "83A10-TCBcv" as used herein refer to a bispecific antibody specifically binding to BCMA and CD3 as specified by its heavy and light chain combination of SEQ ID NO:45, SEQ ID NO:46, SEQ ID NO:47 (2×), and SEQ ID NO:48, and as shown in FIG. 2A and described in EP14179705. The terms "21-TCBcv, 22-TCBcv, 42-TCBcv" as used herein refer to the respective bispecific antibodies of Mab21, as specified by its heavy and light chain combination of SEQ ID NO:48, SEQ ID NO:49, SEQ ID NO:50, and SEQ ID NO:51 (2×), Mab 22 as specified by its heavy and light chain combinations of SEQ ID NO:48, SEQ ID NO:52, SEQ ID NO:53, and SEQ ID NO:54 (2×), and Mab42 as specified by its heavy and light chain combination of SEQ ID NO:48 of SEQ ID NO:55, SEQ ID NO:56, and SEQ ID NO:57-(2×).

The term "naked antibody" as used herein refers to an antibody which is specifically binding to BCMA, comprising an Fc part and is not conjugated with a therapeutic agent e.g. with a cytotoxic agent or radiolabel. The term "conjugated antibody, drug conjugate" as used herein refers to an antibody which is specifically binding to BCMA, and is conjugated with a therapeutic agent e.g. with a cytotoxic agent or radiolabel.

The term "bispecific single-chain antibody" as used herein refers to a single polypeptide chain comprising in one embodiment two binding domains, one specifically binding to BCMA and the other one in one embodiment specifically binding to CD3. Each binding domain comprises one variable region from an antibody heavy chain ("VH region"), wherein the VH region of the first binding domain specifically binds to the CD3 molecule, and the VH region of the second binding domain specifically binds to BCMA. The two binding domains are optionally linked to one another by a short polypeptide spacer. A non-limiting example for a polypeptide spacer is Gly-Gly-Gly-Gly-Ser (G-G-G-G-S) and repeats thereof. Each binding domain may additionally comprise one variable region from an antibody light chain ("VL region"), the VH region and VL region within each of the first and second binding domains being linked to one another via a polypeptide linker, long enough to allow the VH region and VL region of the first binding domain and the VH region and VL region of the second binding domain to pair with one another such that, together, they are able to specifically bind to the respective first and second binding domains (see e.g. EP0623679). Bispecific single-chain antibodies are also mentioned e.g. in Choi B D et al., Expert Opin Biol Ther. 2011 July; 11(7):843-53 and Wolf E. et al., Drug Discov Today. 2005 Sep. 15; 10(18):1237-44.

The term "diabody" as used herein refers to a small bivalent and bispecific antibody fragment comprising a heavy (VH) chain variable domain connected to a light chain variable domain (VL) on the same polypeptide chain (VH-VL) connected by a peptide linker that is too short to allow pairing between the two domains on the same chain (Kipriyanov, Int. J. Cancer 77 (1998), 763-772). This forces pairing with the complementary domains of another chain and promotes the assembly of a dimeric molecule with two functional antigen binding sites. To construct bispecific diabodies of the invention, the V-domains of an anti-CD3 antibody and an anti-BCMA antibody are fused to create the two chains VH(CD3)-VL(BCMA), VH(BCMA)-VL(CD3). Each chain by itself is not able to bind to the respective antigen, but recreates the functional antigen binding sites of anti-CD3 antibody and anti-BCMA antibody on pairing with the other chain. The two scFv molecules, with a linker between heavy chain variable domain and light chain variable domain that is too short for intramolecular dimerization, are co-expressed and self-assemble to form bi-specific molecules with the two binding sites at opposite ends. By way of example, the variable regions encoding the binding domains for BCMA and CD3, respectively, can be amplified by PCR from DNA constructs obtained as described, such that they can be cloned into a vector like pHOG, as described in Kipiriyanov et al., J. Immunol, Methods, 200, 69-77 (1997a). The two scFV constructs are then combined in one expression vector in the desired orientation, whereby the VH-VL linker is shortened to prevent backfolding of the chains onto themselves. The DNA segments are separated by a STOP codon and a ribosome binding site (RBS). The RBS allows for the transcription of the mRNA as a bi-cistronic message, which is translated by ribosomes into two proteins which non-covalently interact to form the diabody molecule. Diabodies, like other antibody fragments, have the advantage that they can be expressed in bacteria (*E. coli*) and yeast (*Pichia pastoris*) in functional form and with high yields (up to 1g/l).

The term "tandem scFVs" as used herein refers to a single chain Fv molecule (i.e. a molecule formed by association of the immunoglobulin heavy and light chain variable domains, VH and VL, respectively) as described e.g, in WO 03/025018 and WO 03/048209. Such Fv molecules, which are known as TandAbs® comprise four antibody variable domains, wherein (i) either the first two or the last two of the four variable domains bind intramolecularly to one another within the same chain by forming an antigen binding scFv in the orientation VH/VL or VL/VH (ii) the other two domains bind intermolecularly with the corresponding VH or VL domains of another chain to form antigen binding VH/VL pairs. In a preferred embodiment, as mentioned in WO 03/025018, the monomers of such Fv molecule comprise at least four variable domains of which two neighboring domains of one monomer form an antigen-binding VH-VL or VL-VH scFv unit.

The term "DARPins" as used herein refers to a bispecific ankyrin repeat molecule as described e.g. in US 2009082274. These molecules are derived from natural ankyrin proteins, which can be found in the human genome and are one of the most abundant types of binding proteins. A DARPin library module is defined by natural ankyrin repeat protein sequences, using 229 ankyrin repeats for the initial design and another 2200 for subsequent refinement. The modules serve as building blocks for the DARPin libraries. The library modules resemble human genome sequences. A DARPin is composed of 4 to 6 modules. Because each module is approx. 3.5 kDa, the size of an average DARPin is 16-21 kDa. Selection of binders is done by ribosome display, which is completely cell-free and is described in He M and Taussig M J., Biochem Soc Trans. 2007, November; 35(Pt 5):962-5.

The term "T cell bispecific engager" are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to a BCMA.

There are five types of mammalian antibody heavy chains denoted by the Greek letters: α, δ, ε, γ, and μ (Janeway C A, Jr et al (2001). Immunobiology. 5th ed., Garland Publishing). The type of heavy chain present defines the class of antibody; these chains are found in IgA, IgD, IgE, IgG, and IgM antibodies, respectively (Rhoades R A, Pflanzer R G (2002). Human Physiology, 4th ed., Thomson Learning). Distinct heavy chains differ in size and composition; α and γ contain approximately 450 amino acids, while μ and ε have approximately 550 amino acids.

Each heavy chain has two regions, the constant region and the variable region. The constant region is identical in all antibodies of the same isotype, but differs in antibodies of different isotype. Heavy chains γ, α and δ have a constant region composed of three constant domains CH1, CH2, and CH3 (in a line), and a hinge region for added flexibility (Woof J, Burton D Nat Rev Immunol 4 (2004) 89-99); heavy chains μ and ε have a constant region composed of four constant domains CH1, CH2, CH3, and CH4 (Janeway C A, Jr et al (2001). Immunobiology. 5th ed., Garland Publishing). The variable region of the heavy chain differs in antibodies produced by different B cells, but is the same for all antibodies produced by a single B cell or B cell clone. The variable region of each heavy chain is approximately 110 amino acids long and is composed of a single antibody domain.

In mammals there are only two types of light chain, which are called lambda (λ) and kappa (κ). A light chain has two successive domains: one constant domain CL and one variable domain VL. The approximate length of a light chain is 211 to 217 amino acids. In one embodiment the light chain is a kappa (κ) light chain, and the constant domain CL is in one embodiment derived from a kappa (K) light chain (the constant domain CK).

"aa substitution" as used herein refer to independent amino acid substitution in the constant domain CH1 at the amino acid at positions 147 and 213 by glutamic acid (E), or aspartic acid (D) and in the constant domain CL the amino acid at position 124 is substituted by lysine (K), arginine (R) or histidine (H). In one embodiment in addition in the constant domain CL the amino acid at position 123 is independently substituted by lysine (K), arginine (R) or histidine (H). In one embodiment amino acid 124 is K, amino acid 147 is E, amino acid 213 is E, and amino acid 123 is R. The aa substitutions are either in the CD3 Fab or in one or two BCMA Fabs. Bispecific antibodies against BCMA and CD3 as charge variants are described in EP14179705, disclosed by reference (further called as "charge variants resp. charge variant exchange").

All amino acid numbering herein is according to Kabat (Kabat, E. A. et al, Sequences of Proteins of Immunological Interest, 5th ed. Public Health Service, National Institutes of Health, Bethesda, Md. (1991), NIH Publication 91-3242).

The terms "monoclonal antibody" or "monoclonal antibody composition" as used herein refer to a preparation of antibody molecules of a single amino acid composition.

The "antibodies" according to the invention can be of any class (e.g. IgA, IgD, IgE, IgG, and IgM, preferably IgG or IgE), or subclass (e.g., IgG1, IgG2, IgG3, IgG4, IgA1 and IgA2, preferably IgG1), whereby both antibodies, from which the bivalent bispecific antibody according to the invention is derived, have an Fc part of the same subclass (e.g. IgG1, IgG4 and the like, preferably IgG1), preferably of the same allotype (e.g. Caucasian).

A "Fc part of an antibody" is a term well known to the skilled artisan and defined on the basis of papain cleavage of antibodies. The antibodies according to the invention contain as Fc part, in one embodiment a Fc part derived from human origin and preferably all other parts of the human constant regions. The Fc part of an antibody is directly involved in complement activation, C1q binding, C3 activation and Fc receptor binding. While the influence of an antibody on the complement system is dependent on certain conditions, binding to C1q is caused by defined binding sites in the Fc part. Such binding sites are known in the state of the art and described e.g. by Lukas, T J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434.

Such binding sites are e.g. L234, L235, D270, N297, E318, K320, K322, P331 and P329 (numbering according to EU index of Kabat). Antibodies of subclass IgG1, IgG2 and IgG3 usually show complement activation, C1q binding and C3 activation, whereas IgG4 do not activate the complement system, do not bind C1q and do not activate C3. In one embodiment the Fc part is a human Fc part.

In one embodiment an antibody according to the invention comprises an Fc variant of a wild-type human IgG Fc region, said Fc variant comprising an amino acid substitution at position Pro329 and at least one further amino acid substitution, wherein the residues are numbered according to the EU index of Kabat, and wherein said antibody exhibits a reduced affinity to the human FcγRIIIA and/or FcγRIIA and/or FcγRI compared to an antibody comprising the wildtype IgG Fc region, and wherein the ADCC induced by said antibody is reduced to at least 20% of the ADCC induced by the antibody comprising a wild-type human IgG Fc region. In a specific embodiment Pro329 of a wild-type human Fc region in the antibody according to the invention is substituted with glycine or arginine or an amino acid residue large enough to destroy the proline sandwich within the Fc/Fcγ receptor interface, that is formed between the proline329 of the Fc and tryptophane residues Trp 87 and Trp 110 of FcγRIII (Sondermann et al.: Nature 406, 267-273 (20 Jul. 2000)). In a further aspect of the invention the at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region. Such Fc variants are described in detail in WO2012130831.

By "effector function" as used herein is meant a biochemical event that results from the interaction of an antibody Fc region with an Fc receptor or ligand. Effector functions include but are not limited to ADCC, ADCP, and CDC. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys. By "library" herein is meant a set of Fc variants in any form, including but not limited to a list of nucleic acid or amino acid sequences, a list of nucleic acid or amino acid substitutions at variable positions, a physical library comprising nucleic acids that encode the library sequences, or a physical library comprising the Fc variant proteins, either in purified or unpurified form.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

"Fc variant with increased effector function" as used herein is meant an Fc sequence that differs from that of a parent Fc sequence by virtue of at least one amino acid modification or relates to other modifications like amendment of glycosylation at e.g. Asn279 that increase effector functions. Such modifications are e.g. mentioned in Duncan et al., 1988, Nature 332:563-564; Lund et al., 1991, J Immunol 147:2657-2662; Lund et al., 1992, Mol Immunol 29:53-59; Alegre et al., 1994, Transplantation 57:1537-1543; Hutchins et al., 1995, Proc Natl Acad Sci USA 92:11980-11984; Jefferis et al., 1995, //77muno/Lett 44:111-117; Lund et al., 1995, Faseb J 9:115-119; Jefferis et al., 1996, Immunol Lett 54:101-104; Lund et al., 1996, J Immunol 157:4963-4969; Armour et al., 1999, Eur J Immunol 29:2613-2624; Idusogie et al., 2000, J Immunol 164:4178-4184; Reddy et al., 2000, J Immunol 164:1925-1933; Xu et al., 2000, Cell Immunol 200: 16-26; Idusogie et al., 2001, J Immunol 166:2571-2575; Shields et al., 2001, J Biol Chem 276:6591-6604; Jefferis et al., 2002, Immunol Lett 82:57-65; Presta et al., 2002, Biochem Soc Trans 30:487-490; U.S. Pat. Nos. 5,624,821; 5,885,573; 6,194,551; WO200042072; WO199958572. Such Fc modifications also include according to the invention engineered glycoforms of the Fc part. By "engineered glycoform" as used herein is meant a carbohydrate composition that is covalently attached to an Fc polypeptide, wherein said carbohydrate composition differs chemically from that of a parent Fc polypeptide. Engineered glycoforms may be generated by any method, for example by using engineered or variant expression strains, by co-expression with one or more enzymes, for example D1-4-N-acetylglucosaminyltransferase III (GnTIII), by expressing an Fc polypeptide in various organisms or cell lines from various organisms, or by modifying carbohydrate(s) after the Fc polypeptide has been expressed.

Methods for generating engineered glycoforms are known in the art and mentioned in Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473) U.S. Pat. No. 6,602,684; WO200061739; WO200129246; WO200231140; WO200230954; Potelligent™ technology (Biowa, Inc., Princeton, N.J.); GlycoMAb™ glycosylation engineering technology (GLYCART biotechnology AG, Zurich, Switzerland)). Engineered glycoform typically refers to the different carbohydrate or oligosaccharide composition than the parent Fc polypeptide.

Antibodies according to the invention comprising a Fc variant with increased effector function show high binding affinity to the Fc gamma receptor III (FcγRIII, CD 16a). High binding affinity to FcγRIII denotes that binding is enhanced for CD16a/F158 at least 10-fold in relation to the parent antibody (95% fucosylation) as reference expressed in CHO host cells, such as CHO DG44 or CHO K1 cells, or/and binding is enhanced for CD16a/V158 at least 20-fold in relation to the parent antibody measured by Surface Plasmon Resonance (SPR) using immobilized CD 16a at an antibody concentration of 100 nM. FcγRIII binding can be increased by methods according to the state of the art, e.g. by modifying the amino acid sequence of the Fc part or the glycosylation of the Fc part of the antibody (see e.g. EP2235061). Mori, K et al., Cytotechnology 55 (2007)109 and Satoh M, et al., Expert Opin Biol Ther. 6 (2006) 1161-1173 relate to a FUT8 (α-1,6-fucosyltransferase) gene knockout CHO line for the generation of afucosylated antibodies.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. MoI. Biol. 227 (1992) 381-388; Marks, J. D., et al., J. MoI. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH)) as used herein denotes each of the pair of light and heavy chains which is involved directly in binding the antibody according to the invention. The domains of variable human light and heavy chains have the same general structure and each domain comprises four framework (FR) regions whose sequences are widely conserved, connected by three "hypervariable regions" (or complementarity determining regions, CDRs).

The framework regions adopt a β-sheet conformation and the CDRs may form loops connecting the β-sheet structure. The CDRs in each chain are held in their three-dimensional structure by the framework regions and form together with the CDRs from the other chain the binding site. The antibody heavy and light chain CDR3 regions play a particularly important role in the binding specificity/affinity of the antibodies according to the invention and therefore provide a further object of the invention.

The terms "hypervariable region" or "target-binding portion of an antibody" when used herein refer to the amino acid residues of an antibody which are responsible for target-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to target binding. CDR and FR regions are determined according to the standard definition of Kabat et al., Sequences of Proteins of Immunological Interest, 5th ed., Public Health Service, National Institutes of Health, Bethesda, Md. (1991). The terms "CDR1H, CDR2H and CDR3H" as used herein refer to the respective CDRs of the heavy chain located in the variable domain VH. The terms "CDR1L, CDR2L and CDR3L" as used herein refer to the respective CDRs of the light chain located in the variable domain VL.

The constant heavy chain domain CH1 by which the heavy chain domain CH3 is replaced can be of any Ig class (e.g. IgA, IgD, IgE, IgG, and IgM), or subclass (e.g., IgG1, IgG2, IgG3, IgG4, IgA1 and IgA2). The constant light chain domain CL by which the heavy chain domain CH3 is replaced can be of the lambda ($\lambda$) or kappa ($\kappa$) type, preferably the kappa ($\kappa$) type.

The term "target" or "target molecule" as used herein are used interchangeable and refer to human BCMA. In regard to bispecific antibodies the term refers to BCMA and the second target. Preferably in regard to bispecific antibodies the term refers to BCMA and CD3.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of a target that is bound by an antibody.

In general there are two vectors encoding the light chain and heavy chain of an antibody according to the invention. In regard to a bispecific antibody there are two vectors encoding the light chain and heavy chain of said antibody specifically binding to the first target, and further two vectors encoding the light chain and heavy chain of said antibody specifically binding to the second target. One of the two vectors is encoding the respective light chain and the other of the two vectors is encoding the respective heavy chain. However in an alternative method for the preparation of an antibody according to the invention, only one first vector encoding the light chain and heavy chain of the antibody specifically binding to the first target and only one second vector encoding the light chain and heavy chain of the antibody specifically binding to the second target can be used for transforming the host cell.

The term "nucleic acid or nucleic acid molecule", as used herein, is intended to include DNA molecules and RNA molecules. A nucleic acid molecule may be single-stranded or double-stranded, but preferably is double-stranded DNA.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen S N, et al, PNAS 1972, 69 (8): 2110-2114.

Recombinant production of antibodies using transformation is well-known in the state of the art and described, for example, in the review articles of Makrides, S. C, Protein Expr. Purif. 17 (1999) 183-202; Geisse, S., et al., Protein Expr. Purif. 8 (1996) 271-282; Kaufman, R J., MoI. Biotechnol. 16 (2000) 151-161; Werner, R. G., et al., Arzneimittelforschung 48 (1998) 870-880 as well as in U.S. Pat. Nos. 6,331,415 and 4,816,567.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NSO cells, SP2/0 cells, HEK293 cells, COS cells, yeast, or E. coli cells, and the antibody is recovered from the cells (supernatant or cells after lysis). The bispecific antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed., Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

The antibodies are suitably separated from the culture medium by conventional immunoglobulin purification procedures such as, for example, protein A-Sepharose, hydroxylapatite chromatography, gel electrophoresis, dialysis, or affinity chromatography. DNA or RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK293 cells, CHO cells, or myeloma cells that do not otherwise produce immunoglobulin protein, to obtain the synthesis of recombinant monoclonal antibodies in the host cells.

Amino acid sequence variants (or mutants) of an antibody according to the invention are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and target binding, but may improve the yield of the recombinant production, protein stability or facilitate the purification.

The invention provides in one embodiment an isolated or purified nucleic acid sequence encoding a chimeric antigen receptor (CAR), wherein the CAR comprises an antigen recognition moiety directed against BCMA, a transmembrane moiety and a T-cell activation moiety, characterized in that the antigen recognition moiety is an antibody according to the invention (here not the bispecific antibody). The encoded antibody can be also an antigen binding fragment thereof as specified. Structures and generation of such "BCMA CARs" are described e.g. in WO2013154760, WO2015052538, WO2015090229, and WO2015092024.

In one embodiment the invention comprises a chimeric antigen receptor (CAR) comprising:
(i) a B cell maturation antigen (BCMA) recognition moiety;
(ii) a spacer domain; and
(ii) a transmembrane domain; and
(iii) an intracellular T cell signaling domain,
characterized in that the BCMA recognition moiety is a monoclonal antibody specifically binding to BCMA, characterized in comprising a CDR3H region of SEQ ID NO:17 and a CDR3L region of SEQ ID NO:20 and a CDR1H, CDR2H, CDR1L, and CDR2L region combination selected from the group of
a) CDR1H region of SEQ ID NO:21 and CDR2H region of SEQ ID NO:22, CDR1L region of SEQ ID NO:23, and CDR2L region of SEQ ID NO:24,
b) CDR1H region of SEQ ID NO:21 and CDR2H region of SEQ ID NO:22, CDR1L region of SEQ ID NO:25, and CDR2L region of SEQ ID NO:26,
c) CDR1H region of SEQ ID NO:21 and CDR2H region of SEQ ID NO:22, CDR1L region of SEQ ID NO:27, and CDR2L region of SEQ ID NO:28,
d) CDR1H region of SEQ ID NO:29 and CDR2H region of SEQ ID NO:30, CDR1L region of SEQ ID NO:31, and CDR2L region of SEQ ID NO:32,
e) CDR1H region of SEQ ID NO:34 and CDR2H region of SEQ ID NO:35, CDR1L region of SEQ ID NO:31, and CDR2L region of SEQ ID NO:32, and
f) CDR1H region of SEQ ID NO:36 and CDR2H region of SEQ ID NO:37, CDR1L region of SEQ ID NO:31, and CDR2L region of SEQ ID NO:32.

The T-cell activation moiety can be any suitable moiety derived or obtained from any suitable molecule. In one embodiment, for example, the T-cell activation moiety comprises a transmembrane domain. The transmembrane domain can be any transmembrane domain derived or obtained from any molecule known in the art. For example, the transmembrane domain can be obtained or derived from a CD8a molecule or a CD28 molecule. CD8 is a transmembrane glycoprotein that serves as a co-receptor for the T-cell receptor (TCR), and is expressed primarily on the surface of cytotoxic T-cells. The most common form of CD8 exists as a dimer composed of a CD8 alpha and CD8 beta chain. CD28 is expressed on T-cells and provides co-stimulatory signals required for T-cell activation. CD28 is the receptor for CD80 (B7.1) and CD86 (B7.2). In a preferred embodiment, the CD8 alpha and CD28 are human. In addition to the transmembrane domain, the T-cell activation moiety further comprises an intracellular (i.e., cytoplasmic) T-cell signaling domain. The intercellular T-cell signaling domain can be obtained or derived from a CD28 molecule, a CD3 zeta molecule or modified versions thereof, a human Fc receptor gamma (FcRy) chain, a CD27 molecule, an OX40 molecule, a 4-IBB molecule, or other intracellular signaling molecules known in the art. As discussed above, CD28 is a T-cell marker important in T-cell co-stimulation. CD3 zeta, associates with TCRs to produce a signal and contains immunoreceptor tyrosine-based activation motifs (ITAMs). 4-1BB, also known as CD137, transmits a potent costimulatory signal to T-cells, promoting differentiation and enhancing long-term survival of T lymphocytes. In one embodiment, the CD28, CD3 zeta, 4-1BB, OX40, and CD27 are human The invention provides in one embodiment an isolated or purified nucleic acid sequence encoding a chimeric antigen receptor (CAR) as specified above.

T cell bispecific (TCB) binders have very high concentration/tumor-cell-receptor-occupancy dependent potency in cell killing (e.g. $EC_{50}$ in in vitro cell killing assays in the sub- or low picomolar range; Dreier et al. Int J Cancer 2002), T-cell bispecific binder (TCB) are given at much lower doses than conventional monospecific antibodies. For example, blinatumomab (CD19×CD3) is given at a continuous intravenous dose of 5 to 15 µg/m$^2$/day (i.e. only 0.35 to 0.105 mg/m²/week) for treatment of acute lymphocytic leukemia or 60 μg/m²/day for treatment of Non Hodgkin Lymphoma, and the serum concentrations at these doses are in the range of 0.5 to 4 ng/ml (Klinger et al., Blood 2012; Topp et al., J Clin Oncol 2011; Goebeler et al. Ann Oncol 2011). Because low doses of TCB can exert high efficacy in patients, it is envisaged that for an antibody according to the invention subcutaneous administration is possible and preferred in the clinical settings (preferably in the dose range of 0.1 to 2.5, preferably 25 mg/m²/week, preferably 250 mg/m2/week). Even at these low concentrations/doses/receptor occupancies, TCB can cause considerable adverse events (Klinger et al., Blood 2012). Therefore it is critical to control tumor cell occupancy/coverage. In patients with high and variable levels of serum APRIL and BAFF (e.g. multiple myeloma patients, Moreaux et al. 2004; Blood 103(8): 3148-3157) number of TCB bound to the tumor cells resp. tumor cell occupancy may be considerably influenced by APRIL/BAFF. But by using said antibody of this invention, tumor cell occupancy respectively efficacy/safety it may not be required to increase the dose for an antibody according to this invention as said antibody may not be affected by APRIL/BAFF ligand competition. Another advantage of the antibody according to the invention is based on the inclusion of an Fc portion, which increases the elimination half-life to about 4 to 12 days and allows at least once or twice/week administrations as compared to TCBs without an Fc portion (e.g. blinatumomab) which are required to be given intravenously and continuously with a pump carried by patients.

Figure 8:
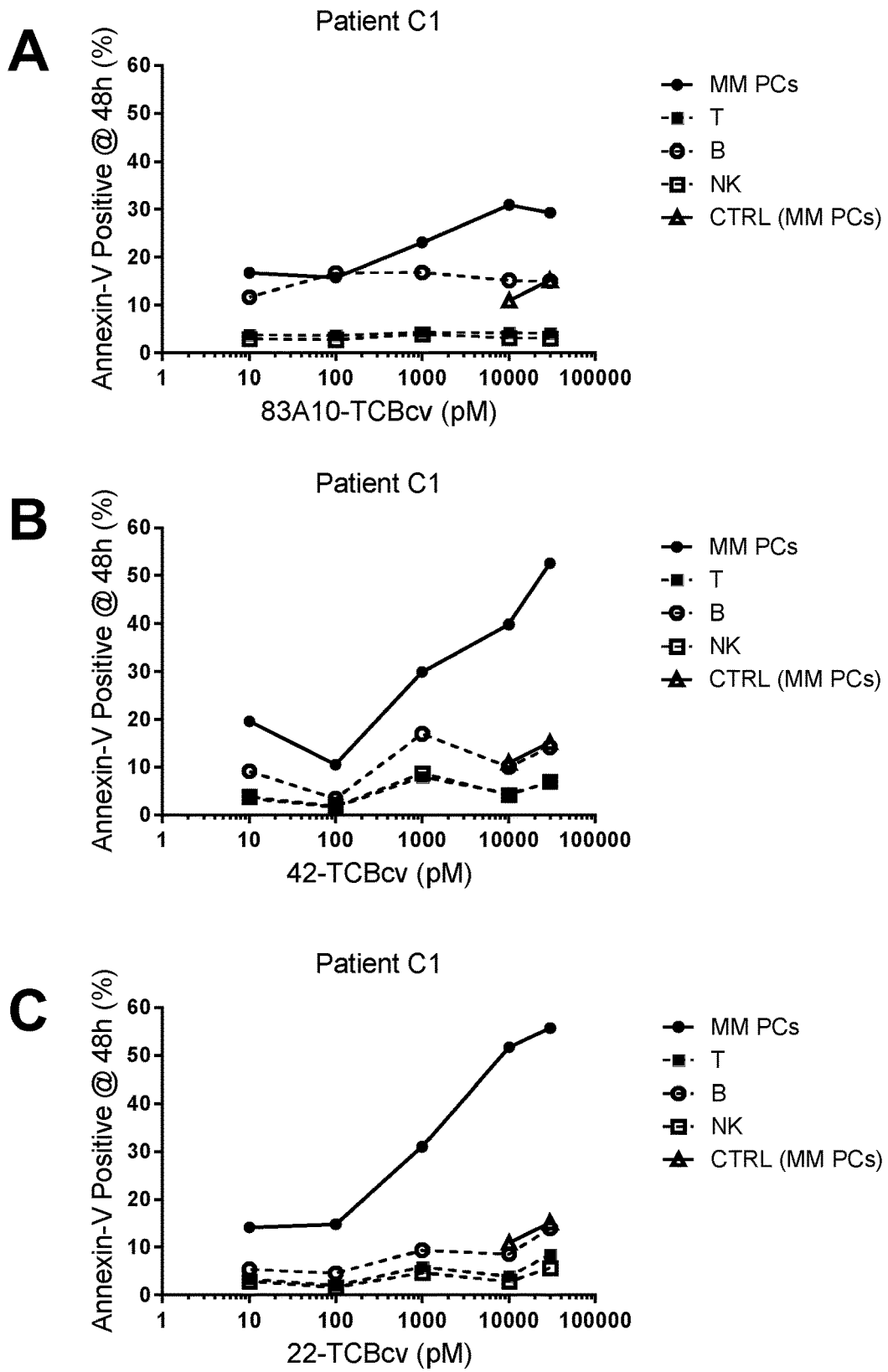
FIG. 8. Redirected T-cell lysis of multiple myeloma patient bone marrow myeloma plasma cells in presence of autologous bone marrow infiltrating T cells (patient's whole bone marrow aspirates) induced by anti-BCMA/anti-CD3 T-cell bispecific antibodies as measured by multiparameter flow cytometry. Percentage of annexin-V positive myeloma plasma cells was determined and plotted against TCB concentrations. Concentration-dependent and specific lysis of patient myeloma plasma cells were observed while lysis of T cells, B cells, and NK cells was not observed based on an 8-color multiparameter panel. No induction of cell death of myeloma plasma cells with control-TCB at the highest concentration of TCB antibodies tested. As compared to 83A10-TCBcv (A), 42-TCBcv (B) and 22-TCBcv (C) were more potent to induce killing of patient bone marrow myeloma plasma cells (see example 13).
Figure 9:
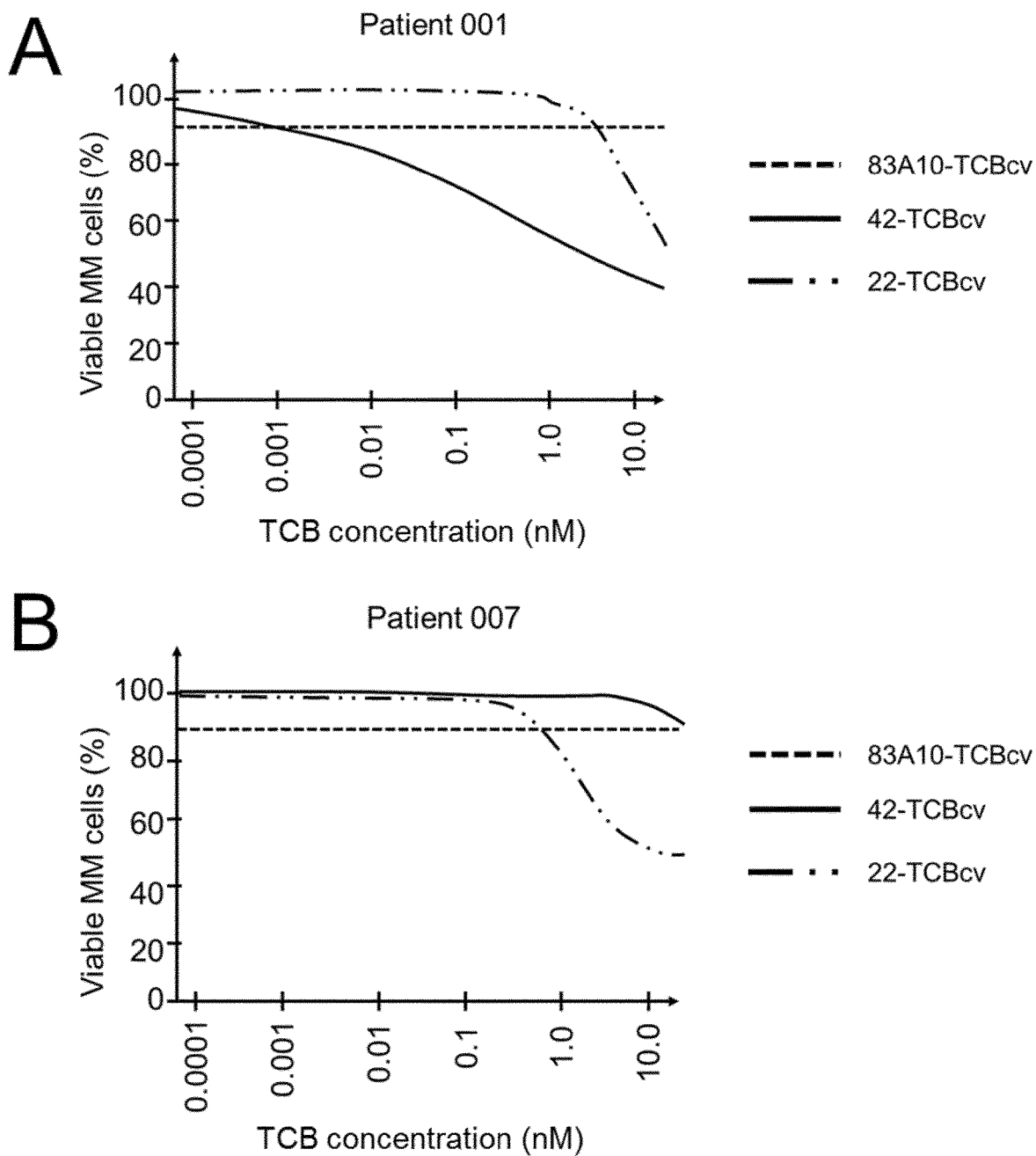
FIG. 9. Redirected T-cell lysis of multiple myeloma patient bone marrow myeloma plasma cells in presence of autologous bone marrow infiltrating T cells (patient's whole bone marrow aspirates) induced by anti-BCMA/anti-CD3 T-cell bispecific antibodies as measured by flow cytometry. Percentage of annexin-V negative myeloma plasma cells was determined and plotted against TCB concentrations. Concentration-dependent and specific lysis of patient myeloma plasma cells were observed while lysis of non-malignant bone marrow cells was not observed (data not shown). No induction of cell death of myeloma plasma cells observed with control-TCB at the highest concentration of TCB antibodies tested (data not shown). As compared to 83A10-TCBcv, 42-TCBcv and 22-TCBcv were more potent to induce killing of patient bone marrow myeloma plasma cells as reflected by the concentration-dependent reduction of viable (annexin-V negative) myeloma plasma cells. Representative experiments in patient 001 (A) and patient 007 (B) (see example 13).
Figure 10:
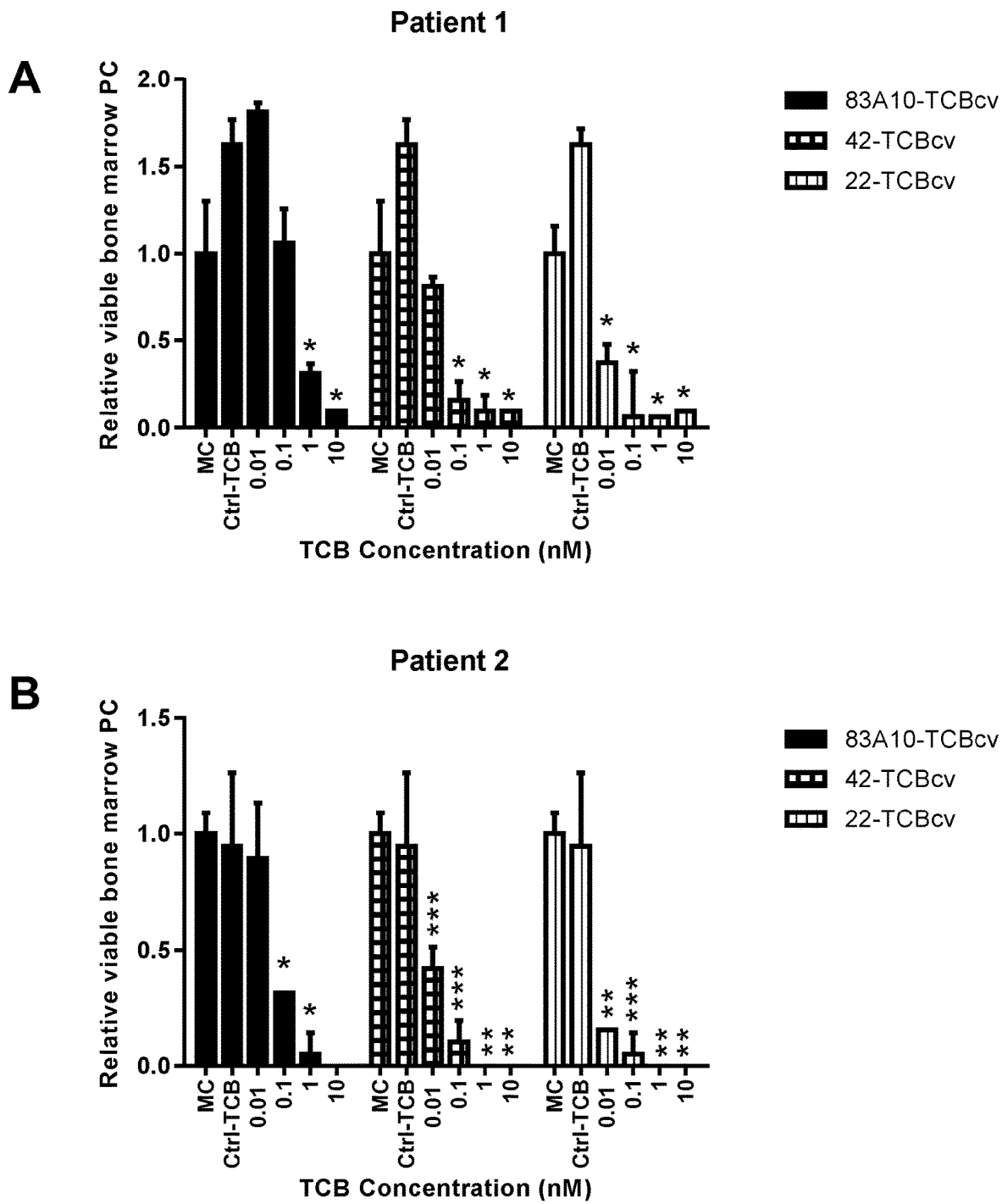
FIG. 10. Redirected T-cell lysis of multiple myeloma patient bone marrow myeloma plasma cells in presence of autologous bone marrow infiltrating T cells induced by anti-BCMA/anti-CD3 T-cell bispecific antibodies as measured by flow cytometry. Percentage of propidium iodide negative myeloma plasma cells was determined and the percentage of viable bone marrow plasma cells relative to the medium control (MC) was plotted against TCB concentrations. Concentration-dependent and specific lysis of patient myeloma plasma cells were observed (A-G) while lysis of bone marrow microenvironment (BMME) was not observed (H). No induction of cell death of myeloma plasma cells observed with control-TCB at the highest concentration of TCB antibodies tested. As compared to 83A10-TCBcv, 42-TCBcv and 22-TCBcv were more potent to induce killing of patient bone marrow myeloma plasma cells as reflected by the concentration-dependent reduction of viable (propidium iodide negative) myeloma plasma cells. An effect was considered statistically significant if the P-value of its corresponding statistical test was <5% (*), <1% () or <0.1% (*). Experiments performed using bone marrow aspirate samples collected from patient 1 (A), patient 2 (B), patient 3 (C), patient 4 (D), patient 5 (E), patient 6 (F), and patient 7 (G, H) (see example 13).

The biological properties of the antibodies according to the invention respectively their anti-BCMA/anti-CD3 TCB antibodies have been investigated in several studies in comparison to 83A10-TCBcv. The potency to induce T-cell redirected cytotoxicity of e.g. anti-BCMA/anti-CD3 TCB antibodies 21-TCBcv, 22-TCBcv, 42-TCBcv in comparison to 83A10-TCBcv was measured on H929 MM cell line (Example 8, Table 12, FIG. 4). The antibodies of this invention were studied and analysis showed that concentration dependent killing of H929 cells resp. the EC50 values were found to be higher than EC50 values determined for 83A10-TCBcv; suggesting that the anti-BCMA antibodies according to the invention as TCBs were less potent to induce killing of H929 MM cells than Mab 83A10 as TCB. Surprisingly a turnover was observed when T-cell redirected cytotoxicity was measured on RPMI-8226 MM cell line and also JJN-3 cell line (respectively, examples 10 and 11, Tables 13, and 14 and 15, FIGS. 6 and 7): the antibodies according to the invention as TCBs showed lower EC50 and therefore higher potency than 83A10-TCBcv. To the surprise of the inventors, the antibodies according to the invention as TCBs showed several advantages in a direct comparison with 83A10 TCBcv in bone marrow aspirates freshly taken from MM patients (note: to get the best possible comparison, in all bone marrow aspirates always all T-cell bispecific (TCB) antibodies have been tested at same concentrations);

Higher killing potency of myeloma cells, i.e. same % of killing already at lower concentrations than with 83A10-TCBcv respectively concentration response curves for killing shifted to the left (Example 13, Tables 18, 19 and 20, FIGS. 8, 9 and 10). Already at a concentration of 1 nM of antibodies as TCBs according to the invention in seven different patient bone marrow aspirates reduction relative to control of propidium iodide negative viable multiple myeloma cancer cells was between 77.1 and 100%. With 1 nM 83A10-TCBcv in same seven bone marrow aspirates reductions of only 37.1 to 98.3% have been achieved (Tables 20 and 21).

Higher maximal killing as compared to 83A10-TCBcv was achieved at the highest concentration tested (10 nM) in the same experiment with the seven (7) bone marrow aspirates for antibodies as TCBs according to the invention (Tables 20 and 21).

Non responders to 83A10-TCBcv can be turned to responders if 22-TCBcv/42-TCBcv are used: In two (2) bone marrow patient samples in which no killing response to 83A10-TCBcv was observed, surprisingly killing could be found with antibodies as TCBs according to the invention (FIGS. 9A and 9B).

The BCMAxCD3 TCB of this invention bind to human and cynomolgus monkeys (cyno) BCMA and to BCMA of mice and rat, appropriate for toxicological examination in cynomolgus monkeys if the CD3 binder also binds to cynomolgus CD3 or in mouse/rat if the CD3 binder also binds to mouse/rat BCMA. Surprisingly the binding affinity to cyno BCMA is very close to the binding affinity to human BCMA. SPR has been used to measure binding affinities to human and cyno BCMA (Example 2, Table 4). Cyno/human gap (ratio of affinity for cyno to human BCMA, KD) has been calculated from measured affinity data by dividing affinity to cyno BCMA through affinity to human BCMA (Example 3, Table 5). For 83A10 a cyno/human gap of 15.3 was found (i.e. 15.3 times lower binding affinity to cyno than to human BCMA). To the surprise of the inventors the antibodies according to the invention showed cyno/human gaps between 15.4 and 1.7, which is similar or in majority more favorable cyno/human gap than that of 83A10 (Table 5). Because the CD3 binder used in the BCMAxCD3 TCB according to the invention is cross-reactive to cynomolgus monkey CD3, pharmacokinetics and pharmacodynamics investigations can be obtained from cynomolgus monkeys (see Example 16). Also toxicological investigations in cynomolgus monkeys are predictive of the pharmacological and toxicological effects in humans and the cross-reactivity to cynomolgus monkeys feature is to the benefit of patients. The BCMA antibodies of this invention also bind to murine BCMA (e.g. Kd of clones 22 and 42 measured by SPR as 0.9 nM and 2.5 nM) see table 2D in Example 1.1.1A.4). The CD3 binder of the BCMAxCD3 TCB is not cross-reactive to murine CD3.

In summary the potency and efficacy advantages for killing of low BCMA expressing MM cell lines like RPMI-8226 and JJN-3 and especially for killing of MM cells in patient bone marrow aspirates and in addition the very favorable cyno/human gap in binding affinities to BCMA make the antibodies of this invention and respective TCBs essentially promising agents for treatment of MM patients. In addition the anti-BCMAxCD3 TCBcv of this invention have, as 83A10-TCBcv, favorable properties like long elimination half-life, efficacy at once a week administration (intravenously, subcutaneously), low or no tendency to aggregation and can be manufactured with high purity and good yield.

TABLE 1A

Antibody sequences

| SEQ ID NO: | Name(s) | aa sequences |
|---|---|---|
| 1 | CD3 CDR1H | TYAMN |
| 2 | CD3 CDR2H | RIRSKYNNYATYYADSVKG |
| 3 | CD3 CDR3H | HGNFGNSYVSWFAY |
| 4 | CD3 CDR1L | GSSTGAVTTSNYAN |
| 5 | CD3 CDR2L | GTNKRAP |
| 6 | CD3 CDR3L | ALWYSNLWV |
| 7 | CD3 VH | EVQLLESGGGLVQPGGSLRLSCAASGFTFSTYAMNWVRQAPGKGLEWVSRIRSKYNNYATYYADSVKGRFTISRDDSKNTLYLQMNSLRAEDTAVYYCVRHGNFGNSYVSWFAYWGQGTLVTVSS |
| 8 | CD3 VL | QAVVTQEPSLTVSPGGTVTLTCGSSTGAVTTSNYANWVQEKPGQAFRGLIGGTNKRAPGTPARFSGSLLGGKAALTLSGAQPEDEAEYYCALWYSNLWVFGGGTKLTVL |
| 9 | 83A10 VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKVLGWFDYWGQGTLVTVSS |
| 10 | Mab21 VH<br>Mab22 VH<br>Mab42 VH | EVQLLESGGGLVQPGGSLRLSCAASGFTFSDNAMGWVRQAPGKGLEWVSAISGPGSSTYYADSVKGRFTISRDNSKNTLYLQMNSLRAEDTAVYYCAKVLGWFDYWGQGTLVTVSS |
| 11 | 83A10 VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGYPPDFTFGQGTKVEIK |
| 12 | Mab21 VL<br>Mab27 VL<br>Mab33 VL<br>Mab39 VL | EIVLTQSPGTLSLSPGERATLSCRASQSVSEYYLAWYQQKPGQAPRLLIEHASTRATGIPDRFSGSGSGTDFTLTISRLEPEDFAVYYCQQYGYPPDFTFGQGTKVEIK |
| 13 | Mab22 VL | EIVLTQSPGTLSLSPGERATLSCRASQSVSSYYLAWYQQKPGQAPRLLISGAGSRATGIPDRFSGSGSGTDFTLTISRLEPEDFAVYYCQQYGYPPDFTFGQGTKVEIK |
| 14 | Mab42 VL | EIVLTQSPGTLSLSPGERATLSCRASQSVSDEYLSWYQQKPGQAPRLLIHSASTRATGIPDRFSGSGSGTDFTLAISRLEPEDFAVYYCQQYGYPPDFTFGQGTKVEIK |
| 15 | 83A10 CDR1H | SYAMS |
| 16 | 83A10 CDR2H | AISGSGGSTYYADSVKG |
| 17 | 83A10 CDR3H<br>Mab21 CDR3H<br>Mab22 CDR3H<br>Mab42 CDR3H<br>Mab27 CDR3H<br>Mab33 CDR3H<br>Mab39 CDR3H | VLGWFDY |
| 18 | 83A10 CDR1L | RASQSVSSSYLAW |
| 19 | 83A10 CDR2L | YGASSRAT |
| 20 | 83A10 CDR3L<br>Mab21 CDR3L<br>Mab22 CDR3L<br>Mab42 CDR3L | QQYGYPPDFT |
| 21 | Mab21 CDR1H<br>Mab22 CDR1H<br>Mab42 CDR1H | DNAMG |
| 22 | Mab21 CDR2H<br>Mab22 CDR2H<br>Mab42 CDR2H | AISGPGSSTYYADSVKG |

TABLE 1A-continued

Antibody sequences

| SEQ ID NO: | Name(s) | aa sequences |
|---|---|---|
| 23 | Mab21 CDR1L | RASQSVSEYYLAW |
| 24 | Mab21 CDR2L | EHASTRAT |
| 25 | Mab22 CDR1L | RASQSVSSYYLAW |
| 26 | Mab22 CDR2L | SGAGSRAT |
| 27 | Mab42 CDR1L | RASQSVSDEYLSW |
| 28 | Mab42 CDR2L | HSASTRAT |
| 29 | Mab27 CDR1H | SAPMG |
| 30 | Mab27 CDR2H | AISYIGHTYYADSVKG |
| 31 | Mab27 CDR1L<br>Mab33 CDR1L<br>Mab39 CDR1L | RASQSVSEYYLA |
| 32 | Mab27 CDR2L<br>Mab33 CDR2L<br>Mab39 CDR2L | HASTRAT |
| 33 | Mab27 CDR3L<br>Mab33 CDR3L<br>Mab39 CDR3L | QQYGYPPDFT |
| 34 | Mab33 CDR1H | TNAMG |
| 35 | Mab33 CDR2H | AINRFGGSTYYADSVKG |
| 36 | Mab39 CDR1H | QNAMG |
| 37 | Mab39 CDR2H | AISPTGFSTYYADSVKG |
| 38 | Mab27 VH | EVQLLESGGGLVQPGGSLRLSCAASGFTFSSAPMGWVR<br>QAPGKGLEWVSAISYIGHTYYADSVKGRFTISRDNSKNT<br>LYLQMNSLRAEDTAVYYCAKVLGWFDYWGQGTLVTV<br>SS |
| 39 | Mab33 VH | EVQLLESGGGLVQPGGSLRLSCAASGFTFYTNAMGWV<br>RQAPGKGLEWVSAINRFGGSTYYADSVKGRFTISRDNS<br>KNTLYLQMNSLRAEDTAVYYCAKVLGWFDYWGQGTL<br>VTVSS |
| 40 | Mab39 VH | EVQLLESGGGLVQPGGSLRLSCAASGFTFTQNAMGWV<br>RQAPGKGLEWVSAISPTGFSTYYADSVKGRFTISRDNSK<br>NTLYLQMNSLRAEDTAVYYCAKVLGWFDYWGQGTLV<br>TVSS |
| 41 | 83A10 BCMA CH1<br>Mab21 BCMA CH1<br>Mab22 BCMA CH1<br>Mab42 BCMA CH1 | ASTKGPSVFPLAPSSKSTSGGTAALGCLVEDYFPEPVTV<br>SWNSGALTSGVHTFPAVLQSSGLYSLSSVVTVPSSSLGT<br>QTYICNVNHKPSNTKVDEKVEPKSC |
| 42 | 83A10 BCMA CL<br>Mab21 BCMA CL<br>Mab22 BCMA CL<br>Mab42 BCMA CL | RTVAAPSVFIFPPSDRKLKSGTASVVCLLNNFYPREAKV<br>QWKVDNALQSGNSQESVTEQDSKDSTYSLSSTLTLSKA<br>DYEKHKVYACEVTHQGLSSPVTKSFNRGEC |
| 43 | CD3 CH1 | ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSC |
| 44 | CD3 CL | ASVAAPSVFIFPPSDEQLKSGTASVVCLLNNFYPREAKV<br>QWKVDNALQSGNSQESVTEQDSKDSTYSLSSTLTLSKA<br>DYEKHKVYACEVTHQGLSSPVTKSFNRGEC |
| 45 | 83A10 knob HC | EVQLLESGGGLVQPGGSLRLSCAASGFTFSSYAMSWVR<br>QAPGKGLEWVSAISGSGGSTYYADSVKGRFTISRDNSK<br>NTLYLQMNSLRAEDTAVYYCAKVLGWFDYWGQGTLV<br>TVSSASTKGPSVFPLAPSSKSTSGGTAALGCLVEDYFPEP<br>VTVSWNSGALTSGVHTFPAVLQSSGLYSLSSVVTVPSSS<br>LGTQTYICNVNHKPSNTKVDEKVEPKSCDGGGSGGG |

TABLE 1A-continued

Antibody sequences

| SEQ ID NO: | Name(s) | aa sequences |
|---|---|---|
| | | GSQAVVTQEPSLTVSPGGTVTLTCGSSTGAVTTSNYAN<br>WVQEKPGQAFRGLIGGTNKRAPGTPARFSGSLLGGKAA<br>LTLSGAQPEDEAEYYCALWYSNLWVFGGGTKLTVLSS<br>ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSCDKTHTCPPCPAPE<br>AAGGPSVFLFPPKPKDTLMISRTPEVTCVVVDVSHEDPE<br>VKFNWYVDGVEVHNAKTKPREEQYNSTYRVVSVLTVL<br>HQDWLNGKEYKCKVSNKALGAPIEKTISKAKGQPREPQ<br>VYTLPPCRDELTKNQVSLWCLVKGFYPSDIAVEWESNG<br>QPENNYKTTPPVLDSDGSFFLYSKLTVDKSRWQQGNVF<br>SCSVMHEALHNHYTQKSLSLSPGK |
| 46 | 83A10 hole HC | EVQLLESGGGLVQPGGSLRLSCAASGFTFSSYAMSWVR<br>QAPGKGLEWVSAISGSGGSTYYADSVKGRFTISRDNSK<br>NTLYLQMNSLRAEDTAVYYCAKVLGWFDYWGQGTLV<br>TVSSASTKGPSVFPLAPSSKSTSGGTAALGCLVEDYFPEP<br>VTVSWNSGALTSGVHTFPAVLQSSGLYSLSSVVTVPSSS<br>LGTQTYICNVNHKPSNTKVDEKVEPKSCDKTHTCPPCP<br>APEAAGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALGAPIEKTISKAKGQPR<br>EPQVCTLPPSRDELTKNQVSLSCAVKGFYPSDIAVEWES<br>NGQPENNYKTTPPVLDSDGSFFLVSKLTVDKSRWQQGN<br>VFSCSVMHEALHNHYTQKSLSLSPGK |
| 47 | 83A10 LC | EIVLTQSPGTLSLSPGERATLSCRASQSVSSSYLAWYQQ<br>KPGQAPRLLIYGASSRATGIPDRFSGSGSGTDFTLTISRLE<br>PEDFAVYYCQQYGYPPDFTFGQGTKVEIKRTVAAPSVFI<br>FPPSDRKLKSGTASVVCLLNNFYPREAKVQWKVDNAL<br>QSGNSQESVTEQDSKDSTYSLSSTLTLSKADYEKHKVY<br>ACEVTHQGLSSPVTKSFNRGEC |
| 48 | CD3 LC | EVQLLESGGGLVQPGGSLRLSCAASGFTFSTYAMNWVR<br>QAPGKGLEWVSRIRSKYNNYATYYADSVKGRFTISRDD<br>SKNTLYLQMNSLRAEDTAVYYCVRHGNFGNSYVSWFA<br>YWGQGTLVTVSSASVAAPSVFIFPPSDEQLKSGTASVVC<br>LLNNFYPREAKVQWKVDNALQSGNSQESVTEQDSKDS<br>TYSLSSTLTLSKADYEKHKVYACEVTHQGLSSPVTKSFN<br>RGEC |
| 49 | Mab21 knob HC | EVQLLESGGGLVQPGGSLRLSCAASGFTFSDNAMGWV<br>RQAPGKGLEWVSAISGPGSSTYYADSVKGRFTISRDNSK<br>NTLYLQMNSLRAEDTAVYYCAKVLGWFDYWGQGTLV<br>TVSSASTKGPSVFPLAPSSKSTSGGTAALGCLVEDYFPEP<br>VTVSWNSGALTSGVHTFPAVLQSSGLYSLSSVVTVPSSS<br>LGTQTYICNVNHKPSNTKVDEKVEPKSCDGGGSGGG<br>GSQAVVTQEPSLTVSPGGTVTLTCGSSTGAVTTSNYAN<br>WVQEKPGQAFRGLIGGTNKRAPGTPARFSGSLLGGKAA<br>LTLSGAQPEDEAEYYCALWYSNLWVFGGGTKLTVLSS<br>ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSCDKTHTCPPCPAPE<br>AAGGPSVFLFPPKPKDTLMISRTPEVTCVVVDVSHEDPE<br>VKFNWYVDGVEVHNAKTKPREEQYNSTYRVVSVLTVL<br>HQDWLNGKEYKCKVSNKALGAPIEKTISKAKGQPREPQ<br>VYTLPPCRDELTKNQVSLWCLVKGFYPSDIAVEWESNG<br>QPENNYKTTPPVLDSDGSFFLYSKLTVDKSRWQQGNVF<br>SCSVMHEALHNHYTQKSLSLSPGK |
| 50 | Mab21 hole HC | EVQLLESGGGLVQPGGSLRLSCAASGFTFSDNAMGWV<br>RQAPGKGLEWVSAISGPGSSTYYADSVKGRFTISRDNSK<br>NTLYLQMNSLRAEDTAVYYCAKVLGWFDYWGQGTLV<br>TVSSASTKGPSVFPLAPSSKSTSGGTAALGCLVEDYFPEP<br>VTVSWNSGALTSGVHTFPAVLQSSGLYSLSSVVTVPSSS<br>LGTQTYICNVNHKPSNTKVDEKVEPKSCDKTHTCPPCP<br>APEAAGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALGAPIEKTISKAKGQPR<br>EPQVCTLPPSRDELTKNQVSLSCAVKGFYPSDIAVEWES<br>NGQPENNYKTTPPVLDSDGSFFLVSKLTVDKSRWQQGN<br>VFSCSVMHEALHNHYTQKSLSLSPGK |
| 51 | Mab21 LC | EIVLTQSPGTLSLSPGERATLSCRASQSVSEYYLAWYQQ<br>KPGQAPRLLIEHASTRATGIPDRFSGSGSGTDFTLTISRLE<br>PEDFAVYYCQQYGYPPDFTFGQGTKVEIKRTVAAPSVFI |

TABLE 1A-continued

Antibody sequences

| SEQ ID NO: | Name(s) | aa sequences |
|---|---|---|
| | | FPPSDRKLKSGTASVVCLLNNFYPREAKVQWKVDNAL QSGNSQESVTEQDSKDSTYSLSSTLTLSKADYEKHKVY ACEVTHQGLSSPVTKSFNRGEC |
| 52 | Mab22 knob HC | EVQLLESGGGLVQPGGSLRLSCAASGFTFSDNAMGWV RQAPGKGLEWVSAISGPGSSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDGGGGSGGG GSQAVVTQEPSLTVSPGGTVTLTCGSSTGAVTTSNYAN WVQEKPGQAFRGLIGGTNKRAPGTPARFSGSLLGGKAA LTLSGAQPEDEAEYYCALWYSNLWVFGGGTKLTVLSS ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALGAPIEKTISKAKGQPREPQ VYTLPPCRDELTKNQVSLWCLVKGFYPSDIAVEWESNG QPENNYKTTPPVLDSDGSFFLYSKLTVDKSRWQQGNVF SCSVMHEALHNHYTQKSLSLSPGK |
| 53 | Mab22 hole HC | EVQLLESGGGLVQPGGSLRLSCAASGFTFSDNAMGWV RQAPGKGLEWVSAISGPGSSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDKTHTCPPCP APEAAGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALGAPIEKTISKAKGQPR EPQVCTLPPSRDELTKNQVSLSCAVKGFYPSDIAVEWES NGQPENNYKTTPPVLDSDGSFFLVSKLTVDKSRWQQGN VFSCSVMHEALHNHYTQKSLSLSPGK |
| 54 | Mab22 LC | EIVLTQSPGTLSLSPGERATLSCRASQSVSSYYLAWYQQ KPGQAPRLLISGAGSRATGIPDRFSGSGSGTDFTLTISRLE PEDFAVYYCQQYGYPPDFTFGQGTKVEIKRTVAAPSVFI FPPSDRKLKSGTASVVCLLNNFYPREAKVQWKVDNAL QSGNSQESVTEQDSKDSTYSLSSTLTLSKADYEKHKVY ACEVTHQGLSSPVTKSFNRGEC |
| 55 | Mab42 knob HC | EVQLLESGGGLVQPGGSLRLSCAASGFTFSDNAMGWV RQAPGKGLEWVSAISGPGSSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDGGGGSGGG GSQAVVTQEPSLTVSPGGTVTLTCGSSTGAVTTSNYAN WVQEKPGQAFRGLIGGTNKRAPGTPARFSGSLLGGKAA LTLSGAQPEDEAEYYCALWYSNLWVFGGGTKLTVLSS ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALGAPIEKTISKAKGQPREPQ VYTLPPCRDELTKNQVSLWCLVKGFYPSDIAVEWESNG QPENNYKTTPPVLDSDGSFFLYSKLTVDKSRWQQGNVF SCSVMHEALHNHYTQKSLSLSPGK |
| 56 | Mab42 hole HC | EVQLLESGGGLVQPGGSLRLSCAASGFTFSDNAMGWV RQAPGKGLEWVSAISGPGSSTYYADSVKGRFTISRDNSK NTLYLQMNSLRAEDTAVYYCAKVLGWFDYWGQGTLV TVSSASTKGPSVFPLAPSSKSTSGGTAALGCLVEDYFPEP VTVSWNSGALTSGVHTFPAVLQSSGLYSLSSVVTVPSSS LGTQTYICNVNHKPSNTKVDEKVEPKSCDKTHTCPPCP APEAAGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALGAPIEKTISKAKGQPR EPQVCTLPPSRDELTKNQVSLSCAVKGFYPSDIAVEWES NGQPENNYKTTPPVLDSDGSFFLVSKLTVDKSRWQQGN VFSCSVMHEALHNHYTQKSLSLSPGK |

TABLE 1A-continued

Antibody sequences

| SEQ ID NO:Name(s) | aa sequences |
|---|---|
| 57   Mab42 LC | EIVLTQSPGTLSLSPGERATLSCRASQSVSDEYLSWYQQ KPGQAPRLLIHSASTRATGIPDRFSGSGSGTDFTLAISRLE PEDFAVYYCQQYGYPPDFTFGQGTKVEIKRTVAAPSVFI FPPSDRKLKSGTASVVCLLNNFYPREAKVQWKVDNAL QSGNSQESVTEQDSKDSTYSLSSTLTLSKADYEKHKVY ACEVTHQGLSSPVTKSFNRGEC |

Remark: SEQ ID NO: 20 and SEQ ID NO: 33 are identical

TABLE 1B

Antibody sequences (short list)

| | | | | SEQ ID NO: | | | | |
|---|---|---|---|---|---|---|---|---|
| CD3 antibody | VH | VL | CDR1H | CDR2H | CDR3H | CDR1L | CDR2L | CDR3L |
| | 7 | 8 | 1 | 2 | 3 | 4 | 5 | 6 |
| BCMA antibody | VH | VL | CDR1H | CDR2H | CDR3H | CDR1L | CDR2L | CDR3L |
| 83A10 | 9 | 11 | 15 | 16 | 17 | 18 | 19 | 20 |
| Mab21 | 10 | 12 | 21 | 22 | 17 | 23 | 24 | 20 |
| Mab22 | 10 | 13 | 21 | 22 | 17 | 25 | 26 | 20 |
| Mab42 | 10 | 14 | 21 | 22 | 17 | 27 | 28 | 20 |
| Mab27 | 38 | 12 | 29 | 30 | 17 | 31 | 32 | 33 |
| Mab33 | 39 | 12 | 34 | 35 | 17 | 31 | 32 | 33 |
| Mab39 | 40 | 12 | 36 | 37 | 17 | 31 | 32 | 33 |

TABLE 2A

Additional constructs

| Fragment/ | SEQ ID NO: | | | |
|---|---|---|---|---|
| Construct | 83A10 | Mab21 | Mab22 | Mab42 |
| BCMA CH1 | 41 | 41 | 41 | 41 |
| BCMA CL | 42 | 42 | 42 | 42 |
| CD3 CH1 | 43 | 43 | 43 | 43 |
| CD3 CL | 44 | 44 | 44 | 44 |

TABLE 2B

Additional constructs

| Construct | SEQ ID NO: | | | |
|---|---|---|---|---|
| | 83A10 | Mab21 | Mab22 | Mab42 |
| BCMA VH_CH1cv × CD3 VL_CH1 Fc knob LALA PG (knob HC) | 45 | 49 | 52 | 55 |
| BCMAcv HC hole LALA PG (hole HC) | 46 | 50 | 53 | 56 |
| BCMAcv hum IgG1 LC (BCMA LC) | 47 | 51 | 54 | 57 |
| CD3 VH_CL (CD3 LC) | 48 | 48 | 48 | 48 |

To make the following (2+1) Fc-containing anti-BCMA/anti-CD3 TCBs, the respective constructs/sequence IDs as mentioned in the table 2B above were used:
83A10-TCBcv: 45, 46, 47 (×2), 48 (FIG. 2A)
21-TCBcv: 48, 49, 50, 51 (×2) (FIG. 2A)
22-TCBcv: 48, 52, 53, 54 (×2) (FIG. 2A)
42-TCBcv: 48, 55, 56, 57 (×2) (FIG. 2A)
In the following specific embodiments of the invention are listed:

1. A monoclonal antibody specifically binding to BCMA, characterized in comprising a CDR3H region of SEQ ID NO:17 and a CDR3L region of SEQ ID NO:20 and a CDR1H, CDR2H, CDR1L, and CDR2L region combination selected from the group of
a) CDR1H region of SEQ ID NO:21 and CDR2H region of SEQ ID NO:22, CDR1L region of SEQ ID NO:23, and CDR2L region of SEQ ID NO:24,
b) CDR1H region of SEQ ID NO:21 and CDR2H region of SEQ ID NO:22, CDR1L region of SEQ ID NO:25, and CDR2L region of SEQ ID NO:26,
c) CDR1H region of SEQ ID NO:21 and CDR2H region of SEQ ID NO:22, CDR1L region of SEQ ID NO:27, and CDR2L region of SEQ ID NO:28,
d) CDR1H region of SEQ ID NO:29 and CDR2H region of SEQ ID NO:30, CDR1L region of SEQ ID NO:31, and CDR2L region of SEQ ID NO:32,
e) CDR1H region of SEQ ID NO:34 and CDR2H region of SEQ ID NO:35, CDR1L region of SEQ ID NO:31, and CDR2L region of SEQ ID NO:32, and
f) CDR1H region of SEQ ID NO:36 and CDR2H region of SEQ ID NO:37, CDR1L region of SEQ ID NO:31, and CDR2L region of SEQ ID NO:32.

2. A monoclonal antibody specifically binding to BCMA, characterized in comprising a VH region comprising a CDR1H region of SEQ ID NO:21, a CDR2H region of SEQ ID NO:22 and a CDR3H region of SEQ ID NO:17 and a VL region comprising a CDR3L region of SEQ ID NO:20 and a CDR1L and CDR2L region combination selected from the group of
a) CDR1L region of SEQ ID NO:23 and CDR2L region of SEQ ID NO:24,
b) CDR1L region of SEQ ID NO:25 and CDR2L region of SEQ ID NO:26, or c) CDR1L region of SEQ ID NO:27 and CDR2L region of SEQ ID NO:28.

3. The antibody according to embodiment for 2, characterized in comprising as VL region a VL region selected from the group consisting of VL regions of SEQ ID NO:12, 13, and 14.

4. The antibody according to any one of embodiments 1 to 3, characterized in comprising as VH region a VH region of SEQ ID NO:10 and as VL region a VL region of SEQ ID NO:12.

5. The antibody according to any one of embodiment 1 to 3, characterized in comprising as VH region a VH region of SEQ ID NO:10 and as VL region a VL region of SEQ ID NO:13.

6. The antibody according to any one of embodiment 1 to 3, characterized in comprising as VH region a VH region of SEQ ID NO:10 and as VL region a VL region of SEQ ID NO:14.

7. The antibody according to embodiment 1 or 2, characterized in that amino acid 49 of the VL region is selected from the group of amino acids tyrosine (Y), glutamic acid (E), serine (S), and histidine (H).

8. The antibody according to embodiment 7, characterized in that amino acid 74 of the VL region is threonine (T) or alanine (A).

9. A monoclonal antibody specifically binding to BCMA, characterized in comprising a VH region comprising a CDR3H region of SEQ ID NO:17 and a VL region comprising a CDR1L region of SEQ ID NO:31, a CDR2L region of SEQ ID NO:32 and a CDR3L region of SEQ ID NO:20 and a CDR1L and CDR2L region combination selected from the group of a) CDR1H region of SEQ ID NO:29 and CDR2H region of SEQ ID NO:30, b) CDR1H region of SEQ ID NO:34 and CDR2H region of SEQ ID NO:35, or c) CDR1H region of SEQ ID NO:36 and CDR2H region of SEQ ID NO:37.

10. The antibody according to embodiment 9, characterized in comprising a VL region of SEQ ID NO:12 and a VH region selected from the group comprising the VH regions of SEQ ID NO:38, 39, and 40.

11. The antibody according to embodiment 9 or 10, characterized in comprising in in that amino acid 49 of the VL region is selected from the group of amino acids tyrosine (Y), glutamic acid (E), serine (S), and histidine (H).

12. The antibody according to embodiment 9 or 10, characterized in that amino acid 74 of the VL region is threonine (T) or alanine (A).

13. The antibody according to any one of embodiments 1 to 12, characterized in that it binds also specifically to cynomolgus BCMA and comprises an additional Fab fragment specifically binding to CD3ε.

14. The antibody according to any one of embodiments 1 to 13, characterized in being an antibody with an Fc or without an Fc part.

15. A bispecific antibody specifically binding to BCMA and CD3ε, characterized in comprising a CDR3H region of SEQ ID NO:17 and a CDR3L region of SEQ ID NO:20 and a CDR1H, CDR2H, CDR1L, and CDR2L region combination selected from the group of a) CDR1H region of SEQ ID NO:21 and CDR2H region of SEQ ID NO:22, CDR1L region of SEQ ID NO:23, and CDR2L region of SEQ ID NO:24, b) CDR1H region of SEQ ID NO:21 and CDR2H region of SEQ ID NO:22, CDR1L region of SEQ ID NO:25, and CDR2L region of SEQ ID NO:26, c) CDR1H region of SEQ ID NO:21 and CDR2H region of SEQ ID NO:22, CDR1L region of SEQ ID NO:27, and CDR2L region of SEQ ID NO:28, d) CDR1H region of SEQ ID NO:29 and CDR2H region of SEQ ID NO:30, CDR1L region of SEQ ID NO:31, and CDR2L region of SEQ ID NO:32, e) CDR1H region of SEQ ID NO:34 and CDR2H region of SEQ ID NO:35, CDR1L region of SEQ ID NO:31, and CDR2L region of SEQ ID NO:32, and f) CDR1H region of SEQ ID NO:36 and CDR2H region of SEQ ID NO:37, CDR1L region of SEQ ID NO:31, and CDR2L region of SEQ ID NO:32.

16. A bispecific antibody specifically binding to the two targets which are the extracellular domain of human BCMA (further named also as "BCMA") and human CD3E (further named also as "CD3"), characterized in comprising a VH region comprising a CDR1H region of SEQ ID NO:21, a CDR2H region of SEQ ID NO:22 and a CDR3H region of SEQ ID NO:17 and a VL region comprising a CDR3L region of SEQ ID NO:20 and a CDR1L and CDR2L region combination selected from the group of a) CDR1L region of SEQ ID NO:23 and CDR2L region of SEQ ID NO:24, b) CDR1L region of SEQ ID NO:25 and CDR2L region of SEQ ID NO:26, or c) CDR1L region of SEQ ID NO:27 and CDR2L region of SEQ ID NO:28.

17. The bispecific antibody according to embodiment 15 or 16, characterized in comprising as VH region a VH region of SEQ ID NO:10.

18. The bispecific antibody according to any one of embodiments 15 to 16, characterized in that the BCMA VL is selected from the group consisting of VL regions of SEQ ID NO:12, 13, and 14.

19. The bispecific antibody according to any one of embodiments 14 to 18, characterized in comprising as BCMA VH region a VH region of SEQ ID NO:10 and as VL region a VL region of SEQ ID NO:12, or as BCMA VH a VH region of SEQ ID NO:10 and as VL region a VL region of SEQ ID NO:13, or as BCMA VH a VH region of SEQ ID NO:10 and as VL region a VL region of SEQ ID NO:14.

20. The bispecific antibody according to any one of embodiments 15 or 19, characterized in comprising in in that amino acid 49 of the VL region is selected from the group of amino acids tyrosine (Y), glutamic acid (E), serine (S), and histidine (H).

21. The bispecific antibody according to any one of embodiments 15 to 20, characterized in that amino acid 74) of the VL region is threonine (T) or alanine (A).

22. A bispecific antibody specifically binding to BCMA and CD3, characterized in comprising a VH region comprising a CDR3H region of SEQ ID NO:17 and a VL region comprising a CDR1L region of SEQ ID NO:31, a CDR2L region of SEQ ID NO:32 and a CDR3L region of SEQ ID NO:20 and a CDR1L and CDR2L region combination selected from the group of a) CDR1H region of SEQ ID NO:29 and CDR2H region of SEQ ID NO:30, b) CDR1H region of SEQ ID NO:34 and CDR2H region of SEQ ID NO:35, or c) CDR1H region of SEQ ID NO:36 and CDR2H region of SEQ ID NO:37.

23. The bispecific antibody according to embodiment 22, characterized in comprising a VL region of SEQ ID NO:12 and a VH region selected from the group comprising the VH regions of SEQ ID NO:38, 39, and 40.

24. The bispecific antibody according to embodiment 22 or 23, characterized in comprising in in that amino acid 49 of the VL region is selected from the group of amino acids tyrosine (Y), glutamic acid (E), serine (S), and histidine (H).

25. The bispecific antibody according to any one of embodiments 22 to 24, characterized in that amino acid 74 of the VL region is threonine (T) or alanine (A).

26. The bispecific antibody according to any one of embodiments 15 to 25, characterized in comprising an anti BCMA antibody according to the invention and an anti CD3 antibody, wherein
a) the light chain and heavy chain of an antibody according to any one of embodiments 1 to 7; and
b) the light chain and heavy chain of an antibody specifically binding to CD3, wherein the variable domains VL and VH or the constant domains CL and CH1 are replaced by each other.

27. The bispecific antibody according to any one of embodiments 15 to 26, characterized in comprising not more than one Fab fragment of an anti-CD3 antibody portion, not more than two Fab fragments of an anti-BCMA antibody portion and not more than one Fc part.

28. The bispecific antibody according to any one of embodiments 15 to 27, characterized in comprising a Fc part linked with its N-terminus to the C-terminus of said CD3 antibody Fab fragment and to the C-terminus of one of said BCMA antibody Fab fragments.

29. The bispecific antibody according to any one of embodiments 15-28, characterized in comprising a second Fab fragment of said anti-BCMA antibody (BCMA antibody portion) linked with its C-terminus to the N-terminus of said Fab fragment of said anti-CD3 antibody (CD3 antibody portion) of said bispecific antibody.

30. The bispecific antibody according to embodiment 29, characterized in that the VL domain of said anti-CD3 antibody Fab fragment is linked to the CH1 domain of said second anti-BCMA antibody Fab fragment.

31. The bispecific antibody according to any one of embodiments 15 to 30, characterized in that the variable domain VH of the anti-CD3 antibody portion (further named as "CD3 VH") comprises the heavy chain CDRs of SEQ ID NO: 1, 2 and 3 as respectively heavy chain CDR1, CDR2 and CDR3 and the variable domain VL of the anti-CD3 antibody portion (further named as "CD3 VL") comprises the light chain CDRs of SEQ ID NO: 4, 5 and 6 as respectively light chain CDR1, CDR2 and CDR3.

32. The bispecific antibody according to any one of embodiments 15 to 31, characterized in that the variable domains of the anti CD3E antibody portion are of SEQ ID NO:7 and 8.

33. A bispecific antibody specifically binding to the two targets which are the extracellular domain of human BCMA and human CD3E, characterized in comprising
a) the first light chain and the first heavy chain of a first antibody according to any one of claims 1 to 7; and
b) the second light chain and the second heavy chain of a second antibody which specifically binds to CD3, and wherein the variable domains VL and VH in the second light chain and second heavy chain of the second antibody are replaced by each other; and
c) wherein in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 and the amino acid at position 213 is substituted independently by glutamic acid (E), or aspartic acid (D) (numbering according to EU index of Kabat) (see e.g. FIGS. 1A, 2A, 2C, 3A, 3C).

34. A bispecific antibody specifically according to claim 33, characterized in comprising in addition a Fab fragment of said first antibody (further named also as "BCMA-Fab") and in the constant domain CL said BCMA-Fab the amino acid at position 124 is substituted independently by lysine (K), arginine (R) or histidine (H) (numbering according to Kabat), and wherein in the constant domain CH1 of said BCMA-Fab the amino acid at positions 147 and the amino acid at position 213 is substituted independently by glutamic acid (E), or aspartic acid (D) (numbering according to EU index of Kabat) (see e.g. FIGS. 2A, 2C).

35. A bispecific antibody specifically binding to the two targets which are the extracellular domain of human BCMA and human CD3E, characterized in comprising
a) the first light chain and the first heavy chain of a first antibody according to any one of claims 1 to 7; and
b) the second light chain and the second heavy chain of a second antibody which specifically binds to CD3, and wherein the variable domains VL and VH in the second light chain and second heavy chain of the second antibody are replaced by each other; and wherein
c) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at positions 147 and the amino acid at position 213 is substituted independently by glutamic acid (E), or aspartic acid (D) (numbering according to EU index of Kabat).

36. A bispecific antibody specifically binding to the two targets which are the extracellular domain of human BCMA and human CD3E, characterized in comprising a heavy and light chain set selected from the group consisting of polypeptides
i) SEQ ID NO:48, SEQ ID NO:49, SEQ ID NO:50, and SEQ ID NO:51 (2×); (set 1 TCB of antibody 21),
ii) SEQ ID NO:48, SEQ ID NO:52, SEQ ID NO:53, and SEQ ID NO:54 (2×) (set 2 TCB of antibody 22), and
iii) SEQ ID NO:48, SEQ ID NO:55, SEQ ID NO:56, and SEQ ID NO:57 (2×) (set 3 TCB of antibody 42).

37. A method for the preparation of an antibody according to any one of claims 1 to 36 comprising the steps of
a) transforming a host cell with
b) vectors comprising nucleic acid molecules encoding the light chain and heavy chains of an antibody according to any one of claims 1 to 36,
c) culturing the host cell under conditions that allow synthesis of said antibody molecule; and
d) recovering said antibody molecule from said culture.

38. A host cell comprising vectors comprising nucleic acid molecules encoding an antibody according to any one of claims 1 to 36.

39. A pharmaceutical composition comprising an antibody according to any one of claims 1 to 36 and a pharmaceutically acceptable excipient.

40. A pharmaceutical composition comprising an antibody according to any one of claims 1 to 36 for use as a medicament.

41. A pharmaceutical composition comprising an antibody according to any one of claims 1 to 36 for use as a medicament in the treatment of plasma cell disorders.

42. A pharmaceutical composition comprising an antibody according to any one of claims 1 to 36 for use as a medicament in the treatment of Multiple Myeloma, Plasma Cell Leukemia and AL-Amyloidosis 43. A pharmaceutical composition comprising an antibody according to any one of claims 1 to 36 for use as a medicament in the treatment of systemic lupus erythematosus.

44. A pharmaceutical composition comprising an antibody according to any one of claims 1 to 36, including a monospecific antibody, an ADCC enhanced naked antibody, an antibody-drug conjugate or a bispecific antibody for use as a medicament in the treatment of antibody-mediated rejection.

45. A chimeric antigen receptor (CAR) comprising: an antigen recognition moiety directed against BCMA and a T-cell activation moiety, characterized in that the antigen recognition moiety is a monoclonal antibody or antibody fragment according to any one of embodiments 1 to 14.

46. A chimeric antigen receptor (CAR) according to embodiment 45, characterized in comprising:
(i) a B cell maturation antigen (BCMA) recognition moiety;
(ii) a spacer domain; and
(ii) a transmembrane domain; and
(iii) an intracellular T cell signaling domain.

47. A chimeric antigen receptor (CAR) according to embodiment 45 or 46, characterized in that the antigen recognition moiety is a monoclonal antibody or antibody fragment specifically binding to BCMA, characterized in comprising a CDR3H region of SEQ ID NO:17 and a CDR3L region of SEQ ID NO:20 and a CDR1H, CDR2H, CDR1L, and CDR2L region combination selected from the group of
a) CDR1H region of SEQ ID NO:21 and CDR2H region of SEQ ID NO:22, CDR1L region of SEQ ID NO:23, and CDR2L region of SEQ ID NO:24,
b) CDR1H region of SEQ ID NO:21 and CDR2H region of SEQ ID NO:22, CDR1L region of SEQ ID NO:25, and CDR2L region of SEQ ID NO:26,
c) CDR1H region of SEQ ID NO:21 and CDR2H region of SEQ ID NO:22, CDR1L region of SEQ ID NO:27, and CDR2L region of SEQ ID NO:28,
d) CDR1H region of SEQ ID NO:29 and CDR2H region of SEQ ID NO:30, CDR1L region of SEQ ID NO:31, and CDR2L region of SEQ ID NO:32,
e) CDR1H region of SEQ ID NO:34 and CDR2H region of SEQ ID NO:35, CDR1L region of SEQ ID NO:31, and CDR2L region of SEQ ID NO:32, and
f) CDR1H region of SEQ ID NO:36 and CDR2H region of SEQ ID NO:37, CDR1L region of SEQ ID NO:31, and CDR2L region of SEQ ID NO:32.

48. An isolated or purified nucleic acid sequence encoding a chimeric antigen receptor (CAR), according to any one of embodiments 45 to 47.

49. A method of generation a monoclonal antibody specifically binding to BCMA, which depletes as bispecific antibody according to any one of embodiments 15 to 36 human malignant plasma cells in multiple myeloma MM bone marrow aspirates in a manner to at least 80% after a 48 hour treatment in a concentration of between 10 nM and 1 fM, anti-BCMA antibody, characterized in
a) panning a variable heavy chain (VH) phage-display library of SEQ ID NO:9 with 1-50 nM cynomolgus BCMA in 1-3 rounds and selecting a variable heavy chain, which when combined with the variable light chain of SEQ ID NO:11 to a bispecific antibody according to any one of embodiments 15 to 36 which depletes such human malignant plasma cells in such manner,
c) panning a variable light chain (VL) phage-display library of SEQ ID NO:11 with 1-50 nM cynomolgus BCMA in 1-3 rounds and b) selecting a variable light chain, which when combined with the variable heavy chain of SEQ ID NO:9 to a bispecific antibody according to any one of embodiments 15 to 36 which depletes such human malignant plasma cells in such manner, and
combining said selected variable heavy chain and selected variable light chain to a bispecific antibody according to any one of embodiments 4 to 16 which depletes such human malignant plasma cells in such manner 50. A pharmaceutical composition comprising an antibody according to any one of claims 1 to 36 and 45 to 47 for use as a medicament in the treatment of multiple myeloma or systemic lupus erythematosus or plasma cell leukemia or AL-amyloidosis.

In one embodiment the binding of the antibody according to the invention is not reduced by 100 ng/ml APRIL for more than 20% measured in an ELISA assay as OD at 405 nm compared to the binding of said antibody to human BCMA without APRIL, does not alter APRIL-dependent NF-κB activation for more than 20%, as compared to APRIL, and does not alter NF-κB activation without APRIL for more than 20%, as compared without said antibody.

In one embodiment the binding the antibody in a concentration of 6.25 nM is not reduced by 140 ng/ml murine APRIL for more than 10%, preferably not reduced by for more than 1% measured in an ELISA assay as OD at 450 nm compared to the binding of said antibody to human BCMA without APRIL. The binding of said antibody in a concentration of 50 nM is not reduced by 140 ng/ml murine APRIL for more than 10%, measured in an ELISA assay as OD at 450 nm, compared to the binding of said antibody to human BCMA without APRIL.

In one embodiment the binding of said antibody is not reduced by 100 ng/ml APRIL and not reduced by 100 ng/ml BAFF for more than 20% measured in an ELISA assay as OD at 405 nm compared to the binding of said antibody to human BCMA without APRIL or BAFF respectively, the antibody does not alter APRIL-dependent NF-κB activation for more than 20%, as compared to APRIL alone, does not alter BAFF-dependent NF-κB activation for more than 20%, as compared to BAFF alone, and does not alter NF-κB activation without BAFF and APRIL for more than 20%, as compared without said antibody.

In one embodiment the binding of said antibody to human BCMA is not reduced by 100 ng/ml APRIL for more than 15%, measured in said ELISA, not reduced by 1000 ng/ml APRIL, for more than 20%, measured in said ELISA, and not reduced by 1000 ng/ml APRIL for more than 15%, measured in said ELISA.

In one embodiment the binding of said antibody to human BCMA is not reduced by 100 ng/ml APRIL and not reduced by 100 ng/ml BAFF for more than 15%, measured in said ELISA, not reduced by 1000 ng/ml APRIL and not reduced by 1000 ng/ml BAFF, for more than 20%, measured in said ELISA, not reduced by 1000 ng/ml APRIL and not reduced by 1000 ng/ml BAFF for more than 15%, measured in said ELISA.

In one embodiment the antibody according to the invention does not alter APRIL-dependent NF-kB activation for more than 15%, does not alter BAFF-dependent NF-kB activation for more than 15%, and does not alter NF-κB activation without APRIL and BAFF for more than 15%.

In one embodiment the binding of the antibody to BCMA is not reduced by APRIL, not reduced by BAFF for more than 25%, not more than 20%, and not more than 10%, measured as binding of said antibody in a concentration of 5 nM, preferably 50 nM, and 140 nM to NCI-H929 cells (ATCC® CRL-9068™) in presence or absence of APRIL or respectively BAFF in a concentration of 2.5 µg/ml compared to the binding of said antibody to NCI-H929 cells without APRIL or BAFF respectively.

In one embodiment the following examples, sequence listing and figures are provided to aid the understanding of the present invention, the true scope of which is set forth in the appended claims. It is understood that modifications can be made in the procedures set forth without departing from the spirit of the invention.

Materials & General Methods
Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulins light and heavy chains is given in: Kabat, E. A. et al., (1991) Sequences of Proteins of Immunological Interest, 5' ed., NIH Publication No. 91-3242. Amino acids of antibody chains were numbered and referred to according to Kabat, E. A., et al., Sequences of Proteins of Immunological Interest, 5th ed., Public Health Service, National Institutes of Health, Bethesda, Md., (1991).

Gene Synthesis a) Desired gene segments were prepared from oligonucleotides made by chemical synthesis. The 600-1800 bp long gene segments, which were flanked by singular restriction endonuclease cleavage sites, were assembled by annealing and ligation of oligonucleotides including PCR amplification and subsequently cloned via the indicated restriction sites e.g. Kpnl/Sad or Ascl/Pacl into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany)

b) Desired gene segments where required were either generated by PCR using appropriate templates or were synthesized by Geneart AG (Regensburg, Germany) from synthetic oligonucleotides and PCR products by automated gene synthesis. The gene segments flanked by singular restriction endonuclease cleavage sites were cloned into standard expression vectors or into sequencing vectors for further analysis. The plasmid DNA was purified from transformed bacteria using commercially available plasmid purification kits. Plasmid concentration was determined by UV spectroscopy. The DNA sequence of the subcloned gene fragments was confirmed by DNA sequencing. Gene segments were designed with suitable restriction sites to allow sub-cloning into the respective expression vectors. If required, protein coding genes were designed with a 5'-end DNA sequence coding for a leader peptide which targets proteins for secretion in eukaryotic cells.

DNA Sequence Determination

DNA sequences were determined by double strand sequencing.

DNA and Protein Sequence Analysis and Sequence Data Management

The Clone Manager (Scientific & Educational Software) software package version 9.2 was used for sequence mapping, analysis, annotation and illustration.

Expression Vectors a) The fusion genes comprising the described antibody chains as described below were generated by PCR and/or gene synthesis and assembled with known recombinant methods and techniques by connection of the according nucleic acid segments e.g. using unique restriction sites in the respective vectors. The subcloned nucleic acid sequences were verified by DNA sequencing. For transient transfections larger quantities of the plasmids are prepared by plasmid preparation from transformed E. coli cultures (Nucleobond AX, Macherey-Nagel).

b) For the generation of anti-BCMA antibody expression vectors, the variable regions of heavy and light chain DNA sequences were subcloned in frame with either the human IgG1 constant heavy chain or the hum IgG1 constant light chain pre-inserted into the respective generic recipient expression vector optimized for expression in mammalian cell lines. The antibody expression is driven by a chimeric MPSV promoter comprising a CMV enhancer and a MPSV promoter followed by a 5' UTR, an intron and a Ig kappa MAR element. The transcription is terminated by a synthetic polyA signal sequence at the 3' end of the CDS. All vectors carry a 5'-end DNA sequence coding for a leader peptide which targets proteins for secretion in eukaryotic cells. In addition each vector contains an EBV OriP sequence for episomal plasmid replication in EBV EBNA expressing cells.

c) For the generation of BCMAxCD3 bispecific antibody vectors, the IgG1 derived bispecific molecules consist at least of two antigen binding moieties capable of binding specifically to two distinct antigenic determinants CD3 and BCMA. The antigen binding moieties are Fab fragments composed of a heavy and a light chain, each comprising a variable and a constant region. At least one of the Fab fragments was a "Crossfab" fragment, wherein VH and VL were exchanged. The exchange of VH and VL within the Fab fragment assures that Fab fragments of different specificity do not have identical domain arrangements. The bispecific molecule design was monovalent for CD3 and bivalent for BCMA where one Fab fragment was fused to the N-terminus of the inner CrossFab (2+1). The bispecific molecule contained an Fc part in order for the molecule to have a long half-life. A schematic representation of the constructs is given in FIG. 2; the preferred sequences of the constructs are shown in SEQ ID NOs 39 to 52. The molecules were produced by co-transfecting HEK293 EBNA cells growing in suspension with the mammalian expression vectors using polymer-based solution. For preparation of 2+1 CrossFab-IgG constructs, cells were transfected with the corresponding expression vectors in a 1:2:1:1 ratio ("vector Fc(knob)": "vector light chain": "vector light chain CrossFab": "vector heavy chain-CrossFab").

Cell Culture Techniques

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Expression in HEK293 Cells (HEK293-EBNA System)

Bispecific antibodies were expressed by transient co-transfection of the respective mammalian expression vectors in HEK293-EBNA cells, which were cultivated in suspension, using polymer-based solution. One day prior to transfection the HEK293-EBNA cells were seeded at 1.5 Mio viable cells/mL in Ex-Cell medium, supplemented with 6 mM of L-Glutamine. For every mL of final production volume 2.0 Mio viable cells were centrifuged (5 minutes at 210×g). The supernatant was aspirated and the cells resuspended in 100 μL of CD CHO medium. The DNA for every mL of final production volume was prepared by mixing 1 μg of DNA (Ratio heavy chain: modified heavy chain: light chain: modified light chain=1:1:2:1) in 100 μL of CD CHO medium. After addition of 0.27 μL of polymer-based solution (1 mg/mL) the mixture was vortexed for 15 seconds and left at room temperature for 10 minutes. After 10 minutes, the resuspended cells and DNA/polymer-based solution mixture were put together and then transferred into an appropriate container which was placed in a shaking device (37° C., 5% $CO_2$). After a 3 hours incubation time 800 μL of Ex-Cell Medium, supplemented with 6 mM L-Glutamine, 1.25 mM valproic acid and 12.5% Pepsoy (50 g/L), was added for every mL of final Production volume. After 24 hours, 70 μL of feed solution was added for every mL of final production volume. After 7 days or when the cell viability was equal or lower than 70%, the cells were separated from the supernatant by centrifugation and sterile filtration. The antibodies were purified by an affinity step and one or two polishing steps, being cation exchange chromatography and size exclusion chromatography. When required, an additional polishing step was used. The recombinant anti-BCMA human antibody and bispecific antibodies were produced in suspension by co-transfecting HEK293-EBNA cells with the mammalian expression vectors using polymer-based solution. The cells were transfected with two or four vectors, depending in the format. For the human IgG1 one plasmid encoded the heavy chain and the other plasmid the light chain. For the bispecific antibodies four plasmids were co-transfected. Two of them encoded the two different heavy chains and the other two encoded the two different light chains. One day prior to transfection the HEK293-EBNA cells were seeded at 1.5 Mio viable cells/mL in F17 Medium, supplemented with 6 mM of L-Glutamine.

Protein Determination

Determination of the antibody concentration was done by measurement of the absorbance at 280 nm, using the theoretical value of the absorbance of a 0.1% solution of the antibody. This value was based on the amino acid sequence and calculated by GPMAW software (Lighthouse data).

SDS-PAGE

The NuPAGE® Pre-Cast gel system (Invitrogen) is used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer is used.

Protein Purification

By Protein A Affinity Chromatography

For the affinity step the supernatant was loaded on a protein A column (HiTrap Protein A FF, 5 mL, GE Healthcare) equilibrated with 6 CV 20 mM sodium phosphate, 20 mM sodium citrate, pH 7.5. After a washing step with the same buffer the antibody was eluted from the column by step elution with 20 mM sodium phosphate, 100 mM sodium chloride, 100 mM Glycine, pH 3.0. The fractions with the desired antibody were immediately neutralized by 0.5 M Sodium Phosphate, pH 8.0 (1:10), pooled and concentrated by centrifugation. The concentrate was sterile filtered and processed further by cation exchange chromatography and/or size exclusion chromatography.

By Cation Exchange Chromatography

For the cation exchange chromatography step the concentrated protein was diluted 1:10 with the elution buffer used for the affinity step and loaded onto a cation exchange colume (Poros 50 HS, Applied Biosystems). After two washing steps with the equilibration buffer and a washing buffer resp. 20 mM sodium phosphate, 20 mM sodium citrate, 20 mM TRIS, pH 5.0 and 20 mM sodium phosphate, 20 mM sodium citrate, 20 mM TRIS, 100 mM sodium chloride pH 5.0 the protein was eluted with a gradient using 20 mM sodium phosphate, 20 mM sodium citrate, 20 mM TRIS, 100 mM sodium chloride pH 8.5. The fractions containing the desired antibody were pooled, concentrated by centrifugation, sterile filtered and processed further a size exclusion step.

By Analytical Size Exclusion Chromatography

For the size exclusion step the concentrated protein was injected in a XK16/60 HiLoad Superdex 200 column (GE Healthcare), and 20 mM Histidine, 140 mM Sodium Chloride, pH 6.0 with or without Tween20 as formulation buffer. The fractions containing the monomers were pooled, concentrated by centrifugation and sterile filtered into a sterile vial.

Measurement of Purity and Monomer Content

Purity and monomer content of the final protein preparation was determined by CE-SDS (Caliper LabChip GXII system (Caliper Life Sciences)) resp. HPLC (TSKgel G3000 SW XL analytical size exclusion column (Tosoh)) in a 25 mM potassium phosphate, 125 mM Sodium chloride, 200 mM L-arginine monohydrochloride, 0.02% (w/v) Sodium azide, pH 6.7 buffer.

Molecular Weight Confirmation by LC-MS Analyses

Deglycosylation

To confirm homogeneous preparation of the molecules final protein solution of was analyzed by LC-MS analyses. To remove heterogeneity introduced by carbohydrates the constructs are treated with PNGaseF (ProZyme). Therefore the pH of the protein solution was adjusted to pH7.0 by adding 2 μl 2 M Tris to 20 μg protein with a concentration of 0.5 mg/ml. 0.8 μg PNGaseF was added and incubated for 12 h at 37° C.

LC-MS Analysis—On Line Detection

The LC-MS method was performed on an Agilent HPLC 1200 coupled to a TOF 6441 mass spectrometer (Agilent). The chromatographic separation was performed on a Macherey Nagel Polysterene column; RP1000-8 (8 μm particle size, 4.6×250 mm; cat. No. 719510). Eluent A was 5% acetonitrile and 0.05% (v/v) formic acid in water, eluent B was 95% acetonitrile, 5% water and 0.05% formic acid. The flow rate was 1 ml/min, the separation was performed at 40° C. and 6 μg (15 μl) of a protein sample obtained with a treatment as described before.

| Time (min.) | % B |
| --- | --- |
| 0.5 | 15 |
| 10 | 60 |
| 12.5 | 100 |
| 14.5 | 100 |
| 14.6 | 15 |
| 16 | 15 |
| 16.1 | 100 |

During the first 4 minutes the eluate was directed into the waste to protect the mass spectrometer from salt contamination. The ESI-source was running with a drying gas flow of 12l/min, a temperature of 350° C. and a nebulizer pressure of 60 psi. The MS spectra were acquired using a fragmentor voltage of 380 V and a mass range 700 to 3200 m/z in positive ion mode using. MS data were acquired by the instrument software from 4 to 17 minutes.

Isolation of Human PBMCs from Blood

Peripheral blood mononuclear cells (PBMCs) were prepared by Histopaque density centrifugation from enriched lymphocyte preparations (huffy coats) obtained from local blood banks or from fresh blood from healthy human donors. Briefly, blood was diluted with sterile PBS and carefully layered over a Histopaque gradient (Sigma, H8889). After centrifugation for 30 minutes at 450×g at room temperature (brake switched off), part of the plasma above the PBMC containing interphase was discarded. The PBMCs were transferred into new 50 ml Falcon tubes and tubes were filled up with PBS to a total volume of 50 ml. The mixture was centrifuged at room temperature for 10 minutes at 400×g (brake switched on). The supernatant was discarded and the PBMC pellet washed twice with sterile PBS (centrifugation steps at 4° C. for 10 minutes at 350×g). The resulting PBMC population was counted automatically (Vi-Cell) and stored in RPMI1640 medium, containing 10% FCS and 1% L-alanyl-L-glutamine (Biochrom, K0302) at 37° C., 5% $CO_2$ in the incubator until assay start.

Isolation of Primary Cynomolgus PBMCs from Heparinized Blood

Peripheral blood mononuclar (PBMCs) were prepared by density centrifugation from fresh blood from healthy cynomolgus donors, as follows: Heparinized blood was diluted 1:3 with sterile PBS, and Lymphoprep medium (Axon Lab #1114545) was diluted to 90% with sterile PBS. Two volumes of the diluted blood were layered over one volume of the diluted density gradient and the PBMC fraction was separated by centrifugation for 30 min at 520×g, without brake, at room temperature. The PBMC band. was transferred into a fresh 50 ml Falcon tube and washed with sterile PBS by centrifugation for 10 min at 400×g at 4° C. One low-speed centrifugation was performed to remove the platelets (15 min at 150×g, 4° C.), and the resulting PBMC population was automatically counted (ViCell) and immediately used for further assays.

EXAMPLES

Example 1: Generation of Anti-BCMA Antibodies

Example 1.1: Production of Antigens and Tool Reagents

Example 1.1.1: Recombinant, Soluble, Human BCMA Extracellular Domain

The extracellular domains of human, cynomolgus and murine BCMA that were used as antigens for phage display selections were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). The extracellular domains of human and cynomolgus BCMA comprised methionine 4 to asparagine 53, and methionine 4 to asparagine 52, respectively. These were N-terminally fused to the hinge of a human IgG1 enabling heterodimerization with an unfused human IgG1 Fc portion (hole chain) by knobs-into-holes technology.

Example 1.1.1A: Generation of Anti-BCMA Antibodies by Maturation 1.1.1A.1 Libraries and Selections Two libraries were constructed. on basis of antibody 83A10. These libraries are randomized in either CDR1 and CDR2 of the light chain (83A10 L1/L2) or CDR1 and CDR2 of the heavy chain (83A10 H1/H2), respectively. Each of these libraries was constructed by 2 subsequent steps of amplification and assembly. Final assembly products have been digested NcoI/BsiWI for 83A10 L1/L2 library, MunI and NheI for 83A10 H1/H2 library, alongside with similarly treated acceptor vectors based on plasmid preparations of clone 83A10. The following amounts of digested randomized (partial) V-domains and digested acceptor vector(s) were ligated for the respective libraries (µg V-domain/µg vector): a.m.83A10 L1/L2 library (3/10), 83A10 µl/H2 library (3/10), Purified ligations of 83A10 L1/L2 and 83A10 H1/H2 libraries were pooled, respectively, and used for 15 transformations of $E.\ coli$ TG1 cells for each of the 2. libraries, to obtain final library sizes of $2.4 \times 10^{11}$ for 83A10 L1/L2 library, and $1.4 \times 10^{10}$ for a.m.83A10 H1/H2 library. Phagemid particles displaying these Fab libraries were rescued and purified.

1.1.1A.2 Selections of clones

Selections were carried out against the ectodomain of human or cyno B-cell maturation antigen (BCMA) to which were cloned upstream a Fc and an avi-tag. Prior to selections, the Fc depleter was coated onto neutravidin plates at a concentration of 500 nM, Selections were carried out according to the following pattern:
1) binding of $\sim 10^{12}$ phagemid particles of library.83A10 L1/L2 library or 83A10 H1/H2 library to immobilized Fe depleter for 1h, 2) transfer of unbound phagemid particles of library.83A1.0 L1/L2 library or 83A10 H1/H2 library to 50 nM, 25 nM, 10 nM, or 2 nM human or cyno BCMA (depending on library and selection round) for 20 min, 3) adding magnetic streptavidin beads for 10 min, 4) washing of magnetic streptavidin beads using 10×1 ml PBS/Tween® 20 and 10×1 ml PBS, 5) elution of phage particles by addition of 1 ml 100 mM TEA (triethylamine) for 10 min and neutralization by addition of 500 ul IM Tris®/HCl pH 7.4 and 6) re-infection of log-phase $E.\ coli$ TG1 cells, infection with helperphage VCSM13 and subsequent PEG/NaCl precipitation of phagemid particles to be used n subsequent selection rounds.

Selections have been carried out over 3 rounds and conditions were adjusted in 5 streamlines for each of the 2 libraries individually. In detail, selection parameters were:
Streamline 1 (50 nM huBCMA for round 1, 25 nM cynoBCMA for round. 2, 10 nM huBCMA for round 3).
Streamline 2 (50 nM huBCMA for round 1, 10 nM huBCMA for round 2, 2 nM huBCMA for round 3).
Streamline 3 (50 nM huBCMA for round 1, 25 nM huBCMA for round 2, 10 nM cynoBCMA for round 3),
Streamline 4 (50 nM huBCMA for round 1, 25 nM cynoBCMA for round 2, 10 nM cynoBCMA for round 3),
Streamline 5 (50 nM cynoBCMA for round 1, 25 nM cynoBCMA for round 2, 10 nM cynoBCMA for round 3).
The heavy chains of Mab 21, Mab 22, Mab 33, and Mab 42 BCMA antibodies were derived from Streamline 5 which used only cynoBCMA.

1.1.1A.3 Screening Method

Individual clones were bacterially expressed as 1 ml cultures in 96-well format and supernatants were subjected to a screening by ELISA. Specific binders were defined as signals higher than 5× background for human and cyno BCMA and signals lower than 3× background for Fc depleter. Neutravidin 96 well strip plates were coated with 10 nM of huBCMA, 10 nM cyBCMA or 50 nM Fc-depleter followed by addition of Fab-containing bacterial supernatants and detection of specifically binding Fabs via their Flag-tags by using an anti-Flag/HRP secondary antibody. ELISA-positive clones were bacterially expressed as cultures in 96-well format and supernatants were subjected to a kinetic screening experiment ProteOn. 500 positive clones were identified, most of them having similar affinity.

1.1.1A.4 Surface Plasmon Resonance Screen with Soluble Fabs and IgGs 70 clones were further tested by SPR. All experiments were performed at 25° C. using PBST as running buffer (10 mM PBS, pH 7.4 and 0.005% (v/v) Tween®20). A ProteOn XPR36 biosensor equipped with GLC and GLM sensor chips and coupling reagents (10 mM sodium acetate, pH 4.5, sulfo-N-hydroxysuccinimide, 1-ethyl-3-(3-dimethylaminpropyl)-carbodiimide hydrochloride [EDC] and ethanolamine) was purchased from BioRad Inc. (Hercules, Calif.) Immobilizations were performed at 30 µl/min on a GLM chip. pAb (goat) anti hu IgG, F(ab)2 specific Ab (Jackson) was coupled in vertical direction using a standard amine-coupling procedure: all six ligand channels were activated for 5 min with a mixture of EDC (200 mM) and sulfa-NHS (50 mM). Immediately after the surfaces were activated, pAb (goat) anti hu IgG, F(ab)2 specific antibody (50 µg/ml, 10 mM sodium acetate, pH 5) was injected across all six channels for 5 min. Finally, channels were blocked with a 5 min injection of 1 M ethanolamine-HCl (pH 8.5). Final immobilization levels were similar on all channels, ranging from 11000 to 11500 RU. The Fab variants were captured from *E. coli* supernatants by simultaneous injection along five of the separate whole horizontal channels (30 µl/min) for 5 min and resulted in levels, ranging from 200 to 900 RU, depending on the concentration of Fab in supernatant; conditioned medium was injected along the sixth channel to provide an 'in-line' blank for double referencing purposes. One-shot kinetic measurements were performed by injection of a dilution series of human, cyno and mouse BCMA (50, 10, 2, 0.4, 0.08, 0 nM, 50 µl/min) for 3 min along the vertical channels. Dissociation was monitored for 5 min. Kinetic data were analyzed in ProteOn Manager v. 2.1. Processing of the reaction spot data involved applying an interspot-reference and a double-reference step using an inline buffer blank (Myszka, 1999). The processed data from replicate one-shot injections were fit to a simple 1:1 Langmuir binding model without mass transport (O'Shannessy et al., 1993).

Figure 17:
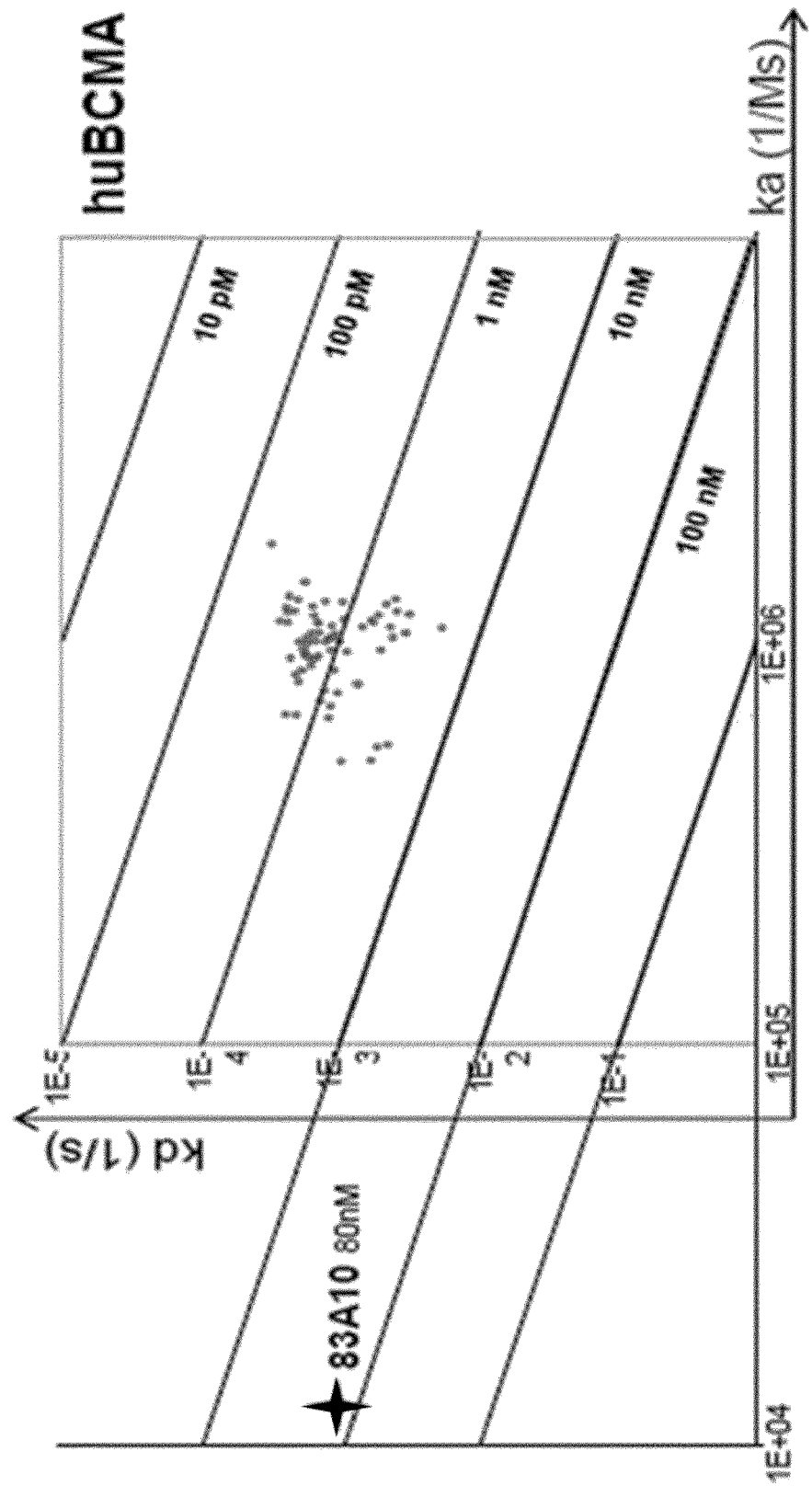
FIG. 17. Surface plasmon resonance (SPR) of 70 clones selected from ELISA. All experiments were performed at 25° C. using PBST as running buffer (10 mM PBS, pH 7.4 and 0.005% (v/v) Tween®20) with a ProteOn XPR36 biosensor equipped with GLC and GLM sensor chips and coupling reagents. Immobilizations were performed at 30 μl/min on a GLM chip. pAb (goat) anti hu IgG, F(ab)2 specific Ab (Jackson) was coupled in vertical direction using a standard amine-coupling procedure: all six ligand channels were activated for 5 min with a mixture of EDC (200 mM) and sulfo-NHS (50 mM) Immediately after the surfaces were activated, pAb (goat) anti hu IgG, F(ab)2 specific antibody (50 μg/ml, 10 mM sodium acetate, pH 5) was injected across all six channels for 5 min. Finally, channels were blocked with a 5 min injection of 1 M ethanolamine-HCl (pH 8.5). Final immobilization levels were similar on all channels, ranging from 11000 to 11500 RU. The Fab variants were captured from E. coli supernatants by simultaneous injection along five of the separate whole horizontal channels (30 μl/min) for 5 min and resulted in levels, ranging from 200 to 900 RU, depending on the concentration of Fab in supernatant; conditioned medium was injected along the sixth channel to provide an 'in-line' blank for double referencing purposes. One-shot kinetic measurements were performed by injection of a dilution series of human and cyno BCMA (50, 10, 2, 0.4, 0.08, 0 nM, 50 µl/min) for 3 min along the vertical channels. Dissociation was monitored for 5 min. Kinetic data were analyzed in ProteOn Manager v. 2.1. Processing of the reaction spot data involved applying an interspot-reference and a double-reference step using an inline buffer blank (Myszka, 1999). The processed data from replicate one-shot injections were fit to a simple 1:1 Langmuir binding model without mass transport (O'Shannessy et al., 1993).
Figure 17:
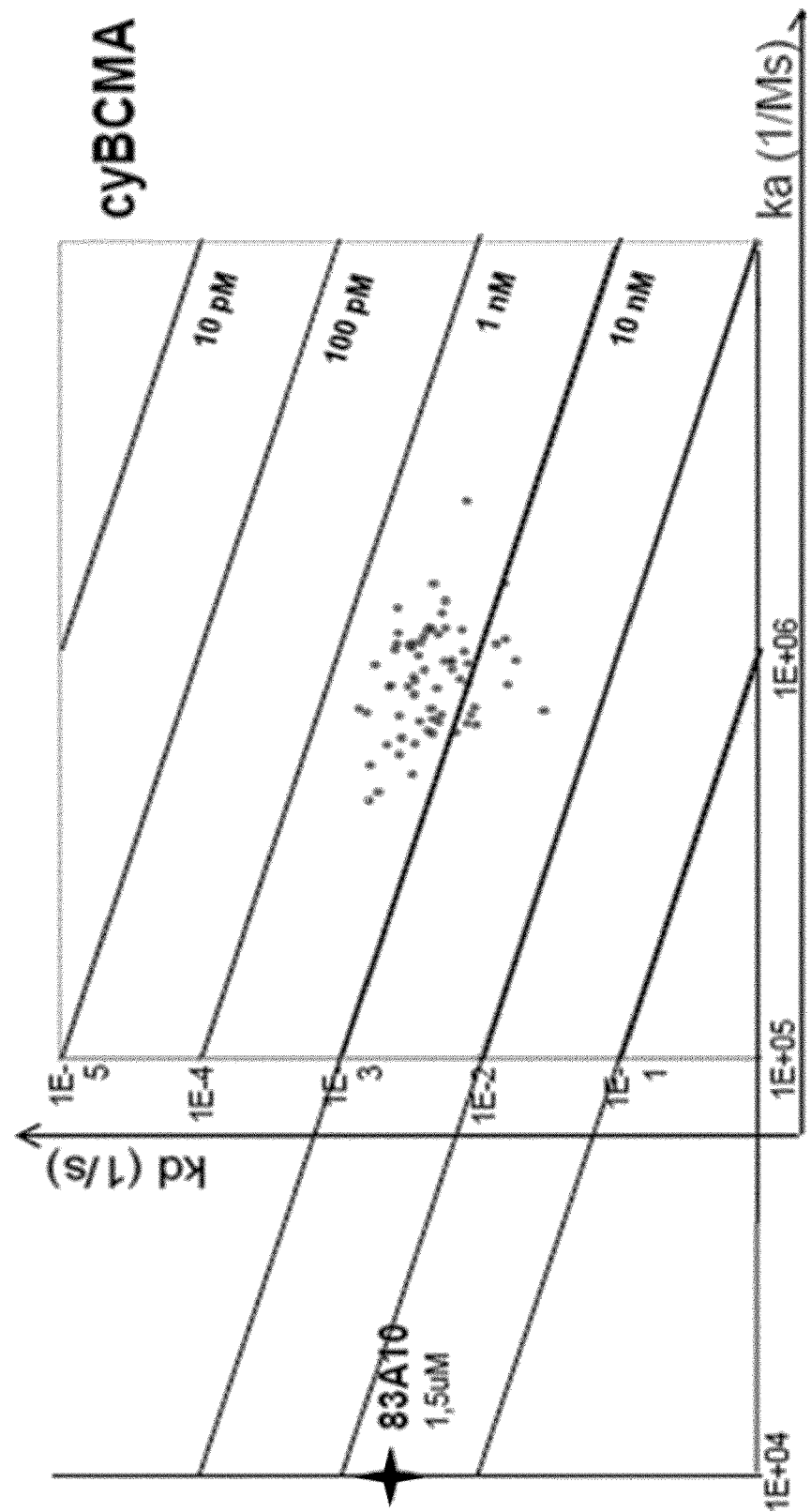

For measurements of IgG from supernatants of HEK productions in 6-well format, the IgG variants were captured from HEK293 supernatants by simultaneous injection along five of the separate whole horizontal channels (30 µl/min) for 5 min and resulted in levels, ranging from 200 to 400 RU; conditioned medium was injected along the sixth channel to provide an 'in-line' blank for double referencing purposes. One-shot kinetic measurements were performed by injection of a dilution series of human, cyno and mouse BCMA (25, 5, 1, 0.2, 0.04, 0 nM, 50 µl/min) for 3 min along the vertical channels. Dissociation was monitored for 5 min. Kinetic data were analyzed as described, above. The OSK measurements are summarized in Table 2D; Um, inconclusive measurement. Affinity to huBCMA was found to be between about 50 pm to 5 nM, Affinity to cynoBCMA was found to be between about 2 nM to 20 nM (few clones fall outside the range, see FIG. 17).

1.1.1A5. Further Selection of HC and LC Clones

Figure 18:
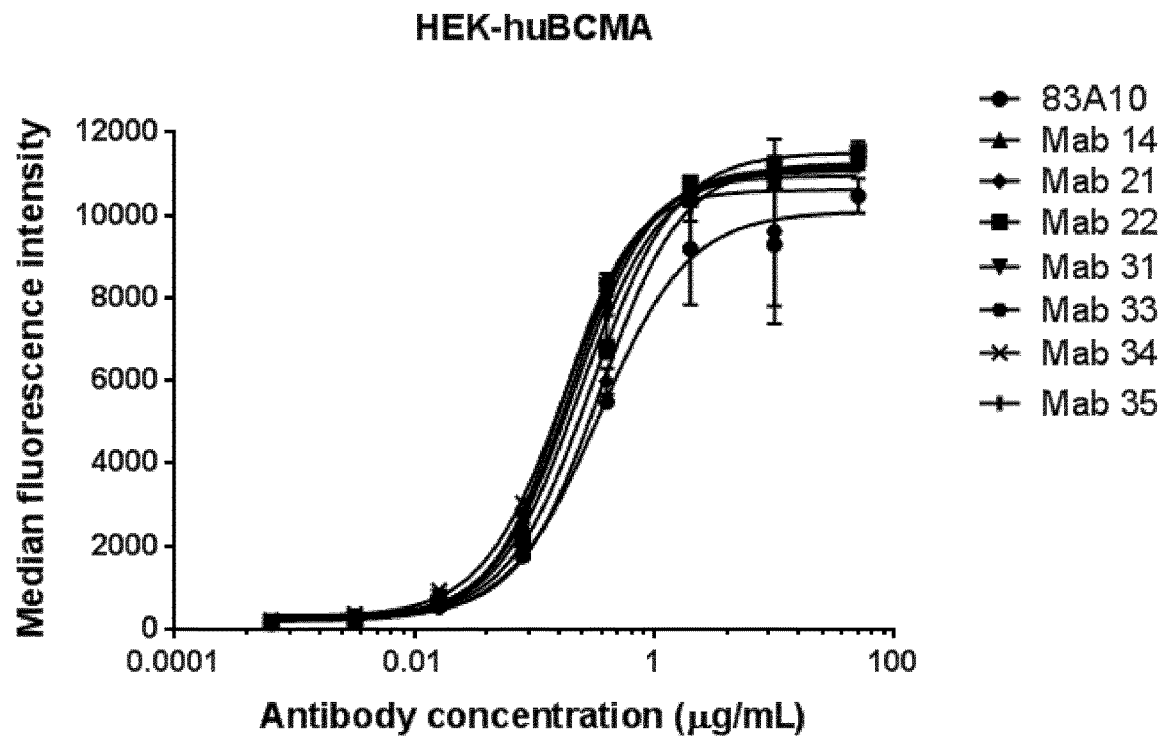
FIG. 18. Binding affinity of BCMA antibodies on HEK-huBCMA cells as measured by flow cytometry. The anti-BCMA antibodies were used as first antibody then a secondary PE-labeled anti-human Fc was used as detection antibody. It was found that binding of antibodies Mab 21, Mab 22, Mab 27, Mab 39 and Mab 42 to huBCMA on HEK cells was not significantly better than the binding of Mab 83A10 to huBCMA-HEK cells.
Figure 18:
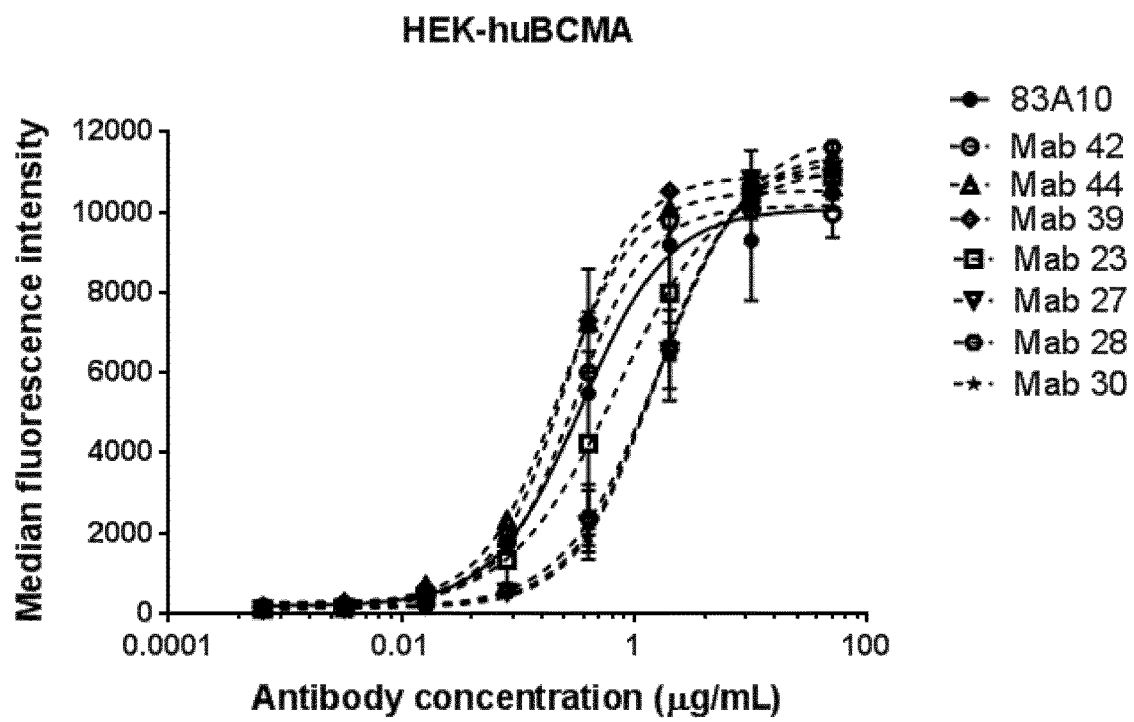

Due to their experience the inventors selected out of these 70 clones further 27 clones based on their binding properties to huBCMA, cynoBCMA, murineBCMA, and ratio, measured in different assays. Out of these clones 4VH and 9VL clones were selected, which results in 34 VH/VL combinations. Binding affinity on HEK-huBCMA cells was measured (FIG. 18 and Table 2E). It was found that binding of antibodies Mab 21, Mab 22, Mab 27, Mab 39 and Mab 42 to huBCMA on HEK cells was not significantly better than the binding of Mab 83A10 to huBCMA-HEK cells. However Mab21, Mab 22, Mab27, Mab33, Mab39, and Mab42 were selected due to their overall properties, like affinity for huBCMA, cynoBCMA, binding as bispecific antibody to BCMA-positive multiple myeloma cell lines H929, L363 and RPMI-8226 by flow cytometry, killing potency of myeloma cells H929, L363 and RPMI-8226, of viable myeloma plasma cells from patient bone marrow aspirates, and pharmacokinetics (PK)) and pharmacodynamics (killing of BCMA positive cells) data in cynomolgus monkeys.

TABLE 2C

Relationship of antibodies to streamlines

| Mab No. | Derived from library 2 (HC) | Clone HC | Derived from library 1 (LC) | Clone LC |
|---|---|---|---|---|
| Mab 21 | Streamline 5 | 5F04 | Streamline 1 | 1D04 |
| Mab 22 | Streamline 5 | 5F04 | Streamline 1 | 1C05 |
| Mab 27 | Streamline 1 | 1A08 | Streamline 1 | 1D04 |
| Mab 33 | Streamline 5 | 5D03 | Streamline 1 | 1D04 |
| Mab 39 | Streamline 2 | 2E12 | Streamline 1 | 1D04 |
| Mab 42 | Streamline 5 | 5F04 | Streamline 5 | 5A11 |

TABLE 2D

One-shot-kinetic affinity measurements to human, cynomolgus and mouse BCMA

| Mab No. | VH | VL | KD huBCMA | KD cyBCMA | KD muBCMA |
|---|---|---|---|---|---|
| 83A10 | pCON1532 | pCON1080 | 1.5E-09 | 1.4E-08 | i/m |
| Mab 21 | pCON1531 | pCON1522 | 2.8E-11 | 5.1E-11 | 7.3E-10 |
| Mab 22 | pCON1531 | pCON1521 | 4.8E-11 | i/m | 9.0E-10 |
| Mab 27 | pCON1520 | pCON1522 | 3.9E-13 | 1.0E-10 | 9.7E-10 |
| Mab 33 | pCON1530 | pCON1522 | 1.7E-11 | 3.4E-11 | 4.9E-10 |
| Mab 39 | pCON1524 | pCON1522 | 6.2E-11 | 2.7E-10 | i/m |
| Mab 42 | pCON1531 | pCON1527 | 2.3E-10 | 3.9E-10 | 2.5E-09 |

TABLE 2E

Binding of IgG variants on HEK-huBCMA cells

| Mab No | VH | VL | Binding EC50 [nM] | Binding EC50 [µg/mL] |
|---|---|---|---|---|
| 83A10 | PCON1532 | PCON1080 | 2.4 | 0.34 |
| Mab 14 | PCON1530 | PCON1527 | 1.47 | 0.21 |
| Mab 21 | pCON1531 | PCON1522 | 2.46 | 0.35 |
| Mab 22 | PCON1531 | pCON1521 | 2.08 | 0.30 |
| Mab 23 | PCON1531 | PCON1519 | 4.97 | 0.71 |
| Mab 27 | PCON1520 | PCOM1522 | 10.57 | 1.52 |
| Mab 28 | PCON1520 | PCOM1521 | 11.34 | 1.63 |
| Mab 30 | PCON1530 | PCON1526 | 10.35 | 1.49 |
| Mab 31 | PCON1530 | PCON1525 | 1.34 | 0.19 |
| Mab 33 | pCOM1530 | PCON1522 | 1.18 | 0.17 |
| Mab 34 | PCON1530 | PCON1521 | 1.24 | 0.18 |
| Mab 35 | PCON1530 | PCON1519 | 1.63 | 0.23 |
| Mab 39 | PCON1524 | PCON1522 | 1.73 | 0.25 |
| Mab 42 | PCON1531 | pCON1527 | 2.10 | 0.30 |
| Mab 44 | PCON1520 | PCON1527 | 1.55 | 0.22 |

Example 1.2: BCMA-Expressing Cells as Tools

Example 1.2.1: Human Myeloma Cell Lines Expressing BCMA on their Surface and Quantification of BCMA Receptor Number on Cell Surface BCMA expression was assessed on five human myeloma cell lines (NCI-H929, RPMI-8226, U266B1, L-363 and JJN-3) by flow cytometry. NCI-H929 cells ((H929) ATCC® CRL-9068™) were cultured in 80-90% RPMI 1640 with 10-20% heat-inactivated FCS and could contain 2 mM L-glutamine, 1 mM sodium pyruvate and 50 µM mercaptoethanol. RPMI-8226 cells ((RPMI) ATCC® CCL-155™) were cultured in a media containing 90% RPMI 1640 and 10% heat-inactivated FCS. U266B1 ((U266) ATCC® TIB-196™) cells were cultured in RPMI-1640 medium modified to contain 2 mM L-glutamine, 10 mM HEPES, 1 mM sodium pyruvate, 4500 mg/L glucose, and 1500 mg/L sodium bicarbonate and 15% heat-inactivated FCS. L-363 cell line (Leibniz Institute DSMZ—German collection of microorganisms and cell cultures; DSMZ No. ACC 49) was cultured in 85% RPMI 1640 and 15% heat-inactivated FCS. JJN-3 cell line (DSMZ No. ACC 541) was cultured in 40% Dulbecco's MEM+40% Iscove's MDM+20% heat-inactivated FBS. Briefly, cells were harvested, washed, counted for viability, resuspended at 50,000 cells/well of a 96-well round bottom plate and incubated with anti-human BCMA antibody (Abcam, #ab54834, mouse IgG1) at 10 µg/ml for 30 min at 4° C. (to prevent internalization). A mouse IgG1 was used as isotype control (BD Biosciences, #554121). Cells were then centrifuged (5 min at 350×g), washed twice and incubated with the FITC-conjugated anti mouse secondary antibody for 30 min at 4° C. At the end of incubation time, cells were centrifuged (5 min at 350×g), washed twice with FACS buffer, resuspended in 100 ul FACS buffer and analyzed on a CantoII device running FACS Diva software. The relative quantification of BCMA receptor number on the surface membrane of H929, RPMI-8226 and U266B1 myeloma cell lines was assessed by QIFIKIT analysis (Dako, #K0078, following manufacturer's instructions). H929 cells expressed human BCMA with the highest density, up to 5-6-fold higher more than other myeloma cell lines. H929 is considered as a high BCMA-expressing myeloma cell line as compared to U266 and L363 which are medium/low BCMA-expressing myeloma cells, RPMI-8226 which are low BCMA-expressing myeloma cells and JJN-3 which are very low BCMA-expressing myeloma cells. Table 3 summarizes the relative BCMA receptor number on the cell surface of human multiple myeloma cell lines per each experiment (n=5).

TABLE 3

Quantification of BCMA receptor number on membrane surface of H929, L363, RPMI-8226, U266B1 and JJN-3 human myeloma cell lines

| Human myeloma cell lines | Specific antigen binding capacity (SABC) | | | | |
| --- | --- | --- | --- | --- | --- |
| | Experiment 1 | Experiment 2 | Experiment 3 | Experiment 4 | Experiment 5 |
| H929 | 19357 | 54981 | 44800 | 100353 | 98050 |
| L363 | 16,970 | / | 11300 | 11228 | / |
| U266(B1) | / | 12852 | 11757 | / | 9030 |
| RPMI-8226 | 1165 | 5461 | / | 11361 | 2072 |
| JJN-3 | / | / | / | / | 650 |

Example 2: BCMA Binding Assays: Surface Plasmon Resonance

Assessment of binding of anti-BCMA antibodies to recombinant BCMA by surface plasmon resonance (SPR) as follow. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). The avidity of the interaction between anti-BCMA antibodies and recombinant BCMA Fc(kih) (human and cynomolgus) was determined. Biotinylated recombinant human and cynomolgus BCMA Fc(kih) were directly coupled on a SA chip following instructions (Biacore, Freiburg/Germany). The immobilization level ranged from 200 to 700 RU. The anti-BCMA antibodies were passed at a 2-fold concentration range (1.95 to 500 nM) with a flow of 30 µL/minutes through the flow cells over 120 seconds. The dissociation was monitored for 180 seconds. Bulk refractive index differences were corrected for by subtracting the response obtained on the reference flow cell. Here, the anti-BCMA antibodies were flown over an empty surface previously activated and deactivated as described in the standard amine coupling kit. Apparent kinetic constants were derived using the Biacore T200 Evaluation Software (vAA, Biacore AB, Uppsala/Sweden), to fit rate equations for 1:1 Langmuir binding by numerical integration, despite the bivalency of the interaction for comparison purposes. The affinity of the interaction between anti-BCMA antibodies and recombinant human BCMA Fc(kih) was also determined. Anti-human Fab antibody (GE Healthcare) was directly coupled on a CM5 chip at pH 5.0 using the standard amine coupling kit (Biacore, Freiburg/Germany) The immobilization level was about 6500 RU. Anti-BCMA antibody was captured for 90 seconds at 25 nM. Recombinant human BCMA Fc(kih) was passed at a 4-fold concentration range (1.95 to 500 nM) with a flow of 30 µL/minutes through the flow cells over 120 seconds. The dissociation was monitored for 120 seconds. Bulk refractive index differences were corrected for by subtracting the response obtained on reference flow cell. Here, recombinant BCMA was flown over a surface with immobilized anti-human Fab antibody but on which HBS-EP has been injected rather than anti-BCMA antibody. Kinetic constants were derived using the Biacore T100 Evaluation Software (vAA, Biacore AB, Uppsala/Sweden), to fit rate equations for 1:1 Langmuir binding by numerical integration (Table 4).

TABLE 4

Affinity constants determined by fitting rate equations for 1:1 Langmuir binding

| Ligand | Analyte | Kon [1/Ms] | Koff [1/s] | KD [M] |
| --- | --- | --- | --- | --- |
| 83A10 IgG | huBCMA Fc(kih) | 5.07E+05 | 2.92E−03 | 5.76E−09 |
| | cynoBCMA Fc(kih) | 2.29E+05 | 2.03E−02 | 8.86E−08 |
| Mab 21 IgG | huBCMA Fc(kih) | 8.51E+05 | 4.39E−05 | 5.16E−11 |
| | cynoBCMA Fc(kih) | 4.91E+05 | 2.35E−04 | 4.78E−10 |
| Mab 22 IgG | huBCMA Fc(kih) | 8.14E+05 | 5.15E−05 | 6.33E−11 |
| | cynoBCMA Fc(kih) | 4.54E+05 | 4.42E−04 | 9.74E−10 |
| Mab 42 IgG | huBCMA Fc(kih) | 8.03E+05 | 2.98E−04 | 3.71E−10 |
| | cynoBCMA Fc(kih) | 7.07E+05 | 4.53E−04 | 6.41E−10 |
| Mab 27 IgG | huBCMA Fc(kih) | 3.59E+05 | 5.93E−05 | 1.65E−10 |
| | cynoBCMA Fc(kih) | 2.16E+05 | 4.55E−04 | 2.11E−09 |
| Mab 33 IgG | huBCMA Fc(kih) | 2.00E+05 | 3.55E−05 | 1.78E−10 |
| | cynoBCMA Fc(kih) | 1.32E+05 | 9.76E−05 | 7.39E−10 |
| Mab 39 IgG | huBCMA Fc(kih) | 3.61E+05 | 5.58E−05 | 1.55E−10 |
| | cynoBCMA Fc(kih) | 2.15E+05 | 4.67E−04 | 2.17E−09 |

Example 3: Human/Cynomolgus (Hu/Cyno) Affinity Gap

Based on the affinity values described in Example 2, the affinity of anti-BCMA antibodies to human BCMA vs. cynomolgus BCMA were compared and cyno/hu affinity ratio (gap) values were calculated (Table 5). Affinity cyno/hu gap was calculated as affinity of antibody to cynomolgus BCMA divided by affinity to human BCMA and means that BCMA antibody binds to human BCMA with x fold binding affinity than to cynomolgus BCMA, where x=cyno/hu gap value. Results are shown in Table 5.

TABLE 5

Affinity of anti-BCMA antibodies to human BCMA vs. cynomolgus BCMA and hu/cyno gap values

| α-BCMA IgG | $K_D$ human BCMA [M] | KD cynomolgus BCMA [M] | Affinity cyno/hu gap |
|---|---|---|---|
| 83A10 | 5.76E−09 | 8.86E−08 | 15.3 |
| Mab 21 | 5.16E−11 | 4.78E−10 | 9.3 |
| Mab 22 | 6.33E−11 | 9.74E−10 | 15.4 |
| Mab 42 | 3.71E−10 | 6.41E−10 | 1.7 |
| Mab 27 | 1.65E−10 | 2.11E−09 | 12.7 |
| Mab 33 | 1.78E−10 | 7.39E−10 | 4.2 |
| Mab 39 | 1.55E−10 | 2.17E−09 | 14 |

Example 4: Generation of Anti-BCMA/Anti-CD3 T Cell Bispecific Antibodies

Anti-BCMA/anti-CD3 T cell bispecific antibodies were generated according to WO2014/122144, which is incorporated by reference.

Example 4.1: Anti-CD3 Antibodies

The term "CD3ε or CD3" as used herein relates to human CD3ε described under UniProt P07766 (CD3E_HUMAN). The term "antibody against CD3, anti CD3 antibody" relates to an antibody binding to CD3ε. Preferably the antibody comprises a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3. Preferably the antibody comprises the variable domains of SEQ ID NO:7 (VH) and SEQ ID NO:8 (VL). Anti-CD3 antibody as described above was used to generate the T cell bispecific antibodies which were used in the following examples.

Example 4.2: Generation of Anti-BCMA/Anti-CD3 T Cell Bispecific Antibodies of Fc-Containing 2+1 Format cDNAs encoding the full heavy and light chains of the corresponding anti-BCMA IgG1 antibodies as well as the anti-CD3 VH and VL cDNAs were used as the starting materials. For each bispecific antibody, four protein chains were involved comprising the heavy and light chains of the corresponding anti-BCMA antibody and the heavy and light chains of the anti-CD3 antibody described above, respectively. In order to minimize the formation of side-products with mispaired heavy chains, for example with two heavy chains of the anti-CD3 antibody, a mutated heterodimeric Fc region is used carrying "knob-into-hole mutations" and an engineered disulphide bond, as described in WO2009080251 and in WO2009080252. In order to minimize the formation of side-products with mispaired light chains, for example with two light chains of the anti-BCMA antibody, a CH1 x constant kappa crossover is applied to the heavy and light chains of the anti-CD3 antibody using the methodology described in WO2009080251 and in WO2009080252.

a) An anti-BCMA/anti-CD3 T cell bispecific antibody with a 2+1 format i.e. bispecific (Fab)$_2$×(Fab) antibody that is bivalent for BCMA and monovalent for CD3 would have advantages on potency, predictability for efficacy and safety because it would preferentially bind to the tumor target BCMA and avoid CD3 antibody sink, thus higher probability for drug exposure focused to the tumor.

Anti-BCMA/anti-CD3 T cell bispecific of the 2+1 format (i.e. bispecific (Fab)$_2$×(Fab) antibody bivalent for BCMA and monovalent for CD3 with Fc were produced for the human BCMA antibodies previously selected. cDNAs encoding the full Fabs (heavy chain VH and CH1 domains plus light chain VL and CL domains) of the corresponding anti-BCMA IgG1 antibodies as well as the anti-CD3 VH and VL cDNAs, were used as the starting materials. For each bispecific antibody, four protein chains were involved comprising the heavy and light chains of the corresponding anti-BCMA antibody and the heavy and light chains of the anti-CD3 antibody described above, respectively, with Fc regions.

Briefly, each bispecific antibody is produced by simultaneous cotransfection of four mammalian expression vectors encoding, respectively: a) the full light chain cDNA of the corresponding BCMA antibody, b) a fusion cDNA generated by standard molecular biology methods, such as splice-overlap-extension PCR, encoding a fusion protein made of (in N- to C-terminal order) secretory leader sequence, Fab (VH followed by CH1 domains) of the corresponding anti-BCMA antibody described above, a flexible glycine(Gly)-serine(Ser) linker with the sequence Gly-Gly-Gly-Gly-Ser-Gly-Gly-Gly-Gly-Ser, Fab (VH followed by CH1 domains) of the corresponding anti-BCMA antibody described above, a flexible glycine(Gly)-serine(Ser) linker with the sequence Gly-Gly-Gly-Gly-Ser-Gly-Gly-Gly-Gly-Ser, the VH of the anti-CD3 antibody described above and the constant kappa domain of a human light chain cDNA, c) a fusion cDNA generated by standard molecular biology methods, such as splice-overlap-extension PC, encoding a fusion protein made of (in N- to C-terminal order) secretory leader sequence, VL of the anti-CD3 antibody described above, constant CH1 domain of a human IgG1 cDNA. Co-transfection of mammalian cells and antibody production and purification using the methods described above for production of human or humanized IgG1 antibodies, with one modification: for purification of antibodies, the first capture step is not done using ProteinA, but instead is done using an affinity chromatography column packed with a resin binding to human kappa light chain constant region, such as KappaSelect (GE Healthcare Life Sciences). In addition, a disulfide can be included to increase the stability and yields as well as additional residues forming ionic bridges and increasing the heterodimerization yields (EP 1870459A1).

For the generation of BCMAxCD3 bispecific antibody vectors, the IgG1 derived bispecific molecules consist at least of two antigen binding moieties capable of binding specifically to two distinct antigenic determinants CD3 and BCMA. The antigen binding moieties were Fab fragments composed of a heavy and a light chain, each comprising a variable and a constant region. At least one of the Fab fragments was a "Crossfab" fragment, wherein the constant domains of the Fab heavy and light chain were exchanged. The exchange of heavy and light chain constant domains within the Fab fragment assures that Fab fragments of different specificity do not have identical domain arrangements and consequently do not interchange light chains. The bispecific molecule design was monovalent for CD3 and bivalent for BCMA where one Fab fragment is fused to the N-terminus of the inner CrossFab (2+1). The bispecific molecule contained an Fc part in order to have a longer half-life. A schematic representation of the constructs is given in FIGS. 1-3; the sequences of the preferred constructs are shown in Table 2A. The molecules were produced by co-transfecting HEK293 EBNA cells growing in suspension with the mammalian expression vectors using polymer-based solution. For preparation of 2+1 CrossFab-IgG constructs, cells were transfected with the corresponding expression vectors in a 1:2:1:1 ratio ("vector Fc(knob)": "vector light chain": "vector light chain CrossFab": "vector heavy chain-CrossFab").

Example 4.3: Generation of Anti-BCMA/Anti-CD3 T Cell Bispecific Antibodies for Comparison The generation of BCMA50-sc(Fv)$_2$ (also known as BCMA50-BiTE®) anti-BCMA/anti-CD3 T cell bispecific antibody and the amino acid sequences used were according to WO2013072406 and WO2013072415.

Example 5: Production and Purification of Anti-BCMA/Anti-CD3 Fc-Containing (2+1) T Cell Bispecific Antibodies with Charge Variants Anti-BCMA/anti-CD3 T cell bispecific antibodies were produced and purified according to WO2014/122144, which is incorporated by reference.

For the production of the bispecific antibodies, bispecific antibodies were expressed by transient co-transfection of the respective mammalian expression vectors in HEK293-EBNA cells, which were cultivated in suspension, using polymer-based solution. One day prior to transfection the HEK293-EBNA cells were seeded at 1.5 Mio viable cells/mL in Ex-Cell medium, supplemented with 6 mM of L-Glutamine. For every mL of final production volume 2.0 Mio viable cells were centrifuged (5 minutes at 210×g). The supernatant was aspirated and the cells resuspended in 100 μL of CD CHO medium. The DNA for every mL of final production volume was prepared by mixing 1 μg of DNA (Ratio heavy chain: modified heavy chain: light chain: modified light chain=1:1:2:1) in 100 μL of CD CHO medium. After addition of 0.27 μL of polymer-based solution (1 mg/mL) the mixture was vortexed for 15 seconds and left at room temperature for 10 minutes. After 10 minutes, the resuspended cells and DNA/polymer-based solution mixture were put together and then transferred into an appropriate container which was placed in a shaking device (37° C., 5% CO$_2$). After a 3 hours incubation time 800 μL of Ex-Cell Medium, supplemented with 6 mM L-Glutamine, 1.25 mM valproic acid and 12.5% Pepsoy (50 g/L), was added for every mL of final Production volume. After 24 hours, 70 μL of feed solution was added for every mL of final production volume. After 7 days or when the cell viability was equal or lower than 70%, the cells were separated from the supernatant by centrifugation and sterile filtration. The antibodies were purified by an affinity step and one or two polishing steps, being cation exchange chromatography and size exclusion chromatography. When required, an additional polishing step was used.

For the affinity step the supernatant was loaded on a protein A column (HiTrap Protein A FF, 5 mL, GE Healthcare) equilibrated with 6 CV 20 mM sodium phosphate, 20 mM sodium citrate, pH 7.5. After a washing step with the same buffer the antibody was eluted from the column by step elution with 20 mM sodium phosphate, 100 mM sodium chloride, 100 mM Glycine, pH 3.0. The fractions with the desired antibody were immediately neutralized by 0.5 M Sodium Phosphate, pH 8.0 (1:10), pooled and concentrated by centrifugation. The concentrate was sterile filtered and processed further by cation exchange chromatography and/or size exclusion chromatography.

For the cation exchange chromatography step the concentrated protein was diluted 1:10 with the elution buffer used for the affinity step and loaded onto a cation exchange colume (Poros 50 HS, Applied Biosystems). After two washing steps with the equilibration buffer and a washing buffer resp. 20 mM sodium phosphate, 20 mM sodium citrate, 20 mM TRIS, pH 5.0 and 20 mM sodium phosphate, 20 mM sodium citrate, 20 mM TRIS, 100 mM sodium chloride pH 5.0 the protein was eluted with a gradient using 20 mM sodium phosphate, 20 mM sodium citrate, 20 mM TRIS, 100 mM sodium chloride pH 8.5. The fractions containing the desired antibody were pooled, concentrated by centrifugation, sterile filtered and processed further a size exclusion step.

For the size exclusion step the concentrated protein was injected in a XK16/60 HiLoad Superdex 200 column (GE Healthcare), and 20 mM Histidine, 140 mM Sodium Chloride, pH 6.0 with or without Tween20 as formulation buffer. The fractions containing the monomers were pooled, concentrated by centrifugation and sterile filtered into a sterile vial.

Determination of the antibody concentration was done by measurement of the absorbance at 280 nm, using the theoretical value of the absorbance of a 0.1% solution of the antibody. This value was based on the amino acid sequence and calculated by GPMAW software (Lighthouse data).

Purity and monomer content of the final protein preparation was determined by CE-SDS (Caliper LabChip GXII system (Caliper Life Sciences)) resp. HPLC (TSKgel G3000 SW XL analytical size exclusion column (Tosoh)) in a 25 mM potassium phosphate, 125 mM Sodium chloride, 200 mM L-arginine monohydrochloride, 0.02% (w/v) Sodium azide, pH 6.7 buffer.

To verify the molecular weight of the final protein preparations and confirm the homogeneous preparation of the molecules final protein solution, liquid chromatography-mass spectometry (LC-MS) was used. A deglycosylation step was first performed. To remove heterogeneity introduced by carbohydrates, the constructs were treated with PNGaseF (ProZyme). Therefore, the pH of the protein solution was adjusted to pH7.0 by adding 2 μl 2 M Tris to 20 μg protein with a concentration of 0.5 mg/ml. 0.8 μg PNGaseF was added and incubated for 12 h at 37° C. The LC-MS online detection was then performed. LC-MS method was performed on an Agilent HPLC 1200 coupled to a TOF 6441 mass spectrometer (Agilent). The chromatographic separation was performed on a Macherey Nagel Polysterene column; RP1000-8 (8 μm particle size, 4.6×250 mm; cat. No. 719510). Eluent A was 5% acetonitrile and 0.05% (v/v) formic acid in water, eluent B was 95% acetonitrile, 5% water and 0.05% formic acid. The flow rate was 1 ml/min, the separation was performed at 40° C. and 6 μg (15 μl) of a protein sample obtained with a treatment as described before.

During the first 4 minutes, the eluate was directed into the waste to protect the mass spectrometer from salt contamination. The ESI-source was running with a drying gas flow of 12 l/min, a temperature of 350° C. and a nebulizer pressure of 60 psi. The MS spectra were acquired using a fragmentor voltage of 380 V and a mass range 700 to 3200 m/z in positive ion mode using. MS data were acquired by the instrument software from 4 to 17 minutes.

FIG. 10 of EP14179705 (incorporated by reference) depicts the CE-SDS (non-reduced) graphs of the final protein preparations after different methods of purification for 83A10-TCB and 83A10-TCBcv antibodies. Protein A (PA) affinity chromatography and size exclusion chromatographic (SEC) purification steps applied to 83A10-TCB antibody resulted in a purity of <30% and 82.8% of monomer content (A). When additional purifications steps including cation exchange chromatography (cIEX) and a final size exclusion chromatographic (re-SEC) steps were applied to the final protein preparations in (A), the purity was increased to 93.4% but the monomer content remained the same and the yield was significantly reduced to 0.42 mg/L. However, when specific charge modifications were applied to 83A10 anti-BCMA Fab CL-CH1, namely 83A10-TCBcv antibody, a superior production/purification profile of the TCB molecule, as demonstrated by a purity of 95.3%, monomer content of 100% and yield of up to 3.3 mg/L, could already be observed even when PA+cIEX+SEC purification steps were applied (C) in comparison to (B) with a production/purification profile showing a 7.9-fold lower yield and 17.2% lower monomer content despite including an additional re-SEC purification step.

Figure 11A:
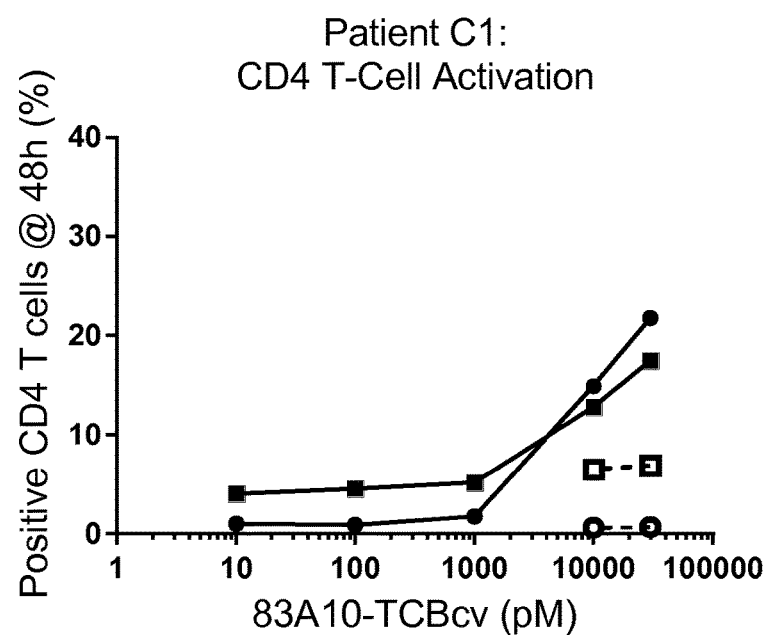
FIG. 11. Activation of myeloma patient bone marrow T cells in presence of bone marrow plasma cells (patient whole bone marrow aspirates) induced by anti-BCMA/anti-CD3 T-cell bispecific antibodies as measured by multiparameter flow cytometry (8-color staining panel). Magnitude of T-cell activation was compared among 83A10-TCBcv (A), 42-TCBcv (B) and 22-TCBcv (C) (see example 14).
Figure 11A:
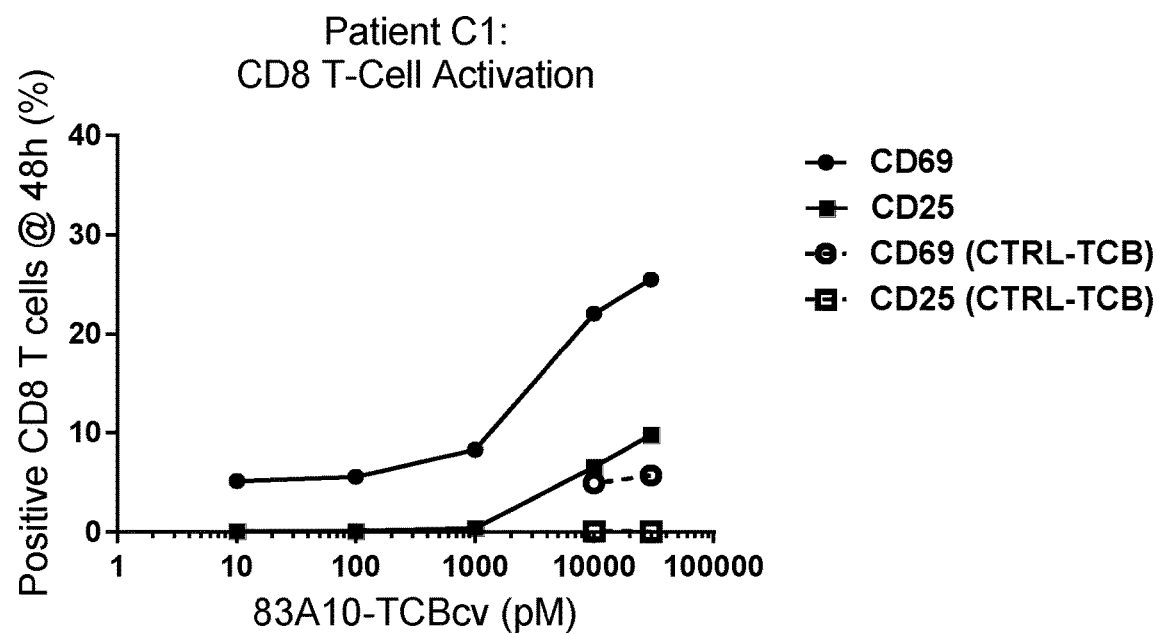
Figure 11B:
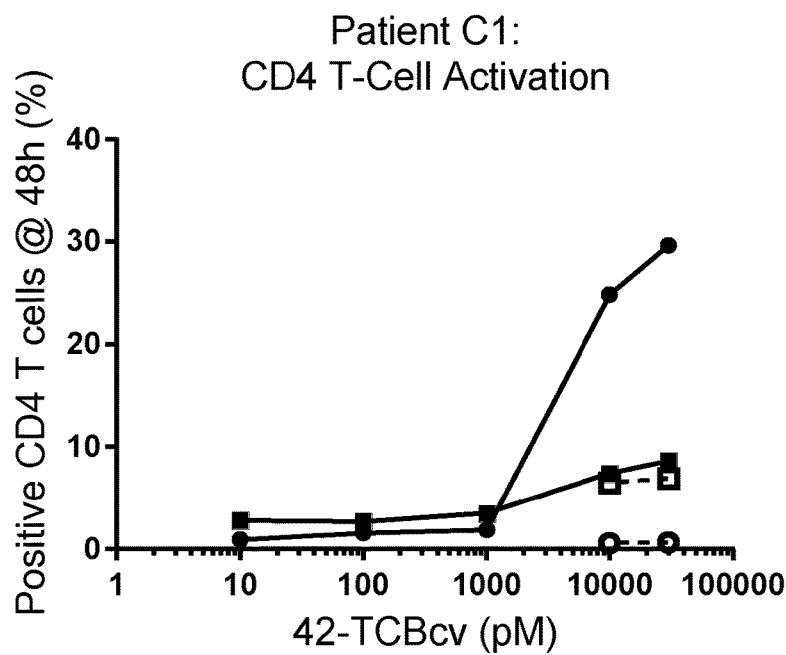
Figure 11B:
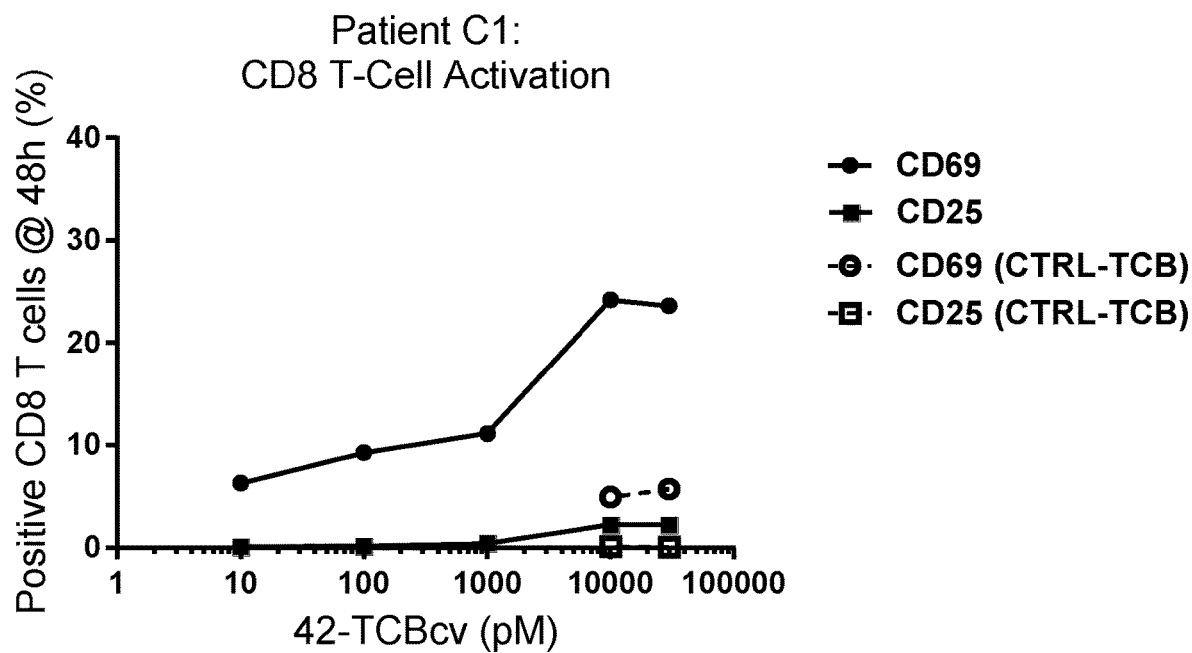
Figure 11C:
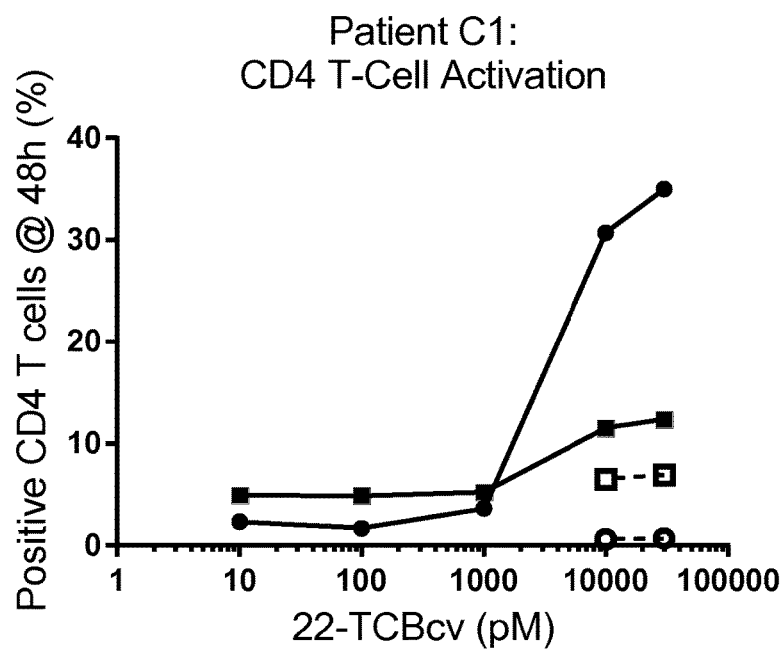
Figure 11C:
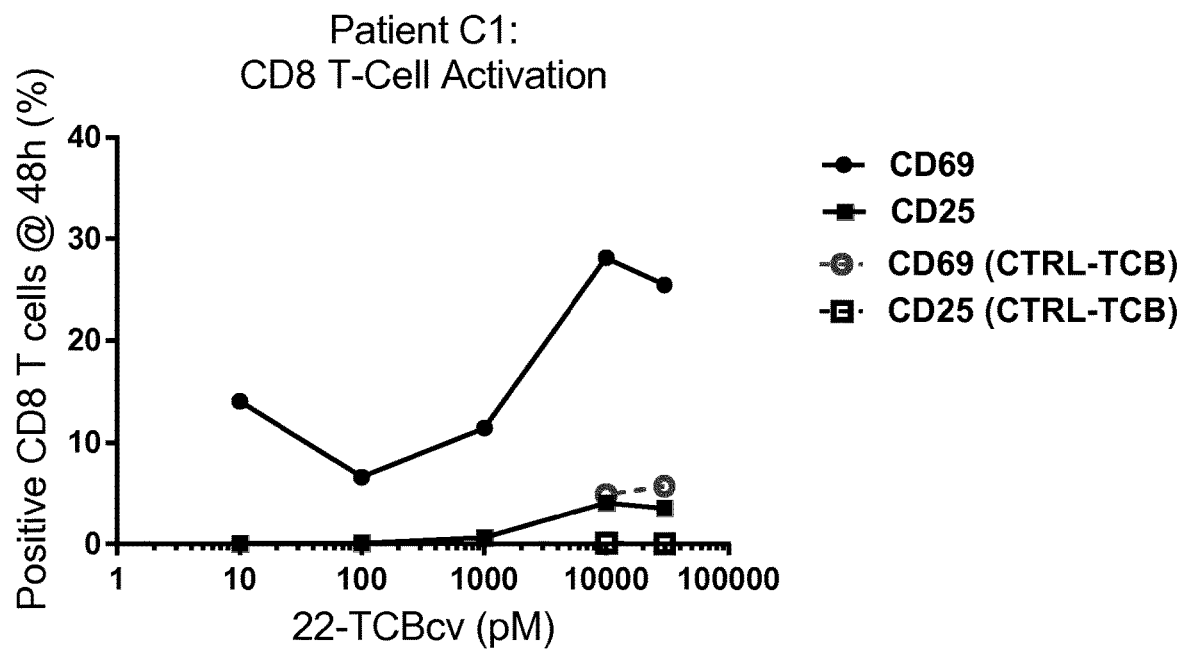

A head-to-head production run to compare the production/purification profile of 83A10-TCB vs. 83A10-TCBcv antibodies was then conducted to further evaluate the advantages of the CL-CH1 charge modifications applied to the antibodies. 83A10-TCB and 83A10-TCBcv molecules are both of molecular format as described in FIG. 2a. As depicted in FIG. 11, properties of 83A10-TCB and 83A10-TCBcv antibodies were measured side-by-side and compared after each purification steps 1) PA affinity chromatography only (A, B), 2) PA affinity chromatography then SEC (C, D) and 3) PA affinity chromatography then SEC then cIEX and re-SEC (E, F). The CE-SDS (non-reduced) graphs of the final protein solutions after the respective methods of purification for 83A10-TCB and 83A10-TCBcv antibodies are demonstrated in FIG. 11 of EP14179705 (incorporated by reference). As shown in FIGS. 11A and 11B of EP14179705 (incorporated by reference), improvements with applying the charge variants to the TCB antibody were already observed after purification by PA affinity chromatography only. In this head-to-head study, PA affinity chromatography purification step applied to 83A10-TCB antibody resulted in a purity of 61.3%, a yield of 26.2 mg/L and 63.7% of monomer content (11A). In comparison, when 83A10-TCBcv antibody was purified by PA affinity chromatography all the properties were improved with a better purity of 81.0%, a better yield of 51.5 mg/L and 68.2% of monomer content (11B). When an additional SEC purification step was applied to the final protein preparations as seen in FIGS. 12A and 12B of EP14179705 (incorporated by reference), 83A10-TCB gained a purity of 69.5%, a yield of 14.1 mg/L and 74.7% of monomer content (C) as compared to 83A10-TCBcv with improved purity and monomer content of up to 91.0% and 83.9% respectively, and a yield of 10.3 mg/L (D). Even though the yield was slightly less (i.e. 27% less) for 83A10-TCBcv than for 83A10-TCB in this particular experiment, the percentage of correct molecule was much better for 83A10-TCBcv than for 83A10-TCB, respectively 90% vs. 40-60%, as measured by LC-MS. In the third head-to-head comparison, 83A10-TCB and 83A10-TCBcv final protein preparations from FIGS. 11C and 11D of EP14179705 (incorporated by reference) were pooled with approximately 1 L (equivolume) of respective final protein preparations from another purification batch (same production) following PA affinity chromatography purification step only. The pooled protein preparations were then being further purified by cIEX and SEC purification methods. As depicted in FIGS. 11E and 11F of EP14179705 (incorporated by reference), improvement of the production/purification profile of the TCB antibody with the charge variants was consistently observed when compared to TCB antibody without charge variant. After several steps of purification methods (i.e. PA+/−SEC+cIEX+SEC) were used to purify 83A10-TCB antibody, only 43.1% purity was reached and 98.3% of monomer content could be achieved but to the detriment of the yield which was reduced to 0.43 mg/L. The percentage of correct molecule as measured by LC-MS was still poor with 60-70%. At the end, the quality of the final protein preparation was not acceptable for in vitro use. In stark contrast, when the same multiple purification steps with the same chronology were applied to 83A10-TCBcv antibody, 96.2% purity and 98.9% of monomer content were reached as well as 95% of correct molecule as measured by LC-MS. The yield however was also greatly reduced to 0.64 mg/L after cIEX purification step. The results show that better purity, higher monomer content, higher percentage of correct molecule and better yield can be achieved with 83A10-TCBcv antibody only after two standard purification steps i.e. PA affinity chromatography and SEC (FIG. 11D of EP14179705) while such properties could not be achieved with 83A10-TCB even when additional purification steps were applied (FIG. 11E of EP14179705).

Table 12 of EP14179705 (incorporated by reference) summarizes the properties of 83A10-TCB as compared to 83A10-TCVcv following PA purification step. Table 13 of EP14179705 (incorporated by reference) summarizes the properties of 83A10-TCB as compared to 83A10-TCVcv following PA and SEC purification steps. Table 14 of EP14179705 (incorporated by reference) summarizes the properties of 83A10-TCB as compared to 83A10-TCVcv following PA and SEC plus PA alone then cIEX and re-SEC purification steps. For Tables 12 to 14 of EP14179705 (incorporated by reference), the values in bold highlight the superior property as compared between 83A10-TCB vs. 83A10-TCVcv. With one exception (i.e. yield respectively amount, see Table 13 of EP14179705 (incorporated by reference)) which may not be representative, all the production/purification parameters and values resulting from the 3 head-to-head comparison experiments were superior for 83A10-TCBcv as compared to 83A10-TCB. The overall results clearly demonstrate that advantages in production/purification features could be achieved with applying CL-CH1 charge modifications to TCB antibodies and that only two purification steps (i.e PA affinity chromatography and SEC) were required to achieve already high quality protein preparations with very good developability properties. Based on the improved production/purification properties of 83A10-TCBcv, 21-TCBcv, 22-TCBcv, 27-TCBcv, 33-TCBcv, 39-TCBcv and 42-TCBcv were generated with charge variants, in a similar way as 83A10-TCBcv.

TABLE 6

Production/purification profile of anti-BCMA/anti-CD3 T cell bispecific antibodies following protein A affinity chromatography purification step

|  | 83A10-TCB | 83A10-TCBcv |
|---|---|---|
| Purity (%) | 61.3 | 81.0 |
| Yield (mg/L) | 26.2 | 51.5 |
| Amount (mg) | 24.3 | 50.2 |
| Monomer (%) | 63.7 | 68.2 |

TABLE 6-continued

Production/purification profile of anti-BCMA/anti-CD3 T cell bispecific antibodies following protein A affinity chromatography purification step

|  | 83A10-TCB | 83A10-TCBcv |
|---|---|---|
| Correct molecule by LC-MS (%) | n.d. | n.d |

TABLE 7

Production/purification profile of anti-BCMA/anti-CD3 T cell bispecific antibodies following protein A affinity chromatography and size exclusion chromatography purification steps

|  | 83A10-TCB | 83A10-TCBcv |
|---|---|---|
| Purity (%) | 69.5 | 91.0 |
| Yield (mg/L) | 14.1 | 10.3 |
| Amount (mg) | 13.1 | 10.0 |
| Monomer (%) | 74.7 | 83.9 |
| Correct molecule by LC-MS (%) | 40-60 | 90 |

TABLE 8

Production/purification profile of anti-BCMA/anti-CD3 T cell bispecific antibodies following 1.a) protein A affinity chromatography and size exclusion chromatography and 1.b) protein A affinity chromatography only pooled together then 2) cation exchange chromatography and 3) final size exclusion chromatography purification steps

|  | 83A10-TCB | 83A10-TCBcv |
|---|---|---|
| Purity (%) | 43.1 | 96.2 |
| Yield (mg/L) | 0.43 | 0.64 |
| Amount (mg) | 0.73 | 1.27 |
| Monomer (%) | 98.3 | 98.9 |
| Correct molecule by LC-MS (%) | 60-70% | >95% |

Example 6: Binding of Anti-BCMA/Anti-CD3 T-Cell Bispecific Antibodies to BCMA-Positive Multiple Myeloma Cell Lines (Flow Cytometry)

Anti-BCMA/anti-CD3 TCB antibodies (21-TCBcv, 22-TCBcv, 42-TCBcv, 83A10-TCBcv) were analyzed by flow cytometry for binding to human BCMA on BCMA-expressing H929, L363 and RPMI-8226 cells. MKN45 (human gastric adenocarcinoma cell line that does not express BCMA) was used as negative control. Briefly, cultured cells are harvested, counted and cell viability was evaluated using ViCell. Viable cells are then adjusted to $2 \times 10^6$ cells per ml in BSA-containing FACS Stain Buffer (BD Biosciences). 100 µl of this cell suspension were further aliquoted per well into a round-bottom 96-well plate and incubated with 30 µl of the anti-BCMA antibodies or corresponding IgG control for 30 min at 4° c. All Anti-BCMA/anti-CD3 TCB antibodies (and TCB controls) were titrated and analyzed in final concentration range between 1-300 nM. Cells were then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 ul BD Fixation buffer per well (#BD Biosciences, 554655) at 4° C. for 20 min, resuspended in 120 µl FACS buffer and analyzed using BD FACS Cantoll. When applicable, EC50 were calculated using Prism GraphPad (La-Jolla, Calif., USA) and EC50 values denoting the antibody concentration required to reaching 50% of the maximal binding for the binding of anti-BCMA/anti-CD3 TCB antibodies to H929 cells, L363 cells and RPMI-8226 cells are summarized in Table 8, Table 9, and Table 10 respectively. Asterix denotes estimated EC50 values as extrapolated and calculated by Prism software. EC50 values for binding of 21-TCBcv to L363 cells and binding of 22-TCBcv to RPMI-8226 cells could not be estimated

TABLE 8

EC50 values for binding of anti-BCMA/anti-CD3 T-cell bispecific antibodies to H929 multiple myeloma cells

| Estimated EC50 | 83A10-TCBcv | 21-TCBcv | 22-TCBcv | 42-TCBcv |
|---|---|---|---|---|
| nM | 12.0 | 11.0 | 7.9 | 13.6 |
| µg/ml | 1.725 | 1.589 | 1.142 | 1.956 |

TABLE 9

EC50 values for binding of anti-BCMA/anti-CD3 T-cell bispecific antibodies to L363 multiple myeloma cells

| Estimated EC50 | 83A10-TCBcv | 21-TCBcv | 22-TCBcv | 42-TCBcv |
|---|---|---|---|---|
| nM | 17.4 | / | 30.0 | 3.8 |
| µg/ml | 2.507 | / | 4.328 | 0.5534 |

TABLE 10

EC50 values for binding of anti-BCMA/anti-CD3 T-cell bispecific antibodies to RPMI-8226 multiple myeloma cells

| Estimated EC50 | 83A10-TCBcv | 21-TCBcv | 22-TCBcv | 42-TCBcv |
|---|---|---|---|---|
| nM | ~188428* | 6.8 | / | 13.2 |
| µg/ml | ~27151* | 0.9817 | / | 1.907 |

Example 7: Cytokine Production from Activated T Cells Upon Binding of Anti-BCMA/Anti-CD3 T Cell Bispecific Antibodies to CD3-Positive T Cells and BCMA-Positive Multiple Myeloma Cell Lines (Cytokine Release Assay CBA Analysis)

Anti-BCMA/anti-CD3 T cell bispecific antibodies are analyzed for their ability to induce T-cell mediated cytokine production de novo in the presence or absence of human BCMA-expressing human myeloma cells (RPMI-8226, JJN-3). Briefly, human PBMCs are isolated from Buffy Coats and 0.3 million cells per well are plated into a round-bottom 96-well plate. Alternatively, 280 µl whole blood from a healthy donor are plated per well of a deep-well 96-well plate. BCMA-positive tumor target cells are added to obtain a final E:T-ratio of 10:1. Anti-BCMA/anti-CD3 TCB antibodies and controls are added for a final concentration of 0.1 pM-10 nM. After an incubation of up to 24 h at 37° C., 5% $CO_2$, the assay plate is centrifuged for 5 min at 350×g and the supernatant is transferred into a new deep-well 96-well plate for the subsequent analysis. The CBA analysis was performed on FACS CantoII according to manufactur'er's instructions, using either the Human Th1/Th2 Cytokine Kit II (BD #551809) or the combination of the following CBA Flex Sets: human granzyme B (BD #560304), human IFN-γ Flex Set (BD #558269), human TNF-α Flex Set (BD #558273), human IL-10 Flex Set (BD #558274), human IL-6 Flex Set (BD #558276), human IL-4 Flex Set (BD #558272), human IL-2 Flex Set (BD #558270). Table 13 shows that 83A10-TCBcv induced a concentration-dependent increase in cytokine production and serine protease granzyme B, a marker of cytotoxic T-cell function. Table 11 shows the EC50 values and amount of secreted cytokines/proteases per anti-BCMA/anti-CD3 T-cell bispecific antibody concentrations.

TABLE 11

Secretion of cytokine and proteases induced by anti-BCMA/anti-CD3 T-cell bispecific antibodies in presence of RPMI-8226 cells

| Cytokines/proteases | EC50 (nM) | 83A10-TCBcv concentration (nM) | | | | | | |
|---|---|---|---|---|---|---|---|---|
| | | 0.00064 | 0.0032 | 0.016 | 0.08 | 0.4 | 2 | 10 |
| TNF-α (pg/mL) | 0.52 | −6.95 | −6.49 | −0.65 | 46.72 | 161.24 | 315.11 | 371.47 |
| IL-10 (pg/mL) | 0.30 | −9.21 | 1.95 | 25.17 | 125.82 | 401.42 | 602.64 | 680.05 |
| Granzyme B (pg/mL) | 0.34 | 220.54 | 331.55 | 889.13 | 5855.02 | 15862.84 | 21270.43 | 27120.52 |

Example 8: Redirected T-Cell Cytotoxicity of BCMA-High Expressing H929 Myeloma Cells Induced by Anti-BCMA/Anti-CD3 T Cell Bispecific Antibodies (Colorimetric LDH Release Assay)

Figure 4:
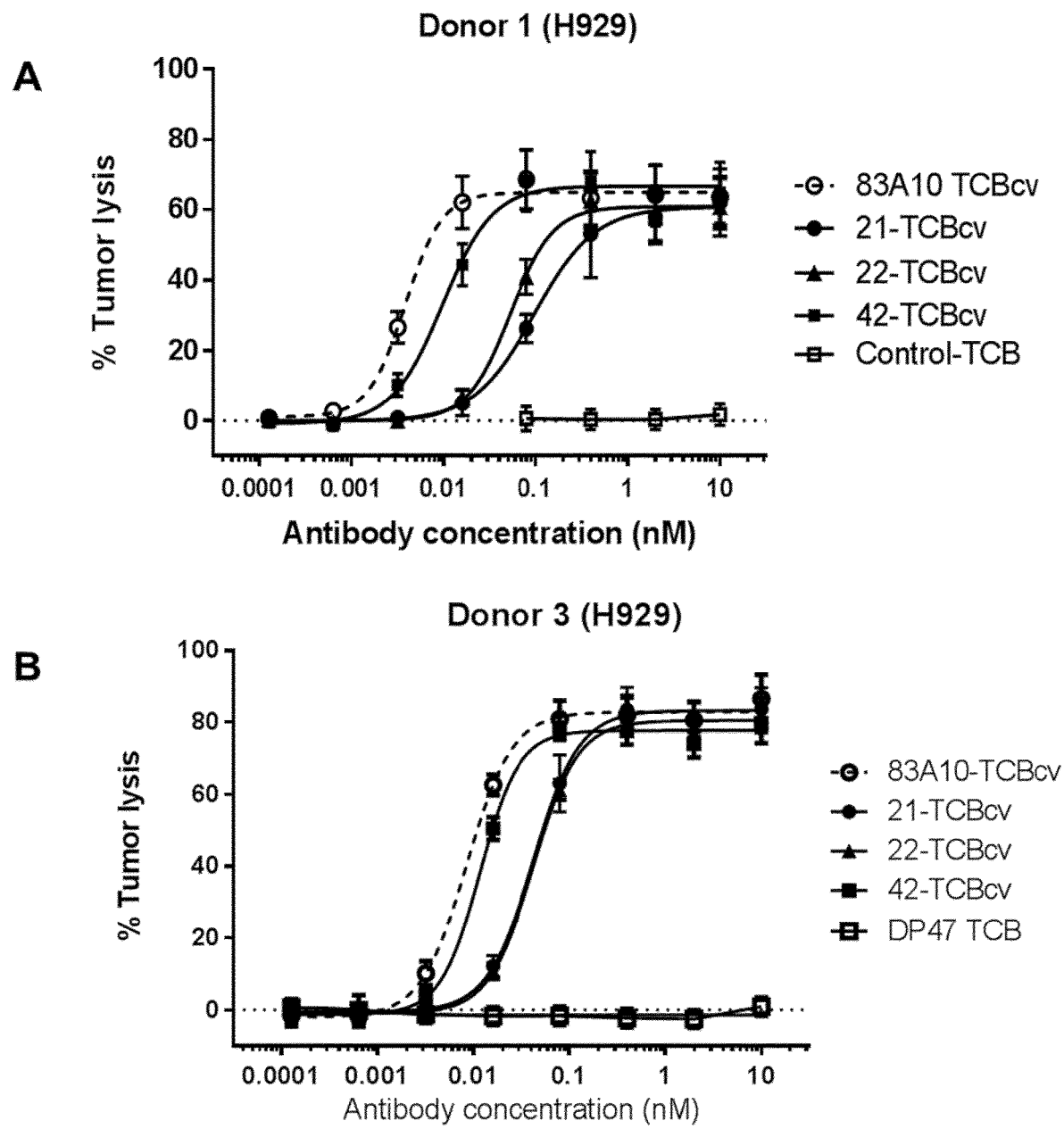
FIG. 4. Redirected T-cell lysis of H929 MM cells induced by anti-BCMA/anti-CD3 T-cell bispecific antibodies as measured by LDH release. Concentration response curves for lysis of H929 MM cells induced by 21-TCBcv (closed circle), 22-TCBcv (closed triangle), 42-TCBcv (closed square) in comparison with 83A10-TCBcv (open circle, dotted line). There was a concentration-dependent killing of H929 cells for all anti-BCMA/anti-CD3 T cell bispecific antibodies while no killing was observed with the control-TCB. Experiments were performed with PBMC donor 1 (A), donor 3 (B), donor 4 (C), donor (D) using an effector cell to tumor target cell (E:T) ratio of 10 PBMCs to 1 MM cell (see example 8).

Anti-BCMA/anti-CD3 TCB antibodies were analyzed for their potential to induce T cell-mediated apoptosis in BCMA high-expressing MM cells upon crosslinking of the construct via binding of the antigen binding moieties to BCMA on cells. Briefly, human BCMA high-expressing H929 multiple myeloma target cells were harvested with Cell Dissociation Buffer, washed and resuspended in RPMI supplemented with 10% fetal bovine serum (Invitrogen). Approximately, 30,000 cells per well were plated in a round-bottom 96-well plate and the respective dilution of the construct was added for a desired final concentration (in triplicates); final concentrations ranging from 0.1 pM to 10 nM. For an appropriate comparison, all TCB constructs and controls were adjusted to the same molarity. Human PBMCs (effector cells) were added into the wells to obtain a final E:T ratio of 10:1, corresponding to a E:T ratio of approximately 3 to 5 T cells for 1 tumor target cells. Negative control groups were represented by effector or target cells only. For normalization, maximal lysis of the H929 MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. After 20-24h or 48h incubation at 37° C., 5% $CO_2$, LDH release from the apoptotic/necrotic MM target cells into the supernatant was then measured with the LDH detection kit (Roche Applied Science), following the manufacturer's instructions. The percentage of LDH release was plotted against the concentrations of anti-BCMA/anti-CD3 T cell bispecific antibodies in concentration-response curves. The EC50 values were measured using Prism software (GraphPad) and determined as the TCB antibody concentration that results in 50% of maximum LDH release. As shown in FIG. 4, all anti-BCMA/anti-CD3 TCB antibodies (21-, 22-, 42-, and 83A10-TCBcv) induced a concentration-dependent killing of BCMA-positive H929 myeloma cells as measured by LDH release. The lysis of H929 cells was specific since control-TCB antibody which does not bind to BCMA-positive target cells but only to CD3 on T cells did not induce LDH release, even at the highest concentration tested. Table 12 summarizes the EC50 values for the redirected T-cell killing of BCMA high-expressing H929 cells induced by anti-BCMA/anti-CD3 TCB antibodies.

TABLE 12

EC50 values for redirected T-cell killing of H929 cells induced by anti-BCMA/anti-CD3 TCB antibodies

| Anti-BCMA/anti-CD3 TCB antibodies | EC50 (pM) | | | | | |
|---|---|---|---|---|---|---|
| | Donor 1 | Donor 2 | Donor 3 | Donor 4 | Donor 5 | Donor 6 |
| 21-TCBcv | 97.1 | / | 42.1 | 53.9 | 38.7 | / |
| 22-TCBcv | 53.2 | / | 42.2 | 23.2 | 28.9 | / |
| 42-TCBcv | 9.7 | / | 11.7 | 7.2 | 6.8 | / |
| 83A10-TCBcv | 3.9 | / | 8.5 | 5.0 | 4.3 | 1.5 |

Figure 5:
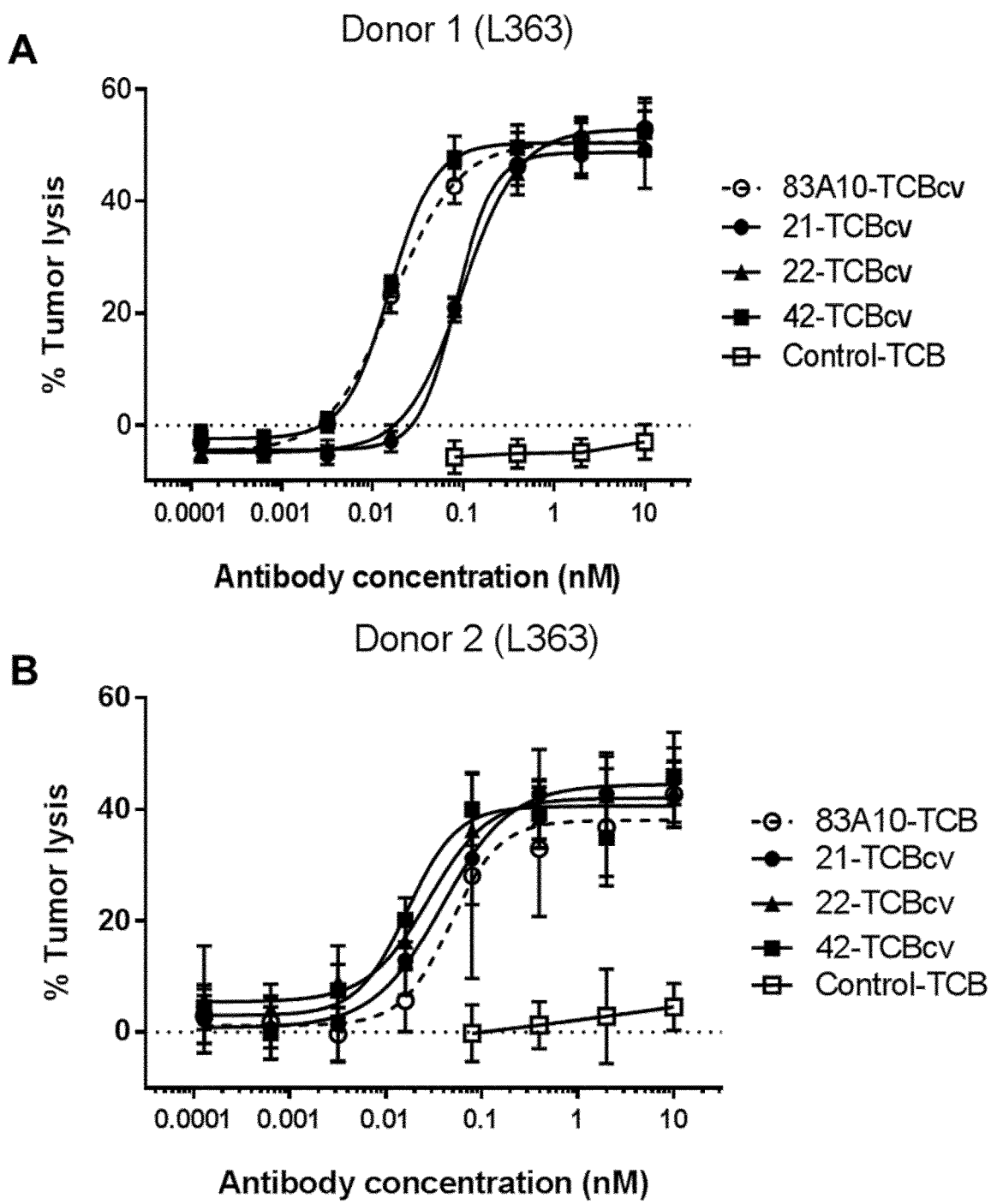
FIG. 5. Redirected T-cell lysis of L363 MM cells induced by anti-BCMA/anti-CD3 T-cell bispecific antibodies as measured by LDH release. Concentration response curves for lysis of L363 MM cells induced by 21-TCBcv (closed circle), 22-TCBcv (closed triangle), 42-TCBcv (closed square) in comparison with 83A10-TCBcv (open circle, dotted line). A concentration-dependent killing of L363 cells was observed for all anti-BCMA/anti-CD3 T cell bispecific antibodies while no killing was observed with the control-TCB. Experiments were performed with PBMC donor 1 (A), donor 2 (B), donor 3 (C), donor 4 (D), donor 5 (E) using an E:T ratio of 10 PBMCs to 1 MM cell (see example 9).

Example 9: Redirected T-Cell Cytotoxicity of BCMA-Medium/Low Expressing L363 Myeloma Cells Induced by Anti-BCMA/Anti-CD3 T Cell Bispecific Antibodies (LDH Release Assay) Anti-BCMA/anti-CD3 TCB antibodies were also analyzed for their ability to induce T cell-mediated apoptosis in BCMA medium/low-expressing MM cells upon crosslinking of the construct via binding of the antigen binding moieties to BCMA on cells. Briefly, human BCMA medium/low-expressing L363 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Human PBMCs (effector cells) were added into the wells to obtain a final E:T ratio of 10:1, corresponding to a E:T ratio of approximately 3 to 5 T cells for 1 tumor target cells. Negative control groups were represented by effector or target cells only. For normalization, maximal lysis of the MM target cells (=100%) is determined by incubation of the target cells with a final concentration of 1% Triton X-100, inducing cell death Minimal lysis (=0%) was represented by target cells co-incubated with effector cells only, i.e. without any T cell bispecific antibody. After 20-24 h incubation at 37° C., 5% $CO_2$, LDH release from the apoptotic/necrotic MM target cells into the supernatant was then measured with the LDH detection kit (Roche Applied Science), following the manufacturer's instructions. The percentage of LDH release was plotted against the concentrations of anti-BCMA/anti-CD3 T cell bispecific antibodies in concentration-response curves. The EC50 values were measured using Prism software (GraphPad) and determined as the TCB antibody concentration that results in 50% of maximum LDH release. As shown in FIG. 5, all anti-BCMA/anti-CD3 TCB antibodies (21-, 22-, 42-, and 83A10-TCBcv) induced a concentration-dependent killing of BCMA-positive L363 myeloma cells as measured by LDH release. The lysis of L363 cells was specific since control-TCB antibody which does not bind to BCMA-positive target cells but only to CD3 on T cells did not induce LDH release, even at the highest concentration tested. Table 13 summarizes the EC50 values for the redirected T-cell killing of BCMA medium/low-expressing L363 cells induced by anti-BCMA/anti-CD3 TCB antibodies.

TABLE 13

EC50 values for redirected T-cell killing of L363 cells induced by anti-BCMA/anti-CD3 TCB antibodies

| Anti-BCMA/anti-CD3 TCB antibodies | EC50 (pM) | | | | |
| --- | --- | --- | --- | --- | --- |
| | Donor 1 | Donor 2 | Donor 3 | Donor 4 | Donor 5 |
| 21-TCBcv | 83.6 | 38.4 | 18.9 | 19.1 | 46.4 |
| 22-TCBcv | 97.5 | 27.7 | 16.5 | 14.6 | 56.0 |
| 42-TCBcv | 15.5 | 16.7 | 5.2 | 2.2 | 10.6 |
| 83A10-TCBcv | 16.8 | 47.8 | 28.4 | 12.6 | 39.0 |

Example 10: Redirected T-Cell Cytotoxicity of BCMA-Medium/Low Expressing RPMI-8226 Myeloma Cells Induced by Anti-BCMA/Anti-CD3 T Cell Bispecific Antibodies (LDH Release Assay)

Figure 6:
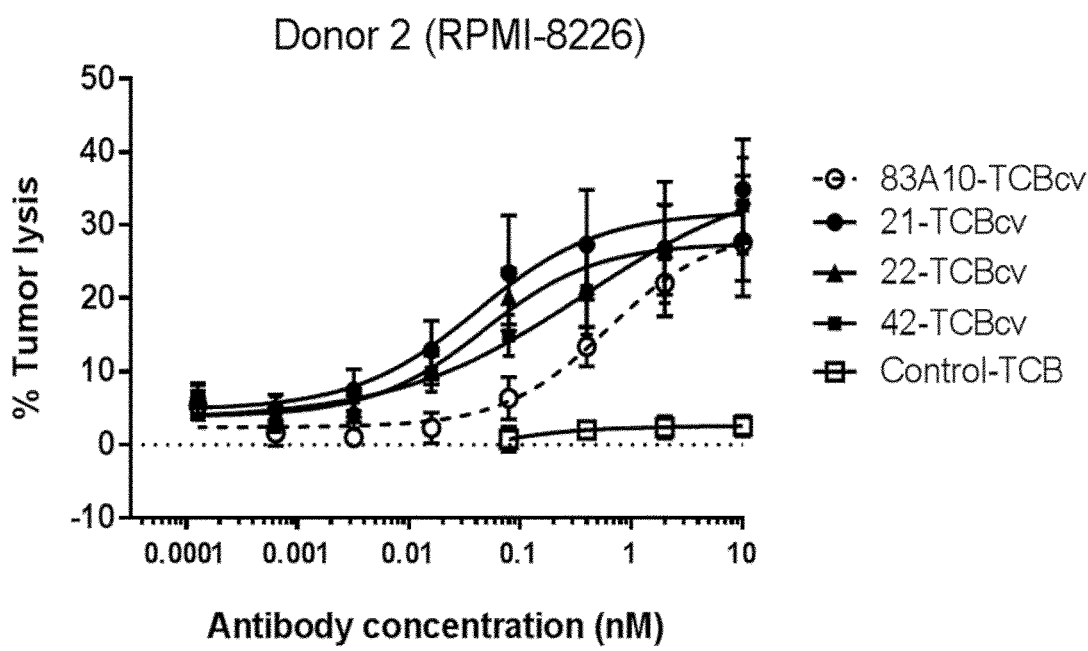
FIG. 6. Redirected T-cell lysis of RPMI-8226 MM cells induced by anti-BCMA/anti-CD3 T-cell bispecific antibodies as measured by LDH release. Concentration response curves for lysis of RPMI-8226 MM cells induced by 21-TCBcv (closed circle), 22-TCBcv (closed triangle), 42-TCBcv (closed square) in comparison with 83A10-TCBcv (open circle, dotted line). A concentration-dependent killing of RPMI-8226 cells was observed for all anti-BCMA/anti-CD3 T cell bispecific antibodies while no killing was observed with the control-TCB. Experiments were performed with PBMC donor 2 (A), donor 3 (B), donor 4 (C), donor 5 (D) using an E:T ratio of 10 PBMCs to 1 MM cell (see example 10).
Figure 6:
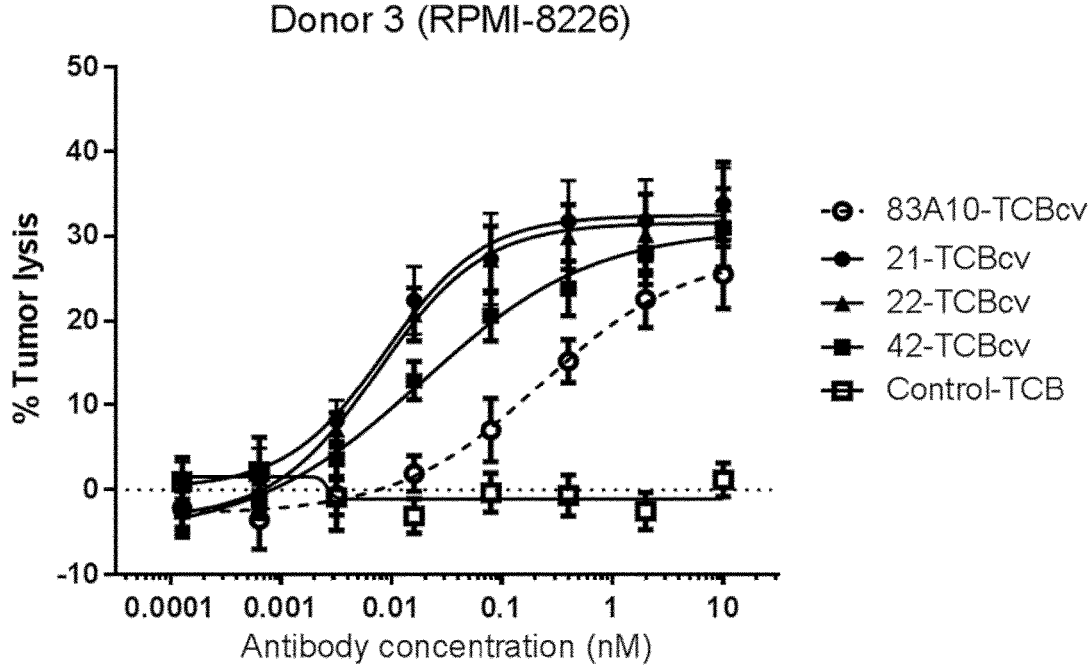

Anti-BCMA/anti-CD3 TCB antibodies were analyzed for their ability to induce T cell-mediated apoptosis in BCMA medium/low-expressing MM cells upon crosslinking of the construct via binding of the antigen binding moieties to BCMA on cells. Briefly, human BCMA medium/low-expressing L363 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Human PBMCs (effector cells) were added into the wells to obtain a final E:T ratio of 10:1, corresponding to a E:T ratio of approximately 3 to 5 T cells for 1 tumor target cells. Negative control groups were represented by effector or target cells only. For normalization, maximal lysis of the MM target cells (=100%) was determined by incubation of the target cells with a final concentration of 1% Triton X-100, inducing cell death Minimal lysis (=0%) was represented by target cells co-incubated with effector cells only, i.e. without any T cell bispecific antibody. After 20-24 h incubation at 37° C., 5% $CO_2$, LDH release from the apoptotic/necrotic MM target cells into the supernatant was then measured with the LDH detection kit (Roche Applied Science), following the manufacturer's instructions. The percentage of LDH release was plotted against the concentrations of anti-BCMA/anti-CD3 T cell bispecific antibodies in concentration-response curves. The EC50 values were measured using Prism software (GraphPad) and determined as the TCB antibody concentration that results in 50% of maximum LDH release. As shown in FIG. 6, all anti-BCMA/anti-CD3 TCB antibodies (21-, 22-, 42-, and 83A10-TCBcv) induced a concentration-dependent killing of BCMA-positive RPMI-8226 myeloma cells as measured by LDH release. The lysis of RPMI-8226 cells was specific since control-TCB antibody which does not bind to BCMA-positive target cells but only to CD3 on T cells did not induce LDH release, even at the highest concentration tested. Table 13 summarizes the EC50 values for the redirected T-cell killing of BCMA medium/low-expressing RPMI-8226 cells induced by anti-BCMA/anti-CD3 TCB antibodies.

TABLE 13

EC50 values for redirected T-cell killing of RPMI-8226 cells induced by anti-BCMA/anti-CD3 TCB antibodies

| Anti-BCMA/anti-CD3 TCB antibodies | EC50 (pM) | | | | |
| --- | --- | --- | --- | --- | --- |
| | Donor 1 | Donor 2 | Donor 3 | Donor 4 | Donor 5 |
| 21-TCBcv | / | 41.3 | 8.8 | 4.0 | 8.4 |
| 22-TCBcv | / | 47.6 | 7.6 | 3.2 | 5.5 |
| 42-TCBcv | / | 382.8 | 18.7 | 3.5 | 1.5 |
| 83A10-TCBcv | / | 620.5 | 229.3 | 35.0 | 64.9 |

Example 11: Redirected T-Cell Cytotoxicity of BCMA-Low Expressing JJN-3 Myeloma Cells Induced by Anti-BCMA/Anti-CD3 T Cell Bispecific Antibodies (Flow Cytometry and LDH Release)

Figure 7:
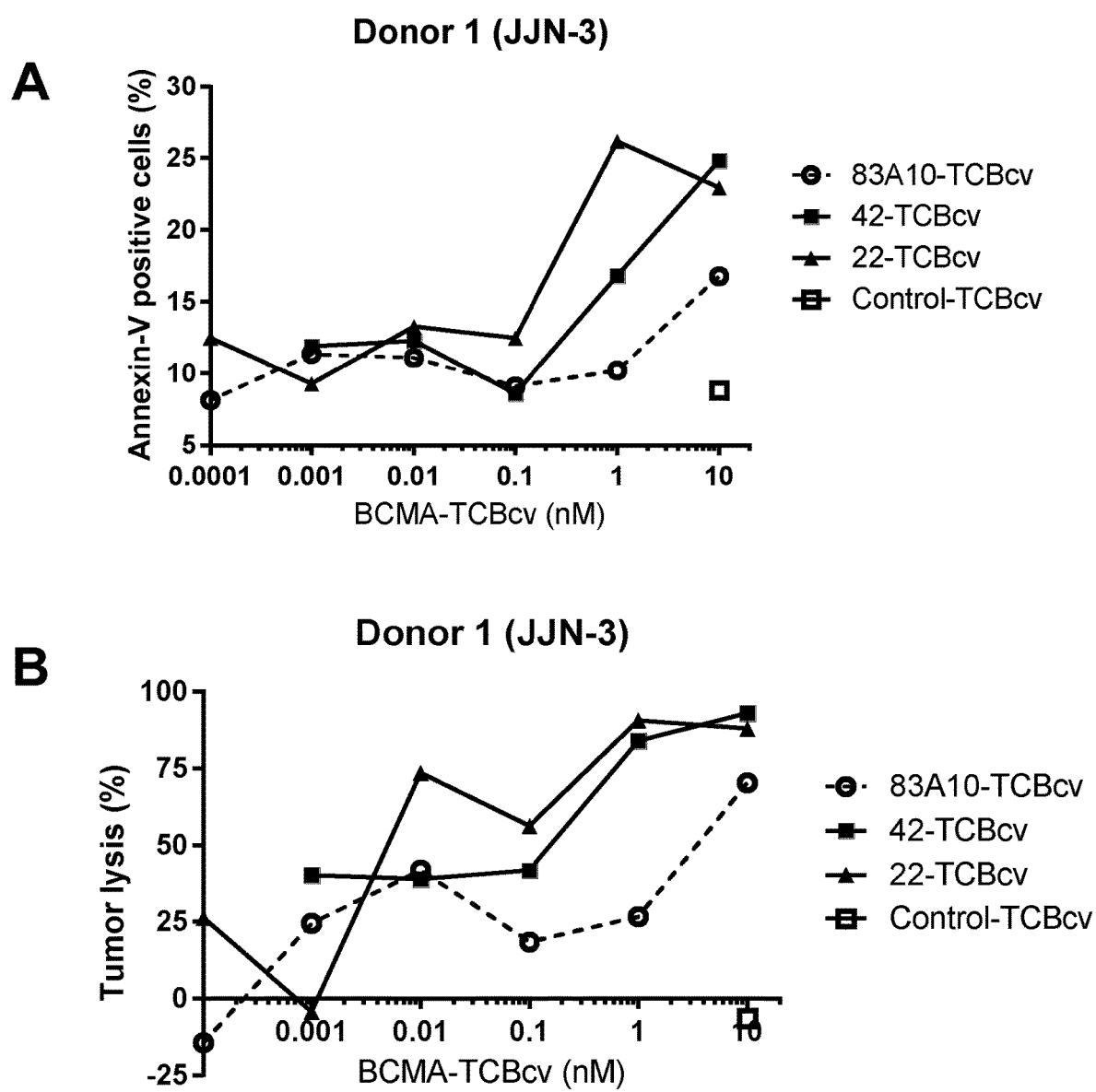
FIG. 7. Redirected T-cell lysis of JJN-3 MM cells induced by anti-BCMA/anti-CD3 T-cell bispecific antibodies as measured by flow cytometry. Concentration-dependent killing of JJN-3 MM cells by 22-TCBcv (closed triangle), 42-TCBcv (closed square) in comparison with 83A10-TCBcv (open circle, dotted line). Percentage of annexin-V positive JJN-3 cells (A, C) and tumor cell lysis (B, D) were determined and plotted. The percentage of lysis of JJN-3 cells induced by a specific concentration of anti-BCMA/anti-CD3 T cell bispecific antibody determined as the following: the absolute count of annexin-V-negative JJN-3 cells at a given TCB concentration and subtracting it from the absolute count of annexin-V-negative JJN-3 cells without TCB; divided by the absolute count of annexin-V-negative JJN-3 cells without TCB. Experiments were performed with 2 PBMC donors: donor 1 (A, B) and donor 2 (C, D) using an E:T ratio of 10 PBMCs to 1 MM cell (see example 11).

Anti-BCMA/anti-CD3 TCB antibodies were analyzed for their ability to induce T cell-mediated apoptosis in BCMA low-expressing MM cells upon crosslinking of the construct via binding of the antigen binding moieties to BCMA on cells. Briefly, human BCMA low-expressing JJN-3 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Human PBMCs (effector cells) were added into the wells to obtain a final E:T ratio of 10:1, corresponding to a E:T ratio of approximately 3 to 5 T cells for 1 tumor target cells. Negative control groups were represented by effector or target cells only. For normalization, maximal lysis of the MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody.

i) After 48 h incubation at 37° C., 5% $CO_2$, the cultured myeloma cells were collected, washed and stained with fluorochrome-conjugated antibodies and Annexin-V for determination of apoptotic myeloma cells. The staining panel comprised CD138-APCC750/CD38-FITC/CD5-BV510/CD56-PE/CD19-PerCP-Cy7/CD45-V450/Annexin-V-PerCP-Cy5.5. Fluorochrome-labelled antibodies used were purchased from BD Biosciences (San Jose, Calif.) and Caltag Laboratories (San Francisco Calif.). Acquisition was performed using a multicolor flow cytometer and installed software (e.g. CantoII device running FACS Diva software or FACSCalibur flow cytometer using the CellQUEST software). The Paint-A-Gate PRO program (BD Biosciences) was used for data analysis. Annexin-V was measured on JJN-3 cells and the percentage of annexin-v-positive JJN-3 cells was plotted against the concentration of anti-BCMA/anti-CD3 T cell bispecific antibodies. The percentage of lysis of JJN-3 cells induced by a specific concentration of anti-BCMA/anti-CD3 T cell bispecific antibody was also determined by measuring the absolute count of annexin-V-negative JJN-3 cells at a given TCB concentration and subtracting it from the absolute count of annexin-V-negative JJN-3 cells without TCB; divided by the absolute count of annexin-V-negative JJN-3 cells without TCB. FIG. 7 shows that anti-BCMA/anti-CD3 TCB antibodies (22-, 42-, and 83A10-TCBcv) induced a concentration-dependent killing of BCMA low-expressing JJN-3 myeloma cells as measured by flow cytometry. The lysis of JJN-3 cells was specific since control-TCB antibody which does not bind to BCMA-positive target cells but only to CD3 on T cells did not induce increase in annexin-v positive JJN-3 cells or JJN-3 cell lysis, even at the highest concentration tested. Table 14 and Table 15 summarize respectively the percentages of annexin-v positive JJN-3 cells and percentages of lysis of JJN-3 cells induced by anti-BCMA/anti-CD3 TCB antibodies.

Detection of LDH is also performed after 20-24 h or 48 h incubation at 37° C., 5% $CO_2$. LDH release from the apoptotic/necrotic JJN-3 MM target cells into the supernatant is then measured with the LDH detection kit (Roche Applied Science), following the manufacturer's instructions. The percentage of LDH release is plotted against the concentrations of anti-BCMA/anti-CD3 T cell bispecific antibodies in concentration-response curves. The EC50 values are measured using Prism software (GraphPad) and determined as the TCB antibody concentration that results in 50% of maximum LDH release.

TABLE 14

Redirected T-cell killing of BCMA low-expressing JJN-3 cells induced by anti-BCMA/anti-CD3 TCB antibodies: percentages of annexin-V positive cells

| Annexin-V positive JJN-3 cells (%) | Anti-BCMA/anti-CD3 TCB concentration (pM) | | | | | | |
|---|---|---|---|---|---|---|---|
| | 10000 | 1000 | 100 | 10 | 1 | 0.1 | 0 |
| Experiment 1 | | | | | | | |
| 83A10-TCBcv | 16.78 | 10.21 | 9.12 | 11.11 | 11.36 | 8.14 | 9.6 |
| 42-TCBcv | 24.83 | 16.84 | 8.62 | 12.3 | 11.9 | / | 9.6 |
| 22-TCBcv | 22.95 | 26.15 | 12.48 | 13.29 | 9.3 | 12.48 | 9.6 |
| Control-TCB | 8.84 | / | / | / | / | / | / |
| Experiment 2 | | | | | | | |
| 83A10-TCBcv | 22.86 | 17.53 | 16.5 | 15.94 | 14.32 | 13.07 | 10.74 |
| 42-TCBcv | 26.88 | 21.68 | 14.42 | 13.6 | 13.47 | 12.75 | 10.74 |
| 22-TCBcv | 29.72 | 26.97 | 18.35 | 15.94 | 15 | 14.8 | 10.74 |
| Control-TCB | 12.82 | / | / | / | / | / | / |

TABLE 15

Redirected T-cell killing of BCMA low-expressing JJN-3 cells induced by anti-BCMA/anti-CD3 TCB antibodies: percentages of lysis of JJN-3 cells

| Lysis of JJN-3 cells (%) | Anti-BCMA/anti-CD3 TCB concentration (pM) | | | | | | |
|---|---|---|---|---|---|---|---|
| | 10000 | 1000 | 100 | 10 | 1 | 0.1 | 0 |
| Experiment 1 | | | | | | | |
| 83A10-TCBcv | 70.30 | 26.66 | 18.43 | 41.88 | 24.42 | −14.45 | 0.00 |
| 42-TCBcv | 92.92 | 84.02 | 41.87 | 38.96 | 40.29 | / | 0.00 |
| 22-TCBcv | 88.02 | 90.54 | 56.26 | 73.56 | −4.29 | 26.28 | 0.00 |
| Control-TCB | −6.55 | / | / | / | / | / | / |
| Experiment 2 | | | | | | | |
| 83A10-TCBcv | 51.18 | 25.30 | 20.12 | 39.58 | −1.88 | 22.28 | 0.00 |
| 42-TCBcv | 90.37 | 81.12 | 55.32 | 39.44 | 34.94 | 17.62 | 0.00 |
| 22-TCBcv | 91.21 | 94.12 | 53.03 | 41.66 | 24.36 | 36.47 | 0.00 |
| Control-TCB | 4.18 | / | / | / | / | / | / |

Example 12: BCMA Expression on Bone Marrow Myeloma Plasma Cells from Multiple Myeloma Patients Human cell lines expressing the tumor target of interest are very useful and practical tools for the measurement of TCB antibody potency to induce tumor cell cytotoxicity in presence of T cells and determination of EC50 values and for the ranking of TCB molecules. However, despite being readily accessible and practical human myeloma cell lines have the caveat of not representing the heterogeneity of multiple myeloma, a very complex disease which is characterized by a significant heterogeneity at the molecular level. In addition, myeloma cell lines do not express BCMA receptor with the same intensity and density as some cells express BCMA more strongly than others (e.g. H929 cells vs. RPMI-8226 cells), and such heterogeneity at the cellular level may also be observed among different patients. Throughout academic collaborations with key opinion leaders in multiple myeloma, determination of BCMA expression and density in patient samples and evaluation of the anti-BCMA/anti-CD3 TCB antibodies with clinical patient samples are being investigated. Blood and bone marrow aspirates are collected from multiple myeloma patients after informed consent is given, in accordance with local ethical committee guidelines and the Declaration of Helsinki.

a) BCMA Expression as Detected by Multiparameter Flow Cytometry (Mean Fluorescence Intensity)

To determine the expression of BCMA receptor on bone marrow myeloma cells, immunophenotypic analyses were performed using freshly isolated whole bone marrow aspirates. Erythrocyte-lysed K3-EDTA (ethylenediaminetetraacetic acid) anticoagulated whole bone marrow samples were used for the immunophenotypic analyses. A total of $2 \times 10^6$ cells per tube were stained, lysed, and then washed using a direct immunofluorescence technique and multicolor staining, which was aimed at the specific identification and immunophenotypic characterization of malignant plasma cells identified as $CD138^+$ $CD38^+$ $CD45^+$ $CD19^-$ $CD56^+$. The cells were then stained using a panel of fluorochrome-conjugated antibodies including at least CD38-FITC/CD56-PE/CD19-PerCP-Cy7/CD45-V450/BCMA-APC. Fluorochrome-labelled antibodies used are purchased from BD Biosciences (San Jose, Calif.) and Caltag Laboratories (San Francisco Calif.). In-house APC-conjugated anti-human BCMA antibody was used in the immunophenotypic analyses. Acquisition was performed using a multicolor flow cytometer and installed software (e.g. Cantoll device running FACS Diva software or FACSCalibur flow cytometer using the CellQUEST software). The Paint-A-Gate PRO program (BD Biosciences) was used for data analysis. BCMA expression was measured gated on the malignant plasma cell population and mean fluorescence intensity (MFI) values were determined and compared among the myeloma patients.

TABLE 16

BCMA expression on patient bone marrow myeloma plasma cells as detected by multiparameter flow cytometry (mean fluorescence intensity)

| Patient N° | $MFI_{BCMA}$ |
|---|---|
| P1 | 2863 |
| P2 | 3528 |
| P3 | 602 |
| P4 | 389 |
| P5 | 955 |
| P6 | 1475 |
| P7 | 282 |
| P8 | 1621 |
| P9 | 116 |
| P10 | 125 |
| P11 | 1495 |
| P12 | 2451 |
| P13 | 398 |
| P14 | 2040 |
| P15 | 678 |
| P16 | 945 |
| P17 | 1672 |
| P18 | 1491 |
| P19 | 2198 |
| P20 | 1058 |
| P21 | 3594 |
| P22 | 615 |
| P23 | 159 | b) Determination of BCMA Specific Antigen Binding Capacity (Quantitative Flow Cytometry Analysis)

The Qifikit (Dako) method was used to quantify BCMA specific antigen binding capacity (SABC) on the cell surface of patient bone marrow myeloma plasma cells. Myeloma plasma cells isolated from whole bone marrow aspirates were stained with 50 μl of mouse anti-human BCMA IgG (BioLegend #357502) or a mouse IgG2a isotype control (BioLegend #401501) diluted in FACS buffer (PBS, 0.1% BSA) to a final concentration of 25 μg/ml (or at saturation concentrations) and staining was performed for 30 min at 4° C. in the dark. Next, 100 μl of the Set-up or Calibration Beads were added in separate wells and the cells, as well as the beads were washed twice with FACS buffer. Cells and beads were resuspended in 25 μl FACS buffer, containing fluorescein conjugated anti-mouse secondary antibody (at saturation concentrations), provided by the Qifikit. Cells and beads were stained for 45 min at 4° C. in the dark. The cells were washed once and all samples were resuspended in 100 μl FACS buffer. Samples were analyzed immediately on a multicolor flow cytometer and installed software (e.g. Cantoll device running FACS Diva software or FACSCalibur flow cytometer using the CellQUEST software).

TABLE 17

BCMA specific antigen binding capacity on patient bone marrow myeloma plasma cells as measured by quantitative flow cytometry analysis

| Patient N° | $SABC_{BCMA}$ |
|---|---|
| P1 | n/a |
| P2 | n/a |
| P3 | 679 |
| P4 | 145 |
| P5 | 957 |
| P6 | 969 |
| P7 | 554 |
| P8 | 4479 |
| P9 | 350 |
| P10 | 414 |
| P11 | 2756 |
| P12 | 2911 |
| P13 | 1267 |
| P14 | 3453 |
| P15 | 1006 |
| P16 | 1097 |
| P17 | 1622 |
| P18 | 429 |
| P19 | 1684 |
| P20 | 383 |
| P21 | 1602 |
| P22 | 799 |
| P23 | 204 |

Example 13: Redirected T-Cell Cytotoxicity of Bone Marrow Patient Myeloma Plasma Cells in Presence of Autologous Bone Marrow Infiltrating T Cells Induced by Anti-BCMA/Anti-CD3 T Cell Bispecific Antibodies (Multiparameter Flow Cytometry)

One of the most meaningful and critical in vitro characterization during preclinical evaluation of TCB antibody candidates for multiple myeloma is whether the TCB molecule could activate the patients' T cells and induce redirected T-cell killing of primary myeloma plasma cells from the patients' bone marrow. To evaluate the effect of anti-BCMA/anti-CD3 TCB antibodies to induce redirected T-cell killing of bone marrow myeloma plasma cells, whole bone marrow aspirates were collected from multiple myeloma patients in EDTA-coated tubes and immediately used for the cell culture assays. The ratio of effector cells to tumor cells (E:T ratio) present in the whole bone marrow samples was determined and measured by flow cytometry. Briefly, 200 μl of bone marrow samples were transferred into 96 deep-well plates. Anti-BCMA/anti-CD3 TCB antibody and control antibody dilutions were prepared in sterile medium and 10 μl of the preparation were added to the respective wells for final concentrations ranging from 0.1 pM to 30 nM. The bone marrow-antibody suspension is mixed by gentle shaking and then incubated at 37° C., 5% $CO_2$ for 48 h, sealed with paraffin film. After the incubation period, 20 μl of a corresponding FACS antibody solution prepared based on an antibody-panel including CD138-APCC750/CD38-FITC/CD5-B V510/CD56-PE/CD19-PerCP-Cy7/CD45-V450/BCMA-APC/Annexin-V-PerCP-Cy5.5 were added into a 96-U-bottom plate. Fluorochrome-labelled antibodies were purchased from BD Biosciences (San Jose, Calif.) and Caltag Laboratories (San Francisco Calif.) and in-house APC-conjugated anti-human BCMA antibody was used. The samples were then incubated for 15 minutes in the dark at room temperature and acquired and analyzed using a multicolor flow cytometer. Cell death of the myeloma cells was determined by evaluating annexin-V positive expression gated on the myeloma cell populations $CD138^+$ $CD38^+$ $CD45^+$ $CD19^-$ $CD56^+$. Percentage of myeloma cell death was then determined. The percentage of lysis of patient bone marrow myeloma plasma cells induced by a specific concentration of anti-BCMA/anti-CD3 T cell bispecific antibody was also determined by measuring the absolute count of annexin-V-negative myeloma plasma cells at a given TCB concentration and subtracting it from the absolute count of annexin-V-negative myeloma plasma cells without TCB; divided by the absolute count of annexin-V-negative myeloma plasma cells without TCB. To verify the specificity of the anti-BCMA/anti-CD3 T cell bispecific antibodies, annexin-V expression was also measured in other bone marrow cell types such as T cells, B cells and NK cells. As shown in FIG. 8, there was a concentration-dependent and specific lysis of patient myeloma plasma cells while lysis of T cells, B cells, and NK cells was not observed. In addition, control-TCB which binds to CD3 only but not to BCMA did not induce cell death of myeloma plasma cells at the highest concentrations of TCB antibodies. As shown in Table 18, percentage of annexin-V positive patient bone marrow myeloma cells at the highest concentration (30 nM) reached up to 52.54% and 55.72% for 42-TCBcv and 22-TCBcv respectively as compared to 29.31% for 83A10-TCBcv, concluding that 42-TCBcv and 22-TCBcv are more potent than 83A10-TCBcv to induce killing of patient bone marrow myeloma plasma cells.

TABLE 18

Percentage of annexin-V positive myeloma plasma cells from patient bone marrow aspirates induced by anti-BCMA/anti-CD3 T cell bispecific antibodies.

| Annexin-V positive myeloma plasma cells (%) | Anti-BCMA/anti-CD3 T cell bispecific antibody concentration (pM) | | | | | |
|---|---|---|---|---|---|---|
| | 30000 | 10000 | 1000 | 100 | 10 | 0 |
| 83A10-TCBcv | 29.31 | 30.95 | 23.14 | 15.74 | 16.76 | 13.11 |
| 42-TCBcv | 52.54 | 39.87 | 29.96 | 10.51 | 19.6 | 13.11 |
| 22-TCBcv | 55.72 | 51.71 | 31.01 | 14.81 | 14.19 | 13.11 |
| Control-TCB | 15.18 | 10.93 | / | / | / | / |

In another study in bone marrow aspirates from 5 different MM patients, the percentage of viable myeloma plasma cells was determined by gating on annexin-V negative cell population and plotted against the concentration of anti-BCMA/anti-CD3 T cell bispecific antibody. The EC50 values were measured and determined as the TCB antibody concentration that results in 50% of maximum viable myeloma plasma cells. EMAX (%) was determined as maximum of viable myeloma plasma cells in presence of respective anti-BCMA/anti-CD3 T cell bispecific antibody. 83A10-TCBcv was much less potent in inducing lysis of myeloma plasma cells than 22-TCBcv and 42-TCBcv in majority of the five myeloma patient bone marrow aspirate samples (Table 26; FIG. 9 shows as example concentration response curves for 2 of the patients). Concentration-dependent reduction of viable myeloma cells was observed in 5/5 patient samples treated with 22-TCBcv or 42-TCBcv, as compared to only ⅕ patient samples for 83A10-TCBcv. Table 19 shows the comparison of 83A10-TCBcv with 22-TCBcv and 42-TCBcv and the effect of the anti-BCMA/anti-CD3 T cell bispecific antibodies on viability of bone marrow myeloma plasma cells. The results clearly show that there were less viable bone marrow myeloma plasma cells with 22-TCBcv and 42-TCBcv (i.e. more lysis of the bone marrow myeloma plasma cells) in ⅘ patient samples as demonstrated by lower EMAX (%) values for 22-TCBcv and 42-TCBcv vs. 83A10-TCBcv in respective patient samples. Concentration-dependent and specific lysis of patient myeloma plasma cells were observed while lysis of non-malignant bone marrow cells was not observed (data not shown).

TABLE 19

EMAX (%) values in respect to annexin-V negative viable myeloma plasma cells from patient bone marrow aspirates in presence of by anti-BCMA/anti-CD3 T cell bispecific antibodies.

| Bone marrow aspirate patient sample (Study 2) | 83A10-TCBcv | 22-TCBcv | 42-TCBcv |
|---|---|---|---|
| | | EMAX (%) | |
| Patient 001 | 100 | 7.6 | 22.6 |
| Patient 003 | 54.3 | 38.9 | 44.6 |
| Patient 004 | 100 | 66.6 | 53.9 |
| Patient 006 | 81.8 | 65.9 | 73.5 |
| Patient 007 | 81.8 | 48.6 | 72.8 |

In a further investigations of the new anti-BCMA/anti-CD3 T cell bispecific antibodies of this invention compared to 83A10-TCBcv, seven freshly taken patient whole bone marrow samples/aspirates were stained with CD138 magnetic microbeads (Miltenyi Biotec, Bergisch Gladbach, Germany), passed through an autoMACS cell separation column and the collected fractions with sufficient remaining number of MM plasma cells of usually >4% myeloma plasma cells were used for further experiments. In 24-well plates, 500,000 cells/well were incubated and cultured for 48 hours. Anti-BCMA/anti-CD3 TCB antibodies and control antibody dilutions were added to the respective wells for a final TCB concentration of 0.1. pM to 10 nM. Each dose point was done in triplicates. Viability of the plasma cells and cells of the bone marrow microenvironment was investigated by propidium iodide/CD138-FITC double-staining using flow cytometry (FACSCalibur; Becton Dickinson). Data analysis was performed using FACSDiva Software (Becton Dickinson). As depicted in FIG. 10, bar plots show mean values normalized on the mean over the triplicates of the respective medium control (MC). For statistical analysis, a one-sided t-test was used. The maximum inhibition of MM plasma cell growth at a concentration of 10 nM (IMAX10) and the inhibition measured at 1 nM (IMAX1), respectively, were given in percent as referred to the medium control. The maximum inhibition of the control-TCB antibody (10 nM) compared to the medium control was also depicted. Computations were performed using R 3.1.19, and Bioconductor 2.1310, but for calculation of the IMAX values (Microsoft Excel®; Microsoft Office Professional 2013). An effect was considered statistically significant if the P-value of its corresponding statistical test was <5% (*), <1% () or <0.1% (*). As shown in FIGS. 10A-10G, the results clearly show that there were less viable bone marrow myeloma plasma cells with 22-TCBcv and 42-TCBcv (i.e. more lysis of the bone marrow myeloma plasma cells) in 7/7 patient samples as compared to 83A10-TCBcv. Table 20 demonstrates the percentage of viable myeloma plasma cells from patient bone marrow aspirates induced by anti-BCMA/anti-CD3 T cell bispecific antibodies relative to medium control. Table 21 shows the IMAX10 and IMAX1 values. The results demonstrate that 22-TCBcv and 42-TCBcv are clearly more potent than 83A10-TCBcv to induce killing of patient bone marrow myeloma plasma cells. Despite specific lysis of bone marrow plasma cells (BMPC) induced by the anti-BCMA/anti-CD3 T cell bispecific antibodies and observed in all bone marrow patient samples, the bone marrow microenvironment (BMME) was unaffected in the respective samples (FIG. 10H, representative of 7 patient samples).

TABLE 20

Relative percentage of propidium iodide negative viable myeloma plasma cells from patient bone marrow aspirates induced by anti-BCMA/anti-CD3 T cell bispecific antibodies.

|  | Anti-BCMA/anti-CD3 T cell bispecific antibody concentration (nM) | | | |
| --- | --- | --- | --- | --- |
|  | 0.01 | 0.1 | 1 | 10 |
| Patient sample No. 1/Viable myeloma plasma cells (%) | | | | |
| 83A10-TCBcv | 181.3 | 106.3 | 31.3 | 9.4 |
| 42-TCVcv | 81.3 | 15.6 | 9.4 | 9.4 |
| 22-TCVcv | 37.5 | 6.3 | 6.3 | 9.4 |
| Ctrl-TCB | / | / | / | 162.5 |
| Patient sample No. 2/Viable myeloma plasma cells (%) | | | | |
| 83A10-TCBcv | 89.5 | 31.6 | 5.3 | 0 |
| 42-TCVcv | 42.1 | 10.5 | 0 | 0 |
| 22-TCVcv | 15.8 | 5.3 | 0 | 0 |
| Ctrl-TCB | / | / | / | 94.7 |

TABLE 20-continued

Relative percentage of propidium iodide negative viable myeloma plasma cells from patient bone marrow aspirates induced by anti-BCMA/anti-CD3 T cell bispecific antibodies.

|  | Anti-BCMA/anti-CD3 T cell bispecific antibody concentration (nM) | | | |
| --- | --- | --- | --- | --- |
|  | 0.01 | 0.1 | 1 | 10 |
| Patient sample No. 3/Viable myeloma plasma cells (%) | | | | |
| 83A10-TCBcv | 76.7 | 35.0 | 1.7 | 0 |
| 42-TCVcv | 13.3 | 0 | 0 | 0 |
| 22-TCVcv | 3.3 | 0 | 0 | 0 |
| Ctrl-TCB | / | / | / | 86.7 |
| Patient sample No. 4/Viable myeloma plasma cells (%) | | | | |
| 83A10-TCBcv | 93.9 | 51.5 | 9.1 | 6.1 |
| 42-TCVcv | 9.1 | 0 | 0 | 0 |
| 22-TCVcv | 15.2 | 15.2 | 0 | 0 |
| Ctrl-TCB | / | / | / | 127.3 |
| Patient sample No. 5/Viable myeloma plasma cells (%) | | | | |
| 83A10-TCBcv | 100 | 91.4 | 62.9 | 20.0 |
| 42-TCVcv | 71.4 | 34.3 | 22.9 | 11.4 |
| 22-TCVcv | 20.0 | 22.9 | 14.3 | 11.4 |
| Ctrl-TCB | / | / | / | 85.7 |
| Patient sample No. 6/Viable myeloma plasma cells (%) | | | | |
| 83A10-TCBcv | 55.6 | 22.2 | 6.7 | 4.4 |
| 42-TCVcv | 35.6 | 6.7 | 4.4 | 4.4 |
| 22-TCVcv | 24.4 | 3.3 | 8.9 | 2.2 |
| Ctrl-TCB | / | / | / | 117.8 |
| Patient sample No. 7/Viable myeloma plasma cells (%) | | | | |
| 83A10-TCBcv | 84.4 | 82.6 | 46.8 | 19.3 |
| 42-TCVcv | 67.0 | 33.9 | 12.8 | 5.5 |
| 22-TCVcv | 24.4 | 3.3 | 8.9 | 2.2 |
| Ctrl-TCB | / | / | / | 106.4 |

TABLE 21

IMAX10 and IMAX1 values in respect to maximal inhibition of MM plasma cell growth at 10 nM IMAX10 and inhibition at 1 nM IMAX1 based on propidium iodide negative viable myeloma plasma cells from patient bone marrow aspirates in presence of by anti-BCMA/anti-CD3 T cell bispecific antibodies.

| Patient Sample No. | 83A10-TCBcv | | 42-TCBcv | | 22-TCBcv | | Ctrl-TCB |
| --- | --- | --- | --- | --- | --- | --- | --- |
|  | IMAX10 (%) | IMAX1 (%) | IMAX10 (%) | IMAX1 (%) | IMAX10 (%) | IMAX1 (%) | IMAX10 (%) |
| 1 | 90.6 | 68.8 | 90.6 | 90.6 | 90.6 | 93.8 | −62.5 |
| 3 | 100 | 94.7 | 100 | 100 | 100 | 100 | 5.3 |
| 4 | 100 | 98.3 | 100 | 100 | 100 | 100 | 13.3 |
| 5 | 93.9 | 90.9 | 100 | 100 | 100 | 100 | −27.3 |
| 6 | 80.0 | 37.1 | 88.6 | 77.1 | 88.6 | 85.7 | 14.3 |
| 7 | 95.6 | 93.3 | 95.6 | 95.6 | 97.8 | 91.1 | −17.8 |
| 8 | 80.7 | 53.2 | 94.5 | 87.2 | 97.2 | 97.2 | −6.4 |

Example 14: T-Cell Activation of Patient Bone Marrow T Cells Induced by Anti-BCMA/Anti-CD3 T Cell Bispecific Antibodies (Multiparameter Flow Cytometry)

To evaluate whether anti-BCMA/anti-CD3 TCB antibodies induce activation of myeloma patient CD4+ and CD8+ T cells (i.e. bone marrow infiltrated T cells (MILs)), the samples from the respective treated, untreated and control groups after 48 h of incubation were also stain with a FACS antibody solution prepared based on an antibody-panel including eight markers: CD8/CD69/TIM-3/CD16/CD25/CD4/HLA-DR/PD-1. The samples were then incubated for 15 minutes in the dark at room temperature and acquired and analyzed using a multicolor flow cytometer. T-cell activation was determined by evaluating CD25, CD69 and/or HLA-DR positive expression gated on CD4+ and CD8+ T-cell populations. Percentages of T-cell activation were then measured. FIG. 11 shows a concentration-dependent upregulation of CD69 and CD25 on bone marrow-infiltrated CD4+ and CD8+ T cells from multiple myeloma patients. Table 22 summarizes the increase of CD69 and CD25 expression on CD4+ and CD8+ T cells induced by anti-BCMA/anti-CD3 TCB antibodies; data from one patient.

TABLE 22

T-cell activation of myeloma patient autologous T cells induced by anti-BCMA/anti-CD3 T-cell bispecific antibodies in presence of patient bone marrow myeloma plasma cells

| | Anti-BCMA/anti-CD3 T cell bispecific antibody concentration (pM) | | | | | |
|---|---|---|---|---|---|---|
| | 30000 | 10000 | 1000 | 100 | 10 | 0 |
| CD69+/CD4 T cells (%) | | | | | | |
| 83A10-TCBcv | 21.8 | 14.93 | 1.80 | 0.93 | 1.02 | 0.85 |
| 42-TCBcv | 29.6 | 24.8 | 1.90 | 1.57 | 0.94 | 0.85 |
| 22-TCBcv | 34.99 | 30.72 | 3.62 | 1.69 | 2.31 | 0.85 |
| Control-TCB | 0.7 | 0.62 | / | / | / | / |
| CD69+/CD8 T cells (%) | | | | | | |
| 83A10-TCBcv | 25.50 | 22.07 | 8.330 | 5.60 | 5.14 | 5.30 |
| 42-TCBcv | 23.61 | 24.22 | 11.125 | 9.26 | 6.28 | 5.30 |
| 22-TCBcv | 25.48 | 28.14 | 11.460 | 6.64 | 14.08 | 5.30 |
| Control-TCB | 5.71 | 4.93 | / | / | / | / |
| CD25+/CD4 T cells (%) | | | | | | |
| 83A10-TCBcv | 17.47 | 12.86 | 5.18 | 4.58 | 4.07 | 7.5 |
| 42-TCBcv | 8.65 | 7.42 | 3.51 | 2.71 | 2.81 | 7.5 |
| 22-TCBcv | 12.34 | 11.52 | 5.23 | 4.89 | 4.90 | 7.5 |
| Control-TCB | 6.90 | 6.50 | / | / | / | / |
| CD25+/CD8 T cells (%) | | | | | | |
| 83A10-TCBcv | 9.79 | 6.560 | 0.42 | 0.13 | 0.12 | 0.12 |
| 42-TCBcv | 2.20 | 2.231 | 0.42 | 0.14 | 0.08 | 0.12 |
| 22-TCBcv | 3.57 | 4.110 | 0.65 | 0.10 | 0.08 | 0.12 |
| Control-TCB | 0.09 | 0.100 | / | / | / | / |

Example 15: Increased T-Cell Function (Cytokine Production) of Patient Bone Marrow T Cells Induced by Anti-BCMA/Anti-CD3 T Cell Bispecific Antibodies (Multiplexed-Bead Based Immunoassay/Flow Cytometry)

To evaluate whether anti-BCMA/anti-CD3 TCB antibodies (83A10-TCBcv, 22-TCBcv and 42-TCBcv) induce T-cell activation and increased function of myeloma patient bone marrow infiltrating CD4+ and CD8+ T cells, supernatant were collected from the culture of the respective treated, untreated and control groups after 48 h of incubation and the content of cytokines and serine proteases were measured. The cytokine bead array (CBA) analysis is performed on a multicolor flow cytometer according to manufacturer's instructions, using either the Human Th1/Th2 Cytokine Kit II (BD #551809) or the combination of the following CBA Flex Sets: human granzyme B (BD #560304), human IFN-γ Flex Set (BD #558269), human TNF-α Flex Set (BD #558273), human IL-10 Flex Set (BD #558274), human IL-6 Flex Set (BD #558276), human IL-4 Flex Set (BD #558272), human IL-2 Flex Set (BD #558270).

Figure 12:
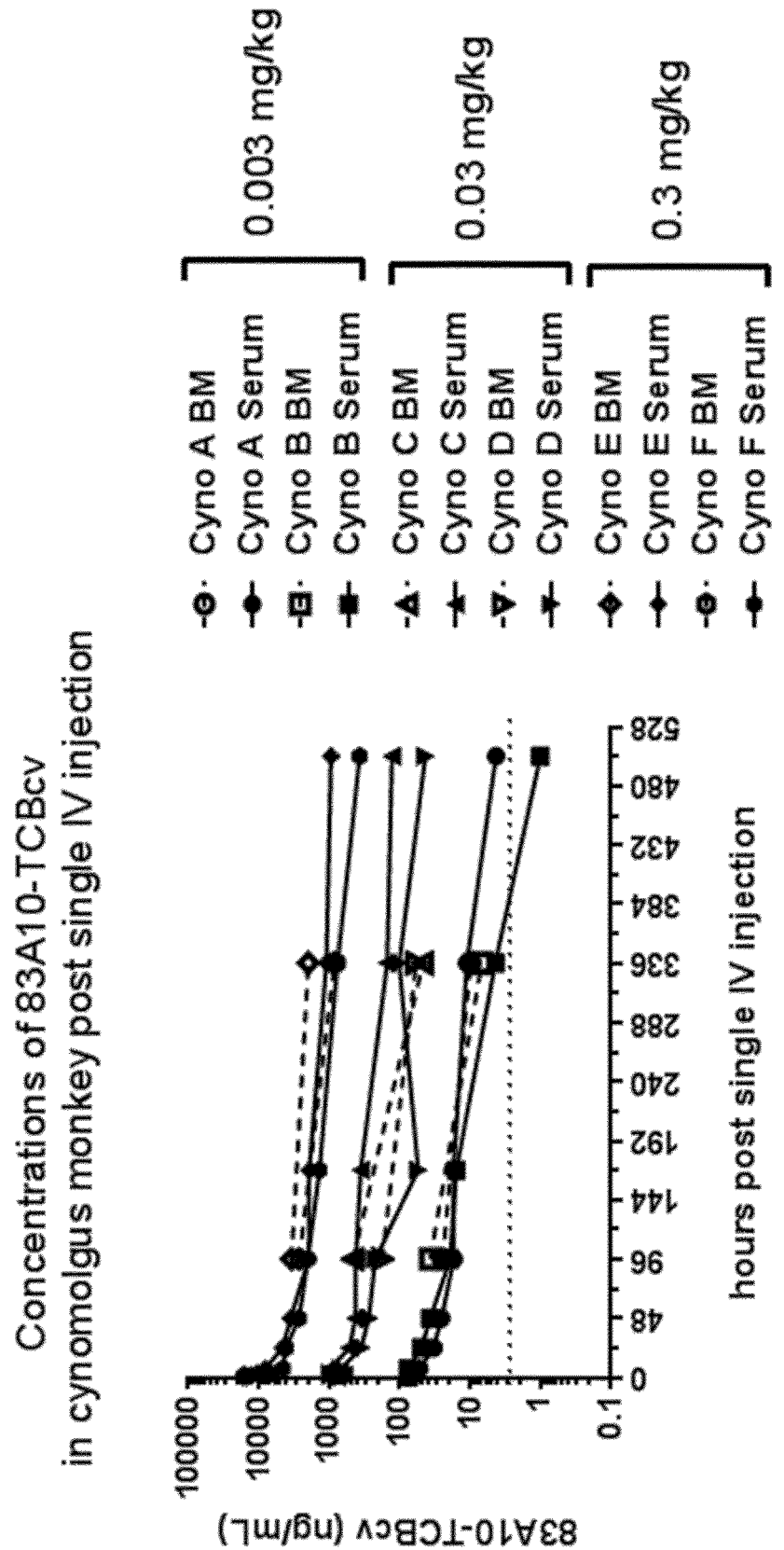
FIG. 12. Concentrations of 83A10-TCBcv measured from serum samples (closed symbols with full lines) and bone marrow samples (open symbols with dotted lines) after single intravenous (IV) injection in cynomolgus monkeys with 0.003, 0.03 and 0.1 mg/kg of 83A10-TCBcv. Serum samples collection was performed at pre-dose and 30, 90, 180 min, 7, 24, 48, 96, 168, 336, 504 h after dosing. Bone marrow samples were collected at pre-dose, and 96 and 336 h after dosing (see example 16).

Example 16: Pharmacokinetic/Pharmacodynamic (PK/PD) Study in Cynomolgus Monkeys A clear advantage an anti-BCMA/anti-CD3 TCBcv antibody could have over other bispecific antibodies such as (scFV)$_2$ (e.g. BCMAxCD3 bispecific T-cell engager BiTE® as described in WO2013072415 and WO2013072406) is the much longer elimination half-life/lower clearance in vivo which could allow a twice or once a week IV or SC administration as compared to the very short elimination half-life of (scFV)$_2$ (e.g. 1 to 4 hours) requiring treatment administered via a pump carried by the patients for weeks to months (Topp et al. J Clin Oncol 2011; 29(18): 2493-8). A twice or once a week administration would be much more convenient for the patients and also much less risky (e.g. failure of pump, issues with the catheter, etc.).

a) To verify the elimination half-life/clearance of anti-BCMA/anti-CD3 83A10-TCBcv antibody in vivo, single dose pharmacokinetic (PK) pharmacodynamic (PD) studies with anti-BCMA/anti-CD3 T-cell bispecific antibodies (83A10-TCBcv, 22-TCBcv and 42-TCBcv) were conducted at experienced AAALAC-accredited CRO. Biologically naïve adult cynomolgus monkeys of about two years old and weighing approximately 3 kg were acclimatized for at least 40 days and selected on the basis of body weight, clinical observations and clinical pathology examinations Animals were identified by Individual tattoos and color-coded cage cards. All the animal procedures (including housing, health monitoring, restrain, dosing, etc) and ethical revision was performed according to the current country legislation enforcing the Directive on the protection of animals used for biomedical research Animals were randomly assigned to the treatment group based on the most recent pretest body weight. After excluding animals with unacceptable pretest findings, a computer program included in the Pristima® system designed to achieve balance with respect to pretest body weights was used to exclude animals from both body weight extremes and randomize the remaining animals to the treatment group. Animals were assigned to three treatment groups with 83A10-TCBcv (n=2 animals i.e. 1 female and 1 male per group) at 0.003; 0.03; and 0.3 mg/kg. Animals received a single i.v. injection of 83A10-TCBcv and at least 0.8 mL of blood samples per timepoint were collected via the peripheral vein for PK evaluations according to the following collection schedule and procedures: Pre-dose, 30, 90, 180 min, 7, 24, 48, 96, 168, 336, 504 h after dosing. Blood samples were allowed to clot in tubes for serum separation for 60 min at room temperature. The clot was spun down by centrifugation (at least 10 min., 1200 g, +4° C.). The resultant serum (about 300 μL) was directly stored at −80° C. until further analysis. Bone marrow samples for PK evaluations were also collected at the femur under anesthesia/analgesic treatment according to the following collection schedule: Pre-dose, 96 and 336 h after dosing. Bone marrow samples were allowed to clot in tubes for serum separation for 60 min at room temperature. The clot was spun down by centrifugation (at least 10 min, 1200 g, +4° C.). The resultant bone marrow (about 1 mL) was directly stored at −80° C. until further analysis. The PK data analysis and evaluation are performed. Standard non compartmental analysis is performed using Watson package (v 7.4, Thermo Fisher Scientific Waltman, MA, USA) or Phoenix WinNonlin system (v. 6.3, Certara Company, USA). As shown in FIG. 12 and Table 23, serum concentrations of 83A10-TCBcv were measured by ELISA from serum samples collected at different timepoints after IV injection. Table 24 shows the concentrations of 83A10-TCBcv in bone marrow as measured by ELISA for each treatment group (BLQ means below level of quantification).

Several information relevant for potential clinical use of a bispecific antibody according to the invention can be taken from FIG. 12, Table 23 and Table 24:

- In bone marrow aspirates from MM patients, concentrations of 1 nM or 10 nM of TCBs of this invention induce significant or even total killing of MM plasma cells; at the dose 0.03 mg/kg in the interval from injection to 168 hours (7 days) plasma concentrations between approx. 1 nM and 4 nM have been achieved showing that once a week therapy with doses of approx. 0.03 mg/kg may well be feasible (200 ng/ml corresponds to approx. 1 nM)
- FIG. 12 shows that in the investigated dose range PK is largely dose linear; that means concentrations are proportional to dose; a useful property for clinical therapy
- MM is a disease mainly located in the bone marrow; Concentrations of 83A10-TCBcv detected in bone marrow are close to serum concentrations (Table 24), e.g. at 96 h after injection bone marrow concentrations of approx. 1 and 2 nM have been measured; these are concentrations of TCB of this invention at which significant killing of MM plasma cells is observed in bone marrow aspirates freshly taken from MM Patients; demonstrating again the opportunity for convenient dosing intervals like once a week
- Between 24 and 504 hours post injection, the elimination is largely first order with an elimination half-life of approx. 6 to 8 days showing again the opportunity for e.g. once a week dosing

TABLE 23

Serum concentrations of 83A10-TCBcv after IV treatment in cynomolgus monkeys 83A10-TCBcv

| Conc. (ng/mL) | 0.003 mg/kg IV | | 0.03 mg/kg IV | | 0.3 mg/kg IV | |
|---|---|---|---|---|---|---|
| | A | B | C | D | E | F |
| Pre-dose | 0.00 | 0.00 | 0.00 | 0.00 | 0.00 | 0.00 |
| 30 min | 75.69 | 74.99 | 668.66 | 796.54 | 17207.20 | 14943.95 |
| 90 min | 70.92 | 74.56 | 951.81 | 628.72 | 12831.54 | 16248.97 |
| 180 min | 76.54 | 62.55 | 981.42 | 722.27 | 10653.28 | 6824.72 |
| 7 h | 53.17 | 77.39 | 700.67 | 972.38 | 8204.77 | 4560.36 |
| 24 h | 33.16 | 50.41 | 358.90 | 532.11 | 4609.28 | 4127.41 |
| 48 h | 26.05 | 37.40 | 279.80 | 433.30 | 3546.09 | 2700.43 |
| 96 h | 17.28 | 19.52 | 226.01 | 429.80 | 1959.96 | 2006.92 |
| 168 h | 17.33 | 15.87 | 55.58 | 365.67 | 1918.06 | 1382.57 |
| 336 h | 11.21 | 4.43 | 102.94 | 153.54 | 1102.96 | 773.55 |
| 504 h | 4.33 | BLQ | 43.99 | 130.14 | 952.03 | 377.04 |

TABLE 24

Bone marrow concentrations of 83A10-TCBcv after single IV treatment in cynomolgus monkeys

| Conc. (ng/mL) | 0.003 mg/kg | | 0.03 mg/kg | | 0.3 mg/kg | |
|---|---|---|---|---|---|---|
| | A | B | C | D | E | F |
| Pre-dose | 0.00 | 0.00 | 0.00 | 0.00 | 0.00 | 0.00 |
| 96 h | 25.07 | 37.15 | 179.87 | 469.08 | 3432.54 | 2674.70 |
| 336 h | 9.92 | 6.90 | 59.39 | 47.22 | 1987.48 | 850.87 |

Figure 13:
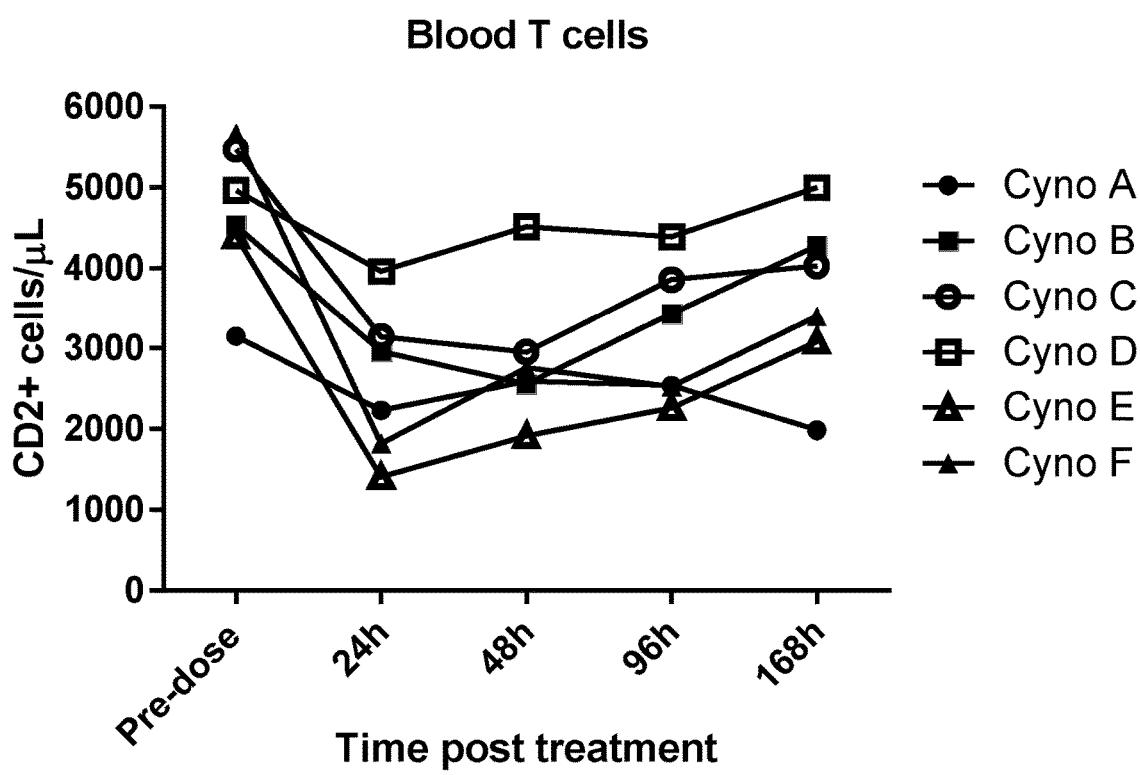
FIG. 13. Peripheral T-cell redistribution observed in cynomolgus monkeys following a single IV injection of 83A10-TCBcv (0.003, 0.03 and 0.3 mg/kg). Animals A and B, C and D, and E and F respectively received an IV injection of 0.003, 0.03 and 0.3 mg/kg of 83A10-TCBcv. Absolute blood T-cell counts (CD2+ cells per μL of blood) were plotted against time post treatment (see example 16).
Figure 14A:
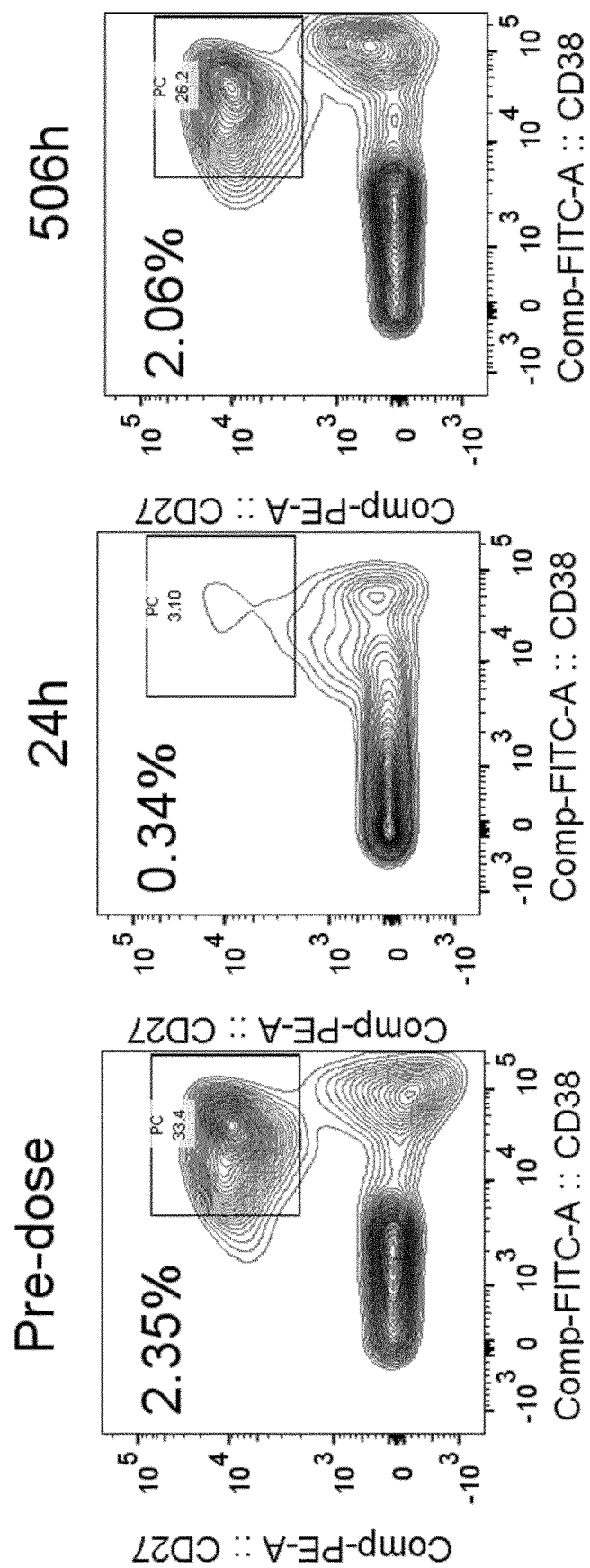
FIG. 14. Reduction of blood plasma cells observed in cynomolgus monkeys following a single IV injection of 83A10-TCBcv (0.3 mg/kg) as measured by multiparameter flow cytometry. Plasma cells (PCs) were identified based on a 6-color staining panel and percentages of PCs over lymphocytes were measured and plotted in contour plots (A). Kinetic of blood plasma cell depletion after treatment with 83A10-TCBcv 0.3 mg/kg in cynomolgus monkeys was plotted (B) (see example 16).
Figure 14B:
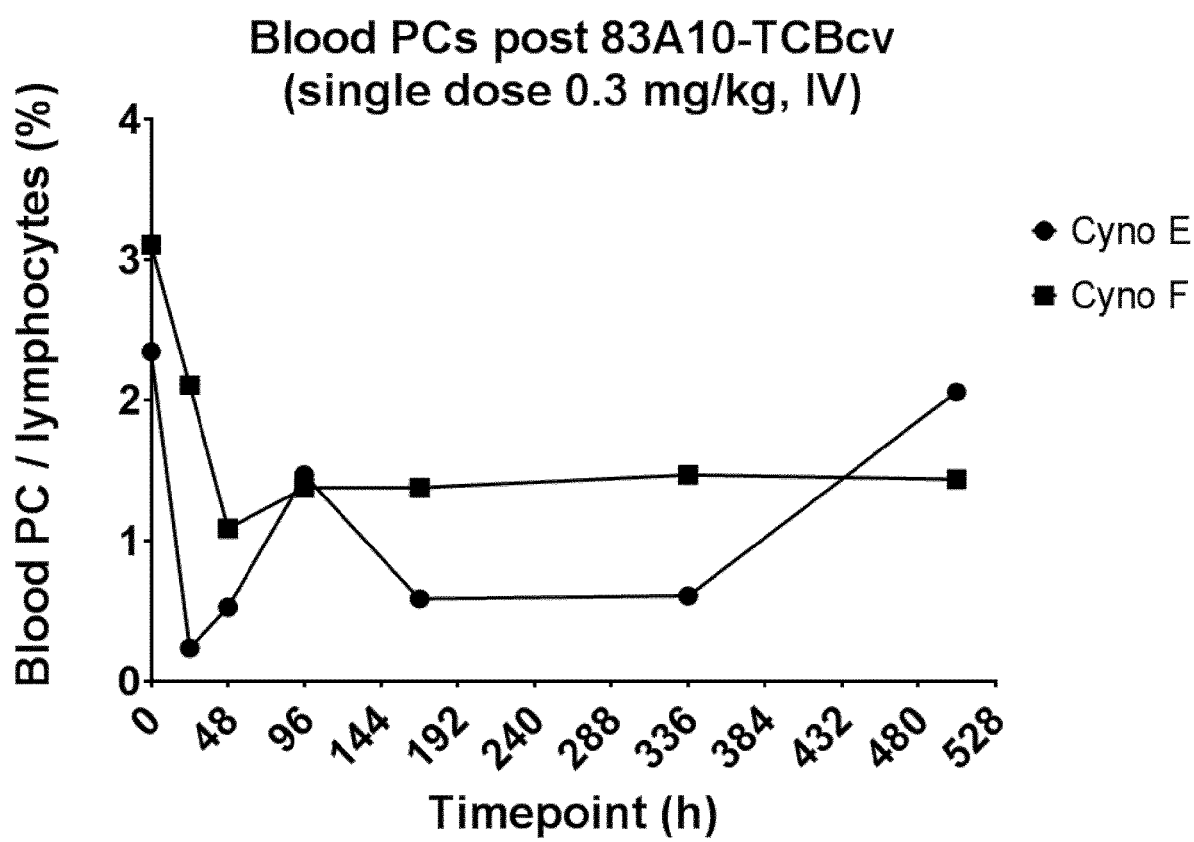

Pharmacodynamics (PD) measurements: Blood samples (timepoints: pre-dose, 24, 48, 96, 168, 336, 504 h after dosing) and bone marrow samples (timepoints: pre-dose, 96 and 336 hs after dosing) were collected in tubes containing 7.5% K3 EDTA for PD evaluation by flow cytometry to evaluate the effect of 83A10-TCBcv give i.v. as single dose on blood and bone marrow plasma cells, B cells, and T cells. A "lyse and wash" direct immunofluorescence staining method of the surface markers was applied. Briefly, 100 µL of blood or bone marrow was incubated with two antibody mixtures including CD45/CD2/CD16/CD20/CD27/CD38 or CD45/CD2/CD16/CD4/CD25/CD8 in the dark for 30 min at +4° C. To lyse red blood cells, 2 mL of lysing buffer solution was added to the sample and incubated 15 min at room temperature in the dark. Cells were collected by centrifugation and washed with staining buffer (PBS 2% Fetal Bovine Serum). The stained samples were kept refrigerated, protected from light, until acquisition with cytometer on the same day. FACS data acquisition was performed with a Becton Dickinson flow cytometer equipped with 488 and 635 laser lines, BD FACS Canto II. BD FACSDiva software was used for data collection and analysis. The absolute cell number enumeration was performed with a double platform, based upon the WBC count obtained by the hematology analyzer (ADVIA™ 120, Siemens). As shown in FIG. 13, peripheral T-cell redistribution was observed in all animals receiving a single dose IV treatment of 83A10-TCBcv as shown by the decrease in circulating T cell counts. As shown in FIG. 14A, already at 24h after treatment with 83A10-TCBcv 0.3 mg/kg a decrease in blood plasma cells (BCMA-positive cells) was observed in animals treated while there was no decrease in total B cells (BCMA-negative cells). FIG. 14b shows the kinetic of plasma cell reduction in blood after treatment with 83A10-TCBcv 0.3 mg/kg in cynomolgus monkeys.

Blood samples were also processed for plasma collection for cytokine analysis (IL-1b, IL-2, IL-6, IL-10, TNF-α and IFN-γ) in accordance with the following collection schedule: Pre-dose, 30, 90, 180 min, 7, 24, 48, 96, 168 h after dosing. Blood samples were put in plastic tubes kept in an ice-water bath, then centrifuged (at least 10 min., 1200 g, +4° C.). The resultant plasma was directly stored at −80° C. until analysis. Cytokines analysis is performed with Multiplex bead-based cytokine immunoassay (Luminex Technology). Data are analyzed using Bio-Plex Manager 4.1 software (Bio-Rad): a five-parameter logistic regression model (5PL) is used.

b) In a further study, cynomolgus monkeys were treated with 42-TCBcv or 22-TCBcv. Animals (n=2/group) received a single IV (0.01; 0.1; and 1.0 mg/kg) or SC (0.01 and 0.1 mg/kg) injection of 42-TCBcv or single IV injection with 22-TCBCv (0.1 mg/kg). Blood and bone marrow samples are collected at timepoints following a defined collection schedule and processed accordingly for PK and PD measurement (immunophenotyping and cytokine production).

Figure 19:
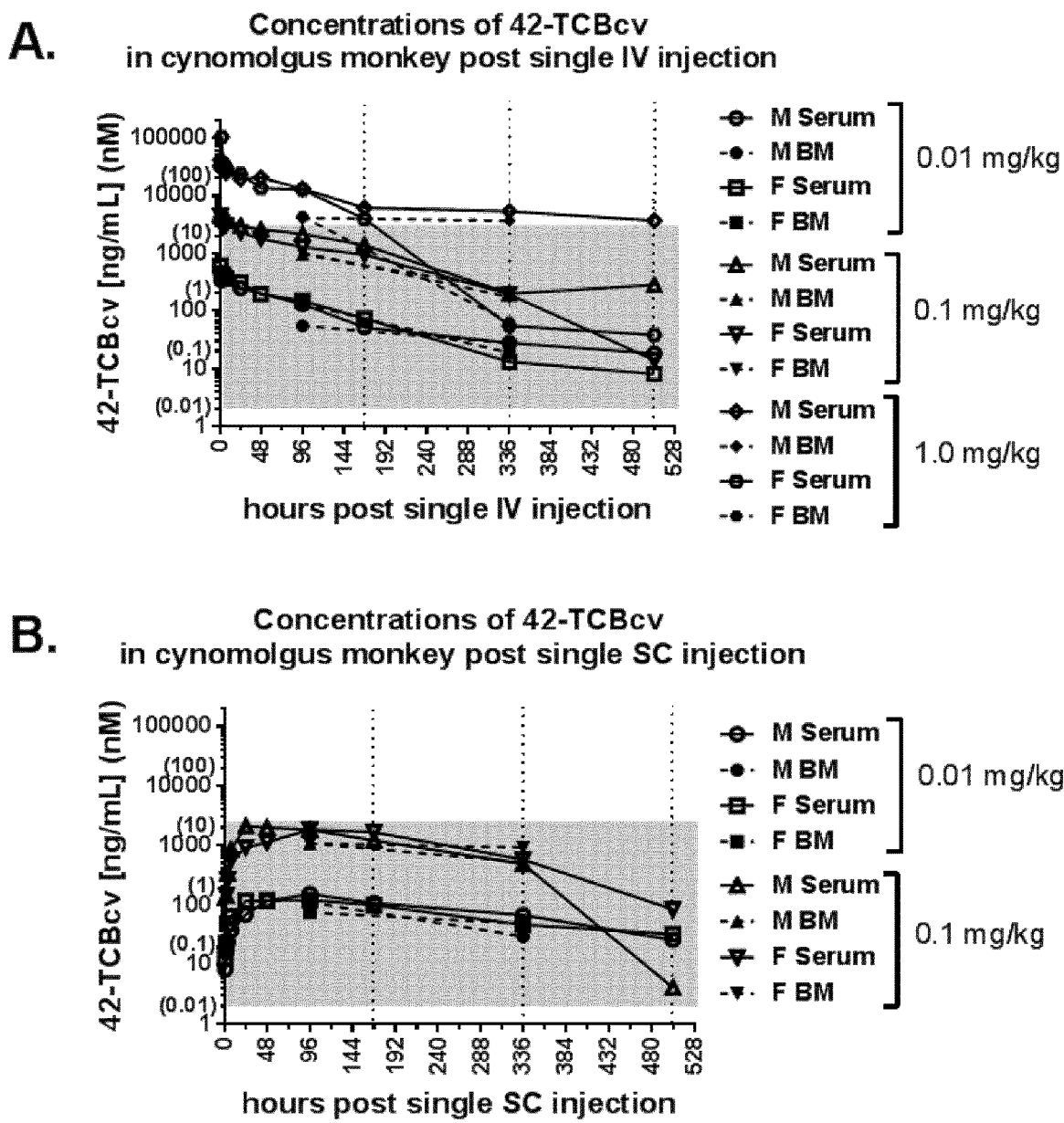
FIG. 19. Concentrations of 42-TCBcv measured in serum and bone marrow after single IV or SC injection in cynomolgus monkeys. Animals received a single IV or SC. injection of 42-TCBcv) and blood samples per timepoint were collected via the peripheral vein for PK evaluations at Pre-dose, 30, 90, 180 min, 7, 24, 48, 96, 168, 336, 504 h after dosing. Blood samples were allowed to clot in tubes for serum separation for 60 min at room temperature. The clot was spun down by centrifugation. The resultant serum was directly stored at −80° C. until further analysis. Bone marrow samples for PK evaluations were also collected at the femur under anesthesia/analgesic treatment at Pre-dose, 96 and 336 h after dosing. Bone marrow samples were allowed to clot in tubes for serum separation for 60 min at room temperature. The clot was spun down by centrifugation. The resultant bone marrow was directly stored at −80° C. until further analysis. The PK data analysis and evaluation were performed. Standard non compartmental analysis was performed using Watson package (v 7.4, Thermo Fisher Scientific Waltman, MA, USA) or Phoenix WinNonlin system (v. 6.3, Certara Company, USA). Effective concentration range of 42-TCBcv in multiple myeloma patient bone marrow aspirates corresponding to 10 pm to 10 nM (grey area). Concentrations in parenthesis are in nM.

Animals received a single IV or SC. injection of 42-TCBcv or 22-TCBcv (only IV) and blood samples per timepoint were collected via the peripheral vein for PK evaluations according to the following collection schedule and procedures: Pre-dose, 30, 90, 180 min, 7, 24, 48, 96, 168, 336, 504 h after dosing. Blood samples were allowed to clot in tubes for serum separation for 60 min at room temperature. The clot was spun down by centrifugation (at least 10 min., 1200 g, +4° C.). The resultant serum (about 300 μL) was directly stored at −80° C. until further analysis. Bone marrow samples for PK evaluations were also collected at the femur under anesthesia/analgesic treatment according to the following collection schedule: Pre-dose, 96 and 336 h after dosing. Bone marrow samples were allowed to clot in tubes for serum separation for 60 min at room temperature. The clot was spun down by centrifugation (at least 10 min, 1200 g, +4° C.). The resultant bone marrow (about 1 mL) was directly stored at −80° C. until further analysis. The PK data analysis and evaluation were performed. Standard non compartmental analysis was performed using Watson package (v 7.4, Thermo Fisher Scientific Waltman, MA, USA) or Phoenix WinNonlin system (v. 6.3, Certara Company, USA). As shown in FIG. 19 and Table 24A-D, concentrations of 42-TCBcv were measured by ELISA from serum and bone marrow samples collected at different timepoints after IV or SC injection. Effective concentration range of 42-TCBcv in multiple myeloma patient bone marrow aspirates corresponding to 10 pm to 10 nM (grey area). Concentrations in parenthesis are in nM. BLQ, below level of quantification; i/m, inconclusive measurement.

TABLE 24A

Serum concentrations of 42-TCBcv after IV treatment in cynomolgus monkeys
42-TCBcv

| Conc. | 0.01 mg/kg IV | | 0.1 mg/kg IV | | 1.0 mg/kg IV | |
|---|---|---|---|---|---|---|
| (ng/mL) | Male | Female | Male | Female | Male | Female |
| Pre-dose | BLQ | BLQ | i/m | BLQ | BLQ | BLQ |
| 30 min | 468.57 | 613.44 | 4720.33 | 4506.64 | 41939.31 | 32677.23 |
| 90 min | 333.09 | 427.16 | 4284.66 | 3214.65 | 30889.73 | 103925.73 |
| 180 min | 392.37 | 422.36 | 4336.89 | 2865.36 | 29201.69 | 36157.78 |
| 7 h | 421.96 | 356.34 | 4028.47 | 3070.84 | 25064.81 | 29962.62 |
| 24 h | 242.64 | 305.74 | 2996.24 | 2321.66 | 19365.86 | 23656.65 |
| 48 h | i/m | 192.97 | 2595.62 | 1781.91 | 20539.59 | 13523.68 |
| 96 h | 128.50 | 148.02 | 2153.34 | 1277.02 | 13147.09 | 12755.58 |
| 168 h | 51.13 | 72.64 | 1388.24 | 948.31 | 6189.79 | 3952.05 |
| 336 h | 27.68 | 13.03 | 195.51 | 190.87 | 5337.85 | 54.15 |
| 504 h | 18.17 | 8.04 | 275.93 | 13.96 | 3678.69 | 37.88 |

TABLE 24B

Bone marrow concentrations of 42-TCBcv after single IV treatment in cynomolgus monkeys
42-TCBcv

| Conc. | 0.01 mg/kg IV | | 0.1 mg/kg IV | | 1.0 mg/kg IV | |
|---|---|---|---|---|---|---|
| (ng/mL) | Female | Male | Female | Female | Male | Female |
| Pre-dose | BLQ | BLQ | 406.99 | BLQ | BLQ | BLQ |
| 96 h | 54.39 | 130.03 | 956.56 | 1022.87 | 4089.88 | 4339.33 |
| 336 h | 27.23 | 18.49 | 227.20 | 170.34 | 3705.74 | 62.44 |

TABLE 24C

Serum concentrations of 42-TCBcv after SC treatment in cynomolgus monkeys
42-TCBcv

| Conc. | 0.01 mg/kg SC | | 0.1 mg/kg SC | |
|---|---|---|---|---|
| (ng/mL) | Male | Female | Male | Female |
| Pre-dose | 4.76 | 12.41 | BLQ | BLQ |
| 30 min | 8.25 | 12.51 | 25.11 | 14.62 |
| 90 min | 16.38 | 22.71 | 140.73 | 145.39 |
| 180 min | 23.75 | 48.51 | 334.95 | 269.66 |
| 7 h | 37.46 | 63.48 | 836.86 | 565.10 |
| 24 h | 68.15 | 115.31 | 2100.42 | 904.22 |
| 48 h | 116.63 | 118.03 | 1956.60 | 1111.06 |
| 96 h | 150.77 | 120.62 | 1810.13 | 1817.52 |
| 168 h | 106.28 | 98.64 | 1192.65 | 1653.26 |
| 336 h | 67.02 | 46.21 | 482.39 | 571.04 |
| 504 h | 25.69 | 31.99 | 4.08 | 83.91 |

TABLE 24D

Bone marrow concentrations of 42-TCBcv after single SC treatment in cynomolgus monkeys
42-TCBcv

| Conc. | 0.01 mg/kg SC | | 0.1 mg/kg SC | |
|---|---|---|---|---|
| (ng/mL) | Female | Male | Female | Female |
| Pre-dose | 5.59 | 10.70 | BLQ | BLQ |
| 96 h | 109.88 | 73.93 | 1064.66 | 1066.79 |
| 336 h | 29.35 | 48.78 | 518.40 | 906.48 |

The results from Tables 24A and 24C show an attractive serum concentration profile suitable for once a week or even once every two weeks treatment with 42-TCBcv. Area under the curve AUC for serum concentrations after IV and SC administration were determined, comparison of the AUC values showed high bioavailability of close to 100% with SC injection of 42-TCBcv. In addition, the results show that concentration of 42-TCBcv in bone marrow is very similar to 42-TCBcv serum concentrations. 42-TCBcv concentrations in the serum could well represent the concentrations of 42-TCBcv available in the bone marrow i.e. at the main location where the myeloma tumor cells are enriched.

Pharmacodynamic (PD) measurements are valuable information to corroborate with PK measurements. Further PD analyses were performed. Cynomolgus $CD20^+$ B cells from blood also express BCMA on the cell surface and are significantly more frequent (higher absolute count) than plasma cells in blood. Blood B-cell depletion was used as a reliable pharmacodynamic effect of anti-BCMA/anti-CD3 TCBcv antibodies and to compare the in vivo efficacy between 83A10-TCBcv, 42-TCBcv and 22-TCBcv.

Absolute B-cell counts were calculated based on the double platform consisting of flow cytometry and WBC count obtained with a hematology analyser and measured at the following timepoints: pre-dose, 24h, 48h, 96h and 196h after 10-min IV infusion. The percentage of B-cell depletion was calculated as followed:

$$= \frac{[\text{absolute } B\text{-cell count at pre-dose}] - [\text{absolute } B\text{-cell count at } timepoint]}{[\text{absolute } B\text{-cell count at pre-dose}] * 100}$$

TABLE 24E

Pharmacodynamic effects of anti-BCMA/anti-CD3 TCBcv antibodies: B-cell depletion

| Time after IV injection (hours) | B-cell depletion relative to pre-dose (%) | | |
|---|---|---|---|
| | 83A10-TCBcv 0.3 mg/kg (n = 2) | 42-TCBcv 0.1 mg/kg (n = 2) | 22-TCBcv 0.1 mg/kg (n = 2) |
| 24 h | 19.9 ± 0.21 | 91.4 ± 3.8 | 77.8 ± 3.7 |
| 48 h | 11.9 ± 17.6 | 88.8 ± 3.9 | 61.5 ± 9.8 |
| 96 h | 5.0 ± 10.8 | 93.0 ± 7.2 | 89.2 ± 4.8 |
| 168 h | −0.23 ± 61.4 | 96.6 ± 3.5 | 91.9 ± 3.9 |

42-TCBcv and 22-TCBcv are more potent than 83A10-TCBcv to induce depletion of BCMA-expressing B cells in cynomolgus monkeys following a single dose IV injection (see Table 24E). Since the three molecules share the same molecular structure and CD3 binder, the difference in efficacy in cynomolgus monkeys could be mainly attributed to the respective BCMA antibody.

To confirm that depletion of BCMA-expressing B cells in cynomolgus monkeys after IV injection is a result of the mechanistic pharmacodynamic effects of anti-BCMA/anti-CD3 TCBcv antibodies, the increase of activated $CD8^+$ cytotoxic T cells (i.e. effector cells) was measured in the bone marrow enriched of BCMA-positive cells (i.e. target cells) 4 days (96 h) and 3 weeks (336h) after IV injection. Absolute $CD8^+$ $CD25^+$ activated T-cell counts were calculated based on the double platform consisting of flow cytometry and WBC count obtained with a hematology analyser

TABLE 24F

Pharmacodynamic effects of anti-BCMA/anti-CD3 TCBcv antibodies: Increase in $CD8^+$ $CD25^+$ activated T cells

| Time after IV injection (hours) | Increase in $CD8^+$ $CD25^+$ activated T cells relative to pre-dose (%) | | |
|---|---|---|---|
| | 83A10-TCBcv 0.3 mg/kg (n = 2) | 42-TCBcv 0.1 mg/kg (n = 2) | 22-TCBcv 0.1 mg/kg (n = 2) |
| 96 h | 284 ± 244% | 585 ± 496% | 1449 ± 1715% |
| 336 h | −0.9 ± 1.3% | 110 ± 187% | −6.6 ± 45.3% |

42-TCBcv and 22-TCBcv are more potent than 83A10-TCBcv to induce T-cell activation in cynomolgus monkeys following a single dose IV injection (see Table 24F). Since the three molecules share the same molecular structure and CD3 binder, the difference in pharmacodynamic effects in cynomolgus monkeys could be mainly attributed to the respective BCMA antibody. The results indicate that depletion of BCMA-positive B cells in bone marrow and in blood is most likely the result of activation of cytotoxic T cells induced by anti-BCMA/anti-CD3 TCBcv antibodies.

Figure 15:
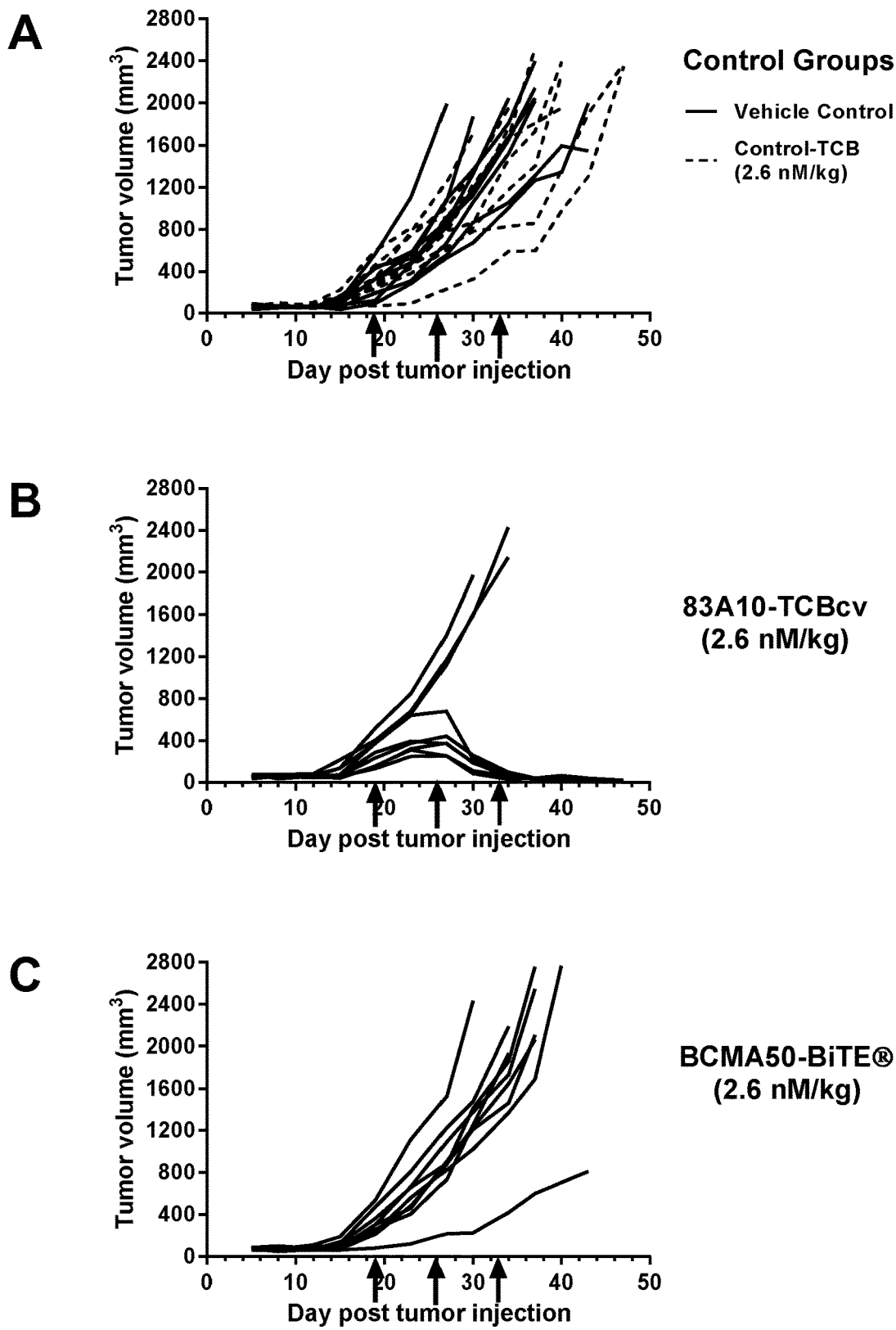
FIG. 15. Antitumoral activity induced by 83A10-TCBcv anti-BCMA/anti-CD3 T cell bispecific antibody in the H929 human myeloma xenograft model using PBMC-humanized NOG mice. Immunodeficient NOD/Shi-scid IL2rgamma (null) (NOG) received on day 0 (d0) human multiple myeloma H929 cells as a subcutaneous (SC) injection into the right dorsal flank. On day 15 (d15), NOG mice received a single intraperitoneal (IP) injection of human PBMCs. Mice were then carefully randomized into the different treatment and control groups (n=9/group) and a statistical test was performed to test for homogeneity between groups. The experimental groups were the control untreated group, control-TCB treated group, 83A10-TCBcv 2.6 nM/kg treated group and BCMA50-BiTE® (BCMAxCD3 (scFv)$_2$) 2.6 nM/kg treated group. Antibody treatment given by tail vein injection started on day 19 (d19), i.e. 19 days after SC injection of H929 tumor cells. The TCB antibody treatment schedule consisted of a once a week IV administration for up to 3 weeks (i.e. total of 3 injections of TCB antibody). Tumor volume (TV) was measured by caliper during the study and progress evaluated by intergroup comparison of TV. TV (mm3) plotted against day post tumor injection. On d19, first day of treatment, the mean tumor volume had reached 300±161 mm3 for the vehicle treated control group (A), 315±148 mm3 for the 2.6 nM/kg control-TCB treated group (A), 293±135 mm3 for the 2.6 nM/kg 83A10-TCBcv group (B) and 307±138 mm3 for the 2.6 nM/kg BCMA50-BiTE® group (C). TV of each individual mouse per experimental group were plotted against day post tumor injection: (A) control groups including vehicle control (full line) and control-TCB (dotted line), (B) 83A10-TCBcv (2.6 nM/kg) group, and (C) BCMA50-BiTE® (2.6 nM/kg). Black arrows show the TCB treatment given by IV injection. In the 83A10-TCBcv (2.6 nM/kg) group, 6 out of 9 mice (67%) had their tumor regressed even below TV recorded at d19 i.e. first TCB treatment and tumor regression was maintained until termination of study. The 3 mice in the 83A10-TCBcv (2.6 nM/kg) treated group which failed to show tumor regression had their TV equal to 376, 402 and 522 mm3 respectively at d19. In contrast, none of the 9 mice (0%) treated with an equimolar dose of BCMA50-BiTE® (2.6 nM/kg) at a once a week schedule for 3 weeks had their tumor regressed at any timepoint (see example 17).
Figure 16:
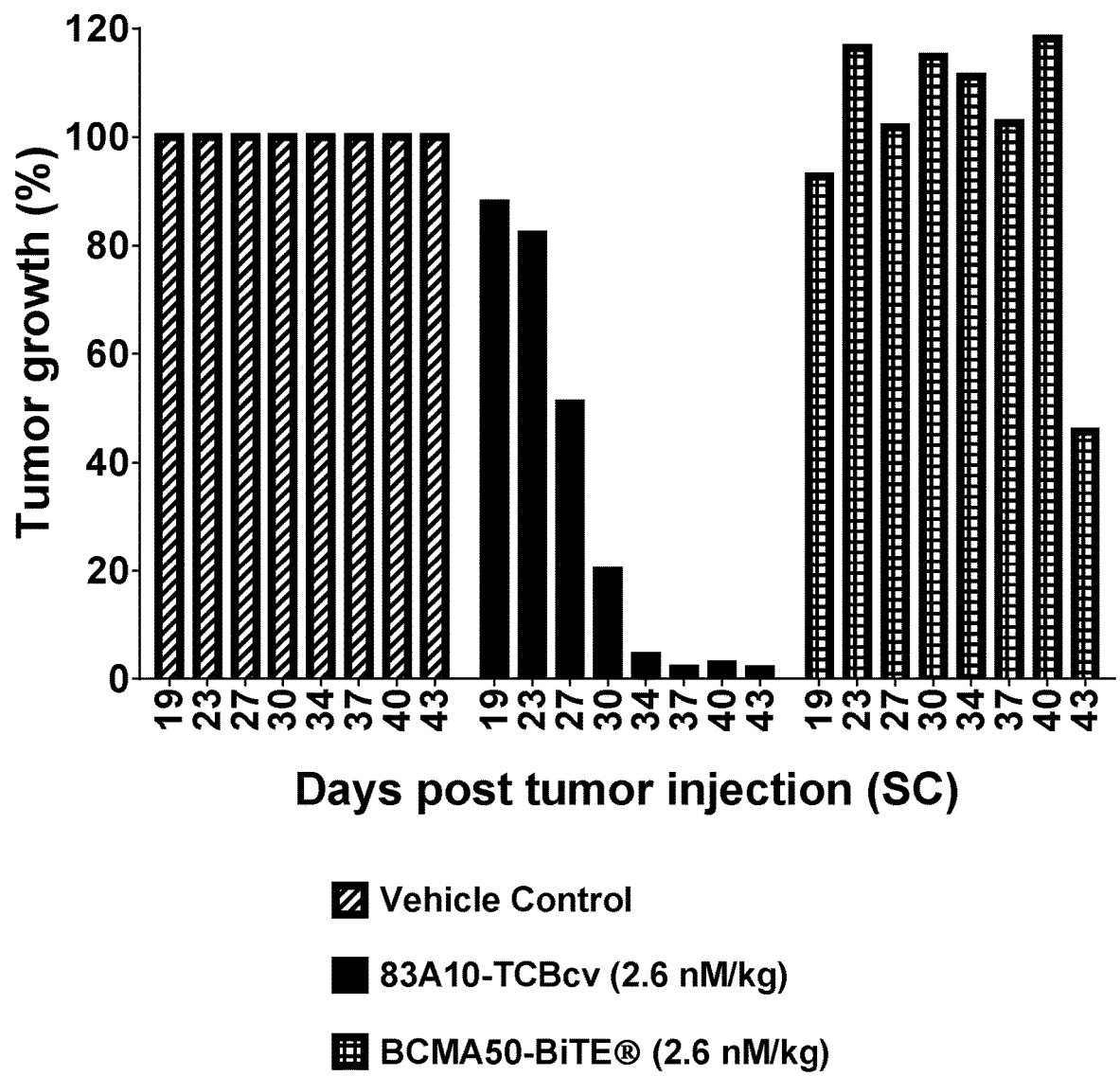
FIG. 16. Percentage of tumor growth (TG) calculated for d19 to d43 and compared between 83A10-TCBcv (2.6 nM/kg) group and BCMA50-BITE® (2.6 nM/kg). The percentage of tumor growth defined as TG (%) was determined by calculating TG (%)=100×(median TV of analyzed group)/(median TV of control vehicle treated group). For ethical reason, mice were euthanized when TV reached at least 2000 mm3 TG (%) was consistently and significantly reduced in the 83A10-TCBcv (2.6 nM/kg) group as well as the TG (%) was always lower when compared to BCMA50-BiTE® (2.6 nM/kg) (see example 17).

Example 17: Antitumoral Activity Induced by Anti-BCMA/Anti-CD3 T Cell Bispecific Antibody in the H929 Human Myeloma Xenograft Model Using PBMC-Humanized NOG Mice With a long elimination half-life, Fc-containing anti-BCMA/anti-CD3 TCBcv antibodies could be more efficacious than $(scFv)_2$-based bispecific antibodies such as BCMA50-BITE® given at equimolar doses, in a once a week schedule. The in vivo effect of 83A10-TCBcv and BCMA50-BiTE® (as described in WO2013072415 and WO2013072406) was compared and evaluated in the H929 human myeloma xenograft model in PBMC-humanized NOG mice. NOG mice are appropriate for humanized mouse models as they completely lack of immune cells including resident NK cell population and are therefore more permissive to tumor engraftment of human xenogeneic cells (Ito et al. Curr Top Microbiol Immunol 2008; 324: 53-76). Briefly, on day 0 (d0) of the study, $5\times10^6$ human myeloma cell line NCI-H929 (NCI-H929, ATCC® CRL-9068™) in 100 μL RPMI 1640 medium containing 50:50 matrigel (BD Biosciences, France) were subcutaneously (SC) injected into the right dorsal flank of immunodeficient NOD/Shi-scid IL2rgamma(null) (NOG) female mice of 8-10 weeks of age (Taconic, Ry, Danemark). Twenty-four to 72 hours prior to H929 tumor cell SC implantation, all mice received a whole body irradiation with a γ-source (1.44 Gy, $^{60}$Co, BioMep, Bretenières, France). On day 15 (d15), NOG mice received a single intraperitoneal (IP) injection of $2\times10^7$ human PBMCs (in 500 μL PBS 1× pH7.4). Characterization of the human PBMC was performed by immunophenotyping (flow cytometry). Mice were then carefully randomized into the different treatment and control groups (n=9/group) using Vivo Manager® software (Biosystemes, Couternon, France) and a statistical test (analysis of variance) was performed to test for homogeneity between groups. Antibody treatment started on day 19 (d19), i.e. 19 days after SC injection of H929 tumor cells when the tumor volume had reached at least 100-150 $mm^3$ in all mice, with a mean tumor volume of 300±161 $mm^3$ for the vehicle treated control group, 315±148 $mm^3$ for the 2.6 nM/kg control-TCB treated group, 293±135 $mm^3$ for the 2.6 nM/kg 83A10-TCBcv group and 307±138 $mm^3$ for the 2.6 nM/kg BCMA50-$(scFv)_2$ (BCMA50-BiTE®) group. The TCB antibody treatment schedule was based on the pharmacokinetic results previously obtained with 83A10-TCBcv and consisted of a once a week IV administration for up to 3 weeks (i.e. total of 3 injections of TCB antibody). Four days after reconstitution of the host mice with human PBMCs (d19), a first dose of the anti-BCMA/anti-CD3 83A10-TCBcv antibody (2.6 nM/kg respectively 0.5 mg/kg) was given via tail vein injection. Blood samples were collected by jugular/mandibular vein puncture (under anesthesia) 1 h before each treatment, 2 h before the second treatment and at termination in mice from all groups treated with 83A10-TCBcv and control-TCBcv. Blood samples were immediately transferred into clot activator containing tubes (T MG tubes, cherry red top, Capiject®, Terumo®). Tubes were left at room temperature for 30 min to allow clotting. Then tubes were centrifuged at 1,300 g for 5 min for clot/serum separation. Serum aliquots were prepared, flash frozen in liquid nitrogen and stored at −80° C. until further analysis. Tumor volume (TV) was measured by caliper during the study and progress evaluated by intergroup comparison of TV. The percentage of tumor growth defined as TG (%) was determined by calculating TG (%)=100×(median TV of analysed group)/(median TV of control vehicle treated group). For ethical reason, mice were euthanized when TV reached at least 2000 $mm^3$. FIG. 15 shows the TV of each individual mouse per experimental group: (A) control groups including vehicle control (full line) and control-TCB (dotted line), (B) 83A10-TCBcv (2.6 nM/kg) group, and (C) BCMA50-BiTE® (2.6 nM/kg). In the 83A10-TCBcv (2.6 nM/kg) group, 6 out of 9 mice (67%) had their tumor regressed even below TV recorded at d19 i.e. first TCB treatment and tumor regression was maintained until termination of study. The 3 mice in the 83A10-TCBcv (2.6 nM/kg) treated group which failed to show tumor regression had their TV equal to 376, 402 and 522 mm³ respectively at d19. In contrast, none of the 9 mice (0%) treated with an equimolar dose of BCMA50-BiTE® (2.6 nM/kg) at a once a week schedule for 3 weeks had their tumor regressed at any timepoints. Table 25 shows progression of tumor volumes over time in all experimental groups. The percentage of tumor growth was calculated for d19 to d43 and compared between 83A10-TCBcv (2.6 nM/kg) group and BCMA50-BiTE® (2.6 nM/kg) (FIG. 16). The results demonstrate that TG (%) is consistently and significantly reduced in the 83A10-TCBcv (2.6 nM/kg) group as well as the TG (%) is always lower when compared to BCMA50-BiTE® (2.6 nM/kg). Table 26 shows the median tumor volume (TV) and percentage of tumor growth (TG (%)) at days 19 to 43. The overall results clearly demonstrated that 83A10-TCBcv is superior to BCMA50-BiTE® to induce antitumor activity in vivo when treatment is given at equimolar dose in once a week schedule for 3 weeks.

TABLE 25

Progression of tumor volumes over time in mice from control vehicle group and mice treated with equimolar doses of control-TCB, 83A10-TCBcv and BCMA50-(scFv)₂ (BCMA50-BiTE ®)

| Tumor volume (mm³) | Control vehicle Group A | | | | | | | | | | |
|---|---|---|---|---|---|---|---|---|---|---|---|
| | A1 | A2 | A3 | A4 | A5 | A6 | A7 | A8 | A9 | Mean | SD |
| Day 5 | 95 | 58 | 63 | 71 | 63 | 68 | 67 | 65 | 36 | 65 | 15 |
| Day 8 | 70 | 61 | 71 | 70 | 56 | 68 | 74 | 70 | 49 | 66 | 8 |
| Day 12 | 66 | 65 | 53 | 50 | 57 | 58 | 60 | 59 | 56 | 58 | 5 |
| Day 15 | 101 | 95 | 131 | 80 | 61 | 65 | 89 | 37 | 161 | 91 | 37 |
| Day 19 | 333 | 327 | 566 | 123 | 197 | 191 | 444 | 92 | 427 | 300 | 161 |
| Day 23 | 565 | 481 | 1105 | 470 | 310 | 309 | 517 | 281 | 581 | 513 | 249 |
| Day 27 | 1071 | 877 | 1989 | 823 | 560 | 675 | 1089 | 530 | 870 | 943 | 440 |
| Day 30 | 1870 | 1129 | x | 419.2 | 867 | 1060 | 1368 | 673 | 1331 | 1090 | 450 |
| Day 34 | x | 1653 | | 507 | 1056 | 1521 | 1805 | 1008 | 2042 | 1370 | 535 |
| Day 37 | | 2140 | | 2043 | 1309 | 2017 | 2394 | 1267 | x | 1862 | 464 |
| Day 40 | | x | | x | 1592 | x | x | 1346 | | 1469 | 174 |
| Day 43 | | | | | 1548 | | | 1994 | | 1771 | 314 |
| Day 47 | | | | | x | | | x | | | |
| Day 51 | | | | | | | | | | | |

| Tumor volume (mm³) | 2.6 nM/kg Control TCB Group B | | | | | | | | | | |
|---|---|---|---|---|---|---|---|---|---|---|---|
| | B1 | B2 | B3 | B4 | B5 | B6 | B7 | B8 | B9 | Mean | SD |
| Day 5 | 68 | 65 | 84 | 83 | 46 | 63 | 73 | 74 | 67 | 69 | 11 |
| Day 8 | 55 | 64 | 54 | 73 | 60 | 103 | 56 | 55 | 76 | 66 | 16 |
| Day 12 | 45 | 92 | 73 | 76 | 83 | 78 | 103 | 69 | 76 | 77 | 16 |
| Day 15 | 72 | 169 | 64 | 99 | 69 | 150 | 223 | 115 | 88 | 117 | 54 |
| Day 19 | 257 | 334 | 71 | 318 | 268 | 460 | 602 | 236 | 285 | 315 | 148 |
| Day 23 | 430 | 773 | 95 | 444 | 553 | 738 | 808 | 381 | 461 | 520 | 227 |
| Day 27 | 924 | 1252 | 232 | 780 | 768 | 1009 | 915 | 606 | 630 | 791 | 289 |
| Day 30 | 1191 | 1714 | 326 | 867 | 1230 | 1349 | 1118 | 817 | 783 | 1044 | 398 |
| Day 34 | 1684 | x | 592 | 1466 | 1660 | 1954 | 1765 | 1180 | 576 | 1359 | 529 |
| Day 37 | 2522 | | 597 | 1735 | 1105 | x | x | 1402 | 861 | 1370 | 691 |
| Day 40 | x | | 978 | 2388 | 1952 | | | 2277 | 1365 | 1792 | 604 |
| Day 43 | | | 1302 | x | x | | | x | 1895 | 1599 | 419 |
| Day 47 | | | 2346 | | | | | | 2373 | 2359 | 19 |
| Day 51 | | | x | | | | | | x | | |

| Tumor volume (mm³) | 2.6 nM/kg 83A10-TCBcv Group C | | | | | | | | | | |
|---|---|---|---|---|---|---|---|---|---|---|---|
| | C1 | C2 | C3 | C4 | C5 | C6 | C7 | C8 | C9 | Mean | SD |
| Day 5 | 78 | 79 | 55 | 77 | 53 | 47 | 39 | 53 | 60 | 60 | 15 |
| Day 8 | 69 | 37 | 67 | 75 | 62 | 59 | 59 | 77 | 75 | 64 | 12 |
| Day 12 | 58 | 61 | 60 | 69 | 48 | 59 | 46 | 63 | 87 | 61 | 12 |
| Day 15 | 136 | 41 | 61 | 138 | 48 | 57 | 76 | 71 | 217 | 94 | 58 |
| Day 19 | 376 | 151 | 238 | 522 | 154 | 133 | 377 | 287 | 402 | 293 | 135 |
| Day 23 | 656 | 322 | 375 | 847 | 311 | 249 | 642 | 395 | 681 | 498 | 210 |
| Day 27 | 1119 | 376 | 443 | 1400 | 253 | 253 | 678 | 371 | 1166 | 673 | 441 |
| Day 30 | 1607 | 187 | 260 | 1975 | 88 | 113 | 219 | 191 | 1590 | 692 | 783 |
| Day 34 | 2143 | 68 | 100 | x | 34 | 54 | 63 | 53 | 2429 | 618 | 1033 |
| Day 37 | x | 41 | 44 | | 43 | 34 | 34 | 35 | x | 38 | 5 |
| Day 40 | | 64 | 40 | | 43 | 38 | 32 | 39 | | 43 | 11 |
| Day 43 | | 40 | 43 | | 33 | 24 | 32 | 25 | | 33 | 8 |
| Day 47 | | 14 | 21 | | 16 | 12 | 19 | 14 | | 16 | 3 |
| Day 51 | | 15 | 30 | | 20 | 20 | 15 | 18 | | 20 | 6 |

TABLE 25-continued

Progression of tumor volumes over time in mice from control vehicle
group and mice treated with equimolar doses of control-TCB, 83A10-TCBcv
and BCMA50-(scFv)₂ (BCMA50-BiTE ®)

| Tumor volume (mm³) | 2.6 nM/kg BCMA50-(scFv)₂ (BCMA50-BiTE ®) Group D | | | | | | | | | | |
|---|---|---|---|---|---|---|---|---|---|---|---|
| | D1 | D2 | D3 | D4 | D5 | D6 | D7 | D8 | D9 | Mean | SD |
| Day 5 | 75 | 92 | 78 | 86 | 57 | 91 | 74 | 58 | 62 | 75 | 13 |
| Day 8 | 51 | 87 | 61 | 99 | 70 | 88 | 90 | 73 | 71 | 77 | 15 |
| Day 12 | 70 | 73 | 63 | 76 | 84 | 76 | 85 | 58 | 113 | 78 | 16 |
| Day 15 | 142 | 72 | 61 | 128 | 87 | 77 | 121 | 60 | 188 | 104 | 44 |
| Day 19 | 232 | 212 | 81 | 474 | 303 | 260 | 360 | 304 | 539 | 307 | 138 |
| Day 23 | 560 | 483 | 121 | 811 | 665 | 408 | 654 | 457 | 1115 | 586 | 278 |
| Day 27 | 827 | 879 | 216 | 1224 | 1092 | 732 | 886 | 908 | 1526 | 921 | 359 |
| Day 30 | 1026 | 1414 | 227 | 1476 | 1373 | 1256 | 1210 | 1228 | 2433 | 1294 | 567 |
| Day 34 | 1368 | 1855 | 418 | 2185 | 1734 | 1936 | 1465 | 1645 | x | 1576 | 535 |
| Day 37 | 1691 | 2754 | 599 | | 2542 | | 2102 | 2062 | | 1958 | 765 |
| Day 40 | 2764 | x | 706 | | x | | x | x | | 1735 | 1455 |
| Day 43 | x | | 807 | | | | | | | 807 | n/a |
| Day 47 | | | x | | | | | | | | |
| Day 51 | | | | | | | | | | | |

TABLE 26

Median tumor volume (TV) and percentage of tumor growth (TG (%)) at
days 19 to 43: 83A10-TCBcv in comparison to BCMA50-BiTE ®.

| Tumor growth inhibition TG$_{inh}$ (%) | Vehicle treated Control | | 83A10-TCBcv 2.6 nM/kg | | BCMA50-BiTE ® 2.6 nM/kg | | Control-TCB 2.6 nM/kg | |
|---|---|---|---|---|---|---|---|---|
| | Median TV | TG (%) | Median TV | TG (%) | Median TV | TG (%) | Median TV | TG (%) |
| Day 19 | 327 | 100 | 287 | 87.8 | 303 | 92.7 | 285 | 87.2 |
| Day 23 | 481 | 100 | 395 | 82.1 | 560 | 116.4 | 461 | 95.8 |
| Day 27 | 870 | 100 | 443 | 50.9 | 886 | 101.8 | 780 | 89.7 |
| Day 30 | 1094.5 | 100 | 219 | 20.0 | 1256 | 114.8 | 1118 | 102.1 |
| Day 34 | 1521 | 100 | 65.5 | 4.3 | 1689.5 | 111.1 | 1563 | 102.8 |
| Day 37 | 2030 | 100 | 38 | 1.9 | 2082 | 102.6 | 1253.5 | 61.7 |
| Day 40 | 1469 | 100 | 39.5 | 2.7 | 1735 | 118.1 | 1952 | 132.9 |
| Day 43 | 1771 | 100 | 32.5 | 1.8 | 807 | 45.6 | 1598.5 | 90.3 |
| Day 47 | / | / | 15 | / | / | / | 2359.5 | / |
| Day 51 | / | / | 19 | / | / | / | / | / |

Example 18: Antitumoral Activity Induced by Anti-BCMA/Anti-CD3 T-Cell Bispecific Antibodies in RPMI-8226 Human Myeloma Xenograft Model in PBMC-Humanized NOG Mice Alternatively to H929 myeloma cell line, human myeloma RPMI-8226 cell line for which the level of expression of surface BCMA is lower than that of H929 and more representative of the level detected on primary myeloma cells is used as tumor xenograft. Briefly, on day 0 (d0) of the study, 10×10⁶-20×10⁶ human myeloma cell line RPMI-8226 (ATCC® CCL-155™) in 200 μL 0.9% NaCl solution containing 50:50 matrigel (BD Biosciences, France) are subcutaneously (SC) injected into the right dorsal flank of immunodeficient NOD/Shi-scid IL2rgamma(null) (NOG) female mice of 8-10 weeks of age (Taconic, Ry, Danemark). Twenty-four to 72 hours prior to RPMI-8226 cell line SC implantation, all mice received a whole body irradiation with a γ-source (1.44 Gy, ⁶⁰Co, BioMep, Bretenières, France). NOG mice receive a single intraperitoneal (IP) injection of 2×10⁷ human PBMCs (in 500 μL PBS 1× pH7.4) once between day 9 (d9) and day 45 (d45) once the tumor volumes reach at least 100-150 mm³. Characterization of the human PBMC is performed by immunophenotyping (flow cytometry). Mice are then carefully randomized into the different treatment and control groups (n=9/group) using Vivo Manager® software (Biosystemes, Couternon, France) and a statistical test (analysis of variance) is performed to test for homogeneity between the groups. Antibody treatment starts at least 24h to 48h after human PBMC IP injection and when the tumor volume reaches at least 100-150 mm³ in all mice. The TCB antibody treatment schedule is based on previous pharmacokinetic results and consisted of a once or twice a week IV administration via the tail vein for up to 3 weeks (i.e. total of 3 injections of TCB antibody). Blood samples are collected by jugular/mandibular vein puncture (under anesthesia) 1 h before each treatment, 2 h before the second treatment and at termination. Blood samples are immediately transferred into clot activator containing tubes (T MG tubes, cherry red top, Capiject®, Terumo®). Tubes are left at room temperature for 30 min to allow clotting. Then tubes are centrifuged at 1,300 g for 5 min for clot/serum separation. Serum aliquots are prepared, flash frozen in liquid nitrogen and stored at −80° C. until further analysis. Tumor volume (TV) is measured by caliper during the study and progress evaluated by intergroup comparison of TV. The percentage of tumor growth as defined as inhibition TG (%) is determined by calculating TG (%)=100×(median TV of analysed group)/(median TV of control vehicle treated group).

Figure 20:
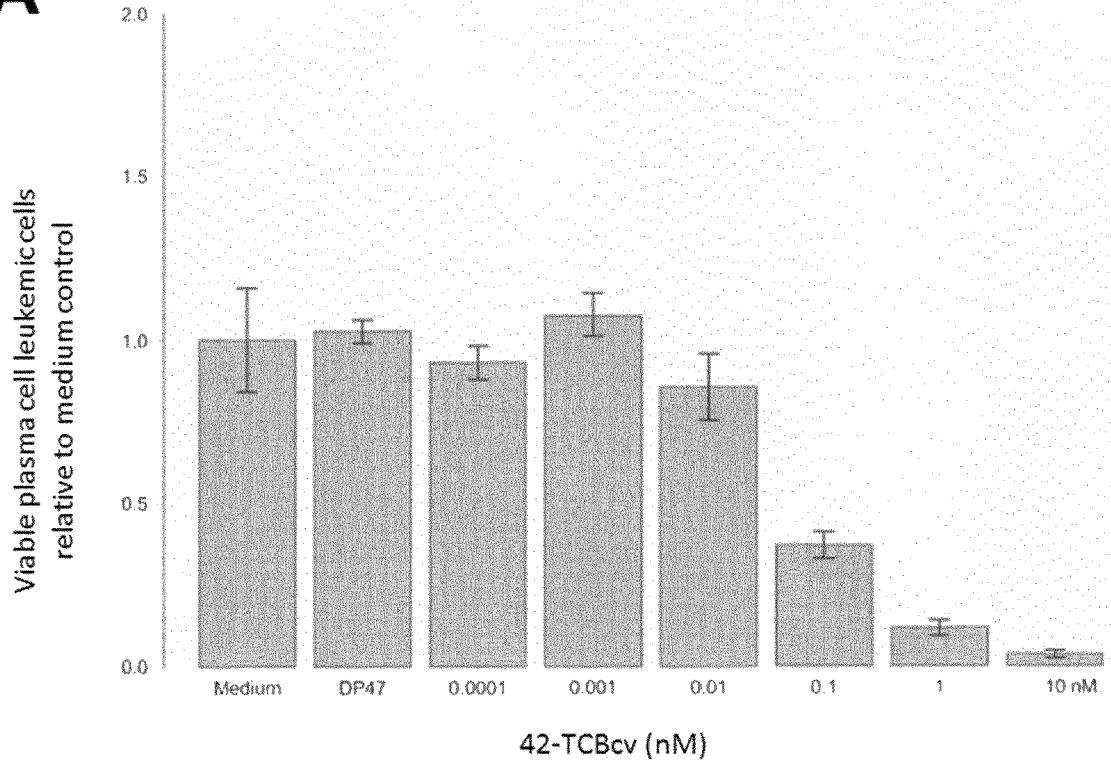
FIG. 20. Redirected T-cell lysis of plasma cell leukemia patient bone marrow leukemic cells in presence of autologous T cells or bone marrow infiltrating T cells induced by anti-BCMA/anti-CD3 T-cell bispecific antibodies as measured by flow cytometry. Percentage of propidium iodide negative myeloma plasma cells was determined and the percentage of viable bone marrow plasma cell leukemic cells relative to the medium control (MC) was plotted against TCB concentrations. Concentration-dependent and specific lysis of patient plasma cell leukemic cells were observed (A, B) while lysis of bone marrow microenvironment (BMME) was not observed (data not shown). No induction of cell death of myeloma plasma cells observed with control-TCB at the highest concentration of TCB antibodies tested. 42-TCBcv was very potent to induce killing of patient bone marrow plasma cell leukemic cells as reflected by the concentration-dependent reduction of viable (propidium iodide negative) myeloma plasma cells. An effect was considered statistically significant if the P-value of its corresponding statistical test was <5% (*), <1% () or <0.1% (*). The figure shows results obtained from bone marrow samples of patient 1(A) and patient 2(B) (see also example 20).
Figure 20:
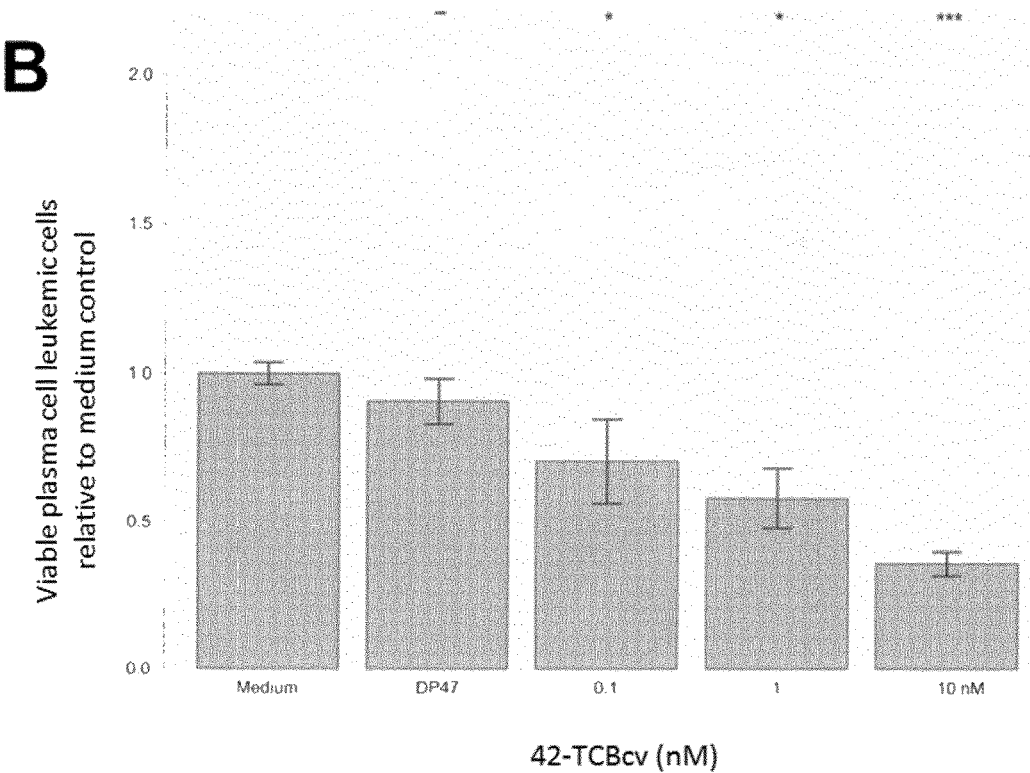

The model development of the RPMI-8226 human myeloma xenograft in PBMC-humanized NOG mice was first performed to ensure that the xenograft model was appropriate for testing anti-BCMA/anti-CD3 T-cell bispecific antibodies. BCMA'w-expressing RPMI-8226 MM cells were injected SC to NOG mice on day 0. At day 22, human PBMCs were injected IP and human T cells could be detected in blood one week later (data not shown). As depicted in FIG. 20, tumor growth and bodyweight were measured until day 50. Unfortunately and unexpectedly, this xenograft model turned out to be unsuitable to test the antitumor activity of anti-BCMA/anti-CD3 T-cell bispecific antibodies for the following reasons: 1) RPMI-8226 human myeloma xenograft failed to grow consistently in the PBMC-humanized NOG mice; 2) the PBMC-humanized NOG mice transplanted with RPMI-8226 xenograft started losing bodyweight soon after IP injection of human PBMC, a sign of graft-versus host disease. These mice were euthanized for ethical reasons; 3) loss of BCMA expression observed in tumor xenograft post SC injection at sacrifice of the host mice.

Example 19: Redirected T-Cell Cytotoxicity of Plasma Cells from Peripheral Blood Mononuclear Cells or Bone Marrow Aspirates of Patient with Plasma Cell Leukemia (PCL) in Presence of Autologous T Cells Induced by Anti-BCMA/Anti-CD3 T Cell Bispecific Antibodies as Measured by Flow Cytometry Plasma cell leukemia (PCL) is a leukemic variant of myeloma arising either de novo or from clinically pre-existent multiple myeloma (MM). The current available treatments are rather limited and consist mainly of combinations of MM drugs and chemotherapy. To date no therapy has ever been explicitly registered for this highly aggressive and deadly disease. BCMA plays an essential role in the survival of normal plasma cells and an anti-BCMA/anti-CD3 T cell bispecific antibodies according to the invention can be used for plasma cell leukemia treatment in a patient suffering from said disease. Freshly taken peripheral blood mononuclear cells (PBMC) from plasma cell leukemia patient samples containing >80% plasma cells at high leucocyte counts are isolated by density gradient using Ficoll or other comparable methods and incubated for 24h and 48h with anti-BCMA/anti-CD3 T cell bispecific antibody concentrations or control antibodies of 0.1 pM to 30 nM at 37° C. in a humidified air atmosphere. Whole bone marrow aspirates from plasma cell leukemia patients can also be used as samples. Each dose point is done in triplicates. Apoptosis is determined by annexin/propidium iodide staining of the whole population and of the CD138 positive cells on a FACSCalibur using Diva software (BD). Viability of the plasma cells and PBMC whole population are investigated by propidium iodide/CD138-FITC double-staining using flow cytometry (FACSCalibur; Becton Dickinson). Data analysis is performed using FACSDiva Software (Becton Dickinson). Mean values are normalized on the mean over the triplicates of the respective medium control (MC). For statistical analysis, a one-sided t-test is used. The maximum inhibition of PCL cell growth at a concentration of 10 nM (IMAX10) and the inhibition measured at 1 nM (IMAX1), respectively, are given in percent as referred to the medium control. The maximum inhibition of the control-TCB antibody (10 or 30 nM) compared to the medium control is also measured. Computations are performed using R 3.1.19, and Bioconductor 2.1310, but for calculation of the IMAX values (Microsoft Excel®; Microsoft Office Professional 2013). An effect is considered statistically significant if the P-value of its corresponding statistical test is <5% (*), <1% () or <0.1% (*). BCMA expression is also measured on PBMC CD138$^+$ plasma cells from plasma cell leukemia patient samples as well as effector cells to tumor cells (E:T) ratio is determined. As shown in FIG. 20, the results clearly show that there was significantly reduced viable bone marrow plasma cell leukemic cells with 42-TCBcv (i.e. more lysis of the bone marrow plasma cell leukemic cells) in two plasma cell leukemia patient samples as compared to the medium control Table 27 demonstrates the percentage of maximum inhibition of plasma cell leukemic cells from patient bone marrow aspirates or peripheral blood induced by 10 nM (IMAX10) and 1 nM (IMAX1) anti-BCMA/anti-CD3 T cell bispecific antibodies relative to medium control. The results demonstrate that 42-TCBcv is very potent to induce killing of patient bone marrow plasma cell leukemic cells. Despite specific lysis of bone marrow plasma cell leukemic cells induced by the anti-BCMA/anti-CD3 T cell bispecific antibodies and observed bone marrow samples (PCL patient 1), the bone marrow microenvironment (BMME) was unaffected in the respective samples (data not shown).

TABLE 27

IMAX10 and IMAX1 values in respect to maximal inhibition of plasma cell leukemia plasma cell growth at 10 nM (IMAX10) and inhibition at 1 nM (IMAX1) based on propidium iodide negative viable plasma cell leukemic cells from patient bone marrow aspirates in presence of by anti-BCMA/anti-CD3 T cell bispecific antibodies.

| Patient Sample No. | 42-TCBcv | | Ctrl-TCB |
| --- | --- | --- | --- |
| | IMAX10 (%) | IMAX1 (%) | IMAX10 (%) |
| 1 | 99.6 | 88.2 | −2.7 |
| 2 | ~60.0 | ~40.0 | ~8.0 |

Example 20: Redirected T-Cell Cytotoxicity of Bone Marrow Plasma Cells from Patient with AL Amyloidosis in Presence of Autologous T Cells Induced by Anti-BCMA/Anti-CD3 T Cell Bispecific Antibodies as Measured by Flow Cytometry AL amyloidosis is a rare disease caused by a disorder of the bone marrow which usually affects people from ages 50-80 and with two-third of the patients being male. AL amyloidosis is reflected by an abnormal production of antibody/immunoglobulin protein by the plasma cells. In AL amyloidosis, the light chains (LC) of the antibody are misfolded and the abnormal LC misfolded protein result is the formation of amyloid. These misfolded amyloid proteins are deposited in and around tissues, nerves and organs. As the amyloid builds up in an organ, nerve or tissue, it gradually causes damage and affects their function. Patients with AL amyloidosis are often affected with more than one organ. Since BCMA plays an essential role in the survival of normal plasma cells, it is highly justified to evaluate the effect of anti-BCMA/anti-CD3 T cell bispecific antibodies in killing plasma cells in AL amyloidosis. Freshly taken AL amyloidosis patient whole bone marrow samples/aspirates are either exposed directly to the anti-BCMA/anti-CD3 TCB antibodies or stained with CD138 magnetic microbeads (Miltenyi Biotec, Bergisch Gladbach, Germany), passed through an autoMACS cell separation column and the collected fractions with sufficient remaining number of AL amyloidosis plasma cells of usually >4% are used for further experiments. In 24-well plates, 500,000 cells/well are incubated and cultured for 48 hours. Anti-BCMA/anti-CD3 TCB antibodies and control antibody dilutions are added to the respective wells for a final TCB concentration of 0.1 pM to 30 nM. Each dose point is done in triplicates. Viability of the plasma cells and cells of the bone marrow microenvironment is investigated by propidium iodide/CD138-FITC double-staining using flow cytometry (FACSCalibur; Becton Dickinson). Data analysis is performed using FACSDiva Software (Becton Dickinson). Mean values are normalized on the mean over the triplicates of the respective medium control (MC). For statistical analysis, a one-sided t-test is used. The maximum inhibition of PCL cell growth at a concentration of 10 nM (IMAX10) and the inhibition measured at 1 nM (IMAX1), respectively, are given in percent as referred to the medium control. The maximum inhibition of the control-TCB antibody (10 or 30 nM) compared to the medium control is also measured. Computations are performed using R 3.1.19, and Bioconductor 2.1310, but for calculation of the IMAX values (Microsoft Excel®; Microsoft Office Professional 2013). An effect is considered statistically significant if the P-value of its corresponding statistical test is <5% (*), <1% () or <0.1% (*). BCMA expression is also measured on bone marrow CD138+ plasma cells from AL amyloidosis patient samples as well as effector cells to tumor cells (E:T) ratio is determined.

The invention claimed is:

1. A monoclonal antibody specifically binding to human B cell maturation antigen (BCMA), characterized in comprising a CDR3H region having SEQ ID NO:17 and a CDR3L region having SEQ ID NO:20 and a CDR1H, CDR2H, CDR1L, and CDR2L region combination selected from the group of:
   a) CDR1H region having SEQ ID NO:21 and CDR2H region having SEQ ID NO:22, CDR1L region having SEQ ID NO:23, and CDR2L region having SEQ ID NO:24,
   b) CDR1H region having SEQ ID NO:21 and CDR2H region having SEQ ID NO:22, CDR1L region having SEQ ID NO:25, and CDR2L region having SEQ ID NO:26,
   c) CDR1H region having SEQ ID NO:21 and CDR2H region having SEQ ID NO:22, CDR1L region having SEQ ID NO:27, and CDR2L region having SEQ ID NO:28,
   d) CDR1H region having SEQ ID NO:29 and CDR2H region having SEQ ID NO:30, CDR1L region having SEQ ID NO:31, and CDR2L region having SEQ ID NO:32,
   e) CDR1H region having SEQ ID NO:34 and CDR2H region having SEQ ID NO:35, CDR1L region having SEQ ID NO:31, and CDR2L region having SEQ ID NO:32, and
   f) CDR1H region having SEQ ID NO:36 and CDR2H region having SEQ ID NO:37, CDR1L region having SEQ ID NO:31, and CDR2L region having SEQ ID NO:32.

2. A monoclonal antibody specifically binding to BCMA, characterized in comprising a VH region comprising a CDR1H region having SEQ ID NO:21, a CDR2H region having SEQ ID NO:22 and a CDR3H region having SEQ ID NO:17 and a VL region comprising a CDR3L region having SEQ ID NO:20 and a CDR1L and CDR2L region combination selected from the group of:
   a) CDR1L region having SEQ ID NO:23 and CDR2L region having SEQ ID NO:24,
   b) CDR1L region having SEQ ID NO:25 and CDR2L region having SEQ ID NO:26, and
   c) CDR1L region having SEQ ID NO:27 and CDR2L region having SEQ ID NO:28.

3. The antibody according to claim 2, characterized in comprising a VH region having SEQ ID NO:10 and a VL region selected from the group consisting of VL regions having SEQ ID NO:12, 13, and 14.

4. A bispecific antibody specifically binding to BCMA and human CD3ε (CD3), characterized in comprising a CDR3H region having SEQ ID NO:17 and a CDR3L region having SEQ ID NO:20 and a CDR1H, CDR2H, CDR1L, and CDR2L region combination selected from the group of:
   a) CDR1H region having SEQ ID NO:21 and CDR2H region having SEQ ID NO:22, CDR1L region having SEQ ID NO:23, and CDR2L region having SEQ ID NO:24,
   b) CDR1H region having SEQ ID NO:21 and CDR2H region having SEQ ID NO:22, CDR1L region having SEQ ID NO:25, and CDR2L region having SEQ ID NO:26,
   c) CDR1H region having SEQ ID NO:21 and CDR2H region having SEQ ID NO:22, CDR1L region having SEQ ID NO:27, and CDR2L region having SEQ ID NO:28,
   d) CDR1H region having SEQ ID NO:29 and CDR2H region having SEQ ID NO:30, CDR1L region having SEQ ID NO:31, and CDR2L region having SEQ ID NO:32,
   e) CDR1H region having SEQ ID NO:34 and CDR2H region having SEQ ID NO:35, CDR1L region having SEQ ID NO:31, and CDR2L region having SEQ ID NO:32, and
   f) CDR1H region having SEQ ID NO:36 and CDR2H region having SEQ ID NO:37, CDR1L region having SEQ ID NO:31, and CDR2L region having SEQ ID NO:32.

5. A bispecific antibody specifically binding to two targets which are the extracellular domain of human BCMA (BCMA) and human CD3ε (CD3), characterized in comprising a VH region comprising a CDR1H region having SEQ ID NO:21, a CDR2H region having SEQ ID NO:22 and a CDR3H region having SEQ ID NO:17 and a VL region comprising a CDR3L region having SEQ ID NO:20 and a CDR1L and CDR2L region combination selected from the group of:
   a) CDR1L region having SEQ ID NO:23 and CDR2L region having SEQ ID NO:24,
   b) CDR1L region having SEQ ID NO:25 and CDR2L region having SEQ ID NO:26, and
   c) CDR1L region having SEQ ID NO:27 and CDR2L region having SEQ ID NO:28.

6. The bispecific antibody according to claim 5, characterized in comprising a BCMA VH region having SEQ ID NO:10 and a VL region having SEQ ID NO:12, or a BCMA VH region having SEQ ID NO:10 and a VL region having SEQ ID NO:13, or a BCMA VH region having SEQ ID NO:10 and a VL region having SEQ ID NO:14.

7. The bispecific antibody according to claim 4, characterized in comprising a light chain and a heavy chain of an antibody specifically binding to CD3, wherein the variable domains VL and VH or the constant domains CL and CH1 are replaced by each other.

8. The bispecific antibody according to claim 4, characterized in that a variable domain VH of an anti-CD3 antibody portion of the bispecific antibody (CD3 VH) comprises heavy chain CDRs having SEQ ID NO: 1, 2 and 3 as respective heavy chain CDR1, CDR2 and CDR3 and the variable domain VL of the anti-CD3 antibody portion (CD3 VL) comprises light chain CDRs having SEQ ID NO: 4, 5 and 6 as respective light chain CDR1, CDR2 and CDR3.

9. A bispecific antibody specifically binding to BCMA and CD3, characterized in comprising a) a first light chain and a first heavy chain of a first anti-BCMA antibody according to claim 1; and
b) a second light chain and a second heavy chain of a second antibody which specifically binds to CD3, and wherein the variable domains VL and VH in the second light chain and second heavy chain of the second antibody are replaced by each other; and
c) wherein in a constant domain CL of the first light chain a) an amino acid at position 124 is substituted independently by lysine (K), arginine (R) or histidine (H) (numbering according to Kabat), and wherein in a constant domain CH1 of the first heavy chain a) an amino acid at position 147 and an amino acid at position 213 are substituted independently by glutamic acid (E), or aspartic acid (D) (numbering according to EU index of Kabat).

10. A bispecific antibody according to claim 9, characterized in comprising in addition a Fab fragment of said first antibody (BCMA-Fab) and in the constant domain CL of said BCMA-Fab the amino acid at position 124 is substituted independently by lysine (K), arginine (R) or histidine (H) (numbering according to Kabat), and wherein in the constant domain CH1 of said BCMA-Fab the amino acid at positions 147 and the amino acid at position 213 are substituted independently by glutamic acid (E), or aspartic acid (D) (numbering according to EU index of Kabat) (see e.g. FIGS. 2A, 2C).

11. A bispecific antibody specifically binding to BCMA and CD3, characterized in comprising
a) a first light chain and a first heavy chain of a first antibody according to claim 1; and
b) a second light chain and a second heavy chain of a second antibody which specifically binds to CD3, and wherein the variable domains VL and VH in the second light chain and second heavy chain of the second antibody are replaced by each other; and wherein
c) in a constant domain CL of the second light chain under b) an amino acid at position 124 is substituted independently by lysine (K), arginine (R) or histidine (H) (numbering according to Kabat), and wherein in a constant domain CH1 of the second heavy chain under b) an amino acid at positions 147 and an amino acid at position 213 are substituted independently by glutamic acid (E), or aspartic acid (D) (numbering according to EU index of Kabat).

12. The bispecific antibody according to claim 4, characterized in comprising not more than one Fab fragment of an anti-CD3 antibody, not more than two Fab fragments of an anti-BCMA antibody and not more than one Fc part.

13. The bispecific antibody according to claim 12 characterized in comprising an Fc part linked with its N-terminus to the C-terminus of said CD3 antibody Fab fragment and to the C-terminus of one of said BCMA antibody Fab fragments.

14. The bispecific antibody according to claim 13, characterized in comprising a second Fab fragment of said anti-BCMA antibody portion linked with its C-terminus to the N-terminus of the CD3 antibody portion of said bispecific antibody.

15. The bispecific antibody according to claim 14, characterized in that a VL domain of said anti-CD3 antibody Fab fragment is linked to a CH1 domain of said second anti-BCMA antibody Fab fragment.

16. A bispecific antibody specifically binding to BCMA and to CD3, characterized in comprising a heavy and light chain set selected from the group consisting of polypeptides:
i) SEQ ID NO:48, SEQ ID NO:49, SEQ ID NO:50, and SEQ ID NO:51 (2×),
ii) SEQ ID NO:48, SEQ ID NO:52, SEQ ID NO:53, and SEQ ID NO:54 (2×), or
iii) SEQ ID NO:48, SEQ ID NO:55, SEQ ID NO:56, and SEQ ID NO:57 (2×).

17. A method of treatment of a plasma cell disorder comprising administering an antibody according to claim 1 to a subject in need thereof.

18. A method of treatment of a plasma cell disorder according to claim 17 wherein the plasma cell disorder is selected from the group consisting of multiple myeloma, systemic lupus erythematosus, plasma cell leukemia, and AL-amyloidosis.

19. A chimeric antigen receptor (CAR), wherein the CAR comprises an antigen recognition moiety directed against BCMA and a T-cell activation moiety, characterized in that the antigen recognition moiety is a monoclonal antibody or antibody fragment according to claim 1.

20. A monoclonal antibody specifically binding to BCMA according to claim 1, characterized in comprising a VH region comprising a CDR1H region having SEQ ID NO:21, a CDR2H region having SEQ ID NO:22 and a CDR3H region having SEQ ID NO:17; and a VL region comprising a CDR1L region having SEQ ID NO:27, a CDR2L region having SEQ ID NO:28 and a CDR3L region having SEQ ID NO:20.

21. A bispecific antibody specifically binding to BCMA and human CD3E (CD3) according to claim 4, characterized in that a variable domain VH of an anti-BCMA antibody portion of the bispecific antibody comprises a CDR1H region having SEQ ID NO:21, a CDR2H region having SEQ ID NO:22 and a CDR3H region having SEQ ID NO:17; and a VL region comprising a CDR1L region having SEQ ID NO:27, a CDR2L region having SEQ ID NO:28 and a CDR3L region having SEQ ID NO:20; and,
wherein the bispecific antibody is further characterized in that a variable domain VH of a n anti-CD3 antibody portion of the bispecific antibody comprises a CDR1H region having SEQ ID NO:1, a CDR2H region having SEQ ID NO:2 and a CDR3H region having SEQ ID NO:3; and a VL region comprising a CDR1L region having SEQ ID NO:4, a CDR2L region having SEQ ID NO:5 and a CDR3L region having SEQ ID NO:6.

* * * * *